US008415357B2

(12) United States Patent
Kawabe et al.

(10) Patent No.: US 8,415,357 B2
(45) Date of Patent: Apr. 9, 2013

(54) COMPOUNDS WITH ANTI-CANCER ACTIVITY

(75) Inventors: Takumi Kawabe, Numazu (JP); Machiyo Ishigaki, Numazu (JP); Takuji Sato, Numazu (JP); Sayaka Yamamoto, Numazu (JP); Yoko Hasegawa, Numazu (JP)

(73) Assignee: Canbas Co., Ltd., Shizuoka (JP)

( * ) Notice: Subject to any disclaimer, the term of this patent is extended or adjusted under 35 U.S.C. 154(b) by 39 days.

(21) Appl. No.: 12/950,297

(22) Filed: Nov. 19, 2010

(65) Prior Publication Data

US 2011/0092514 A1    Apr. 21, 2011

Related U.S. Application Data

(62) Division of application No. 12/082,643, filed on Apr. 11, 2008, now Pat. No. 8,084, 454.

(60) Provisional application No. 60/911,258, filed on Apr. 11, 2007.

(51) Int. Cl.
*A61K 31/497* (2006.01)
*A61K 31/44* (2006.01)
*A61K 31/47* (2006.01)

(52) U.S. Cl.
USPC ...... 514/253.06; 514/290; 514/310; 514/313; 514/343

(58) Field of Classification Search ............. 514/253.06, 514/313, 310, 290, 343
See application file for complete search history.

(56) References Cited

U.S. PATENT DOCUMENTS

| 5,935,966 A | 8/1999 | Suto et al. |
| 6,291,447 B1 | 9/2001 | Andersen et al. |
| 6,476,061 B1 | 11/2002 | Rheinheimer et al. |
| 6,586,369 B1 | 7/2003 | Rheimheimer et al. |
| 8,084,454 B2 | 12/2011 | Kawabe et al. |
| 2004/0198727 A1 | 10/2004 | Kawabe et al. |

FOREIGN PATENT DOCUMENTS

| EP | 1 218 494 B1 | 4/2005 |
| JP | 07 224032 A | 8/1995 |
| WO | 9709325 A1 | 3/1997 |
| WO | WO 97/09325 A1 | 3/1997 |
| WO | WO 00/30445 A1 | 6/2000 |
| WO | WO 01/62087 A2 | 8/2001 |
| WO | WO 2005/024755 A2 | 3/2005 |
| WO | WO 2006/086255 A2 | 8/2006 |
| WO | WO 2007/053765 A | 5/2007 |
| WO | WO 2008/110891 A2 | 9/2008 |

OTHER PUBLICATIONS

Singapore Patent Application No. 200906750-5, Intellectual Property Office of Singapore, Search and Examination Report issued Apr. 6, 2011.
Hartwell, L., Defects in a Cell Cycle Checkpoint May be Responsible for the Genomic Instability of Cancer Cells, Cell, 1992, 71, 543-546.
Kawabe, T., G2 Checkpoint Abrogators as Anticancer Drugs, Mol. Cancer Ther., 2004, 3(4), 513-519.
Maller, J. L., Mitotic Control, Current Opinion in Cell Biology, 1991, 3, 369-275.
Piers, E., et al., Improved Synthesis of Isogranulatimide, a G2 Checkpoint Inhibitor, Syntheses of Didemnimide C, Isodidemnimide A, Neodidemnimide A, 17-Methylgranulatirnide, and dlsogranulatimides A-C, J. Org. Chem., 2000, 65, 530-535.
Sha, S.-K., et al., Cell Cycle Phenotype-Based Optimization of $G_2$-Abrogating Peptides Yields CBP501 With a Unique Mechanism of Action at the $G_2$ Checkpoint, Mol. Cancer Ther., 2007, 6(1), 147-53.
Palanski, M.S., et al., Novel Inhibitors of AP-1 and NF-KappaB Mediated Gene Expression: Structure-Activity Relationship Studies of Ethyl . . . , Bioorganic & Medicinal Chemistry Letters, Pergamon, Elsevier Science, 2000, 10(15):1645-1648, XP004213214.
Palanski, M.S., et al., the Design and Synthesis of Novel Orally Active Inhibitors of AP-1 and NF-kB Mediated Transcriptional Activation. SAR of in vitro and in vivo Studies, Bioorganic & Medicinal Chemistry Letters, 2003 13:4077-4080, XP002518652.
Database Beilstein Beilstein Institute for Organic Chemistry, Frankfurt-Main, DE; XP002518653, Database accession No. BRN:1477866 abstract & Chemical and Pharmaceutical Bulletin, 1967, 15:1101-1104, XP002518653.
CAS Registry entry No. 910441-85-9; entry date Oct. 15, 2006.
CAS Registry entry No. 138949-46-9; entry date Feb. 14, 1992.
CAS Registry entry No. 138949-42-5; entry date Feb. 14, 1992.
CAS Registry entry No. 138949-41-4; entry date Feb. 14, 1992.
CAS Registry entry No. 138949-40-3; entry date Feb. 14, 1992.
CAS Registry entry No. 138949-26-5; entry date Feb. 14, 1992.
CAS Registry entry No. 144173-20-6; entry date Oct. 28, 1992.
CAS Registry entry No. 84686-99-7; entry date Nov. 16, 1984.
CAS Registry entry No. 74180-27-1; entry date Nov. 16, 1984.
CAS Registry entry No. 731832-52-3; entry date Aug. 24, 2004.
CAS Registry entry No. 732257-97-5; entry date Aug. 24, 2004.

*Primary Examiner* — James O Wilson
*Assistant Examiner* — Ebenezer O. Sackey
(74) *Attorney, Agent, or Firm* — Pillsbury Winthrop Shaw Pittman LLP

(57) ABSTRACT

Novel substituted azole diones are provided that kill cells, suppress cell proliferation, suppress cell growth, abrogate the cell cycle G2 checkpoint and/or cause adaptation to G2 cell cycle arrest. Methods of making and using the invention compounds are provided. The invention provides substituted azole diones to treat cell proliferation disorders. The invention includes the use of substituted azole diones to selectively kill or suppress cancer cells without additional anti-cancer treatment. The invention includes the use of cell cycle G2-checkpoint-abrogating substituted azole diones to selectively sensitize cancer cells to DNA damaging reagents, treatments and/or other types of anti-cancer reagents.

104 Claims, 8 Drawing Sheets

# COMPOUNDS WITH ANTI-CANCER ACTIVITY

RELATED APPLICATIONS

This application is a division of U.S. application Ser. No. 12/082,643, filed Apr. 11, 2008 now U.S. Pat. No. 8,084,454, which claims benefit of priority to U.S. Provisional Application No. 60/911,258, filed Apr. 11, 2007, the contents of each of which is hereby incorporated by reference in its entirety.

FIELD OF THE INVENTION

The invention relates to novel substituted azole dione compounds having anti-cancer activity and/or activity against proliferating cells, and to methods of making and using these compounds, wherein the substituted azole dione compounds abrogate the cell cycle G2 checkpoint and/or cause adaptation to cell cycle arrest. The invention includes the use of substituted azole dione compounds to selectively suppress or kill cancer cells, with or without additional anti-cancer treatment. The invention includes the use of cell cycle G2-checkpoint-abrogating substituted azole dione compounds provided herein, to selectively sensitize cancer cells to DNA damaging agents, DNA-damaging treatments and/or other types of anti-cancer agents.

BACKGROUND

The cell cycle comprises S phase (DNA replication), M phase (mitosis), and two gap phases (G1 and G2 phases) between S and M phases. Checkpoints in the cell cycle ensure accurate progression through cell cycle stages, and include monitoring DNA integrity, DNA replication, cell size, and the surrounding environment (Mailer (1991) *Curr. Opin. Cell Biol.*, 3:26). Cell cycle checkpoints that monitor the state of genome include the G1 checkpoint prior to onset of DNA replication and the G2 checkpoint prior to onset of mitosis. The G1 checkpoint allows detection and repair of DNA damage before entering S phase, thereby providing a crucial protective function because, when damaged DNA is replicated, it often gives rise to mutations (Hartwell (1992) *Cell* 71: 543). The G2 checkpoint allows detection and repair of DNA damage before entering mitosis (M phase), thereby providing a crucial function because mitosis without DNA repair may propagate the damage through DNA-damaged daughter cells, or mitosis may fail entirely. Progression through G1 and G2 checkpoints without repairing extensive DNA damage usually results in cell death.

Inhibition of the cell cycle G2 checkpoint by peptides, peptidomimetics, and "small molecules" has been used to selectively target cancer cells because most cancer cells are defective at one or both of the two major checkpoints of the cell cycle that protect cells from the effects of DNA damage, such that inhibition of the G2 checkpoint allows DNA-damaged cells to re-enter the cell cycle without repairing the DNA damage. (Kawabe T. (2004) "G2 checkpoint abrogators as anti-cancer drugs" *Mol Cancer Ther* 3: 513-519). Although the molecular mechanism of the cell cycle G2 checkpoint was extensively studied, no single molecular target for the therapeutic G2 checkpoint abrogation was established in earlier studies. A phenotype-based screening protocol has been developed to efficiently identify potential G2 checkpoint inhibitors. (Suganuma M. & Kawabe T., EP Application No. 00964563; Sha et al. (2007) *Mol Cancer Ther* 6: 147-153), where cell cycle phenotype-based screening of G2 checkpoint abrogating peptides identified CBP501 having a unique mechanism of action at the cell cycle G2 checkpoint. (Sha et al. (2007) *Mol Cancer Ther* 6: 147-153).

SUMMARY OF THE INVENTION

The present invention provides compounds to treat cell proliferation disorders. In particular, the invention provides compounds including: tert-butyl 3-(1-{[6-chloro-5-(trifluoromethyl)(2-pyridyl)]amino}-4-methyl-2,5-dioxoazolin-3-yl) propanoate (interchangeably referred to as S001860, S01860, or S1860, i.e., S001860=S01860=S1860); 1-{[6-chloro-3-(trifluoromethyl)(2-pyridyl)]amino}-3,4-dimethylazoline-2,5-dione (S00109=S0109=S109); 3-(Butoxymethyl)-1-{[6-chloro-5-(trifluoromethyl) (2-pyridyl)]amino}-4-methylazoline-2,5-dione (S03518); 1-{[6-Chloro-5-(trifluoromethyl) (2-pyridyl)]amino}-4-methyl-3-[(3-methylbutoxy)methyl]azoline-2,5-dione (S03405); 3-[(3,3-Dimethylbutoxy)methyl]-1-{[6-chloro-5-(trifluoromethyl) (2-pyridyl)]amino}-4-methylazoline-2,5-dione (S03747); and related compounds, wherein these compounds, when administered to cells or to a subject, have effects that may include killing or suppressing undesirably proliferating cells associated with a cell proliferation disorder.

The present invention provides compounds that kill or suppress undesirably proliferating cells associated with a cell proliferation disorder. The present invention provides compounds that abrogate the cell cycle G2 checkpoint and/or cause adaptation to G2 cell cycle arrest. The present invention provides compounds that abrogate the cell cycle G2 checkpoint and/or cause adaptation to cell cycle arrest, leading to death or suppression of undesirably proliferating cells The present invention provides compounds that abrogate the cell cycle G2 checkpoint and/or cause adaptation to cell cycle arrest, leading to death or suppression of DNA-damaged cells. The present invention provides compounds having cytotoxic activity against cancer cells. The present invention provides compounds having cytotoxic activity against cancer cells, including but not limited to DNA-damaged cancer cells. The present invention provides compounds having cytotoxic activity against cancer cells, including but not limited to cancer cells in G2 cell cycle arrest due to DNA damage. The present invention provides compounds having cytotoxic activity against cancer cells, and little or no cytotoxic activity against normal cells. The present invention provides compounds that can augment the cytotoxic effect of other anti-cancer agents and treatments, especially DNA-damaging anti-cancer agents and DNA-damaging anti-cancer treatments. The present invention provides compounds that can sensitize cells to other anti-cancer agents and treatments, especially DNA-damaging anti-cancer agents and DNA-damaging anti-cancer treatments. The present invention provides methods of making and using the compounds disclosed herein. The present invention provides pharmaceutical compositions containing compounds of the invention.

The present invention provides compounds for use in treating a cell proliferation disorder. The present invention provides compounds for use in treating cancer, e.g., for treating undesirable cell proliferation associated with benign and malignant tumor cells, leukemia cells, lymphoma cells, or multiple myeloma cells. The present invention provides compounds for use in abrogating the cell cycle G2 checkpoint in undesirably proliferating cells such as cancer cells, e.g., benign and malignant tumor cells, leukemia cells, lymphoma cells, or multiple myeloma cells. The present invention provides compounds for use in causing adaptation to G2 cell cycle arrest in undesirably proliferating cells such as cancer cells, e.g., benign and malignant tumor cells, leukemia cells, lymphoma cells, or multiple myeloma cells.

The present invention provides methods for treating a cell proliferation disorder by administering an effective amount of a compound of the invention in vivo, ex vivo, or in vitro. The present invention provides methods for treating a cell proliferation disorder by administering an effective amount of a compound of the invention to a subject. The present invention provides methods for treating a cell proliferation disorder wherein the cell proliferation disorder is cancer, including but not limited to lymphoma, myeloma, or leukemia. The present invention provides methods for treating cancer by administering an effective amount of a compound and administering at least one additional anti-cancer treatment, e.g., a DNA-damaging agent or a DNA-damaging treatment.

The invention provides methods for killing or suppressing cells by contacting cells with a compound of the invention or a pharmaceutical composition of the invention, in combination with a DNA-damaging agent or treatment. The invention provides methods for selectively sensitizing cells to a DNA-damaging agent and/or treatment, by contacting cells with a compound of the invention or a pharmaceutical composition of the invention, in combination with the DNA-damaging agent or treatment. The invention provides methods for inducing apoptosis, necrosis, and/or mitotic catastrophe in undesirably proliferating cells, comprising an administering a compound of the invention or a pharmaceutical composition of the invention to the cells, in an amount sufficient to kill or suppress the undesirably proliferating cells, with or without administering other treatments. The invention provides methods for inducing apoptosis, necrosis, and/or mitotic catastrophe in undesirably proliferating cells in a subject, comprising an administering a compound of the invention or a pharmaceutical composition of the invention to the subject, in an amount sufficient to kill or suppress the undesirably proliferating cells, with or without administering other treatments.

Phenotype-based screening was used to measure the ability of compounds of the invention to cause adaptation to G2 cell cycle arrest in G2-arrested cells. Adaptation to G2 cell cycle arrest and re-entry into the cell cycle can result in death of the previously G2-arrested cell, or suppression (inhibition) of further proliferation of the previously G2-arrested cell. In a non-limiting embodiment, the ability to cause adaptation to G2 cell cycle arrest was measured by contacting cells in which G2 arrest had been induced by irradiation (e.g., gamma (γ) radiation or X-ray radiation), with compounds of the invention at various concentrations and, for each compound at each concentration, determining the percentage of cells that escaped G2 arrest and re-entered the cell cycle, by determining the percentage of cells in G1 phase. The $IC_{50}$ value for each compound was calculated as the dosage (usually in μM) that caused half-maximal increase of the percentage of cells in G1 phase (the G1 increment) measured for that compound. Certain invention compounds were initially identified by phenotype-based screening of small molecule libraries for activity against G2-arrested cells as described above.

The invention provides compounds having the formula of Structure (I):

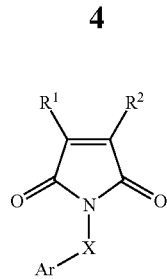

wherein $R^1$ and $R^2$ are independently chosen from alkyl, substituted alkyl, optionally substituted alkoxy, optionally substituted alkylthio, halogen, optionally substituted aryl, optionally substituted aryloxy, optionally substituted arylthio, or H, where $R^1$ and $R^2$ can also be part of a cyclic alkylene chain that form a fused ring structure, X is O, S, $NR^3$, or $CR^4R^5$, Ar is aryl or substituted aryl, including carbocyclic aryl, heterocyclic aryl, monocyclic aryl, polycyclic aryl, and aryl fused with non-aryl (non-aromatic) rings, $R^3$ is H, alkyl, substituted alkyl, optionally substituted acyl, or as part of a ring structure that connects the N to the Ar ring, $R^4$ and $R^5$ are chosen independently from H, alkyl, substituted alkyl, or both can be part of a cyclic alkylene chain that forms a ring structure and $R^4$ or $R^5$ can also be part of a ring structure that connects to the Ar ring, or a salt of any of these compounds.

The invention provides methods for treating a cell proliferation disorder comprising administering to a subject an effective amount of with a compound having the formula of Structure (I):

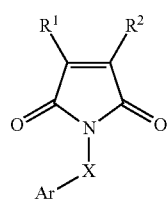

wherein $R^1$ and $R^2$ are independently chosen from alkyl, substituted alkyl, optionally substituted alkoxy, optionally substituted alkylthio, halogen, optionally substituted aryl, optionally substituted aryloxy, optionally substituted arylthio, or H, where $R^1$ and $R^2$ can also be part of a cyclic alkylene chain that form a fused ring structure, X is O, S, $NR^3$, or $CR^4R^5$, Ar is aryl or substituted aryl, including carbocyclic aryl, heterocyclic aryl, monocyclic aryl, polycyclic aryl, and aryl fused with non-aryl (non-aromatic) rings, $R^3$ is H, alkyl, substituted alkyl, optionally substituted acyl, or as part of a ring structure that connects the N to the Ar ring, $R^4$ and $R^5$ are chosen independently from H, alkyl, substituted alkyl, or both can be part of a cyclic alkylene chain that forms a ring structure and $R^4$ or $R^5$ can also be part of a ring structure that connects to the Ar ring, or a salt of any of these compounds. The invention provides methods for treating a cell proliferation disorder comprising administering an effective amount of a compound having the formula of Structure (I) in vivo, ex vivo, or in vitro.

The present invention provides compounds that abrogate the cell cycle G2 checkpoint and/or cause adaptation to cell cycle G2 arrest, wherein these compounds when administered to cells or to a subject have effects that may include killing or suppress the growth of undesirably proliferating cells, the compounds including:

tert-butyl 3-(1-{[6-chloro-5-(trifluoromethyl)(2-pyridyl)] amino}-4-methyl-2,5-dioxoazolin-3-yl) propanoate (S01860);

Ethyl 3-(1-{[6-chloro-5-(trifluoromethyl)(2-pyridyl)] amino}-4-methyl-2,5-dioxoazolin-3-yl) propanoate (S01861);

3,4-dimethyl-1-[(4,7,8-trichloro(2-quinolyl))amino]azoline-2,5-dione (S01078);

1-[(8-bromo-4-chloro(2-quinolyl))amino]-3,4-dimethylazoline-2,5-dione (S01247);

tert-butyl 4-({2-[(3,4-dimethyl-2,5-dioxoazolinyl)amino]-7-bromo-4-quinolyl}methyl)piperazinecarboxylate (S01589);

Methyl 3-(1-{[6-chloro-5-(trifluoromethyl)(2-pyridyl)] amino}-4-methyl-2,5-dioxoazolin-3-yl)propanoate (S01648);

3-(1-{[6-chloro-5-(trifluoromethyl)(2-pyridyl)]amino}-4-methyl-2,5-dioxoazolin-3-yl)-N-methoxy-N-methylpropanamide (S01796);

1-{[7-bromo-4-({4-[(2-methoxyphenyl)carbonyl] piperazinyl}methyl) (2-quinolyl)]amino}-3,4-dimethylazoline-2,5-dione (S01879);

1-{[3-bromo-6-chloro-5-(trifluoromethyl)(2-pyridyl)] amino}-3,4-dimethylazoline-2,5-dione (S01981);

1-{[6-chloro-3-(trifluoromethyl)(2-pyridyl)]amino}-3,4-dimethylazoline-2,5-dione (S00109);

1-{([6-chloro-5-(trifluoromethyl)(2-pyridyl)]methylamino}-3,4-dimethylazoline-2,5-dione (S00170);

1-{[6-bromo-5-(trifluoromethyl)(2-pyridyl)]methylamino}-3,4-dimethylazoline-2,5-dione (S01007);

1-{[6-chloro-5-(trifluoromethyl)(2-pyridyl)]amino}-4-methyl-3-(3-methylbutyl)azoline-2,5-dione (S01554);

1-{[6-chloro-5-(trifluoromethyl)(2-pyridyl)]amino}-3-(methoxymethyl)-4-methylazoline-2,5-dione (S01599);

1-{[7,8-dichloro-4-(trifluoromethyl)(2-quinolyl)]amino}-3,4-dimethylazoline-2,5-dione (S01455);

3-(1-{[6-chloro-5-(trifluoromethyl)(2-pyridyl)]amino}-4-methyl-2,5-dioxoazolin-3-yl)-N,N-diethylpropanamide (S01711);

Diethyl 2-[(1-{[6-chloro-5-(trifluoromethyl)(2-pyridyl)] amino}-4-methyl-2,5-dioxoazolin-3-yl)methyl]propane-1,3-dioate (S01712);

N-(tert-butyl)-3-(1-{[6-chloro-5-(trifluoromethyl)(2-pyridyl)]amino}-4-methyl-2,5-dioxoazolin-3-yl)propanamide (S01758);

1-{[7-bromo-4-({4-[(3-methoxyphenyl)carbonyl] piperazinyl}methyl) (2-quinolyl)]amino}-3,4-dimethylazoline-2,5-dione (S01925);

1-{[6-bromo-5-(trifluoromethyl)(2-pyridyl)]amino}-3,4-dimethylazoline-2,5-dione (S00994);

1-[(4,8-dichloro(2-quinolyl))amino]-3,4-dimethylazoline-2,5-dione (S01005);

3,4-dimethyl-1-{[6-phenyl-5-(trifluoromethyl)(2-pyridyl)] amino}azoline-2,5-dione (S01266);

1-{[6-chloro-5-(trifluoromethyl)(2-pyridyl)]amino}-3-(hydroxymethyl)-4-methylazoline-2,5-dione (S01470);

N-(3,4-dimethyl-2,5-dioxoazolinyl)-N-[6-chloro-5-(trifluoromethyl) (2-pyridyl)]acetamide (S01473);

1-{[7-bromo-4-({4-[(2-chlorophenyl)carbonyl] piperazinyl}methyl) (2-quinolyl)]amino}-3,4-dimethylazoline-2,5-dione (S01878);

3-(1-{[6-chloro-5-(trifluoromethyl)(2-pyridyl)]amino}-4-methyl-2,5-dioxoazolin-3-yl)-N-methylpropanamide (S01883);

1-[(8-chloro(2-quinolyl))amino]-3,4-dimethylazoline-2,5-dione (S00585);

3,4-dimethyl-1-[(3,4,5-trichlorophenyl)amino]azoline-2,5-dione (S00832);

3,4-dimethyl-1-{[4-(trifluoromethyl)(2-quinolyl)] amino}azoline-2,5-dione (S00873);

1-[(7-bromo-4-chloro(2-quinolyl))amino]-3,4-dimethylazoline-2,5-dione (S01311);

1-{[6-(3-chloro-4-fluorophenyl)-5-(trifluoromethyl)(2-pyridyl)]amino}-(3,4-dimethyl (3,4-dimethyl methylazoline-2,5-dione (S01313);

3,4-dimethyl-1-{[6-(2-methylpropyl)-5-(trifluoromethyl)(2-pyridyl)]amino}azoline-2,5-dione (S01457);

1-{[6-chloro-4-(trifluoromethyl)(2-pyridyl)]amino}-3,4-dimethylazoline-2,5-d1one (S01737);

Methyl 3-(1-{[4-({4-[(tert-butyl)oxycarbonyl] piperazinyl}methyl)-7-bromo (2-quinolyl)]amino}-4-methyl-2,5-dioxoazolin-3-yl)propanoate (S01865);

1-({4-[(4-{[4-(dimethylamino)phenyl] carbonyl}piperazinyl)methyl]-7-bromo (2-quinolyl) }amino)-3,4-dimethylazoline-2,5-dione (S01880);

1-[(3-chloroisoquinolyl)amino]-3,4-dimethylazoline-2,5-dione (S01098);

1-{[6-chloro-5-(trifluoromethyl)(2-pyridyl)]amino}-3-ethyl-4-methylazoline-2,5-dione (S01553);

1-{[4-chloro-6-phenyl-5-(trifluoromethyl)(2-pyridyl)] amino}-3,4-dimethylazoline-2,5-dione (S01734);

N-[1-({2-[(3,4-dimethyl-2,5-dioxoazolinyl)amino]-7-bromo(4-quinolyl)}methyl)pyrrolidin-3-yl] (tert-butoxy)carboxamide (S01864);

1-{[7-bromo-4-({4-[(4-fluorophenyl)carbonyl] piperazinyl}methyl) (2-quinolyl)]amino}-3,4-dimethylazoline-2,5-dione (S01877);

6-[(3,4-dimethyl-2,5-dioxoazolinyl)amino]-3-(trifluoromethyl)pyridine-2-carbonitrile (S01475);

2-{[6-chloro-5-(trifluoromethyl)-2-pyridyl]amino}-4,5,6,7-tetrahydroisoindole-1,3-dione (S00186);

1-{[4-bromo-3-(trifluoromethyl)phenyl]amino}-3,4-dimethylazoline-2,5-dione (S00516);

1-[(4-chloronaphthyl)amino]-3,4-dimethylazoline-2,5-dione (S00738);

1-[(4-chloro-6-methyl(2-quinolyl))amino]-3,4-dimethylazoline-2,5-dione (S00935);

1-[(4-bromonaphthyl)amino]-3,4-dimethylazoline-2,5-dione (S00942);

1-{[7-bromo-4-(hydroxymethyl)(2-quinolyl)]amino}-3,4-dimethylazoline-2,5-dione (S01037);

{2-[(3,4-dimethyl-2,5-dioxoazolinyl)amino]-7-bromo-4-quinolyl}methylacetate (S01047);

1-{[8-chloro-4-(4-methoxyphenyl)(2-quinolyl)]amino}-3,4-dimethylazoline-2,5-dione (S01191);

1-[(4-chlorobenzo[h]quinolin-2-yl)amino]-3,4-dimethylazoline-2,5-dione (S01207);

1-[(7-bromo-4-{[4-benzylpiperazinyl]methyl}(2-quinolyl)) amino]-3,4-dimethylazoline-2,5-dione (S01268);

1-{[6-(4-chlorophenyl)-5-(trifluoromethyl)(2-pyridyl)] amino}-3,4-dimethylazoline-2,5-dione (S01371);

3,4-dimethyl-1-{[6-(4-methylphenyl)-5-(trifluoromethyl) (2-pyridyl)]amino}azoline-2,5-dione (S01393);

1-{[6-(3-chlorophenyl)-5-(trifluoromethyl)(2-pyridyl)] amino}-3,4-dimethylazoline-2,5-dione (S01474);

1-{[6-chloro-5-(trifluoromethyl)(2-pyridyl)]methylamino}-3-(methoxymethyl)-4-methylazoline-2,5-dione (S01600);

Phenylmethyl4-({2-[(3,4-dimethyl-2,5-dioxoazolinyl) amino]-7-bromo-4-quinolyl}methyl)piperazinecarboxylate (S01683);

1-{[6-chloro-2-phenyl-3-(trifluoromethyl)(4-pyridyl)] amino}-3,4-dimethylazoline-2,5-dione (S01688);

3,4-dimethyl-1-({6-[3-(trifluoromethyl)phenyl](2-pyridyl)}amino)azoline-2,5-dione (S01691);
1-[(7-bromo-4-{[4-(phenylcarbonyl)piperazinyl]methyl}(2-quinolyl))amino]-3,4-dimethylazoline-2,5-dione (S01699);
3-(1-{[6-chloro-5-(trifluoromethyl)(2-pyridyl)]amino}-4-methyl-2,5-dioxoazolin-3-yl)-N-methyl-N-phenylpropanamide (S01759);
3,4-dimethyl-1-{[6-benzyl-5-(trifluoromethyl)(2-pyridyl)]amino}azoline-2,5-dione (S01762);
1-{[4-({4-[(2,4-dimethylphenyl)carbonyl]piperazinyl}methyl)-7-bromo (2-quinolyl)]amino}-3,4-dimethylazoline-2,5-dione (S01800);
1-{[7-bromo-4-({4-[(4-methoxyphenyl)carbonyl]piperazinyl}methyl) (2-quinolyl)]amino}-3,4-dimethylazoline-2,5-dione (S01801);
N-[6-chloro-5-(trifluoromethyl)(2-pyridyl)]-N-[4-(hydroxymethyl)-3-methyl-2,5-dioxoazolinyl]acetamide (S01820);
1-[(7-bromo-4-{[4-(phenylsulfonyl)piperazinyl]methyl}(2-quinolyl))amino]-3,4-dimethylazoline-2,5-dione (S01822);
1-[(4-chloro-8-methyl(2-quinolyl))amino]-3,4-dimethylazoline-2,5-dione (S00871);
tert-butyl 4-[({2-[(3,4-dimethyl-2,5-dioxoazolinyl)amino]-7-bromo-4-quinolyl}methyl)amino]piperidinecarboxylate (S01862);
tert-butyl 4-[4-({2-[(3,4-dimethyl-2,5-dioxoazolinyl)amino]-7-bromo-4-quinolyl}methyl)piperazinyl]piperidinecarboxylate (S01928);
1-[(4-{[4-(3,3-dimethylbutanoyl)piperazinyl]methyl}-7-bromo(2-quinolyl)) amino]-3,4-dimethylazoline-2,5-dione (S01929);
Methylethyl 3-(1-{[6-chloro-5-(trifluoromethyl) (2-pyridyl)]amino}-4-methyl-2,5-dioxoazolin-3-yl) propanoate (S02022);
Methylpropyl 3-(1-{[6-chloro-5-(trifluoromethyl) (2-pyridyl)]amino}-4-methyl-2,5-dioxoazolin-3-yl) propanoate (S02264);
tert-butyl 2-(1-{[6-chloro-5-(trifluoromethyl) (2-pyridyl)]amino}-4-methyl-2,5-dioxoazolin-3-yl)acetate (S02225);
1-{[6-chloro-5-(trifluoromethyl) (2-pyridyl)]amino}-3-(ethoxymethyl)-4-methylazoline-2,5-dione (S02366);
3-butyl-1-{[6-chloro-5-(trifluoromethyl) (2-pyridyl)]amino}-4-methylazoline-2,5-dione (S03448);
1-{[6-chloro-5-(trifluoromethyl) (2-pyridyl)]amino}-4-methyl-3-[2-(2-methyl (1,3-dioxolan-2-yl)) ethyl]azoline-2,5-dione (S03456);
1-{[6-chloro-5-(trifluoromethyl)(2-pyridyl)]amino}-3-[(2-methoxyethoxy)methyl]-4-methylazoline-2,5-dione (S03742);
1-{[6-chloro-5-(trifluoromethyl)(2-pyridyl)]amino}-4-(3-hydroxyhexyl)-3-methylazoline-2,5-dione (S03552);
1-{[6-chloro-5-(trifluoromethyl)(2-pyridyl)]amino}-4-(3-hydroxypentyl)-3-methylazoline-2,5-dione (S03745);
1-{[6-chloro-5-(trifluoromethyl)(2-pyridyl)]amino}-4-methyl-3-[(3-methylbutoxy)methyl]azoline-2,5-dione (S03405);
3-(butoxymethyl)-1-{[6-chloro-5-(trifluoromethyl)(2-pyridyl)]amino}-4-methylazoline-2,5-dione (S03518);
3-[(3,3-dimethylbutoxy)methyl]-1-{[6-chloro-5-(trifluoromethyl) (2-pyridyl)]amino}-4-methylazoline-2,5-dione (S03747);
1-{[6-chloro-5-(trifluoromethyl)(2-pyridyl)]amino}-3-(2-ethoxyethyl)-4-methylazoline-2,5-dione (S03960);
1-{[6-chloro-5-(trifluoromethyl)(2-pyridyl)]amino}-4-methyl-3-[(2-methylpropoxy)methyl]azoline-2,5-dione (S03963);
3-[(2,2-dimethylpropoxy)methyl]-1-{[6-chloro-5-(trifluoromethyl) (2-pyridyl)]amino}-4-methylazoline-2,5-dione (S03962);
4-[(1,3-dimethylbutoxy)methyl]-1-{[6-chloro-5-(trifluoromethyl) (2-pyridyl)]amino}-3-methylazoline-2,5-dione (S03964);
4-[(tert-butoxy)methyl]-1-{[6-chloro-5-(trifluoromethyl)(2-pyridyl)]amino}-3-methylazoline-2,5-dione (S03873);
1-{[6-chloro-5-(trifluoromethyl)(2-pyridyl)]amino}-4-methyl-3-[2-(2-methylpropoxy)ethyl]azoline-2,5-dione (S03955);
1-{[6-chloro-5-(trifluoromethyl)(2-pyridyl)]amino}-4-methyl-3-[2-(3-methylbutoxy)ethyl]azoline-2,5-dione (S03956);
1-{[6-chloro-5-(trifluoromethyl)(2-pyridyl)]amino}-3-methyl-4-(2-propoxyethyl)azoline-2,5-dione (S04034);

or a salt of any of these compounds.

Additional embodiments of the invention have been synthesized and tested, and details are set forth in the description below and in the examples, tables, and figures (drawings) presented herein. Other features, objects, and advantages of the invention will be apparent from the description, examples, tables, drawings, and from the claims.

Compositions containing compounds having any of the following structures are not being claimed:

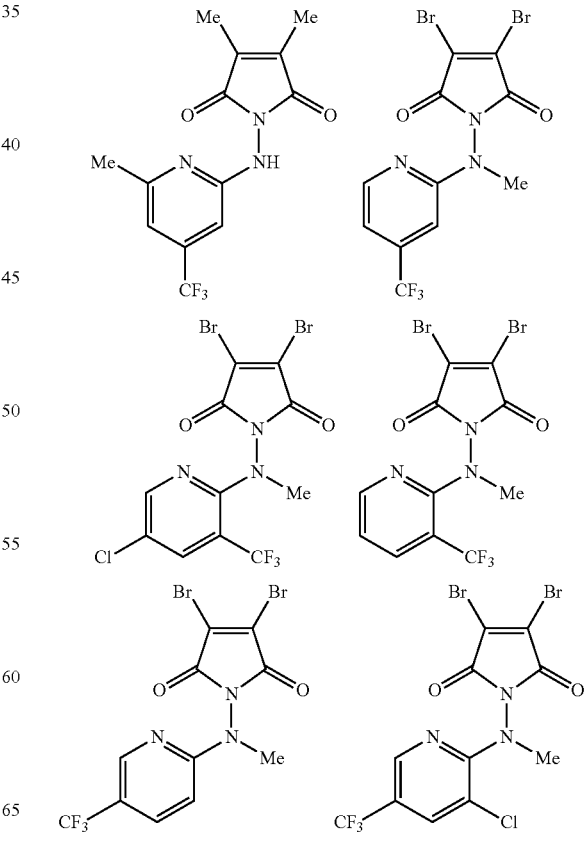

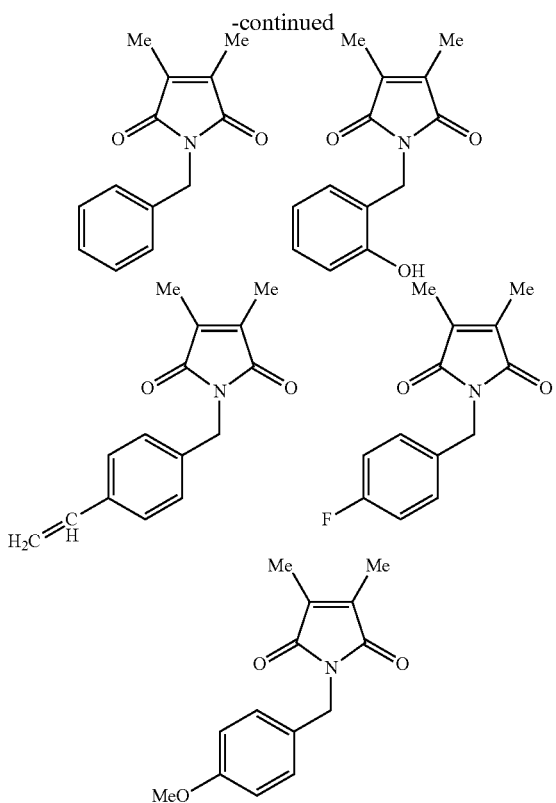

DETAILED DESCRIPTION OF THE INVENTION

Definitions

Figure 1:
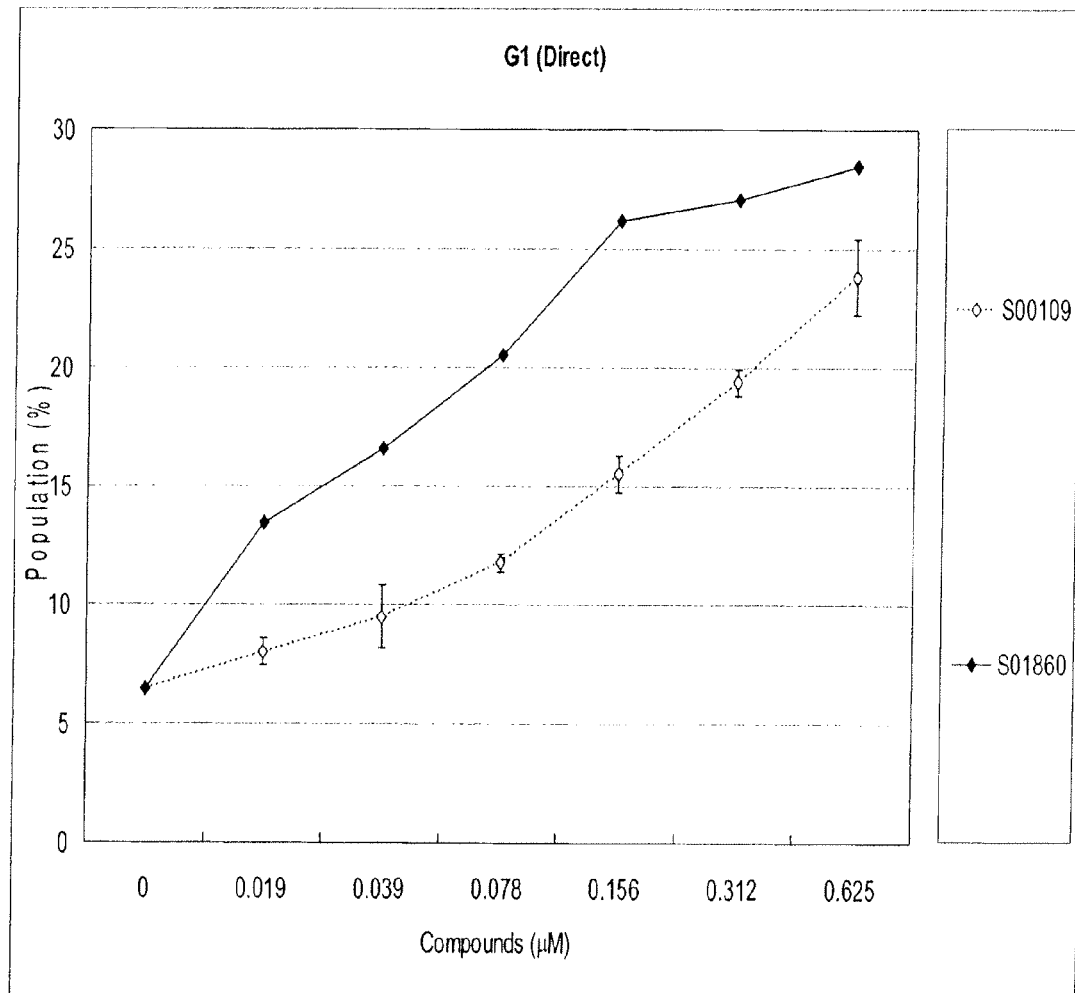
FIG. 1 shows the percentage of cells in G1 phase after Jurkat cells pre-arrested at the G2 phase by X-ray irradiation (10 Gy) are treated with compounds S00109 (unfilled diamonds) and S01860 (solid diamonds), at the indicated dosages, for 24 hours.

Unless defined otherwise, technical and scientific terms used herein have the meaning commonly understood by a person skilled in the art to which this invention belongs. As used herein, the following terms have the meanings ascribed to them unless specified otherwise.

All publications, patents, and patent applications and ATCC deposits cited herein, are hereby expressly incorporated by reference for all purposes.

The terms "DNA-damaging treatment" and "DNA-damaging agent" refer to any agent or treatment that directly or indirectly damages DNA, including but not limited to, DNA-damaging drugs (agents), irradiation with DNA-damaging levels of X, gamma (γ), or UV radiation, various kinds of environmental shock, and the like. It is understood that a DNA-damaging treatment or DNA-damaging agent may act directly on DNA, e.g., to disrupt DNA structure or interfere with DNA synthesis, or may act indirectly on DNA by its effects on other cellular systems involved in DNA synthesis and replication, e.g., to disrupt or inhibit the functions of microtubules or DNA topoisomerase. Specific examples of DNA-damaging agents include but are not limited to alkylating agents, nitrosoureas, anti-metabolites, plant alkaloids, plant extracts, radioisotopes, steroid hormones. Additional examples of DNA-damaging agents also include but are not limited to agents known as "DNA-damaging drugs" or "anti-cancer drugs" or "anti-cancer agents" or "DNA-damaging anti-cancer agents," e.g., 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine (Gemzar®), bortezomib (Velcade®) pentostatin, allopurinol, 2-fluoro-arabinosyl-adenine (2F-ara-A), hydroxyurea, sulfur mustard (bischloroethylsulfide), mechlorethamine, melphalan, melpharan, vincristine, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclines such as doxorubicin (adriamycin; ADR), daunorubicin (Cerubicine), idarubicin (Idamycin) and epirubicin (Ellence), anthracycline analogues such as mitoxantrone, actinomycin D, non intercalating topoisomerase inhibitors such as epipodophyllotoxins (etoposide=VP16, teniposide=VM-26), podophylotoxin, bleomycin (Bleo), pepleomycin, taxanes, compounds that form adducts with nucleic acid including platinum derivatives, e.g., cisplatin (CDDP), trans analogue of cisplatin, carboplatin, iproplatin, tetraplatin and oxaliplatin, as well as camptothecin, topotecan, irinotecan (CPT-11), and SN-38. Specific examples of DNA-damaging treatments include radiation e.g., ultraviolet (UV), infrared (IR), X-ray, α-(alpha), β-(beta), or γ-(gamma) radiation, as well as environmental shock, e.g., hyperthermia. One of skill in the art can identify and use other DNA-damaging agents and treatments.

The term "compound of the invention" is intended to refer to a molecule having the structure and activity disclosed herein. A compound of the invention can be isolated, pure, substantially pure, or may be in a composition containing a mixture of other components. Purity of a composition containing a compound of the invention can be determined, for example, using analytical chemistry techniques such as high performance liquid chromatography (HPLC), or liquid chromatography-mass spectrometry (LC-MS) or gas chromatography-mass spectrometry (GS-MS), or other analytical techniques known to one of skill in the art. A composition as provided herein may contain one or more compounds of the invention, in a mixture with suitable vehicles, carriers, excipients, inert ingredients, and the like. If desired, a composition as provided herein may contain additional active ingredients including DNA-damaging agents and the like, as well as one or more compounds of the invention, in a mixture with suitable vehicles, carriers, excipients, inert ingredients, and the like.

The terms "pharmaceutical composition" or "medicament" refer to a composition suitable for pharmaceutical use in a subject, e.g., as a anti-cancer agent. The subject may be any animal wherein compounds of the invention abrogate the cell cycle G2 checkpoint and/or cause adaptation to G2 arrest. In particular, the subject may be a mammal, e.g., a horse, cow, dog, cat, or human. A pharmaceutical composition of the invention is a formulation that can comprise a pharmacologically effective amount of at least one compound of the invention and a pharmaceutically acceptable carrier.

The terms "cell proliferation disorder" or "proliferative disorder" or "cell proliferative disorder" or "proliferative condition" or "condition characterized by undesirable cell proliferation" or any grammatical equivalent thereof, are understood to refer any pathological or non-pathological physiological condition characterized by aberrant or undesirable proliferation of at least one cell, including but not limited to conditions characterized by undesirable or unwanted or aberrant cell proliferation, conditions characterized by undesirable or unwanted or aberrant cell survival, and conditions characterized by deficient or aberrant apoptosis. The term "cell proliferation" and grammatical equivalents thereof, is understood to encompass both an increase in the number of cells as a result of cell division, as well as an increase in the total mass of cells as a result of cell growth, e.g., by growth of daughter cells after mitosis. One non-limiting example of a "cell proliferation disorder" or "proliferative disorder" or "proliferative condition" or "condition characterized by undesirable cell proliferation" is cancer, e.g., undesirable or unwanted or aberrant proliferation and survival of cancer cells such as cells associated with lymphoma, myeloma, sarcoma, leukemia, or other neoplastic disorders disclosed elsewhere herein and known to one of skill in the art.

The terms "kill or suppress cells" or "killing or suppressing cells" or "kill or suppress undesirably proliferating cells" or "kill or suppress target cells" or any grammatical equivalent thereof, are understood to refer to results of being contacted with an effective amount of a compound of the invention. The terms "kill" or "killing" are understood to refer to cell death resulting from the effects of a compound of the invention on a cell, in particular death of an undesirably proliferating cell such as a cancer cell, where death may be due to apoptosis, mitotic catastrophe, necrosis, or another cause, depending on the circumstances of the cell. The terms "suppress" or "suppressing" are understood to refer to suppression of cell proliferation resulting from effects of a compound of the invention on a cell, where suppression may be partial or complete. A compound of the invention may cause partial suppression of a cell, such that the cell may cease dividing but continue to grow, or the cell may divide much more slowly, or the cell may grow much more slowly, or a cancer cell may not progress from a pre-metastatic state to a metastatic state, etc. A compound of the invention may cause complete suppression wherein a cell neither divides nor grows, in particular, wherein an undesirably proliferating cell neither divides nor grows.

The terms "effective amount" or "sufficient amount" or any grammatical equivalent thereof, are understood to refer to an amount of a compound of the invention sufficient to produce at least one desired effect. Effective amounts are determined by any of a variety of measurements including but not limited to: cell death; decreased cell proliferation; decreased numbers of cells; inhibition of cell growth; decreased cell size; decreased cell survival; decreased cell metabolism; apoptosis; mitotic catastrophe; adaptation to cell cycle arrest (i.e., escape from cell cycle arrest, usually leading to re-entry into the cell cycle); markers of cell damage or cytotoxicity; indirect indicators of cell damage or cytotoxicity such as tumor shrinkage; improved survival of a subject; or disappearance of markers associated with undesirable, unwanted, or aberrant cell proliferation. For example, where it is desired to inhibit undesirable proliferation of a particular cell or cell type, an effective amount will be an amount that detectably decreases cell division, or decreases cell metabolism, or increases cell death, or decreases cell survival, of that cell or cell type. A desired effect may be a selective effect, e.g., an "effective amount" is an amount that kills or suppresses target cells while having little or no cytotoxic effect on non-target cells, or an amount that produces a desired therapeutic benefit in a subject having a cell proliferation disorder, while having little or no adverse effect on the subject. A cell proliferation disorder can be treated by administering an effective amount of at least one compound of the invention, where the effective amount of at least one compound can be administered in vitro or ex vivo to treat cells, or the compound can be administered in vivo to a subject having a cell proliferation disorder.

The terms "cell cycle G2 checkpoint" or "G2 checkpoint" or any grammatical equivalent thereof, refer to the G2 checkpoint occurring at the end of G2 phase of the cell cycle. During the G2 "gap" phase between DNA synthesis (S phase, DNA replication in preparation for mitosis) and mitosis (M phase, cell division to produce daughter cells), the cell continues to grow and produce new proteins. The G2 checkpoint at the end of the G2 phase is a control checkpoint where a number of factors are checked to ensure the cell is ready to enter mitosis (M phase). Functions of the G2 checkpoint includes detecting DNA damage. If the G2 checkpoint is passed, then entry into M phase is initiated. If the G2 checkpoint detects DNA damage, the G2 checkpoint can generate a signal leading to "cell cycle arrest" or "G2 cell cycle arrest" or "G2 arrest," that restricts the onset of mitosis until DNA replication and repair are complete, thereby preventing transmission of DNA damage to daughter cells. It is understood that, because DNA damage can trigger or activate the G2 checkpoint and certain G2 checkpoint-related cellular activities, the term "DNA damage-induced G2 checkpoint" and grammatical equivalents thereof, can also be used in certain contexts. It is further understood that the DNA damage-induced G2 checkpoint can be induced or triggered by DNA-damaging agents or treatments.

The terms "abrogate the G2 checkpoint" or "abrogate the cell cycle G2 checkpoint" or "abrogation of the G2 checkpoint" or "G2 abrogation" or "G2 checkpoint abrogation" or "disrupt the G2 checkpoint" or "inhibit the G2 checkpoint" or "suppress the G2 checkpoint" or any grammatical equivalent thereof, are intended to refer to the ability of compounds of the invention to abrogate, disrupt, inhibit, repress, or suppress the G2 checkpoint. A cell in which the G2 checkpoint is abrogated may have a complete absence of the activity of the G2 checkpoint (G2 checkpoint arrest, or complete G2 checkpoint abrogation). A cell in which the G2 checkpoint is abrogated may exhibit a decrease in the length of time the cell is in the G2 checkpoint, e.g. a G2 checkpoint having a decrease in duration of minutes, hours, days, weeks or longer under appropriate conditions. For example, a decrease in the length of G2 checkpoint time would mean that a cell which is normally in G2 for a certain time, e.g., 4 hours, when contacted with an invention compound, is in G2 for less than 4 hours, e.g., 3.5, 3, 2.5, 2, 1 or fewer hours. Thus, "G2 checkpoint abrogation" refers to any amount of abrogation of the G2 checkpoint. It is understood that the result of G2 checkpoint abrogation is that the cell will enter mitosis (M phase) without DNA repair, which should have little or no deleterious effect on undamaged (normal) cells, and which should result in severe adverse effects on DNA-damaged cells, often leading to cell death due to apoptosis, mitotic catastrophe, or necrosis.

"Cell cycle arrest" or "G2 cell cycle arrest" or "G2 arrest" "G2-M cell cycle arrest" or any grammatical equivalent thereof, refers to a state wherein a cell does not exit G2 to enter mitosis (M phase) such that the cell is considered to be 'arrested' at the G2 phase. G2 cell cycle arrest is often observed in DNA-damaged cells such as many cancer cells. G2 cell cycle arrest can result from any of a number of cellular activities, including but not limited to certain activities of the G2 checkpoint. The DNA damage found in many cancer cells can trigger G2 cell cycle arrest. G2 cell cycle arrest can be induced or enhanced by treating a cell with DNA-damaging agents such as adriamycin, doxorubicine, or bendamustine (an alkylating agent), or DNA-damaging treatments such as irradiation with a triggering dose of X, gamma ($\gamma$), or UV radiation (sometimes referred to as "radiation-induced G2 arrest").

"Adaptation" or "adaptation to cell cycle arrest" or "adaptation to G2 cell cycle arrest" or "adaptation to G2 arrest" refers to lifting or abrogation of G2 cell cycle arrest, such that formerly arrested cells re-enter the cell cycle. Adaptation to G2 cell cycle arrest likewise refers to escape from G2 cell cycle arrest. Compounds of the present invention can cause adaptation to G2 cell cycle arrest in G2-arrested cells. In accordance with one aspect of the invention, "adaptation" or "adaptation to cell cycle arrest" or "adaptation to G2 cell cycle arrest" or "adaptation to G2 arrest" can refer to escape from a condition of G2 cell cycle arrest imposed by G2 checkpoint activation, in particular, G2 cell cycle arrest imposed by activation of the DNA-damage-induced G2 checkpoint. It is understood that adaptation to G2 cell cycle arrest results in formerly G2-arrested cells re-entering the cell cycle without repairing the DNA damage that triggered the G2 arrest. Adaptation to G2 cell cycle arrest, wherein DNA-damaged cells re-enter the cycle, often results in cell death due to apoptosis, mitotic catastrophe, or necrosis. Because the mechanism that promotes the cell cycle G2 arrest after DNA damage appears to be conserved among species from yeast to human, it is understood that compounds of the present invention can cause adaptation to G2 cell cycle arrest in numerous species, in particular in all eukaryotic species.

While the G2 checkpoint-abrogating activity of the compounds of the invention may be related to the ability to cause adaptation to G2 cell cycle arrest, it is also understood that compounds of the invention may cause adaptation to G2 cell cycle arrest by other mechanisms unrelated to abrogation of the G2 checkpoint. Thus, depending on the particular circumstances and without wishing to be limited by this definition, abrogation of the G2 checkpoint can refer, at least in part, to abrogating the ability of a cell to arrest the cell cycle at the G2 checkpoint, leading to adaptation to G2 cell cycle arrest. In particular, abrogation of the DNA damage-induced G2 checkpoint by compounds of the invention, under conditions that would normally trigger G2 cell cycle arrest, can include abrogation of a G2-checkpoint-generated signal involved in triggering G2 cell cycle arrest.

The term "apoptosis" refers to programmed cell death, and associated changes in cell physiology, including nucleic acid fragmentation, caspase activation, chromosome condensation, etc., as is understood in the art.

The term "mitotic catastrophe" refers to cell death resulting from one or more errors in the mitotic process.

The term "necrosis" refers to cell death, often resulting from damage or accident, often characterized by cell swelling, chromatin digestion, disruption of plasma membrane and organelle membranes, DNA hydrolysis, vacuolation of the endoplasmic reticulum, organelle breakdown, and cell lysis.

The term "subject" is understood to refer to animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., tumor-prone mice, tumor-bearing mice, or mice receiving xenograft tumors).

As used herein, the singular forms "a," "an," "the," and "is" include plural referents unless the context clearly indicates otherwise. Thus, for example, reference to "a compound" includes a plurality of compounds and reference to "a residue" or "an amino acid" includes reference to one or more residues and amino acids.

Chemical Terminology

"Alkyl" refers to an aliphatic hydrocarbon group. An alkyl group may be optionally substituted. "Substituted alkyl" refers to an alkyl group that is substituted by one or more substituents such as halogen (Cl, Br, F, I), C3 to C7 cycloalkyl, optionally substituted aryl, optionally substituted heteroaryl, C1 to C6 alkoxy, optionally substituted aryloxy, hydroxy, optionally substituted amino, optionally substituted cyclic amino, nitro, thio, cyano, oxo, C1 to C7 acyl, C1 to C7 acyloxy, carboxy, C1 to C6 alkoxycarbonyl, optionally substituted carbamoyl, optionally substituted cyclic aminocarbonyl, β-mercapto, C1 to C4 alkylthio, C1 to C4 alkylsulfinyl, or C1 to C4 alkylsulfonyl groups. Substituted alkyl groups may have one, two, three, four, five, or more substituents, and multiply substituted alkyl groups may be substituted with the same or with different substituents. The alkyl group may be a saturated alkyl without any alkene or alkyne moieties, or an unsaturated alkyl having at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether substituted or unsubstituted, saturated or unsaturated, may be branched, straight chain, or cyclic. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

"Alkoxy" refers to an OR group, wherein R is an alkyl or substituted alkyl. Preferred alkoxy groups are "C1 to C6 alkoxy" such as methoxy, ethoxy, n-propoxy, isopropoxy, n-butoxy, t-butoxy, and like groups.

The term "alkylthio" refers to sulfide groups such as methylthio, ethylthio, n-propylthio, isopropylthio, n-butylthio, t-butylthio, and like groups. The term "alkylsulfoxide" indicates sulfoxide groups such as methylsulfoxide, ethylsulfoxide, n-propylsulfoxide, isopropylsulfoxide, n-butylsulfoxide, sec-butylsulfoxide, and the like. The term "alkylsulfonyl" encompasses groups such as methylsulfonyl, ethyl sulfonyl, n-propylsulfonyl, isopropylsulfonyl, n-butylsulfonyl, t-butylsulfonyl, and the like.

"Acyl" refers to includes alkyl, heteroalkyl, alkenyl, heteroalkenyl, alkynyl, heteroalkynyl, aryl, or heteroaryl groups coupled to an additional group via a carbonyl group, e.g., —C(O)-alkyl, or —C(O)-aryl. Preferred acyl groups are C1 to C7 acyl such as formyl, acetyl, propionyl, butyryl, pentanoyl, pivaloyl, hexanoyl, heptanoyl, benzoyl, and the like.

The term "amide" refers to a group with the formula C(O)NHR or NHC(O)R, where R is optionally substituted and is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds of the present invention can be amidified.

"Aryl" or "aromatic" refers to a group with at least one ring structure having a conjugated pi electron system, i.e., having the characteristics of aromaticity in terms of electron distribution through the ring system. An aryl may be optionally substituted. Typically, the ring systems contain 5-12 ring atoms in each ring. An aryl group may be monocyclic or a fused-ring polycyclic aryl. An aryl group may be a carbocyclic aryl wherein all ring atoms are carbon, e.g., phenyl. An aryl group may be a heteroaryl or heterocyclic aryl containing at least one ring heteroatom such as oxygen, sulfur and/or nitrogen. Heterocyclic aryl groups may be monocyclic or polycyclic. Examples of heteroaryl groups include maleimidyl, imidazolyl, indolyl, pyrrolidinyl, pyridinyl, pyrimidinyl, pyrazinyl, pyridazinyl, pyrrolyl, furanyl, oxazolyl, dioxazolyl, isoxazolyl, phthalimidyl, thiazolyl, and the like. Aryl groups can be fused to other aryl groups or to non-aryl (non-aromatic) groups.

As examples of the substituents of said "optionally substituted amino" and "optionally substituted carbamoyl," there may be mentioned phenyl, substituted phenyl, C1 to C6 alkyl, C1 to C6 substituted alkyl, C2 to C7 alkenyl, C2 to C7 substituted alkenyl, C2 to C7 alkynyl, C2 to C7 substituted alkynyl, C7 to C12 phenylalkyl, C7 to C12 substituted phenylalkyl, heteroaryl, C1 to C6 alkyl, C1 to C6 substituted alkyl, C1 to C7 acyl, C1 to C7 alkoxycarbonyl, optionally substituted carbamoyl, C1 to C4 alkylsulfonyl, and the like. The "optionally substituted amino" and "optionally substituted carbamoyl" are may be mono-substituted or di-substituted, with the same or with different substituents.

"Alkoxycarbonyl" refers to an "alkoxy" group attached to a carbonyl group.

"Cycloalkyl" refers to a monocyclic or polycyclic radical which contains only carbon and hydrogen, and may be saturated, partially unsaturated, or fully unsaturated. A cycloalkyl group may be optionally substituted. Preferred cycloalkyl groups include groups having from three to twelve ring atoms, more preferably from 5 to 10 ring atoms.

"Cyclic amino" as in "optionally substituted cyclic amino," refers to cyclic groups containing at least one ring nitrogen including piperazino, morpholino, piperidino, pyrrolidino, and the like.

Examples of "cyclic aminocarbonyl" as in "optionally substituted cyclic aminocarbonyl," include piperazinocarbonyl, morpholinocarbonyl, piperidinocarbonyl, pyrrolidinocarbonyl, and the like.

Substituents of "optionally substituted alkoxy," "optionally substituted alkylthio," "optionally substituted aryl," "optionally substituted aryloxy," "optionally substituted arylthio," "optionally substituted acyl," "optionally substituted heteroaryl," "optionally substituted alkylthio," "optionally substituted alkylsufinyl" "optionally substituted alkylsulfonyl," "optionally substituted alkoxycarbonyl," "optionally substituted cyclic amino," and "optionally substituted cyclic aminocarbonyl" are defined in the same manner as substituents of "substituted alkyl."

"Halogen" refers to fluorine, chlorine, bromine, or iodine atoms. One or more halogens can be present in a compound, where the halogens can be the same or different.

Embodiments of compounds of the present invention may possess one or more chiral centers and each center may exist in the R or S configuration, such that the present invention includes all diastereomeric, enantiomeric, and epimeric forms as well as the appropriate mixtures thereof. Embodiments of the present invention may exist as geometric isomers, such that the present invention includes all cis, trans, syn, anti, entgegen (E), and zusammen (Z) isomers, as well as the appropriate mixtures thereof.

Compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Any salt as disclosed herein can include salts with inorganic bases, salts with organic bases, salts with inorganic acids, salts with organic acids, and salts with basic or acidic amino acids.

Unless otherwise indicated, when a substituent is deemed to be "optionally substituted," it is meant that the substituent is a group that may be substituted with one or more group(s) as recited herein or as known to one of skill in the art.

Descriptions of compounds of the invention are in accordance with principles of chemical bonding known to those skill in the art. Accordingly, where a group may be substituted by one or more of a number of substituents, such substitutions are selected so as to comply with principles of chemical bonding and to give compounds which are not inherently unstable, and/or would be known to one of ordinary skill in the art as likely to be unstable, under ambient conditions such as aqueous, neutral, physiological conditions.

It is understood that compounds of the invention can be described by one of skill in the art using different terminology than the terms used here, without affecting the accuracy of the description. Compounds, structures, substituents, groups, and the like can be described using any of IUPAC nomenclature; chemical name' "trivial" or "common" name; trade name; CAS registry number; SMILES notation; or other descriptors. For example, compounds of the invention described herein as "substituted azole diones" or "substituted azoline diones" could alternately be described as "substituted maleimides" or "substituted 2,5-pyrrolediones" or "substituted pyrroles" in combination with other descriptors, preferably according to standardized chemical terminology, to provide a complete description of one or more invention compounds.

Substituted Azole Dione Compounds

The invention provides substituted azole (azoline) dione compounds that can be used to kill or suppress DNA-damaged cells, or to treat cell proliferation disorders characterized by undesirable or unwanted cell proliferation, where compounds of the invention can be described by the formula of Structure (I):

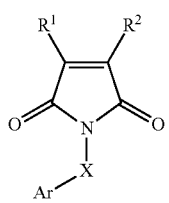

(I)

Wherein

Structure (I) contains an azoline dione heterocycle;

$R^1$ and $R^2$ are independently chosen from alkyl, substituted alkyl, optionally substituted alkoxy, optionally substituted alkylthio, halogen, optionally substituted aryl, optionally substituted aryloxy, optionally substituted arylthio, or H. Both $R^1$ and $R^2$ can also be part of a cyclic alkylene chain that form a fused ring structure;

X is O, S, $NR^3$, or $CR^4R^5$;

Ar is aryl or substituted aryl, including carbocyclic aryl, heterocyclic aryl, monocyclic aryl, polycyclic aryl, and aryl fused with non-aryl (non-aromatic) rings;

$R^3$ is H, alkyl, substituted alkyl, optionally substituted acyl, or as part of a ring structure that connects the N to the Ar ring;

$R^4$ and $R^5$ are chosen independently from H, alkyl, substituted alkyl, or both can be part of a cyclic alkylene chain that forms a ring structure; $R^4$ or $R^5$ can also be part of a ring structure that connects to the Ar ring; or a salt thereof.

In one aspect, compounds of the invention are provided having Structure (II):

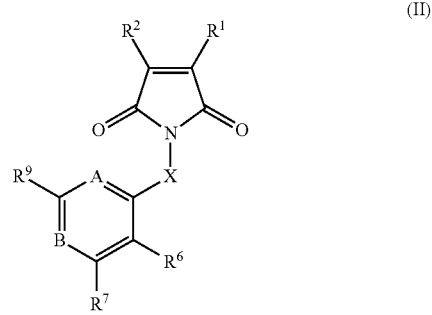

(II)

Wherein

Structure (II) contains an azoline dione heterocycle;

$R^1$, $R^2$, and X are defined as above;

A is N or CH;

B is $CR^8$ or N;

$R^6$, $R^7$, $R^8$, and $R^9$ are independently chosen from H, alkyl, substituted alkyl, halogen, optionally substituted aryl, optionally substituted heteroaryl, optionally substituted alkoxy, optionally substituted aryloxy, cyano, nitro, optionally substituted alkylthio, optionally substituted alkylsufinyl, optionally substituted alkylsulfonyl, optionally substituted arylthio, optionally substituted acyl, optionally substituted amino, carboxyl, optionally substituted alkoxycarbonyl, optionally substituted carbamoyl, etc. Also included are the structures wherein two adjacent substitutions ($R^6$ and $R^7$, $R^7$ and $R^8$, $R^8$ and $R^9$) are part of a cyclic alkylene group that form a fused ring structure; or a salt thereof.

In one aspect, compounds of the invention are provided having Structure (III):

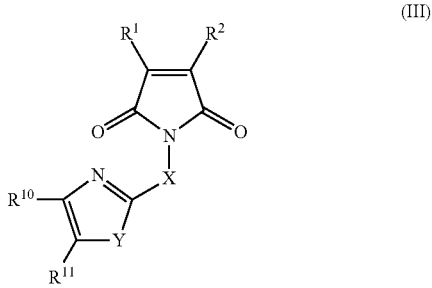

(III)

Wherein

Structure (III) contains an azoline dione heterocycle;

$R^1$, $R^2$, and X are defined as above;

Y is O, S, or $NR^{12}$;

$R^{10}$ and $R^{11}$ are independently chosen from H, alkyl, substituted alkyl, halogen, optionally substituted aryl, optionally substituted heteroaryl, optionally substituted alkoxy, optionally substituted aryloxy, cyano, nitro, optionally substituted alkylthio, optionally substituted alkylsufinyl, optionally substituted alkylsulfonyl, optionally substituted arylthio, optionally substituted acyl, optionally substituted amino, carboxyl, optionally substituted alkoxycarbonyl, optionally substituted carbamoyl, etc; $R^{10}$ and $R^{11}$ could also be an alkylene group that form a "fused" ring with the heterocycle structure;

$R^{12}$ is H, alkyl, substituted alkyl, aryl, acyl, or sulfonyl groups; or a salt thereof.

In certain non-limiting embodiments of compounds having Structure (II), X is $NR^3$, A is N, and B is $CR^8$ and compounds are provided having Structure (IV), wherein $R^1$, $R^2$, $R^3$, $R^6$, $R^7$, $R^8$, and $R^9$ are defined above:

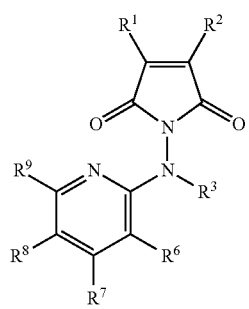

(IV)

In certain non-limiting embodiments of compounds having Structure (II), X is $NR^3$, A is N, B is $CR^8$; $R^8$ and $R^9$ form a fused and substituted benzene ring, providing compounds having Structure (V), wherein $R^1$, $R^2$, $R^3$, $R^6$ and $R^7$ are defined above; $R^{13}$, $R^{14}$, $R^{15}$, and $R^{16}$ are defined as for $R^6$-$R^{11}$ above:

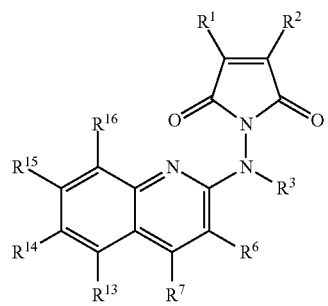

(V)

In certain non-limiting embodiments of compounds having Structure (II), X is $CR^4R^5$, A is N or CH, and B is $CR^8$, providing compounds having Structure (VI), wherein $R^1$, $R^2$, $R^4$, $R^5$, $R^6$, $R^7$, $R^8$, and $R^9$ are defined above:

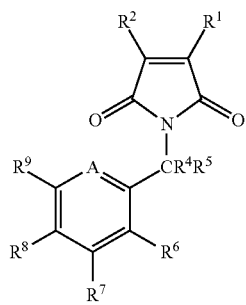

(VI)

In certain non-limiting embodiments of compounds having Structure (III), X is $NR^3$, and Y is S; $R^{10}$ and $R^{11}$ form a fused substituted benzene ring, providing compounds having Structure (VII), wherein $R^1$, $R^2$, and $R^3$ are defined above; $R^{17}$, $R^{18}$, $R^{19}$, and $R^{20}$ are defined as for $R^6$-$R^{11}$ above:

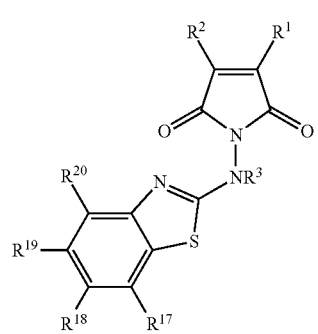

(VII)

In certain non-limiting embodiments of compounds having Structure (II), X is $NR^3$, A is N or CH, and B is $CR^8$; $R^6$ and $R^7$ form a fused and substituted benzene ring, providing compounds having Structure (VIII), wherein $R^1$, $R^2$, $R^3$, $R^8$ and $R^9$ are defined above; $R^{21}$, $R^{22}$, $R^{23}$, and $R^{24}$ are defined as for $R^6$-$R^{11}$ above:

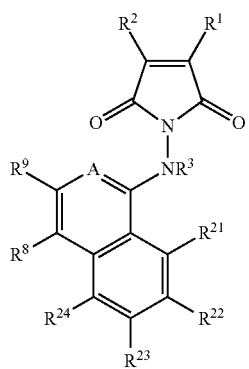

(VIII)

In certain non-limiting embodiments of compounds having Structure (II), X is $NR^3$, A is N, and B is $CR^8$; $R^9$ is a substituted benzene ring, providing compounds having Structure (IX), wherein $R^1$, $R^2$, $R^3$, $R^6$, $R^7$ and $R^8$ are defined above; $R^{25}$, $R^{26}$, $R^{27}$, $R^{28}$, and $R^{29}$ are defined as for $R^6$-$R^{11}$ above:

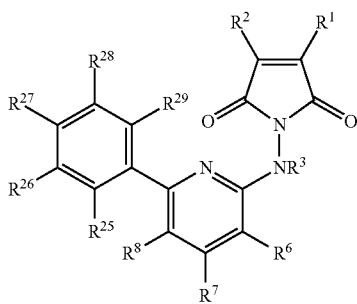

(IX)

In certain non-limiting embodiments of compounds having Structure (III), X is $NR^3$, and Y is S; $R^{10}$ is a substituted benzene ring, providing compounds having Structure (X), wherein $R^1$, $R^2$, $R^3$ and $R^{11}$ are defined above; $R^{30}$, $R^{31}$, $R^{32}$, $R^{33}$, and $R^{34}$ are defined as for $R^6$-$R^{11}$ above:

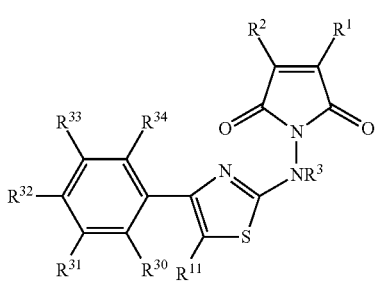

(X)

In certain non-limiting embodiments of compounds having Structure (II), X is $NR^3$, A is N or CH, and B is N, providing compounds having Structure (IV), wherein $R^1$, $R^2$, $R^3$, $R^6$, $R^7$, and $R^9$ are defined above:

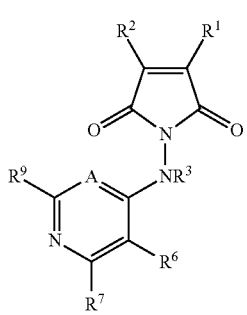

(XI)

Representative compounds are shown in Tables 1, 2, and 3 herein. It is generally understood that the compounds disclosed in Tables 1, 2, and 3 are for the purpose of illustration only, and by no means restrict the scope of the invention.
Representative Synthesis Schemes Representative schemes for synthesis of compounds of the invention having any of Structures (I) to (XI) are presented below. The representative schemes presented here do not restrict the scope of the invention in any way. It is understood that one of skill in the art can adapt methods presented herein, and/or different methods known in the art, to synthesize additional compounds within the scope of the present invention, including analogs having different substitutions or substitution patterns. It is further understood that, although certain substitutions have been observed to produce structures with higher activity than other structures, the present invention provides compounds with all substitutions having all levels of activity.

In Method 1 (Scheme 1), an anhydride (1) is reacted with a substituted hydrazine (2) or a benzylamine (3) to form the compounds having the general structure shown as (4) below:

Scheme 1

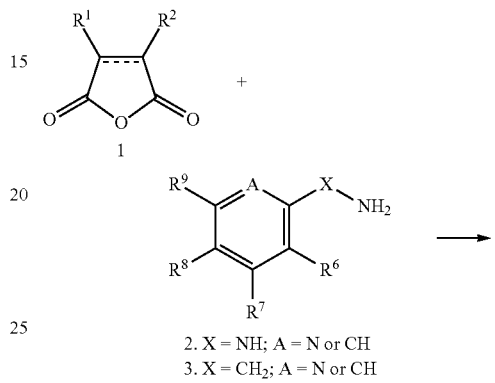

2. X = NH; A = N or CH
3. X = $CH_2$; A = N or CH

The reaction can be carried out in common organic solvents such as THF, chloroform, DMF, acetic acid, etc., at temperatures ranging from ambient to elevated, for times ranging from several hours to a few days. Usually, no other additives are needed. The required anhydrides and hydrazines/benzylamines are either purchased from commercial sources, or synthesized according to procedures known in the literature. In cases where the starting materials are unknown in the literature, synthetic methods are developed, as illustrated by certain syntheses described in the Examples.

In Method 2 (Scheme 2), an imide (5) is reacted with a benzylalcohol (6) under typical Mitsunobu conditions to form compounds having the general structure shown as (7) below:

Scheme 2

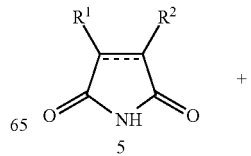

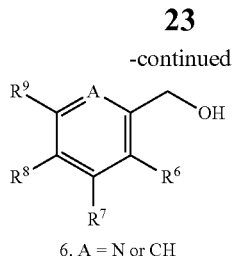

6. A = N or CH

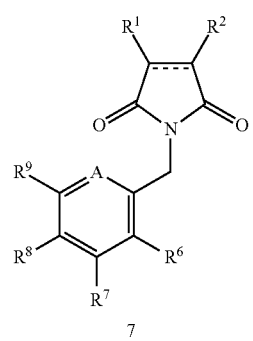

7

Typical Mitsunobu conditions include the use of a phosphine (triphenylphosphine, tributylphosphine etc.), and an azo compound (diethyl azo-dicarboxalate, diisopropyl azo-dicarboxylate, etc.). The reaction can be carried out with an added base, usually triethylamine, or without an added base, in solvents such as THF, at ambient or elevated temperature for several hours. The required imides and benzylalcohols are either purchased from commercial sources, or synthesized according to procedures known in the literature. In cases where the starting materials are unknown in the literature, synthetic methods are developed, as illustrated by certain syntheses described in the Examples.

In Method 3 (Scheme 3), an imide (5) is reacted with a benzylbromide (8) under typical nucleophilic replacement reaction condition to form the compounds having the general structure shown as (9) below:

Scheme 3

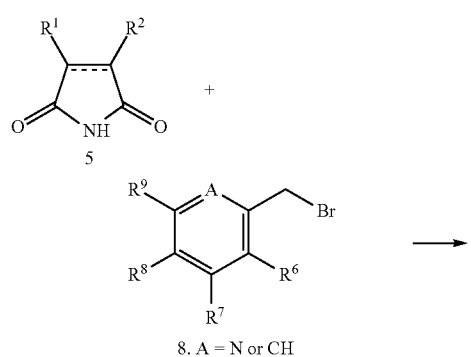

8. A = N or CH

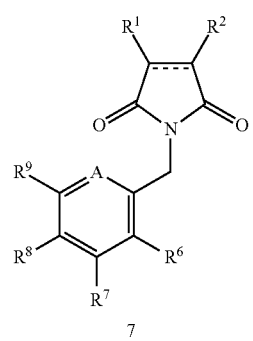

9

The typical reaction condition is: refluxing in a suitable solvent (acetone, DMF, etc.) in the presence of an added base (potassium carbonate, cesium carbonate, etc.) for several hours to a few days. The required imides and benzylbromides are either purchased from commercial sources, or synthesized according to procedures known in the literature. In cases where the starting materials are unknown in the literature, synthetic methods are developed, as illustrated by certain syntheses described in the Examples.

In Method 4 (Scheme 4), an aryl boronic acid (10) is reacted with an N-hydroxyimide (11) under Cu(I) mediated coupling condition to form compounds having the general structure shown as (12) below:

Scheme 4

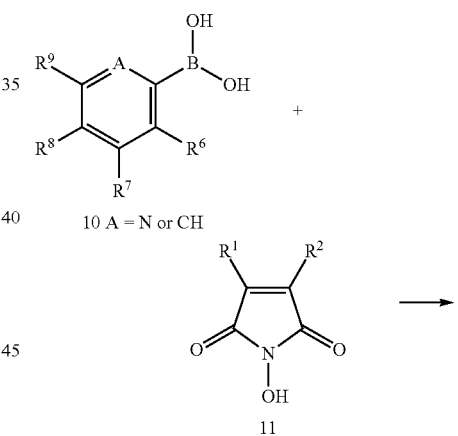

12

The typical reaction condition is: stirring at room temperature in suitable solvents (DCE, THF, DMF, etc.) in the presence of an added base (pyridine, triethylamine, etc.), with added Cu(I) species such as CuCl, for several hours to overnight. The required aryl boronic acids and N-hydroxyimides are either purchased from commercial sources, or synthesized according to procedures known in the literature. In cases where the starting materials are unknown in the literature, synthetic methods are developed, as illustrated by certain syntheses described in the Examples.

Syntheses of particular embodiments are disclosed in the Examples. Representative synthesized compounds presented as embodiments in Tables 1 and 2 are presented solely for illustration and by no means restricts the scope of the invention disclosed herein.

Biological Activities of Compounds of the Invention

The present invention provides compounds to treat cell proliferation disorders. The present invention provides compounds that can be used to kill or suppress undesirably proliferating cells. The present invention provides compounds that can be used to treat cell proliferation disorders by selectively killing or suppressing undesirably proliferating cells. The present invention provides compounds that can be used to treat cell proliferation disorders by selectively killing or suppressing undesirably proliferating cells that have accumulated DNA damage ("DNA-damaged cells"). In mixed populations of normal cells and undesirably proliferating cells, compounds of the invention can be used to selectively kill or suppress undesirably proliferating cells while having little or no cytotoxic effect on the normal cells. In mixed populations of normal cells and undesirably proliferating DNA-damaged cells, compounds of the invention can be used to selectively kill or suppress undesirably proliferating DNA-damaged cells while having little or no cytotoxic effect on the normal cells. In particular, compounds of the invention can be used to selectively kill cancer cells or suppress proliferation of cancer cells, while having little or no cytotoxic effect on "normal" non-cancerous cells. The present invention provides methods for selectively targeting DNA-damaged cells using compounds of the invention. The present invention provides methods for selectively targeting cells with an impaired G1 cell cycle checkpoint using compounds of the invention. The present invention provides methods for selectively targeting cancer cells using compounds of the invention.

Conventional treatments for cell proliferation disorders often include DNA-damaging agents and treatments as described elsewhere herein. These conventional treatments, often used as anti-cancer treatments, have been selected to kill rapidly cycling (proliferating) cells in hopes of killing the undesirably proliferating cells characteristic of the proliferation disorder. Examples of such conventional treatments include, but are not limited to, cytotoxic agents and/or irradiation with $\alpha$, $\beta$, $\gamma$, X- and/or UV radiation. However, conventional treatments often cause patients to suffer adverse effects on normal cells that are also proliferating, e.g., diarrhea due to damage to intestinal epithelial cells, hair loss due to damage to hair follicle cells, and anemia due to damage to blood cell progenitors, all of which are among the most rapidly proliferating cells in the normal body. These adverse effects often hamper treatments. Thus, medicines that specifically target undesirably proliferating cells such as cancer cells, without harming normal cells, have been long awaited in the clinic.

While the invention is not limited by any particular mechanism of action, and without wishing to be limited by this theory, compounds of the invention may kill or suppress undesirably proliferating cells by abrogating the G2 checkpoint in proliferating cells, and/or by causing adaptation to G2 cell cycle arrest in G2-arrested cells. Thus, the invention provides methods for killing or suppressing undesirably proliferating cells by contacting the cells with at least one compound of the invention in an amount sufficient to abrogate G2 cell cycle checkpoint and/or cause adaptation to G2 cell cycle arrest.

Without wishing to be limited by this theory, abrogation of the G2 checkpoint in DNA-damaged cells would cause the DNA-damaged cells to progress through the cell cycle without repairing the DNA damage. Likewise, adaptation to G2 cell cycle arrest in DNA-damaged cells would cause the formerly-arrested DNA-damaged cells to enter mitosis without repairing the DNA damage. It is generally understood that normal cells rely on the G1 checkpoint as the main checkpoint for detecting DNA damage or defects during the cell cycle, and do not appear to use the G2 checkpoint as much for detecting DNA damage or defects, whereas cells having an impaired or defective G1 checkpoint, e.g., most cancer cells, have to depend on the G2 checkpoint to detect DNA damage or defects, and to initiate repair before the cell enters mitosis. Thus, abrogation of the G2 checkpoint in cells with an impaired G1 checkpoint would cause the cells to progress through the cell cycle with out repairing any accumulated DNA damage. Likewise, adaptation to G2 cell cycle arrest in cells with an impaired G1 checkpoint would cause the formerly-arrested cells to enter mitosis without repairing any accumulated DNA damage. The term "DNA damage" is understood to encompass DNA damage unrelated to the G1 checkpoint, as well as DNA damage resulting from an impaired G1 checkpoint, such that cells with an impaired G1 checkpoint can be considered "DNA-damaged cells." In all the situations described above, progressing through the cell cycle without repairing DNA damage is expected to result in suppression or death of the DNA-damaged cells.

While the invention is not limited to a particular mechanism of action, it has been observed that compounds of the invention can abrogate the G2 checkpoint in proliferating cells, and can cause adaptation to G2 cell cycle arrest. Abrogation of the G2 checkpoint in proliferating DNA-damaged cells allow the DNA-damaged cell to progress through G2 and enter mitosis without sufficient repair of DNA damage. Adaptation to G2 arrest of DNA-damaged cells, resulting in re-entry of the formerly arrested DNA-damaged cells into the cell cycle, allows the DNA-damaged cell to enter mitosis without sufficient repair of DNA damage. It is further understood that if a DNA-damaged cell progresses further into the cell cycle with a impaired G1 checkpoint and enters S phase, additional damage, defects, and errors are expected. In all the situations described above, the accumulation of damage could result in apoptosis, mitotic catastrophe, necrosis, or cell suppression. Because most cancer cells have DNA damage and/or an impaired (defective) G1 checkpoint, compounds of the invention can be used to kill or suppress cancer cells because abrogation of the G2 checkpoint or adaptation to G2 arrest will have cytotoxic effects on the cancer cells, e.g., death or suppression of the cancer cells.

For normal cells without DNA damage, it is expected that abrogation of the cell cycle G2 checkpoint by compounds of the invention will have little or no cytotoxic effect. Furthermore, as normal cells without DNA damage are not likely to be in G2 arrest, it is expected that the ability of compounds of the invention to cause adaptation to G2 arrest will have little or no cytotoxic effect. Thus, in a population of cells that includes undesirably proliferating DNA-damaged cells and normal cells, compounds of the invention can be used to selectively kill or suppress DNA-damaged cells, while having little or no cytotoxic effect on normal cells. In a population of cells including undesirably proliferating cancer cells and normal cells, compounds of the invention can be used to selectively kill or suppress the cancer cells, while having little or no cytotoxic effect on normal cells.

Use of Compounds of the Invention to Treat Cells

Any cell whose proliferation is undesired can be treated in vitro, ex vivo or in vivo with compounds of the invention. Candidate cells can be identified by contacting a test cell with an invention compound alone, or in combination with a DNA-damaging treatment or other anti-cancer treatment, and determining if the contacted cell exhibits decreased proliferation, increased cell death, or adaptation to cell cycle arrest. Candidate cells can be identified on the basis of features including but not limited to, DNA damage, aberrant growth or proliferation (in vivo or in vitro) cellular morphology, or expression of cancer markers. A clinical diagnosis of a proliferative disorder such as cancer can be relied upon as evidence of cells to be treated in vitro, ex vivo, or in vivo with compounds of the invention.

Cells can be treated in vitro with compounds of the invention. Cells can be removed from a subject, treated ex vivo using compounds of the invention, and returned to the subject. Cells can be treated in vivo using compounds of the invention, where compounds of the invention may be administered systemically to a subject, e.g. orally or intravenously, or by a targeted administration method, e.g., injection into a tumor site, intraperitoneal injection, or by associating compounds of the invention with delivery devices such as ligands, antibodies, molecular cages, or liposomes capable of targeting at least one cell to be treated.

Use of Compounds of the Invention to Treat Subjects

Subjects appropriate for treatment using compounds of the invention include subjects currently undergoing treatment for a cell proliferation disorder, or candidates for treatment for a cell proliferation disorder, e.g., subjects currently undergoing, or designated as candidates for, anti-cancer treatment. Subjects appropriate for treatment include those having a cell proliferation disorder, e.g., a diagnosis of cancer. Candidate subjects include subjects at risk of developing a cell proliferation disorder. The invention methods are therefore applicable to treating a subject who is at risk of developing a cell proliferation disorder but who has not yet exhibited overt symptoms of the disorder and/or who has not yet received a diagnosis of a cell proliferation disorder.

Use of Compounds of the Invention to Treat Cell Proliferation Disorders.

Cell proliferation disorders amenable to treatment using compositions and methods provided herein include pathological conditions (diseases), both benign and neoplastic, and non-pathological physiological conditions, characterized by abnormal or undesirable cell numbers, cell growth or cell survival. Pathological disorders or conditions may constitute a disease state, in particular all types of cancer, including cancerous growths, oncogenic processes, metastases, metastatic cells and tissues, and malignantly transformed cells, tissues, or organs. Cell proliferation disorders can be non-pathologic, including some types of fibrotic tissue growth (e.g., during wound repair resulting in scarring), certain blood vessel proliferative disorders, and certain benign hyperplasias. The present disclosure provides sufficient guidance and exemplary embodiments to enable of skill in the art to identify cell proliferation disorders suitable for treatment using compositions and methods provided herein, and to develop protocols for such treatment.

Cells comprising the proliferative disorder may be aggregated in a cell mass or may be dispersed. The term "solid tumor" refers to hyperplasias, neoplasias or metastases that typically aggregate together and form a mass. Particular examples include visceral tumors such as gastric or colon cancer, hepatomas, venal carcinomas, lung and brain tumors/cancers. A "liquid tumor" generally refers to neoplasias of the haematopoetic system, such as lymphomas, myelomas and leukemias, or neoplasias that are diffuse in nature, as they do not typically form a solid mass. Particular examples of leukemias include acute and chronic lymphoblastic, myeloblastic and multiple myeloma.

Such disorders include neoplasms or cancers, which can affect virtually any cell or tissue type, e.g., carcinoma, sarcoma, melanoma, metastatic disorders or haematopoietic neoplastic disorders. A metastatic tumor can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, etc.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the cervix, lung, prostate, breast, head and neck, colon, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, and fibrosarcoma.

As used herein, the term "haematopoietic proliferative disorder" means a disease involving hyperplastic/neoplastic cells of haematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The invention provides compositions and methods for treating cell proliferation disorders using compounds of the invention. The invention provides compositions and methods for treating cancer using compounds of the invention. The invention provides compositions and methods for killing or suppressing cancer cells using compounds of the invention. The invention provides compounds of the invention, for use in for treating cell proliferation disorders in vivo, in vitro, and ex vivo. The invention provides compounds of the invention, for use in treating cancer in vivo, in vitro, and ex vivo. The invention provides pharmaceutical compounds of the invention, for use in killing or suppressing cancer cells in vivo, in vitro, and ex vivo. The invention provides pharmaceutical compositions (medicaments) containing compounds on the invention, for all uses described herein, including but not limited to, treating cell proliferation disorders, killing or suppressing cancer cells, and treating cancer.

The invention provides compositions and methods that include at least one compound of the invention in combination with at least one additional active ingredient. The invention provides pharmaceutical compositions (medicaments) including at least one compound of the invention in combination with at least one additional active ingredient, for use in treating cell proliferation disorders. In particular, the invention provides compositions and methods that include compounds of the invention in combination with at least one anti-cancer treatment. The term "anti-cancer treatment" for use in combination with compounds of the invention includes any anti-cancer, anti-proliferative, DNA-damaging, or anti-tumor treatment as disclosed herein, including the "DNA-damaging treatments" and "DNA-damaging agents" recited above, or any such treatment known in the art. For example, an anti-cancer (anti-cell proliferative, anti-tumor) treatment may comprise radiation treatment or surgical resection, optionally in combination with drug treatment. The treatment may comprise administration of a chemical substance, such as a radioisotope, an anti-cancer drug such as a chemotherapeutic agent, or genetic therapy, such as an anti-oncogene (e.g., Rb, DCC, p53, etc.), a dominant negative oncogene or an antisense to an oncogene. The compounds of the invention can be administered prior to, contemporaneously with or following other treatment protocols. For example, a candidate subject for anti-cell proliferative therapy (e.g., radiation therapy, chemotherapy, gene therapy, surgical resection, etc.) can be administered an invention compound prior to initiating the anti-cell proliferative therapy. Thus, prophylactic treatment methods are provided.

As demonstrated in exemplary embodiments described in the Examples and discussed below, compounds of the invention can be used alone or in combination, in vivo, ex vivo, and in vitro, to treat cell proliferation disorders. As demonstrated in exemplary embodiments described in the Examples and discussed below, compound compounds of the invention can be used alone or in combination, in vivo, ex vivo, and in vitro, to treat cancer. As demonstrated in exemplary embodiments described in the Examples and discussed below, compound compounds of the invention can be used alone or in combination, in vivo and in vitro, to kill or suppress cancer cells.

Effects of Compounds of the Invention

Typically an "effective amount" or "sufficient amount" of a compound of the invention is administered, where that is an amount (concentration, dose, level) sufficient to produce a desired effect. Effective amounts are determined by any of a variety of measurements including: cell death (e.g., increase in percentage of cells in subG1 phase), decreased cell proliferation, decreased numbers of cells, decreased cell mass, increased apoptosis, decreased survival, or adaptation to cell cycle arrest (escape from cell cycle arrest). For example, where it is desired to inhibit cell proliferation, an effective amount will be an amount that detectably decreases cell proliferation, or increases cell death, or decreases cell survival. The amount can therefore be sufficient to reduce target cell numbers, stabilize target cell numbers or inhibit increases in target cell numbers. An effective amount can be an amount sufficient to increase survival time of a subject having a cell proliferation disorder.

For example, where the disorder comprises a solid tumor, an effective amount of a compound of the invention could reduce tumor size, stabilize tumor size, or increase the survival time of a subject having the tumor. As shown in the exemplary embodiment in Example 4, five (5) representative compounds of the invention showed selective cytotoxicity in vivo against cancer cells, and no detectable cytotoxicity in vivo against normal cells, as illustrated by dramatic increases in tumor host survival.

Where the disorder comprises a "liquid tumor" an effective amount of a compound of the invention could reduce numbers of tumor cells, stabilize the number of tumor cells, inhibit further increases in the number of tumor cell, or cause cell-cycle-arrested cancer cells to re-enter the cell cycle (adaptation to cell cycle arrest). In addition, effective amounts of compounds of the invention could prevent or inhibit progression of the proliferative disorder, e.g., reduce, inhibit, or prevent metastasis.

An effective amount of a compound of the invention may be an amount that produces a desired effect without producing an unacceptable or undesirable effect. An effective amount of a compound of the invention may be an amount that kills or suppresses target cells (e.g., cancer cells) while having little or no cytotoxic effect on non-target cells (e.g., normal cells), or an amount that produces a desired therapeutic benefit in a subject having a cell proliferation disorder, while having little or no adverse effect on the subject. Further, an effective amount of a compound of the invention may be an amount that, in combination another treatment, produces a desired effect without producing an unacceptable undesirable effect. As shown in exemplary embodiments in Example 7 and illustrated in Tables 4-11 below, compound S00109 has little or no cytotoxic effect on normal cells at concentrations can kill or suppress cancer cells. Further as shown in exemplary embodiments in Example 7 and illustrated in Tables 4-11 below, compound S00109 can be used in combination with another anti-cancer treatment to kill or suppress cancer cells, at a concentration of S00109 that has little or no cytotoxic effect on normal cells.

Effective amounts of compounds of the invention can objectively or subjectively reduce or decrease the severity or frequency of symptoms associated with the disorder or condition. For example, an effective amount of an invention compound could reduce pain, nausea or other discomfort, or increase appetite or subjective well-being.

Effective amounts of compounds of the invention could reduce the amount (e.g., dosage) or frequency of treatment with another protocol. For example, a cancer patient treated with an invention compound may require less anti-cancer DNA-damaging agent or treatment in order to achieve the desired level of inhibition of cancer cell proliferation, i.e., a desired level of killing or suppression of proliferating cancer cells.

Methods of the invention that lead to an improvement in the subject's condition or a therapeutic benefit that may be permanent, may extend over a longer period of time, e.g., months or years, or may be relatively short in duration, e.g., the improvement may last several hours, days or weeks. An effective amount need not achieve a complete ablation of any or all symptoms of the condition or disorder. An amount effective to provide one or more beneficial effects, as described herein or known in the art, is referred to as an "improvement" of the subject's condition or "therapeutic benefit" to the subject.

An effective amount of an invention compound can be determined based upon animal studies or optionally in human clinical trials. The skilled artisan will appreciate the various factors that may influence the dosage and timing required to treat a particular subject including, for example, the general health, age, or gender of the subject, the severity or stage of the disorder or condition, previous treatments, susceptibility to undesirable side effects, clinical outcome desired and the presence of other disorders or conditions. Such factors may influence the dosage and timing required to provide an amount sufficient for therapeutic benefit. The dosage regimen also takes into consideration the pharmacokinetics, i.e., the pharmaceutical composition's rate of absorption, bioavailability, metabolism, and clearance. In addition, doses or treatment protocols may be specifically tailored to the subject or modified based on pharmacogenomic data.

Adaptation to DNA-Damage-Induced G2 Cell Cycle Arrest

While the invention is not limited to a particular mechanism of action, it has been determined that compounds of the invention can cause adaptation to G2 cell cycle arrest. Thus, the invention provides composition and methods for abrogating or escaping from the G2 cell cycle arrest, in particular G2 cell cycle arrest triggered by DNA damage. In DNA-damaged cells, the functions of the DNA-damage-induced G2 checkpoint are understood to include recognition of DNA damage and generation of a signal that produces cell cycle-arrest, such that the DNA-damaged cells are arrested in G2 phase until repair is completed. Compounds of the invention can cause cells in G2 cell cycle arrest to re-enter the cell cycle, possibly by abrogating the DNA-damage-induced G2 checkpoint in the G2-arrested cells. As demonstrated in embodiments presented in the examples, tables and figures of the present disclosure, compounds of the invention can induce cells in G2 cell cycle arrest (i.e., cells having pre-existing DNA damage) to re-enter the cell cycle, proceeding through the G2 and M phases and entering G1 (DNA doubling) phases with unrepaired DNA damage, leading to cell death or cell suppression, usually by mitotic catastrophe or apoptosis.

In an exemplary embodiment described in Example 1 and shown in FIG. 1, Jurkat cells (a human T-cell lymphoma-derived cell line) were "pre-arrested" at the G2 phase by X-ray irradiation and treated with S00109 or S01860 at various dosages. Adaptation to G2 cell cycle arrest was determined by measuring the percentage of cells in G1 phase, where cells in G1 were identified by having 2N DNA. In these embodiments, cells exposed to S00109 or S01860 showed a dose-dependent increase in the percentage of cells in G1 phase (the "G1 increment"), These results indicated that exposure to S00109 or S01860 at concentrations from 0.019 µM to 0.625 µM caused G2-arrested cells to re-enter the cell cycle and proceed through the M phase and enter the G1 phase. In contrast, only a few percent of cells in the population of untreated G2-arrested cells (i.e., no S00109 or S01860 exposure) entered G1 phase.

Additional non-limiting exemplary embodiments of adaptation to G2 cell cycle arrest by compounds of the invention, are presented in Examples 5 and 6, and illustrated in Tables 1, 2 and 3, setting forth the structures and $IC_{50}$ values (the concentration causing half-maximal G1 increment) for approximately 144 compounds of the invention. The extensive data provided in Tables 1, 2 and 3 permitted structure-activity determinations.

Other measurements of cell cycle activity can also be relied upon to demonstrate the ability of the compounds of the invention to abrogate the G2 cell cycle and/or cause adaptation to DNA-damage-induced cell cycle arrest. In an exemplary embodiment described in Example 1 and illustrated in FIG. 2, histone H3 phosphorylation was measured, where increased phosphorylation of histone H3 indicated adaptation to (escape from) DNA-damage-induced cell cycle arrest. G2 cell cycle arrest was induced in Jurkat cells by DNA damage, i.e., by delivering a 10 Gy dose of X rays to produce "pre-arrested" cells. Pre-arrested cells were exposed to compound S00109 (also called S109) at 0.3 µM or 1 µM, and significant increases in histone H3 phosphorylation were observed over a 24-hour treatment period. Without wishing to be limited by this theory, compounds of the invention presumably caused adaptation to (escape from) DNA-damage-induced cell cycle arrest by abrogating the DNA-damage-induced G2 checkpoint.

Compounds on the Invention have Cytotoxic Effects on Cancer Cells

Compounds of the invention can have a cytotoxic effect on cancer cells, without any additional treatment. Thus, the invention provides compositions and methods for killing or suppressing cancer cells without any additional treatment. In an exemplary embodiment described in Example 2 and shown in FIG. 4, exposure of human cancer cells to S00109 alone has a dose-dependent cytotoxic effect on the cancer cells as measured by a colony formation assay (FIG. 4, "0 Gy" unfilled circles, solid line, indicating no radiation treatment).

Figure 6:
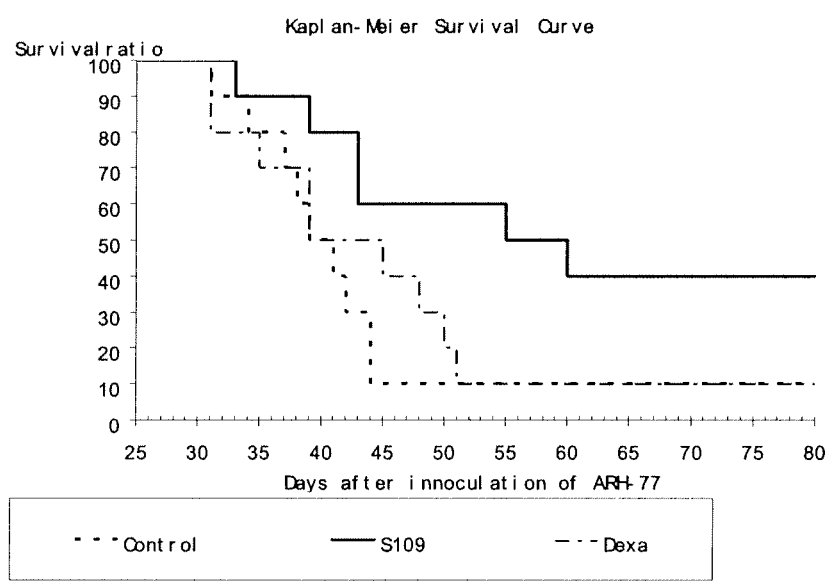
FIG. 6 shows a survival analysis for SCID mice intraperitoneally transplanted with $1.9 \times 10^6$ ARH-77 cells, for up to 80 days after transplantation (x-axis, days after transplantation; y-axis, % of mice surviving) for mice treated by intraperitoneal injection on Day 1, Day 2, and Day 3 after transplantation as follows: control mice treated with vehicle alone ("Control" dashed line); mice treated with 50 mg/kg compound S00109 ("S109" solid line); and mice treated with 2 mg/kg dexamethasone ("Dexa" dot-dash line).
Figure 7:
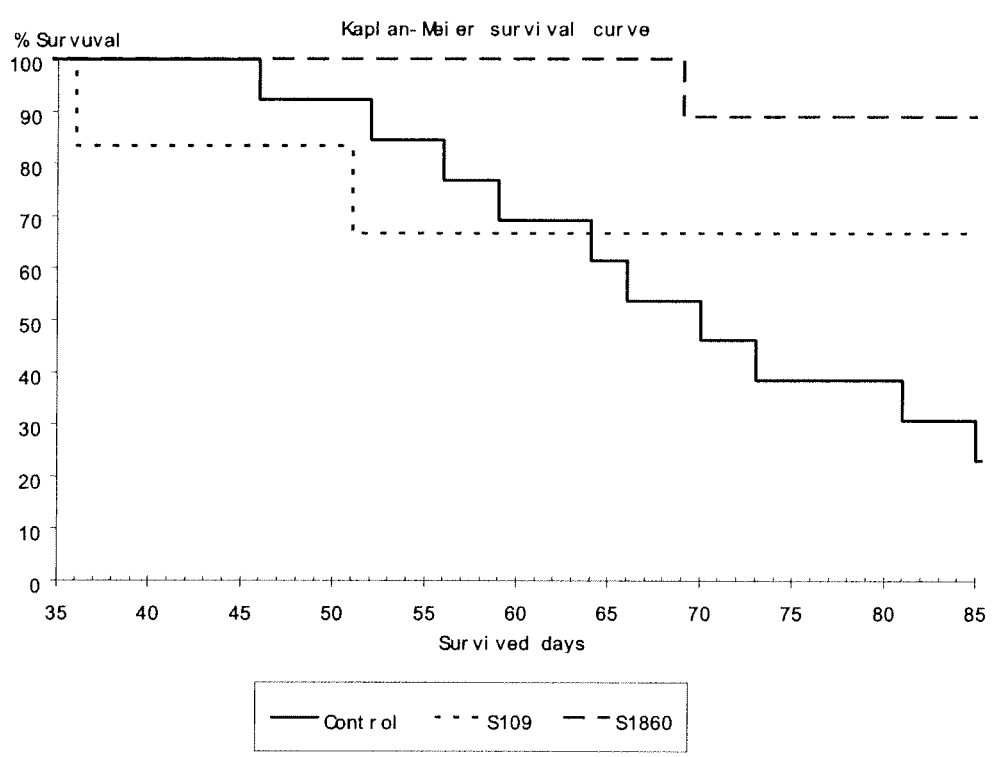
FIG. 7 shows a survival analysis for SCID mice intraperitoneally transplanted with $0.8 \times 10^6$ ARH-77 cells, for up to 85 days after transplantation (x-axis, days after transplantation; y-axis, % of mice surviving), for mice treated by a single oral administration of compounds on Day 1 after transplantation as follows: control mice orally treated with vehicle alone ("Control" solid line); mice orally treated with 750 mg/kg compound S00109 ("S109" dot line); and mice orally treated with 750 mg/kg compound S001860 ("S1860" dash line).
Figure 8:
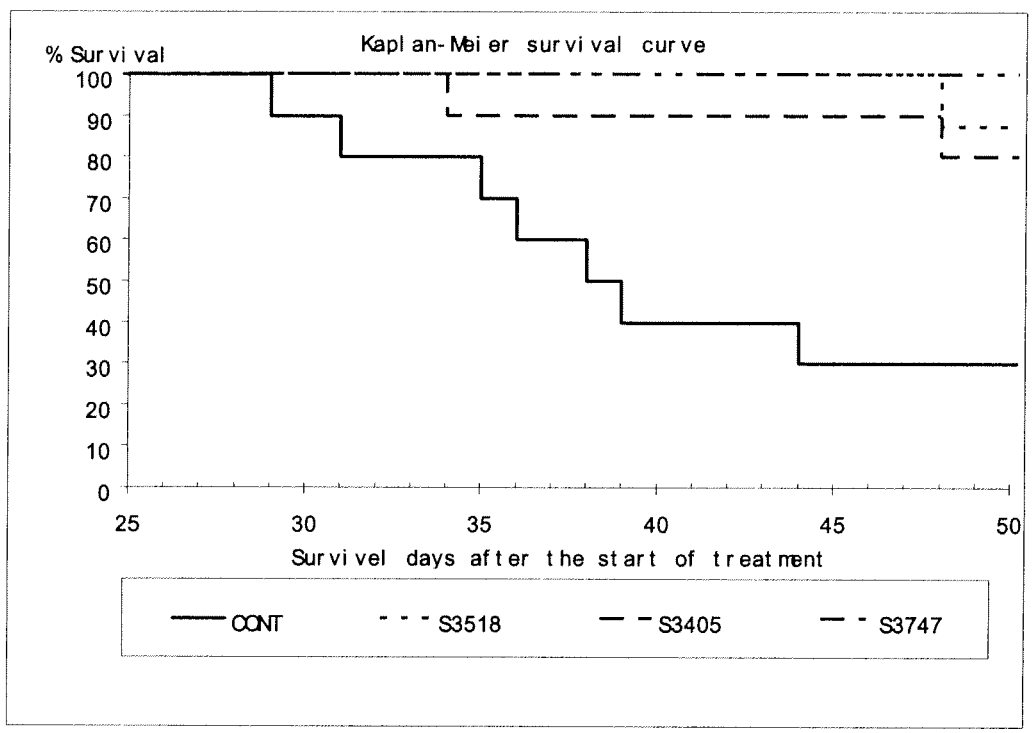
FIG. 8 shows a survival analysis for SCID mice intraperitoneally transplanted with $4.1 \times 10^6$ ARH-77 cells, for up to 50 days after transplantation (x-axis, days after transplantation; y-axis, % of mice surviving), for mice treated by once-daily oral administration of compounds on Day 1 and on Day 2 after transplantation as follows: control mice orally treated once daily for two days with vehicle alone ("CONT" solid line); mice orally treated once daily for two days with 250 mg/kg compound S003518 ("S3518" dot line); mice orally treated once daily for two days with 250 mg/kg compound S003405 ("S3405" dash line); and mice orally treated once daily for two days with 250 mg/kg compound S003747 ("S3747" dot-dash line).

In non-limiting exemplary embodiments described in Example 4 and shown in FIGS. 6, 7, and 8, compounds of the invention are provided that have a cytotoxic effect on cancer cells, without any additional anti-cancer treatment, and without cytotoxic effects on normal cells. In the exemplary embodiments in FIG. 4, mice received xenografts of human myeloma cells by intraperitoneal transplantation, and the effects of compounds of the invention on survival rates were measured. As described in Example 4 and shown in FIGS. 6, 7, and 8, treatment with S00109, S01860, S03518, S03405 or S03747 alone was sufficient to prolong the survival of mice with xenografts of human myeloma cells, indicating that S00109, S01860, S03518, S03405 or S03747 had cytotoxic effects on the transplanted cancer cells in the xenograft. As shown in the embodiment in FIG. 6, treatment with S00109 (by intraperitoneal injection) had a much greater therapeutic effect on survival than the "standard" dexamethasone treatment, or no treatment at all. As shown in FIGS. 7 and 8, oral administration of various representative compounds of the invention produced dramatic increases in survival rates, where some treatments had 100% survival rates at the end of the experiment. These results demonstrate that compounds of the invention, as illustrated by the five (5) distinct representative compounds tested in Example 4, can have selective cytotoxicity against cancer cells, and no detectable cytotoxicity against normal cells (i.e., the normal cells of the mouse tumor graft host). These in vivo results demonstrate that compounds of the invention, as illustrated by the five (5) distinct representative compounds tested in Example 4, can have selective cytotoxicity in vivo against cancer cells, and no detectable cytotoxicity in vivo against normal cells. These results demonstrate that compounds of the invention, as illustrated by the five (5) distinct representative compounds of the present invention administered by different routes in Example 4, can be administered to a subject in an effective amount to treat a proliferative disorder in a subject.

Compounds of the Invention can Sensitize Cells to Anti-Cancer Treatments

Figure 4:
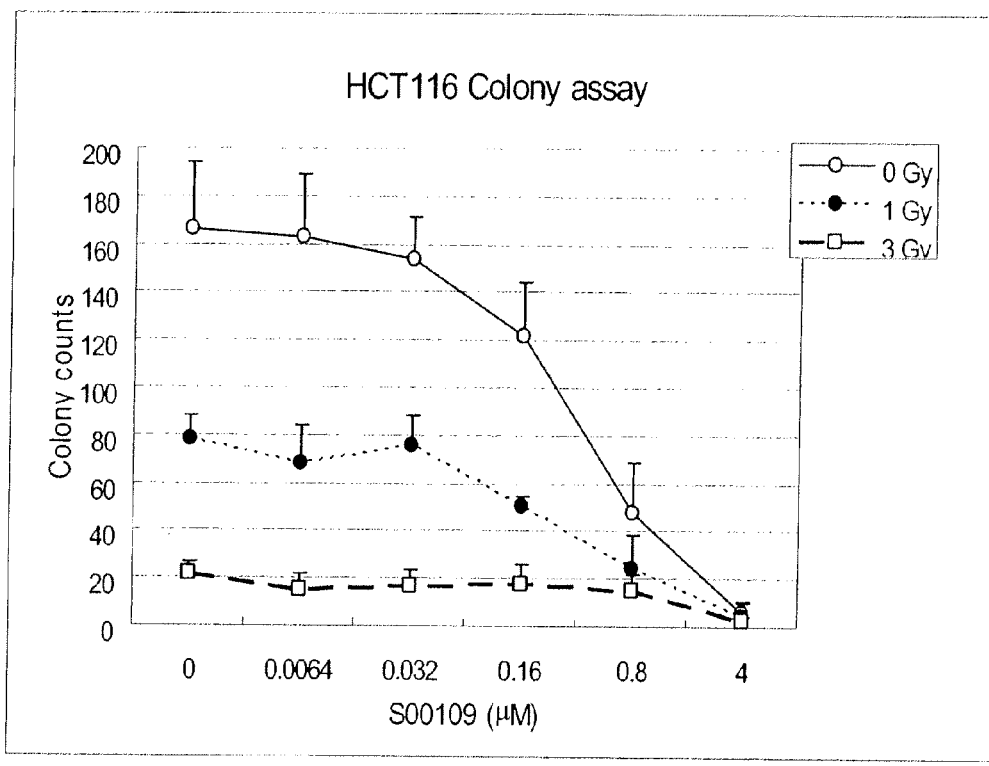
FIG. 4 shows colony counts (y-axis) after treatment of HCT 116 cells with compound S00109 at concentrations from 0 to 4 μM (x-axis) for cells treated with compound S00109 alone and no irradiation (0 Gy represented by unfilled circles) and cells treated with compound S00109 in combination with X-ray irradiation (total dose 1 Gy, represented by solid circles; total dose 3 Gy, represented by unfilled squares), where the decrease in colony counts is a measure of cell growth suppression and/or cell death.

Compounds of the invention can increase, or exacerbate, the cytotoxic effects of other treatments. Thus, the invention provides compositions and methods for sensitizing cells to anti-cancer treatments, in particular for sensitizing cells to DNA-damaging agents and treatments. In exemplary embodiments described in Example 2 and shown in FIG. 4, when human cancer cells that have been "pre-arrested" in G2 by X-ray irradiation are also exposed to S00109, the combination treatment has a higher cytotoxic effect on the cells as measured by a colony formation assay. In FIG. 4, the sensitizing effect of compounds of the invention is best illustrated for cells that received a dose of 1 Gy ("1 Gy" solid circles, dashed line) and treatment with various doses of S00109, where S00109 showed a dose-dependent additive effect on cytotoxicity. In an exemplary embodiment described in Example 3 and shown in FIG. 5, combination treatments of S00109 and dexamethasone have much greater cytotoxicity than either treatment alone, as measured by the percentage of cells in subG1 phase, i.e., the percentage of dead cells.

Figure 3:
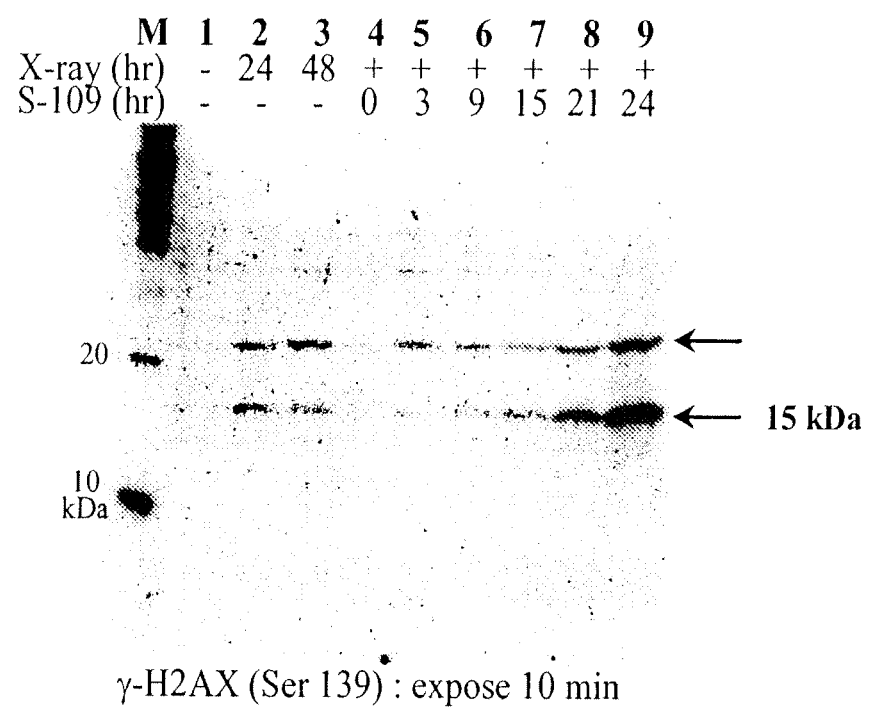
FIG. 3 is an image of an immunoblot showing levels of phosphorylated γH2AX after sequential treatment of Jurkat cells with X-ray irradiation (total dose 10 Gy) and compound S00109 at 1 μM at and for the times indicated, where phosphorylated γH2AX was detected using anti-phospho-histone H2AX and 10 minute exposure of the immunoblot, from left to right: M shows labelled molecular weight standards; Lane 1 shows cells that received no irradiation and no S00109 treatment (control cells); Lane 2 shows irradiated cells at 24 hours after irradiation and no S00109 treatment; Lane 3 shows irradiated cells at 48 hours after irradiation and no S00109 treatment; Lane 4 shows irradiated cells after 0 hours of S00109 treatment (at 24 hours after irradiation); Lane 5 shows irradiated cells after 3 hours of S00109 treatment (at 27 hours after irradiation); Lane 6 shows irradiated cells after 9 hours of S00109 treatment (at 33 hours after irradiation); Lane 7 shows irradiated cells after 15 hours of S00109 treatment (at 39 hours after irradiation); Lane 8 shows irradiated cells after 21 hours of S00109 treatment (at 45 hours after irradiation); Lane 9 shows irradiated cells after 24 hours of S00109 treatment (at 48 hours after irradiation).

In an exemplary embodiment described in Example 2 and shown in FIG. 3, expression of phosphorylated γ-H2AX was measured as an indicator of cytotoxicity. Cells treated with X-ray-irradiation alone showed increased expression of phosphorylated γ-H2AX over a 48-hour period. The sensitizing or "additive" effect of compounds of the invention can be seen in cells treated with X-ray-irradiation followed by exposure to 1 μM S00109 (indicated as "S-109+" in figure legend) resulted in significantly higher levels of phosphorylated γ-H2AX expression over the same 48 hour period, indicating significantly higher levels of cytotoxicity due to administration of S00109.

Compounds of the Invention have Selective Cytotoxicity Toward Cancer Cells

In accordance with yet another aspect of the invention, compounds of the invention can selectively kill or suppress target cells, in particular cancer cells, to the with little or no cytotoxic effect on normal (non-target) cells. Most conventional anti-cancer agents target proliferating cells irrespective of whether they are cancer cells or normal cells, with the result that most conventional anti-cancer medicines give rise to side effects such as nausea, diarrhea, or hair loss. In contrast, compounds of the invention selectively target cells having conditions such as an impaired G1 checkpoint, G2 cell cycle arrest, or other types of DNA damage, selectively killing or suppressing the target cells while having little or no cytotoxic effect on normal cells.

Non-limiting exemplary embodiments of the selectivity of compounds of invention are described in Example 7 and shown in Tables 4 to 11, where compounds of the invention were not cytotoxic for normal cells at concentrations at which compounds of the invention had severe cytotoxic effects on cancer cells and DNA-damaged cells (e.g., irradiated cells). Thus, the invention provides methods for selectively targeting DNA-damaged cells such as cancer cells, with little or no cytotoxic effect on normal (undamaged) cells, by contacting the cells with at least one compound of the invention in an amount sufficient to abrogate the G2 checkpoint. The invention provides pharmaceutical compositions containing at least one compound of the invention, suitable for use in methods for selectively targeting DNA-damaged cells such as cancer cells, with little or no cytotoxic effect on normal (undamaged) cells.

Use of Compounds of the Invention for Screening

Compounds of the invention can be used in cell cycle phenotype-based screening protocols, e.g., as disclosed by Sha et al. ((2007) *Mol Cancer Ther*, 6: 147-153) to identify candidate compounds that may interact with the G2 checkpoint and/or with other processes involved in adaptation to G2 cell cycle arrest. Compounds of the invention can be used in screening protocols to identify candidate compounds for therapeutic G2 checkpoint abrogation and/or therapeutic adaption to G2 arrest. This screening protocol can be used to identify compounds having desired biological activity. Compounds thus identified can be further evaluated for selective cytotoxic activity against cancer cells. Compounds can be evaluated in combination treatments with conventional anti-cancer agents such as dexamethasone.

The following examples are offered to illustrate, but not to limit the claimed invention.

EXAMPLES

Example 1

Effects of Test Compounds S00109 and S01860 on Jurkat Cells Arrested at G2 Phase Jurkat cells (a human T cell lymphoma-derived cell line) were arrested at the G2 phase by X-ray irradiation at 10 Gy, and cultured for 24 hours in 10% fetal calf serum (FCS)/RPMI1640 at 37° C. with 5% $CO_2$/air. (FCS was from Equitech-Bio, Kerrville, Tex., and RPMI1640 was from Sigma-Aldrich, St. Louis, Mo.) Test compounds were added to the medium at the indicated doses, and the cells were cultured under the conditions described above, for an additional 24 hours before harvesting.

Harvested cells were stained with Krishan's buffer (0.1% sodium citrate, 50 μg/ml propidium iodide, 20 μg/ml RNase A, 0.5% Nonidet P-40) and analyzed by flow cytometry (BD Biosciences, Franklin Lakes, N.J.) to identify the cell stage of each cell in the sample. Cells in G1 phase were identified by having doubled (2N) DNA content. FIG. 1 shows the percentage of cells in G1 phase after treatment with each compound at the indicated dosages.

The $IC_{50}$ value for each compound was calculated as the dosage showing half maximal activity to induce the increase of the percentage of cells in G1 phase (the G1 increment). $IC_{50}$ values were used to measure the activity of compounds and to determine structure-activity relationships.

As shown in FIG. 1, populations of pre-arrested Jurkat cells treated with compound S00109 or S01860 for 24 hours showed a significant increase in the number of G1 cells, indicating the cells were able to enter the cell cycle again.

Histone H3 Phosphorylation

Increased numbers of cells in G1 phase ("G1 cells" detected by 2N DNA) after X-ray treatment indicated that the G2 checkpoint had been abrogated and/or cells had adapted to (escaped from) the G2 cell cycle arrest imposed by activation of the G2 checkpoint by the X-ray treatment (i.e., activation of the DNA-damage-induced G2 checkpoint by the X-ray treatment). The level of histone H3 phosphorylation was measured in pre-arrested cells treated with test compounds, to confirm that pre-arrested cells had re-entered the cell cycle and passed through M phase before proceeding to G1 phase. Increased phosphorylation of histone H3 indicated adaptation to (escape from) damage-induced cell cycle arrest or G2/M checkpoint abrogation.

Figure 2:
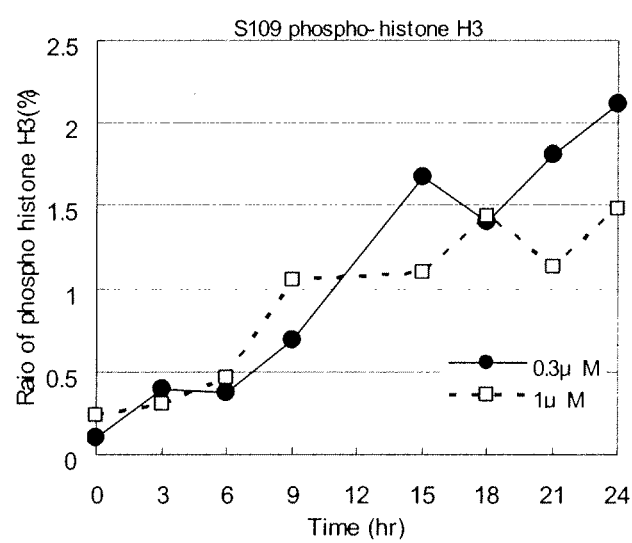
FIG. 2 shows the level of histone H3 phosphorylation (%) in Jurkat cells pre-arrested at the G2 phase by X-ray irradiation (10 Gy) and treated with compound S00109 at 1 μM (unfilled squares) and 0.3 μM (solid circles) for treatment times up to 24 hours.

Jurkat cells were irradiated with 10 Gy X-rays and cultured 24 hour in 10% FCS-RPMI. Test compound S00109 was added to the culture medium at 0.3 or 1 μM and cells were cultured with test compound for treatment times from 0 to 24 hours. The cells were fixed with cold ethanol, treated with 0.1% saponin/PBS, stained with anti-phospho-histone H3 (Ser10) (Upstate Biotechnology, Uppsala, Sweden) and analyzed with flow cytometry (BD Biosciences). In FIG. 2, the X-axis indicates treatment time, i.e., time after S00109 addition, and the Y-axis indicates the ratio (%) of cells that were phospho-histone-H3-positive. The level of histone H3 phosphorylation (%) after sequential treatment of Jurkat cells with X-ray irradiation (10 Gy) and compound S00109 at 1 μM (unfilled squares) and 0.3 μM (solid circles) increased with increasing treatment time up to 24 hours.

Example 2

Cytotoxicity of S00109 Alone or in Combination with Radiation

Phosphorylated Histone H2AX Expression

Expression of phosphorylated histone H2AX (γH2AX phosphorylated on Ser139) was measured as an indicator of cytotoxicity, in particular, DNA-damaged-related cytotoxicity. Jurkat cells were irradiated with 10 Gy X-rays and cultured 24 hour in 10% FCS-RPMI as described above. Then, S00109 was added to the culture medium at 1 μM for the treatment times up to 24 hours. The cells were lysed in a buffer (100 mM NaCl, 10 mM Tris-HCl (pH 8.0), 1 mM DTT, 0.2% NP-40, 10 mM NaF, 10 mM $Na_3VO_4$, 500 nM okadaic acid, and proteinase inhibitors). Aliquots of the lysate (30 μg protein) were electrophoresed on a 15% SDS page gel and transferred to a membrane for Western blot analysis. Anti-phospho-histone H2AX (Ser 139) Ab (Cell Signaling Technology, Beverly, Mass.) was used to detect γ-H2AX on the blotted membrane. As shown in FIG. 3, levels of γH2AX increased treatment time with S00109, indicating that S00109 caused DNA, in addition to DNA damage caused by the irradiation.

Colony Formation Analysis

The cytotoxic activity of S00109 was further confirmed by colony formation analysis using HCT-116 cells, a human colon cancer cell line, where a decrease in colony counts is a measure of cell growth suppression and/or cell death. HCT-116 human colon cancer cells were cultured in McCoy's 5A (Invitrogen, Carlsbad, Calif.) with 10% FCS, 5% $CO_2$/air at 37° C. The cells were seeded at 300 cells per 6 well plate in triplicate, irradiated with X rays as shown in the figure legend, and cultured for 24 hours, then treated with S00109 at the indicated dosages and cultured for 8 days. On day 8, colonies were fixed and stained with crystal violet (Sigma-Aldrich), and the number of colonies was counted. FIG. 4 shows the effect on S00109 dose (x-axis) on colony numbers (y-axis) counted on day 8.

Cells that received no radiation ("0 Gy" open circles, solid line in legend of FIG. 4) were cultured under the same conditions as the irradiated cells, and were treated with S00109 to show the effects of S00109 alone. Thus, as shown in FIG. 4, S00109 alone suppressed colony formation by HCT-116 cells in a dose-dependent manner, indicating that S00109 alone can suppress the growth of cancer cells and/or kill cancer cells at sufficiently high dosage.

The "normal" colony count for untreated control cells is shown by value for 0 Gy and 0 μM S00109.

Cells that received a radiation dose of 1 Gy (filled circles, dotted line) showed an inhibition of colony formation due to radiation alone. Cells that received a radiation dose of 1 and were exposed to S00109 showed further inhibition of colony formation, indicating that S00109 can augment the cytotoxicity of the radiation treatment. Under these conditions of radiation and. S00109 treatment, a strong dose-dependent additive effect of S00109 was seen.

Cells that received a radiation dose of 3 Gy ("3 Gy" open square, solid line) shown strong inhibition of colony formation due to radiation alone. S00109 appears to have a detectable additional inhibitory effect at the highest concentration (4 μM), again indicating that S00109 can augment the cytotoxicity of radiation treatment.

Example 3

Cytotoxicity of S00109 Alone and in Combination with Dexamethasone

Cytotoxicity of S00109 alone and in combination with dexamethasone was measured by identifying the number of cells in subG1 phase after treatment, where subG1 phase indicates cell death, such that the number of cells in subG1 phase after treatment indicates cell killing by the treatment. A human multiple-myeloma-derived cell line, ARH-77, was cultured in the presence or absence of S00109, with or without dexamethasone, for 24 hour in 10% fetal calf serum (FCS)/RPMI1640 at 37° C. with 5% $CO_2$/air using materials and conditions described above. Harvested cells were stained with Krishan's buffer (0.1% sodium citrate, 50 propidium iodide, 20 μg/ml RNase A, 0.5% Nonidet P-40) and analyzed with flow cytometry (BD Biosciences, Franklin Lakes, N.J.).

Figure 5:
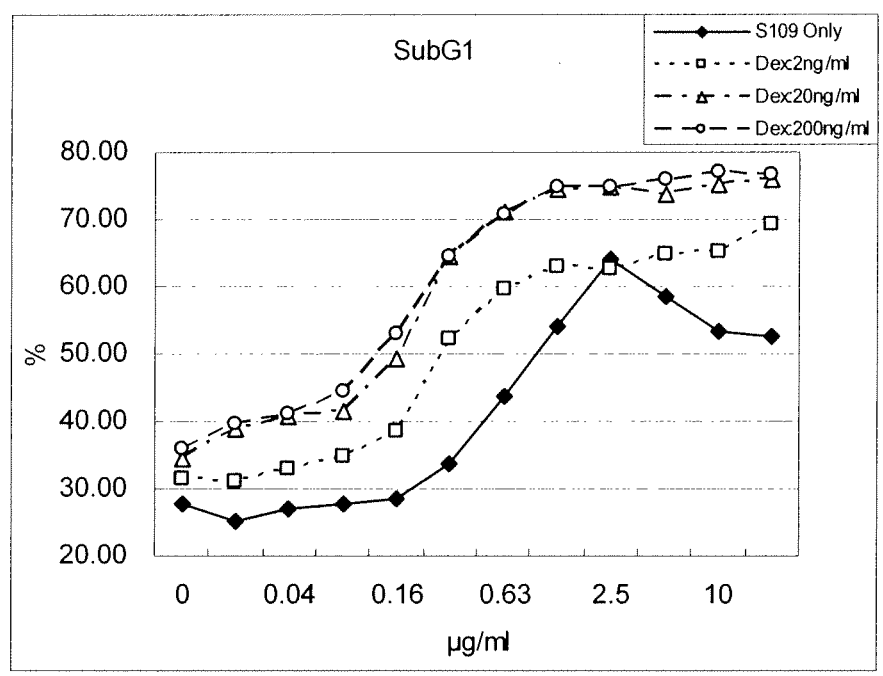
FIG. 5 shows the percentage of cells in subG1 phase (y-axis) after in vitro treatment of ARH-77 with compound S00109 at concentrations from 0 to 10 μg/ml (x-axis) as follows: ARH-77 cells treated with compound S00109 alone at the concentrations indicated on the x-axis ("S109Only" represented by solid diamonds, solid line); ARH-77 cells treated with compound S00109 at the concentrations indicated on the x-axis, in combination with dexamethasone at 2 ng/ml ("Dex2 ng/ml" represented by unfilled squares, short-dash line); ARH-77 cells treated with compound S00109 at the concentrations indicated on the x-axis, in combination with dexamethasone at 20 ng/ml ("Dex20 ng/ml" represented by unfilled triangles, dot-dash line); and ARH-77 cells treated with compound S00109 at the concentrations indicated on the x-axis, in combination with dexamethasone at 200 ng/ml ("Dex200 ng/ml" represented by unfilled circles, long-dash line); where subG1 phase indicates cell death.

FIG. 5 shows the percentage of ARH-77 cells in subG1 phase (y-axis) after treatment with S00109 (x-axis) alone or in combination with dexamethasone. The 'normal' percentage of subG1 cells in a population of untreated control cells is shown by the value for S00109 alone (filled diamonds, solid line, "S109 only" in figure legend) at 0 μg/ml S00109. S00109 treatment alone, at concentrations up to 10 μg/ml, caused cell death in a dose-dependent manner. Dexamethasone treatment alone at 2 ng/ml (open squares, dotted line), 20 ng/ml (open triangles, dot/dash line) and 200 ng/m open circles, dashed line) without S00109 showed slightly increased levels of subG1 cells, i.e., slightly increased cytotoxicity, compared to the control. However, treatment with S00109 in combination with dexamethasone resulted in a dramatic increase in the levels of subG1 cells. The combination effect showed a strong dependence on the S00109 concentration, demonstrating a dose-dependent effect of S00109. The combination of S00109 and dexamethasone resulted in a level of cell death that was significantly higher than the level seen with either compound alone. Thus, S00109 augmented the cytotoxicity of dexamethasone.

Example 4

Effects of Representative Compounds of the Invention, Alone and in Combination, on Survival of Mice with Xenografts of ARH-77 Cells Mice with xenografts of ARH-77 (a human multiple-myeloma-derived cell line) were treated with S00109, S01860, S03518, S03405 or S03747 or with dexamethasone, a recognized "standard" treatment, and their survival was measured and compared with survival of vehicle-treated (control) mice with xenografts. The ability of a treatment to prolong survival was considered to be an indicator of the cytotoxicity of the treatment towards the grafted cancer cells, without significant adverse activity on normal (mouse) cells in vivo.

Male severe combined immune deficiency (SCID) mice at 8 weeks old were transplanted intraperitoneally with $1.9 \times 10^6$ (FIG. 6), $0.8 \times 10^6$ (FIG. 7), $4.1 \times 10^6$ (FIG. 8), cells/animal of ARH-77 cells (n=10).

Animals were housed in accordance with guidelines from the Association for the Assessment and Accreditation of Laboratory Animal Care International, and the protocols were approved by institutional animal care committee of Can-Bas Co. Ltd.

For the experiment shown in FIG. 6, mice received $1.9 \times 10^6$ ARH-77 cells by intraperitoneal transplantation. Mice treated with S00109 ("S109") received an intraperitoneal injection of 50 mg/kg S00109. Mice treated with dexamethasone ("Dexa") received an intraperitoneal injection of 2 mg/kg dexamethasone. Vehicle treated control animals received intraperitoneal vehicle injection. Each injection was performed on day 1, day 2 and day 3 after transplantation of ARH-77 cells. Survival (y-axis, % of mice surviving) was measured for up to 80 days after transplantation (x-axis) for control mice treated with vehicle alone ("Control" dashed line); mice treated with 50 mg/kg compound S00109 ("S109"

solid line); and mice treated with 2 mg/kg dexamethasone ("Dexa" dot-dash line). Mice treated with S00109 had a significantly longer duration of survival than untreated control mice. Although mice treated with dexamethasone had a longer survival duration than untreated control mice, the therapeutic effect of dexamethasone was much smaller than the therapeutic effect of S00109.

For the experiment shown in FIG. 7, mice received $0.8 \times 10^6$ ARH-77 cells by intraperitoneal transplantation. Mice were treated by a single oral administration of compounds on Day 1 after transplantation as follows: control mice orally treated with vehicle alone ("Control" solid line); mice orally treated with 750 mg/kg compound S00109 ("S109" dot line); and mice orally treated with 750 mg/kg compound S01860 ("S1860" dash line). Although mice treated with S00109 initially showed slightly lower survival than the control mice, after about 64 days, mice treated with S00109 showed significantly higher survival than control mice, with almost 70% survival at 85 days, compared with only about 20% of the control mice surviving at 85 days. Mice treated with S01860 showed dramatically higher survival rates than control mice or mice treated with S00109, where the first decrease in survival was not seen until 70 days after transplantation, and almost 90% of the S01860-treated mice survived at 85 days.

For the experiment shown in FIG. 8, mice received $4.1 \times 10^6$ ARH-77 cells by intraperitoneal transplantation. Mice were treated by once-daily oral administration of compounds on Day 1 and once-daily oral administration of compounds on Day 2 after transplantation as follows: control mice orally treated once daily for two days with vehicle alone ("CONT" solid line); mice orally treated once daily for two days with 250 mg/kg compound S003518 ("S3518" dot line); mice orally treated once daily for two days with 250 mg/kg compound S003405 ("S3405" dash line); and mice orally treated once daily for two days with 250 mg/kg compound S003747 ("S3747" dot-dash line). Mice treated with S03518, S03405 or S03747 all showed dramatically higher survival rates than control mice. Control mice showed decreased survival beginning at about 29 days after transplantation, and only about 30% survival at 50 days after transplantation. In contrast, mice treated with S03518, S03405 or S03747 showed very little decrease in survival, and still had extremely high survival rates of between 80-100% by 50 days after transplantation.

These results demonstrated that S00109, S01860, S03518, S03405 or S03747, administered intraperitoneally or orally, had selective cytotoxicity in vivo against cancer cells (ARH 77 cells of the xenograft tumor) while having no detectable cytotoxicity against normal cells (the mouse graft host). These results demonstrated that five different compounds of the present invention were administered to a subject in an effective amount to treat a proliferative disorder in a subject.

Example 5

Ability of Representative Compounds to Cause Adaptation to G2 Cell Cycle Arrest and Induce G2-Arrested Cells to Re-Enter the Cell Cycle Representative compounds were synthesized according to methods provided herein. The structure and other properties of each compound was determined by $^1$H NMR spectroscopy for each synthesized compound.

Pre-arrested Jurkat cells were prepared as described in Example 1. Briefly, Jurkat cells were subjected to X-ray irradiation at a dose of 10 Gy, and cultured for 24 hours in 10% fetal calf serum (FCS)/RPMI1640 at 37° C. with 5% $CO_2$/air, after which time cells were exposed to various concentrations of test compounds, and cultured under the conditions described above for an additional 24 hours before harvesting. Harvested cells were stained with Krishan's buffer (0.1% sodium citrate, 50 μg/ml propidium iodide, 20 μg/ml RNase A, 0.5% Nonidet P-40) and analyzed by flow cytometry (BD Biosciences, Franklin Lakes, N.J.) to identify the cell stage of each cell in the sample. Cells in G1 phase were identified by having doubled (2N) DNA content.

The $IC_{50}$ value for each compound was calculated as the dosage (concentration in μM) that caused half-maximal increase of the percentage of cells in G1 phase (the G1 increment) measured for that test compound. Table 1 below presents the structure, mass, 1H NMR values, and 1050 values for representative compounds.

TABLE 1

Representative Compounds and IC50 values

| | SCID | Structure | MS (m/e) | 1H NMR | IC50 (μM) |
|---|---|---|---|---|---|
| 1 | S00069 | 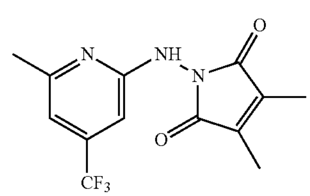 | 300.5 (M + 1) | (CDCl3, 400 MHz) δ: 6.89 (s, 1H), 6.55 (s, 1H), 6.52 (s, 1H), 2.44 (s, 3H), 2.07 (s, 6H) | 5 |
| 2 | S00073 | 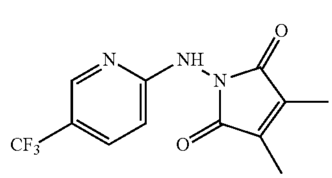 [SMILES: CC1=C(C)C(=O)N(Nc2ccc(C(F)(F)F)cn2)C1=O] | 286.4 (M + 1) | (CDCl3, 300 MHz) δ: 8.37 (s, 1H), 7.70-7.60 (dd, J = 1.8, 8.7 Hz, 1H), 6.96 (s, 1H), 6.60 (d, J = 8.4 Hz, 1H), 2.05 (s, 6H) | 2.5 |

TABLE 1-continued

Representative Compounds and IC50 values

| | SCID | Structure | MS (m/e) | 1H NMR | IC50 (μM) |
|---|---|---|---|---|---|
| 3 | S00084 | 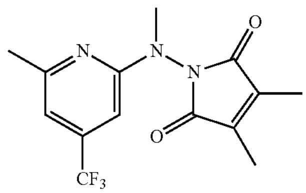 | 314.4 (M + 1) | (CDCl3, 400 MHz) δ: 6.79 (s, 1H), 6.51 (s, 1H), 3.42 (s, 3H), 2.41 (s, 3H), 2.06 (s, 6H) | 5 |
| 4 | S00200 | 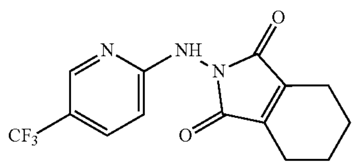 [SMILES: O=C1C2=C(CCCC2)C(=O)N1Nc1ccc(C(F)(F)F)cn1] | | (CDCl3, 300 MHz) δ: 8.37-8.39 (m, 1H), 7.64-7.67 (m, 1H), 7.26 (s, 1H), 6.61-6.64 (d, J = 8.6 Hz, 1H), 2.41 (m, 4H), 1.80-1.84 (m, 4H) | 5 |
| 5 | S00109 | 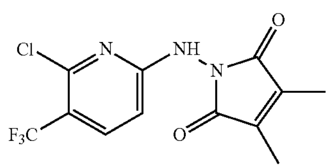 [SMILES: CC1=C(C)C(=O)N(Nc2ccc(C(F)(F)F)c(Cl)n2)C1=O] | 318.0 (M − 1) | (CDCl3, 300 MHz) δ: 7.70 (d, J = 8.7 Hz, 1H), 7.10 (s, 1H), 6.45 (d, J = 8.7 Hz, 1H), 2.07 (s, 6H) | 0.12 |
| 6 | S00170 | 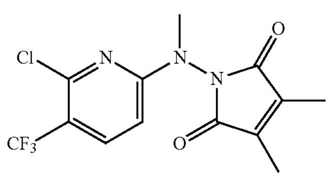 [SMILES: CC1=C(C)C(=O)N(N(C)c2ccc(C(F)(F)F)c(Cl)n2)C1=O] | | (CDCl3, 300 MHz) δ: 7.70 (d, J = 8.4 Hz, 1H), 6.40 (d, J = 8.7 Hz, 1H), 3.44 (s, 3H), 2.08 (s, 6H) | 0.12 |
| 7 | S00186 | 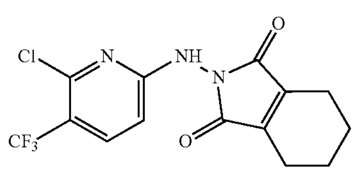 [SMILES: O=C1C2=C(CCCC2)C(=O)N1Nc1ccc(C(F)(F)F)c(Cl)n1] | | (CDCl3, 300 MHz) δ: 7.70 (d, J = 8.7 Hz, 1H), 6.45 (d, J = 8.7 Hz, 1H), 2.50-2.30 (m, 4H), 1.90-1.75 (m, 4H) | 0.63 |
| 8 | S00257 | 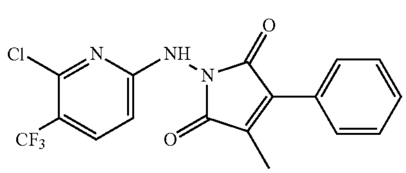 [SMILES: CC1=C(c2ccccc2)C(=O)N(Nc2ccc(C(F)(F)F)c(Cl)n2)C1=O] | | (CDCl3, 300 MHz) δ: 7.79 (d, J = 8.4 Hz, 1H), 7.65-7.62 (m, 2H), 7.53-7.48 (m, 3H), 7.14 (s, 1H), 6.56 (d, J = 8.4 Hz, 1H), 2.31 (s, 3H) | 10 |
| 9 | S00333 | 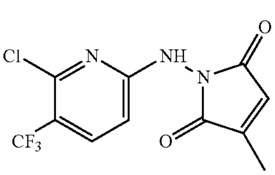 [SMILES: CC1=CC(=O)N(Nc2ccc(C(F)(F)F)c(Cl)n2)C1=O] | 304.2 (M − 1) | (CDCl3, 300 MHz) δ: 8.85-8.75 (br, 1H), 7.95-7.85 (d, J = 8.4 Hz, 1H), 7.24 (s, 1H), 6.20-6.15 (m, 1H), 2.28 (s, 3H). HPLC-MS(m/e): 304.2 (M − 1). | 15 |
| 10 | S00108 | 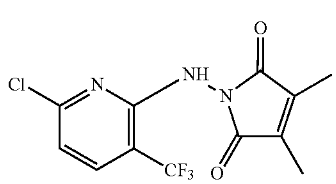 [SMILES: CC1=C(C)C(=O)N(Nc2nc(Cl)ccc2C(F)(F)F)C1=O] | 319.7 (M + 1) | (CDCl3, 300 MHz) δ: 7.80-7.70 (dd, J = 0.6, 7.8 Hz, 1H), 6.95-6.85 (dd, J = 0.6, 7.8 Hz, 1H), 6.82 (s, 1H), 2.07 (s, 6H). HPLC-MS (m/e): 318.0 (M − 1, negative mode) | 20 |

TABLE 1-continued

Representative Compounds and IC50 values

| SCID | Structure | MS (m/e) | 1H NMR | IC50 (µM) |
|---|---|---|---|---|
| 11 S00451 | 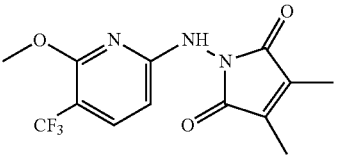 | 314.2 (M − 1) | (CDCl3, 300 MHz) δ: 7.63 (d, J = 8.4 Hz, 1H), 6.82 (s, 1H), 6.26 (d, J = 8.4 Hz, 1H), 3.6l (s, 3H), 2.05 (s, 6H). HPLC-MS (m/e): 314.2 (M − 1) | 60 |
| 12 S00145 | 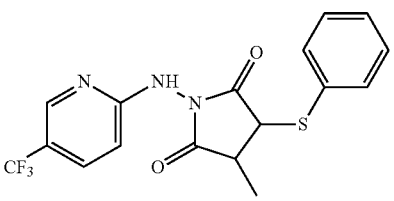<br>Mixture of isomers | 382.1 (M + 1) | (CDCl3, 300 MHz) δ: 8.30 (d, J = 16.6 Hz, 1H), 7.75-7.65 (m, 1H), 7.60-7.50 (m, 2H), 7.50-7.30 (m, 3H), 6.80-6.60 (br, 1H), 6.60-6.45 (dd, J = 8.0, 18.4 Hz, 1H), 3.70 (d, J = 5.6 Hz, 0.5H), 3.20-2.95 (t, J = 18.4, 46.4 Hz, 1H), 2.95-2.90 (t, J = 5.6, 7.6 Hz, 0.5H), 1.72 (s, 1.5H), 1.55-1.45 (d, J = 7.2 Hz, 1.5H). HPLC-MS (m/e): 382.1 (M ++ 1) | 30 |
| 13 S00110 | 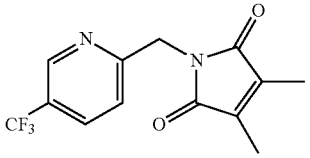 [SMILES: CC1=C(C)C(=O)N(Cc2ccc(C(F)(F)F)cn2)C1=O] | | (CDCl3, 300 MHz) δ: 8.79 (s, 1H), 7.85-7.89 (dd, J = 2.2, 8.3 Hz, 1H), 7.33-7.36 (d, J = 8.0 Hz, 1H), 4.87 (s, 2H), 2.01 (s, 6H) | 60 |
| 14 S00362 | 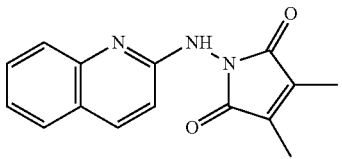 [SMILES: CC1=C(C)C(=O)N(Nc2ccc3ccccc3n2)C1=O] | 268.2 (M + 1) | (CDCl3, 300 MHz) δ: 7.91 (d, J = 8.4 Hz, 1H), 7.69-7.62 (m, 2H), 7.58-7.55 (m, 1H), 7.34-7.29 (m, 1H), 6.79 (d, J = 8.7 Hz, 1H), 2.08 (s, 6H) | 5 |
| 15 S00622 | 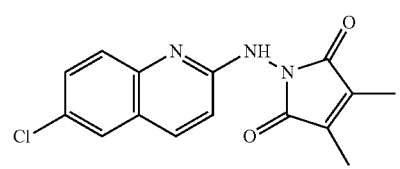 [SMILES: CC1=C(C)C(=O)N(Nc2ccc3cc(Cl)ccc3n2)C1=O] | 302.15 (M + 1) | (CDCl3, 300 MHz) δ: 7.88 (d, J = 8.7 Hz, 1H), 7.62 (m, 2H), 7.51 (d, J = 2.4 Hz, 1H), 6.84 (d, J = 9 Hz, 1H), 5.38 (m, 1H), 2.09 (s, 6H) | 5 |
| 16 S00585 | 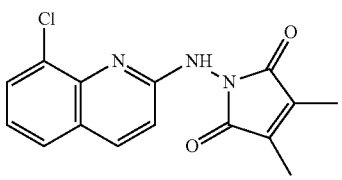 | 302.13 (M + 1) | (CDCl3, 300 MHz) δ: 7.90 (d, J = 6.9 Hz, 1H), 7.64-7.66 (dd, J = 0.8, 5.4 Hz, 1H), 7.53-7.56 (dd, J = 0.8, 6.3 Hz, 1H), 7.19-7.23 (dd, J = 5.7, 6 Hz, 1H), 6.86 (d, J = 6.6 Hz, 1H), 2.10 (s, 6H) | 0.45 |
| 17 S00295 | 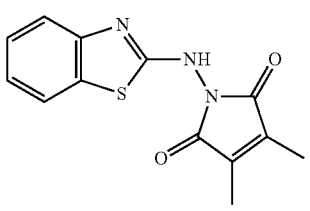 [SMILES: CC1=C(C)C(=O)N(Nc2nc3ccccc3s2)C1=O] | | (CDCl3, 300 MHz) δ: 7.51-7.55 (m, 2H), 7.29-7.35 (m, 1H), 7.12-7.17 (m, 1H), 2.07 (s, 6H) | 5 |

TABLE 1-continued

Representative Compounds and IC50 values

| | SCID | Structure | MS (m/e) | 1H NMR | IC50 (μM) |
|---|---|---|---|---|---|
| 18 | S00454 | (6-fluoro-benzothiazol-2-yl)-NH-(3,4-dimethyl-pyrrole-2,5-dione) | 292.2 (M + 1) | (CDCl3, 300 MHz) δ: 7.50 (dd, J = 4.8, 9.0 Hz, 1H), 7.28 (m, 1H), 7.05 (td, J = 2.1, 9.0, 17.7 Hz, 1H), 2.02 (s, 6H) | 4 |
| 19 | S00590 | (6-chloro-benzothiazol-2-yl)-NH-(3,4-dimethyl-pyrrole-2,5-dione) | 307.8 (M + 1) | (CDCl3, 300 MHz) δ: 7.53 (d, J = 1.2 Hz, 1H), 7.48 (d, J = 6.3 Hz, 1H), 7.30 (d, J = 1.5 Hz, 1H), 2.07 (s, 6H) | 5 |
| 20 | S00756 | (4-chloro-benzothiazol-2-yl)-NH-(3,4-dimethyl-pyrrole-2,5-dione) | | (CDCl3, 300 MHz) δ: 2.02 (s, 6H), 7.07 (d, J = 12 Hz, 1H), 7.32 (d, J = 6.9 Hz, 1H), 7.46 (d, J = 6.9 Hz, 1H) | 1.25 |
| 21 | S00319 | (2-methyl-5-chloro-phenyl)-NH-(3,4-dimethyl-pyrrole-2,5-dione) | | (CDCl3, 300 MHz) δ: 7.05-6.95 (d, J = 7.8 Hz, 1H), 6.90-6.80 (dd, J = 2.1, 7.8 Hz, 1H), 6.50-6.45 (d, J = 2.1 Hz, 1H), 5.77 (s, 1H), 2.25 (s, 3H), 2.04 (s, 6H) | 10 |
| 22 | S00512 | (2-methyl-5-trifluoromethyl-phenyl)-NH-(3,4-dimethyl-pyrrole-2,5-dione) | 297.1 (M − 1) | (CDCl3, 300 MHz) δ: 7.18 (d, J = 8.1 Hz, 1H), 7.10 (d, J = 7.8 Hz, 1H), 6.70 (s, 1H), 5.87 (s, 1H), 2.35 (s, 3H), 2.07 (s, 6H) | 5 |
| 23 | S00623 | (2-bromo-5-trifluoromethyl-phenyl)-NH-(3,4-dimethyl-pyrrole-2,5-dione) | | (CDCl3, 300 MHz) δ: 7.60 (dd, J = 0.3, 6.3 Hz, 1H), 7.04-7.07 (m, 1H), 6.75 (d, J = 1.8 Hz, 1H), 6.44 (s, 1H), 2.08 (s, 6H) | 10 |
| 24 | S00649 | (2-bromo-5-tert-butyl-phenyl)-NH-(3,4-dimethyl-pyrrole-2,5-dione) | 350.9 (M + 1) | (CDCl3, 300 MHz) δ: 7.36 (d, J = 8.4 Hz, 1H), 6.85-6.82 (dd, J = 2.4, 8.4 Hz, 1H), 6.54 (d, J = 2.4 Hz, 1H), 6.32 (s, 1H), 2.06 (s, 6H), 1.20 (s, 9H) | 10 |

TABLE 1-continued

Representative Compounds and IC50 values

| | SCID | Structure | MS (m/e) | 1H NMR | IC50 (μM) |
|---|---|---|---|---|---|
| 25 | S00305 | 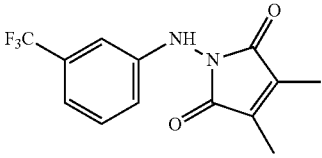 [SMILES: CC1=C(C)C(=O)N(Nc2cccc(C(F)(F)F)c2)C1=O] | | (CDCl3, 300 MHz) δ: 7.34 (t, J = 8.1 Hz, 1H), 7.20 (d, J = 8.1 Hz, 1H), 6.95 (s, 1H), 6.90 (dd, J = 2.4, 8.1 Hz, 1H), 6.02 (s, 1H), 2.06 (s, 6H) | 5 |
| 26 | S00515 | 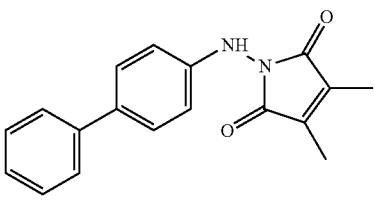 [SMILES: CC1=C(C)C(=O)N(Nc2ccc(-c3ccccc3)cc2)C1=O] | 292.9 (M + 1) | (CDCl3, 300 MHz) δ: 7.52-7.37 (m, 6H), 7.39 (d, J = 7.2 Hz, 1H), 6.83-6.80 (dd, J = 2.1, 6.6 Hz, 2H), 5.98 (s, 1H), 2.05 (s, 6H). HPLC-MS (m/e): 292.9 (M + 1). | 20 |
| 27 | S00406 | 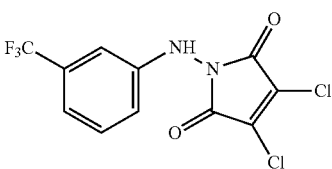 [SMILES: O=C1C(Cl)=C(Cl)C(=O)N1Nc1cccc(C(F)(F)F)c1] | | (CDCl3, 300 MHz) δ: 7.30 (m, 1H), 7.26 (d, J = 9.3 Hz, 1H), 7.01 (s, 1H), 6.94 (d, J = 8.1 Hz, 1H), 6.16 (s, 1H) | 80 |
| 28 | S00294 | 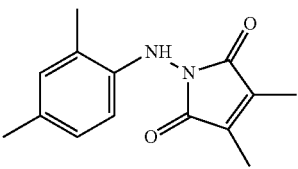 | | (CDCl3, 300 MHz) δ: 6.91 (s, 1H), 6.87 (d, J = 7.8 Hz, 1H), 6.44 (d, J = 7.8 Hz, 1H), 5.75 (s, 1H), 2.30 (s, 3H), 2.23 (s, 3H), 2.03 (s, 6H) | 5 |
| 29 | S00499 | 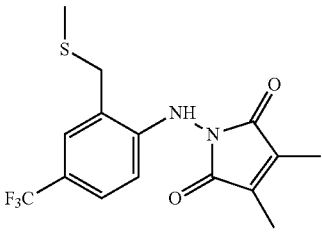 [SMILES: CSCc1cc(C(F)(F)F)ccc1NN1C(=O)C(C)=C(C)C1=O] | | (CDCl3, 300 MHz) δ: 7.60 (s, 1H), 7.40 (d, J = 8.4 Hz, 1H), 7.34 (s, 1H), 6.61 (d, J = 8.4 Hz, 1H), 3.88 (s, 2H), 2.03 (s, 6H), 1.59 (s, 3H) | 5 |
| 30 | S00699 | 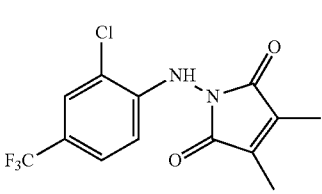 [SMILES: CC1=C(C)C(=O)N(Nc2ccc(C(F)(F)F)cc2Cl)C1=O] | | (CDCl3, 300 MHz) δ: 2.05 (s, 6H), 6.50 (s, 1H), 6.62 (d, J = 8.7 Hz, 1H), 7.36 (d, J = 8.4, 1H), 7.59 (s, 1H) | 10 |
| 31 | S00624 | 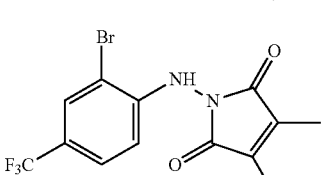 | | (CDCl3, 300 MHz) δ: 7.75 (d, J = 1.2 Hz, 1H), 7.39-7.42 (m, 1H), 6.59 (d, J = 8.7 Hz, 1H), 6.50 (s, 1H), 2.06 (s, 6H) | 10 |
| 32 | S00627 | 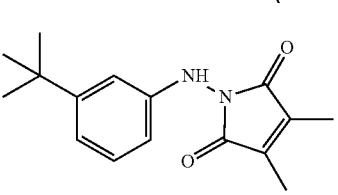 | 271.1 (M − 1) | (CDCl3, 300 MHz) δ: 7.16-7.11 (t, J = 8.1 Hz, 1H), 6.95 (d, J = 7.8 Hz, 1H), 6.84-6.82 (t, J = 7.8 Hz, 1H), 6.45 (d, J = 8.1 Hz, 1H), 5.90 (s, 1H), 2.04 (s, 6H), 1.27 (s, 9H) | 2 |

TABLE 1-continued

Representative Compounds and IC50 values

| | SCID | Structure | MS (m/e) | 1H NMR | IC50 (μM) |
|---|---|---|---|---|---|
| 33 | S00452 | 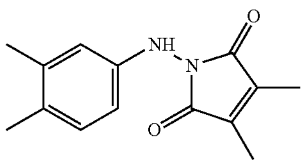 | 245.0 (M + 1) | (CDCl3, 300 MHz) δ: 6.95 (d, J = 8.4 Hz, 1H), 6.56 (d, J = 2.4 Hz, 1H), 6.52-6.48 (dd, J = 2.4, 7.8 Hz, 1H), 5.81 (s, 1H), 2.18 (s, 3H), 2.15 (s, 3H), 2.03 (s, 6H) | 10 |
| 34 | S00697 | 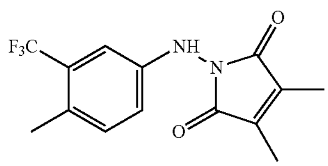 [SMILES: CC1=C(C)C(=O)N(Nc2ccc(C)c(C(F)(F)F)c2)C1=O] | | (CDCl3, 300 MHz) δ: 7.12 (d, J = 8.1 Hz, 1H), 6.99 (d, J = 2.4 Hz, 1H), 6.79 (d, J = 8.4 Hz, 1H), 5.93 (s, 1H), 2.37 (s, 3H), 2.05 (s, 6H) | 2.5 |
| 35 | S00405 | 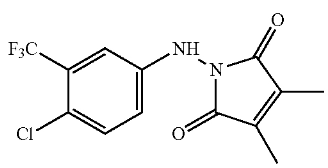 [SMILES: CC1=C(C)C(=O)N(Nc2ccc(Cl)c(C(F)(F)F)c2)C1=O] | | (CDCl3, 300 MHz) δ: 7.33 (m, 1H), 7.04 (m, 1H), 6.82 (m, 1H), 6.01 (s, 1H), 2.05 (s, 6H) | 2.5 |
| 36 | S00516 | 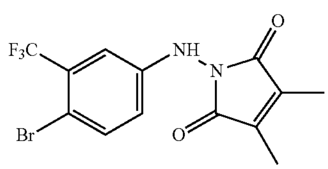 [SMILES: CC1=C(C)C(=O)N(Nc2ccc(Br)c(C(F)(F)F)c2)C1=O] | | (CDCl3, 300 MHz) δ: 7.50 (d, J = 9.0 Hz, 1H), 7.05 (d, J = 3.0 Hz, 1H), 6.76-6.72 (dd, J = 2.7, 8.4 Hz, 1H), 6.10 (s, 1H), 2.05 (s, 6H) | 1.25 |
| 37 | S00479 | 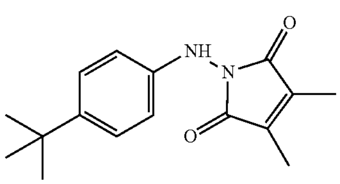 [SMILES: CC1=C(C)C(=O)N(Nc2ccc(C(C)(C)C)cc2)C1=O] | 273 (M + 1) | (CDCl3, 300 MHz) δ: 7.24 (s, 1H), 7.21 (s, 1H), 6.70 (s, 1H), 6.67 (s, 1H), 5.87 (s, 1H), 2.03 (s, 6H), 1.25 (s, 9H) | 2.5 |
| 38 | S00456 | 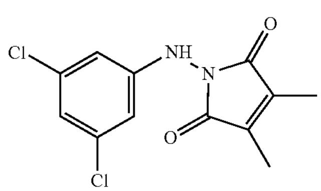 [SMILES: CC1=C(C)C(=O)N(Nc2cc(Cl)cc(Cl)c2)C1=O] | | (CDCl3, 300 MHz) δ: 6.90 (s, 1H), 6.59 (s, 2H), 6.05 (s, 1H), 2.05 (s, 6H) | 2.5 |
| 39 | S00587 | 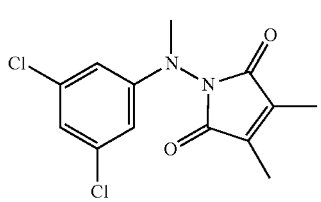 [SMILES: CC1=C(C)C(=O)N(N(C)c2cc(Cl)cc(Cl)c2)C1=O] | 296.9 (M − 1) | (CDCl3, 300 MHz) δ: 6.86-6.85 (t, J = 1.5 Hz, 1H), 6.55 (d, J = 1.2 Hz, 2H), 3.24 (s, 3H), 2.03 (s, 6H) | 2.5 |
| 40 | S00474 | 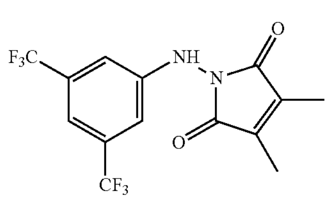 [SMILES: CC1=C(C)C(=O)N(Nc2cc(C(F)(F)F)cc(C(F)(F)F)c2)C1=O] | | (CDCl3, 300 MHz) δ: 7.42 (s, 1H), 7.11 (s, 2H), 6.24 (s, 1H), 2.08 (s, 6H) | 2.5 |

TABLE 1-continued

Representative Compounds and IC50 values

| | SCID | Structure | MS (m/e) | 1H NMR | IC50 (μM) |
|---|---|---|---|---|---|
| 41 | S00475 | 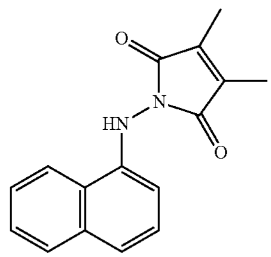 [SMILES: CC1=C(C)C(=O)N(Nc2cccc3ccccc23)C1=O] | 267.5 (M + 1) | (CDCl3, 300 MHz) δ: 7.96-7.99 (t, J = 4.5, 5.1 Hz, 1H), 7.82-7.85 (m, 1H), 7.46-.752 (m, 3H), 7.27-7.32 (t, J = 7.8, 8.1 Hz, 1H), 6.62 (d, J = 7.8 Hz, 1H), 6.57 (s, 1H), 2.07 (s, 6H) | 3.75 |
| 42 | S00738 | 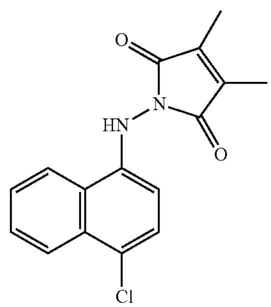 [SMILES: CC1=C(C)C(=O)N(Nc2ccc(Cl)c3ccccc23)C1=O] | | (CDCl3, 300 MHz) δ: 8.24-8.27 (dd, J = 0.6, 8.1 Hz, 1H), 7.97-8.00 (d, J = 8.4 Hz, 1H), 7.52-7.64 (m, 2H), 7.35-7.38 (d, J = 8.4 Hz, 1H), 6.60 (s, 1H), 6.54-6.56 (d, J = 8.4 Hz, 1H), 2.07 (s, 6H) | 0.63 |
| 43 | S00651 | 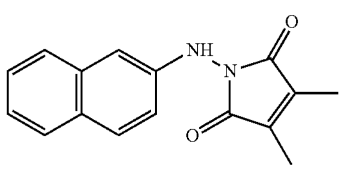 [SMILES: CC1=C(C)C(=O)N(Nc2ccc3ccccc3c2)C1=O] | | (CDCl3, 300 MHz) δ: 7.73 (d, J = 8.7 Hz, 1H), 7.63 (d, J = 8.1 Hz, 1H), 7.28-7.42 (m, 2H), 7.02-7.07 (dd, J = 2.1, 8.7 Hz, 1H), 6.98 (s, 1H), 6.07 (s, 1H), 2.07 (s, 6H) | 10 |
| 44 | S00698 | 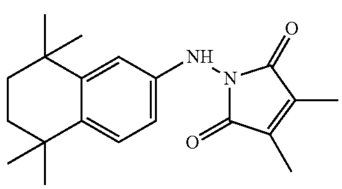 [SMILES: CC1=C(C)C(=O)N(Nc2ccc3c(c2)C(C)(C)CCC3(C)C)C1=O] | 326.9 (M + 1) | (CDCl3, 300 MHz) δ: 7.13 (d, J = 8.4 Hz, 1H), 6.73 (s, 1H), 6.46 (d, J = 7.8 Hz, 1H), 5.82 (s, 1H), 2.03 (s, 6H), 1.63 (s, 4H), 1.20-1.24 (m, 12H) | 5 |
| 45 | S00663 | 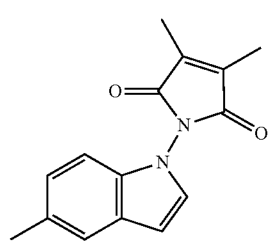 [SMILES: CC1=C(C)C(=O)N(n2ccc3cc(C)ccc32)C1=O] | | (CDCl3, 300 MHz) δ: 9.96 (s, 1H), 6.84 (d, J = 7.5 Hz, 1H), 6.33 (d, J = 8.1 Hz, 1H), 3.80 (m, 2H), 3.09 (m, 2H), 2.25 (s, 3H), 2.02 (s, 6H) | 40 |
| 46 | S00662 | 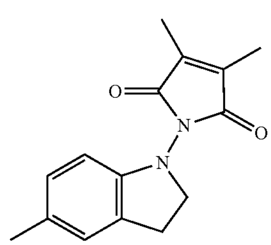 [SMILES: CC1=C(C)C(=O)N(N2CCc3cc(C)ccc32)C1=O] | | (CDCl3, 300 MHz) δ: 7.42 (d, J = 0.9 Hz, 1H), 7.04 (d, J = 8.4 Hz, 1H), 6.95 (d, J = 14.7 Hz, 2H), 6.56 (d, J = 4.2 Hz, 1H), 2.43 (s, 3H), 2.12 (s, 6H) | 60 |

TABLE 1-continued

Representative Compounds and IC50 values

| | SCID | Structure | MS (m/e) | 1H NMR | IC50 (μM) |
|---|---|---|---|---|---|
| 47 | S00412 | 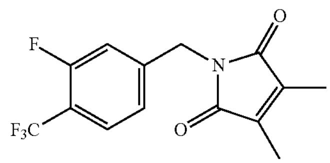 [SMILES: CC1=C(C)C(=O)N(Cc2ccc(C(F)(F)F)c(F)c2)C1=O] | | (CDCl3, 300 MHz) δ: 7.51-7.56 (m, 1H), 7.14-7.21 (m, 2H), 4.66 (s, 2H), 2.00 (s, 6H) | 10 |
| 48 | S00513 | 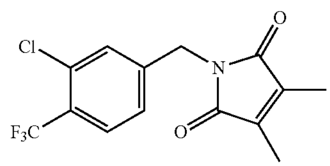 [SMILES: CC1=C(C)C(=O)N(Cc2ccc(C(F)(F)F)c(Cl)c2)C1=O] | | (CDCl3, 300 MHz) δ: 7.60 (d, J = 8.1 Hz, 1H), 7.46 (s, 1H), 7.30 (d, J = 8.1 Hz, 1H), 4.64 (s, 2H), 1.98 (s, 6H) | 5 |
| 49 | S00201 | 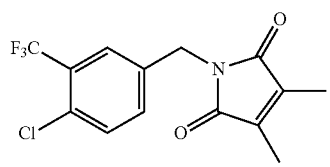 [SMILES: CC1=C(C)C(=O)N(Cc2ccc(Cl)c(C(F)(F)F)c2)C1=O] | | (CDCl3, 300 MHz) δ: 7.65 (s, 1H), 7.45 (d, J = 3 Hz, 2H), 4.64 (s, 2H), 1.97 (s, 6H) | 10 |
| 50 | S00088 | 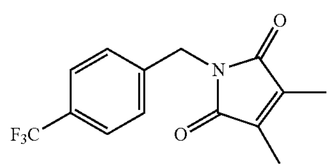 [SMILES: CC1=C(C)C(=O)N(Cc2ccc(C(F)(F)F)cc2)C1=O] | | (CDCl3, 300 MHz) δ: 7.50 (d, J = 8.1 Hz, 2H), 7.40 (d, J = 8.7 Hz, 2H), 4.69 (s, 2H), 1.97 (s, 6H) | 10 |
| 51 | S00408 | 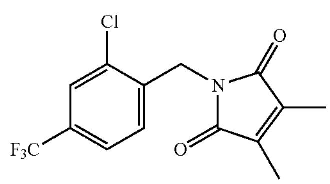 [SMILES: CC1=C(C)C(=O)N(Cc2ccc(C(F)(F)F)cc2Cl)C1=O] | | (CDCl3, 300 MHz) δ: 7.63 (s, 1H), 7.44-7.46 (d, J = 8.0 Hz, 1H), 7.26-7.27 (d, J = 6.2 Hz, 2H), 4.82 (s, 2H), 2.01 (s, 6H) | 10 |
| 52 | S00543 | 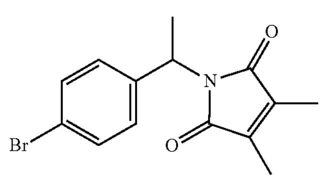 [SMILES: CC1=C(C)C(=O)N(C(C)c2ccc(Br)cc2)C1=O] | | (CDCl3, 300 MHz) δ: 7.43 (m, 2H), 7.30 (m, 2H), 5.25 (m, 1H), 1.92 (s, 6H), 1.77 (d, J = 5.4 Hz, 3H) | 60 |
| 53 | S00628 | 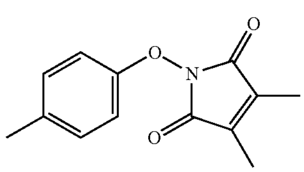 | 230.0 (M − 1) | (CDCl3, 300 MHz) δ: 7.09 (d, J = 8.4 Hz, 2H), 7.00 (d, J = 9.0 Hz, 2H), 2.30 (s, 3H), 2.02 (s, 6H). HPLC-MS (m/e): 230.0 (M − 1). | 60 |
| 54 | S00409 | 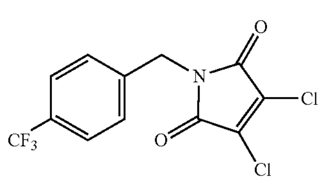 [SMILES: O=C1C(Cl)=C(Cl)C(=O)N1Cc1ccc(C(F)(F)F)cc1] | 324.1 (M + 1) | (CDCl3, 300 MHz) δ: 7.60 (d, J = 8.1 Hz, 2H), 7.48 (d, J = 8.4 Hz, 2H), 4.78 (s, 2H) | 20 |

TABLE 1-continued

Representative Compounds and IC50 values

| SCID | Structure | MS (m/e) | 1H NMR | IC50 (μM) |
|---|---|---|---|---|
| 55 S00410 | | 299.3 (M + 1) | (CDCl3, 300 MHz) δ: 7.56 (d, J = 8.1 Hz, 2H), 7.44 (d, J = 8.1 Hz, 2H), 4.67 (s, 2H), 4.16 (s, 3H), 1.98 (s, 3H) | 10 |

Example 6

Ability of Representative Compounds to Cause Adaptation to G2 Cell Cycle Arrest and Induce G2-Arrested Cells to Re-Enter the Cell Cycle Representative compounds were synthesized according to methods provided herein. The structure and other physicochemical properties of each compound was determined by 1H NMR spectroscopy for each synthesized compound.

Pre-arrested Jurkat cells were prepared as described in Example 1. Briefly, Jurkat cells were subjected to X-ray irradiation at a dose of 10 Gy, and cultured for 24 hours in 10% fetal calf serum (FCS)/RPMI1640 at 37° C. with 5% $CO_2$/air, after which time cells were exposed to various concentrations of test compounds, and cultured under the conditions described above for an additional 24 hours before harvesting. Harvested cells were stained with Krishan's buffer (0.1% sodium citrate, 50 μg/ml propidium iodide, 20 μg/ml RNase A, 0.5% Nonidet P-40) and analyzed by flow cytometry (BD Biosciences, Franklin Lakes, N.J.) to identify the cell stage of each cell in the sample. Cells in G1 phase were identified by having doubled (2N) DNA content.

The $IC_{50}$ value for each compound was calculated as the dosage (concentration in μM) that caused half-maximal increase of the percentage of cells in G1 phase (the G1 increment) measured for that test compound. Table 2 below presents structures, IUPAC name, molecular formula, ID number ("SCID"), mass, 1H NMR values, and $IC_{50}$ values for representative compounds. Table 3 presents structures, IUPAC name, molecular formula, ID number ("SCID"), mass, 1H NMR values, and $IC_{50}$ values for further representative compounds.

TABLE 2

REPRESENTATIVE COMPOUNDS AND IC50 VALUES
Physicochemical Characters

| SCID | Structure | IUPAC Name | Mass (m/e) | $^1$H NMR | $IC_{50}$ (μM) |
|---|---|---|---|---|---|
| S01860 | 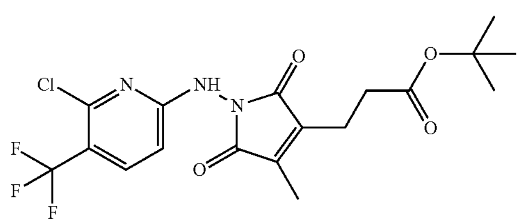 [SMILES: CC1=C(CCC(=O)OC(C)(C)C)C(=O)N(Nc2ccc(C(F)(F)F)c(Cl)n2)C1=O] | tert-butyl 3-(1-{[6-chloro-5-(trifluoromethyl)(2-pyridyl)]amino}-4-methyl-2,5-dioxoazolin-3-yl)propanoate | 432.2 (M⁻ − 1) | (CDCl₃, 300 MHz) δ: 7.79 (d, J = 8.5 Hz, 1H), 6.77 (s, 1H), 6.50 (d, J = 8.5 Hz, 1H), 2.75 (t, J = 7.4 Hz, 2H), 2.58 (t, J = 7.0 Hz, 2H), 2.11 (s, 3H), 1.43 (s, 9H). | 0.03 |
| S01861 | 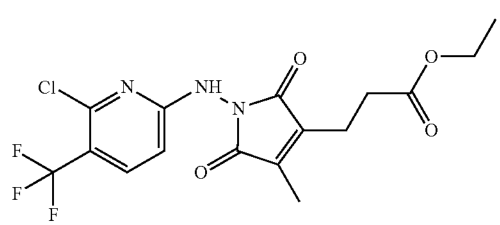 [SMILES: CCOC(=O)CCC1=C(C)C(=O)N(Nc2ccc(C(F)(F)F)c(Cl)n2)C1=O] | ethyl 3-(1-{[6-chloro-5-(trifluoromethyl)(2-pyridyl)]amino}-4-methyl-2,5-dioxoazolin-3-yl)-propanoate | 404.1 (M⁻ − 1) | (CDCl₃, 300 MHz) δ: 7.79 (d, J = 8.4 Hz, 1H), 6.88 (s, 1H), 6.50 (d, J = 8.4 Hz, 1H), 4.14 (q, J = 7.2 Hz, 2H), 2.79-2.65 (m, 4H), 2.12 (s, 3H), 1.26 (t, J = 7.1 Hz, 3H). | 0.05 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01078 | 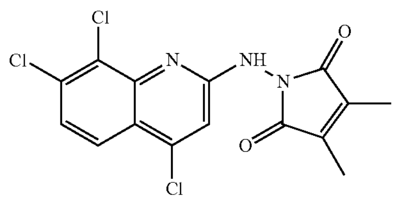 [SMILES: CC1=C(C)C(=O)N(Nc2cc(Cl)c3ccc(Cl)c(Cl)c3n2)C1=O] | 3,4-dimethyl-1-[(4,7,8-trichloro(2-quinolyl))amino]azoline-2,5-dione | 370.2 (M$^+$ + 1) | (CDCl$_3$, 300 MHz) δ: 7.88-7.84 (d, J = 8.7 Hz, 1H), 7.45-7.41 (d, J = 9.3 Hz, 1H), 6.94 (s, 1H), 2.10 (s, 6H) | 0.078 |
| S01247 | 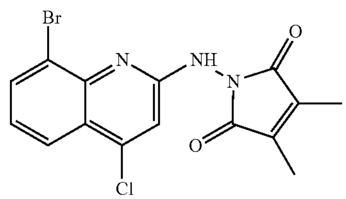 [SMILES: CC1=C(C)C(=O)N(Nc2cc(Cl)c3cccc(Br)c3n2)C1=O] | 1-[(8-bromo-4-chloro(2-quinolyl))amino]-3,4-dimethylazoline-2,5-dione | 380.1 (M$^+$ + 1) | (CDCl$_3$, 300 MHz) δ: 8.00-7.96 (dd, J = 8.4 Hz, 1.2 Hz, 1H), 7.92-7.89 (dd, J = 7.8 Hz, 1.2 Hz, 1H), 7.23-7.20 (d, J = 7.8 Hz, 1H), 7.07 (br, 1H), 6.96 (s, 1H), 2.08 (s, 6H) | 0.078 |
| S01589 | 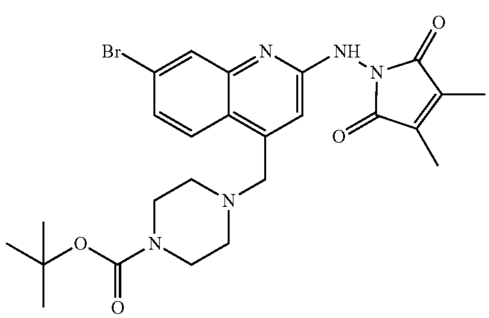 [SMILES: CC1=C(C)C(=O)N(Nc2cc(CN3CCN(C(=O)OC(C)(C)C)CC3)c3ccc(Br)cc3n2)C1=O] | tert-butyl 4-({2-[(3,4-dimethyl-2,5-dioxoazolinyl)amino]-7-bromo-4-quinolyl}methyl)-piperazine-carboxylate | 544.3 (M$^-$ − 1) | (CDCl$_3$, 300 MHz) δ: 7.86-7.83 (d, J = 8.4 Hz, 1H), 7.83 (s, 1H), 7.40-7.37 (dd, J = 8.7 Hz, 2.1 Hz, 1H), 7.00-6.80 (br, 1H), 6.85 (s, 1H), 3.65 (s, 2H), 3.41-3.38 (m, 4H), 2.40-2.35 (m, 4H), 2.09 (s, 6H), 1.46 (s, 9H) | 0.078 |
| S01648 | 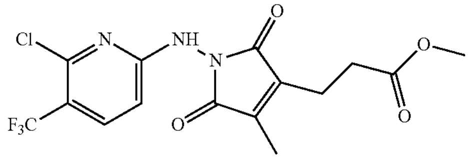 [SMILES: COC(=O)CCC1=C(C)C(=O)N(Nc2ccc(C(F)(F)F)c(Cl)n2)C1=O] | methyl 3-(1-{[6-chloro-5-(trifluoromethyl)(2-pyridyl)]amino}-4-methyl-2,5-dioxoazolin-3-yl)propanoate | 390 (M$^-$ − 1) | (CDCl$_3$, 300 MHz) δ: 7.78 (d, J = 8.8 Hz 1H), 7.11 (s, 1H), 6.50 (d, J = 8.5 Hz, 1H), 2.81-2.66 (m, 4H), 2.11 (s, 3H). | 0.078 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01796 | 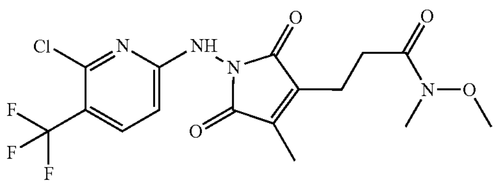 [SMILES: CON(C)C(=O)CCC1=C(C)C(=O)N(Nc2ccc(C(F)(F)F)c(Cl)n2)C1=O] | 3-(1-{[6-chloro-5-(trifluoromethyl)(2-pyridyl)]amino}-4-methyl-2,5-dioxoazolin-3-yl)-N-methoxy-N-methylpropanamide | 419.2 (M$^-$ − 1) | (CDCl$_3$, 300 MHz) δ: 7.76 (d, J = 8.4 Hz, 1H), 7.27 (s, 1H), 6.51 (d, J = 8.5 Hz, 1H), 3.67 (s, 3H), 3.17 (s, 3H), 2.81 (s, 4H), 2.11 (s, 3H). | 0.078 |
| S01879 | 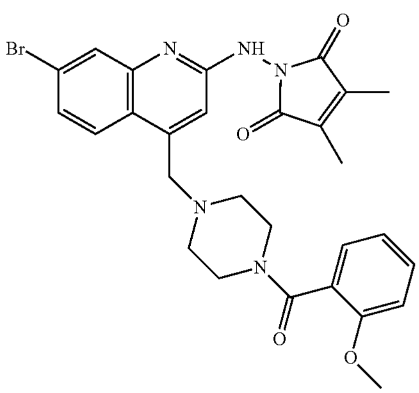 [SMILES: COc1ccccc1C(=O)N1CCN(Cc2cc(NN3C(=O)C(C)=C(C)C3=O)nc3cc(Br)ccc23)CC1] | 1-{[7-bromo-4-({4-[(2-methoxyphenyl)carbonyl]piperazinyl}methyl)(2-quinolyl)]amino}-3,4-dimethylazoline-2,5-dione | 578 (M$^+$ + 1) | (CDCl$_3$, 300 MHz) δ: 7.89-7.83 (m, 2H), 7.41-7.31 (m, 2H), 7.25-7.22 (m, 1H), 7.01-6.98 (m, 1H), 6.96-9.87 (m, 2H), 3.86-3.72 (m, 7H), 3.26-3.20 (m, 2H), 2.63-2.52 (m, 2H), 2.42-2.31 (m, 2H), 2.10 (s, 6H) | 0.078 |
| S01981 | 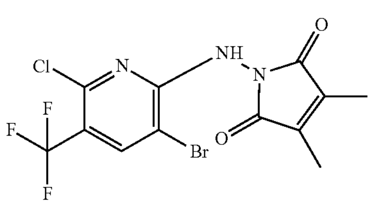 [SMILES: CC1=C(C)C(=O)N(Nc2nc(Cl)c(C(F)(F)F)cc2Br)C1=O] | 1-{[3-bromo-6-chloro-5-(ifluoromethyl)(2-pyridyl)]amino}-3,4-dimethylazoline-2,5-dione | 396 (M$^-$ − 1) | (CDCl$_3$, 300 MHz) δ: 7.97 (s, 1H), 7.07 (s, 1H), 2.07 (s, 6H) | 0.078 |
| S00109 | 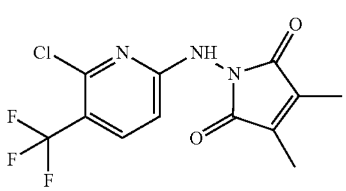 [SMILES: CC1=C(C)C(=O)N(Nc2ccc(C(F)(F)F)c(Cl)n2)C1=O] | 1-{[6-chloro-3-(trifluoromethyl)(2-pyridyl)]amino}-3,4-dimethylazoline-2,5-dione | 318.0 (M$^-$ − 1) | (CDCl$_3$, 300 MHz) δ: 7.80-7.70 (d, J = 8.7 Hz, 1H), 7.10 (s, 1H), 6.55-6.45 (d, 8.7 Hz, 1H), 2.07 (s, 6H) | 0.12 |
| S00170 | 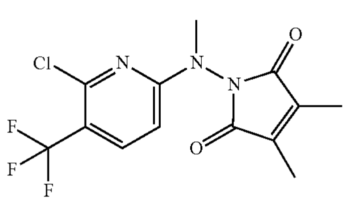 [SMILES: CC1=C(C)C(=O)N(N(C)c2ccc(C(F)(F)F)c(Cl)n2)C1=O] | 1-{[6-chloro-5-{trifluoromethyl)(2-pyridyl)]methylamino}-3,4-dimethylazoline-2,5-dione | | (CDCl$_3$, 300 MHz) δ: 7.70 (d, J = 8.4 Hz, 1H), 6.40 (d, 8.7 Hz, 1H), 3.44 (s, 3H), 2.08 (s, 6H) | 0.12 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01007 | 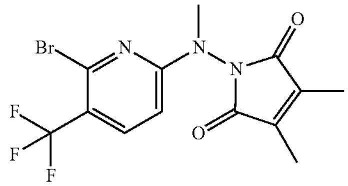 [SMILES: CC1=C(C)C(=O)N(N(C)c2ccc(C(F)(F)F)c(Br)n2)C1=O] | 1-{[6-bromo-5-(trifluoromethyl)(2-pyridyl)]methylamino}-3,4-dimethylazoline-2,5-dione | 375.9 (M$^-$ − 1) | (CDCl$_3$, 300 MHz) δ: 7.70-7.67 (d, J = 8.7 Hz, 1H), 6.48-6.45 (d, J = 8.7 Hz, 1H), 3.44 (s, 3H), 2.06 (s, 6H) | 0.12 |
| S01554 | 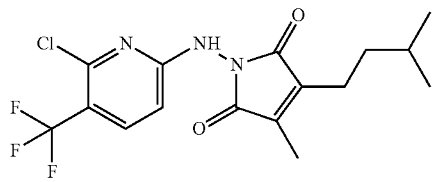 [SMILES: CC1=C(CCC(C)C)C(=O)N(Nc2ccc(C(F)(F)F)c(Cl)n2)C1=O] | 1-{[6-chloro-5-(trifluoromethyl)(2-pyridyl)]amino}-4-methyl-3-(3-methylbutyl)azoline-2,5-dione | 374 (M$^-$ − 1) | (CDCl$_3$, 300 MHz) δ: 7.81-7.77 (d, J = 8.7 Hz, 1H), 6.73 (s, 1H), 6.51-6.47 (d, J = 8.7 Hz, 1H), 2.50-2.44 (m, 2H), 2.07 (s, 3H), 1.50-1.42 (m, 3H), 0.97-0.94 (d, J = 6.6 Hz, 6H) | 0.12 |
| S01599 | 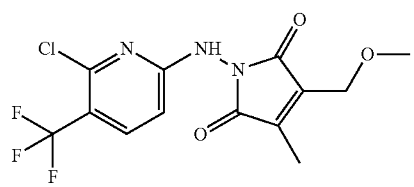 [SMILES: COCC1=C(C)C(=O)N(Nc2ccc(C(F)(F)F)c(Cl)n2)C1=O] | 1-{[6-chloro-5-trifluoromethyl)(2-pyridyl)]amino}-3-(methoxymethyl)-4-methylazoline-2,5-dione | 348 (M$^-$ − 1) | (CDCl$_3$, 300 MHz) δ: 7.80-7.77 (d, J = 8.4 Hz, 1H), 6.92 (s, 1H), 6.53-6.50 (d, J = 8.7 Hz, 1H), 4.38 (s, 2H), 3.44 (s, 3H), 2.20 (s, 3H) | 0.12 |
| S01455 | 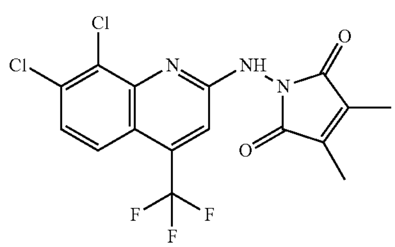 [SMILES: CC1=C(C)C(=O)N(Nc2cc(C(F)(F)F)c3ccc(Cl)c(Cl)c3n2)C1=O] | 1-{(7,8-dichloro-4-(trifluoromethyl)(2-quinolyl)]amino}-3,4-dimethylazoline-2,5-dione | 404 (M$^+$ + 1) | (CDCl$_3$, 300 MHz) δ: 7.78-7.72 (m, 1H), 7.47-7.44 (d, J = 9.4 Hz, 1H), 7.35 (br, 1H), 7.16 (s, 1H), 2.12 (s, 6H) | 0.156 |
| S01711 | 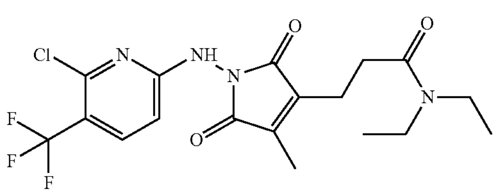 [SMILES: CCN(CC)C(=O)CCC1=C(C)C(=O)N(Nc2ccc(C(F)(F)F)c(Cl)n2)C1=O] | 3-(1-{[6-chloro-5-(trifluoromethyl)(2-pyridyl)]amino}-4-methyl-2,5-dioxoazoline-3-yl)-N,N-diethylpropanamide | 431 (M$^-$ − 1) | (CDCl$_3$, 300 MHz) δ: 7.77 (d, J = 8.7 Hz 1H), 7.13 (s, 1H), 6.52 (d, J = 8.4 Hz 1H), 3.40-3.26 (m, 4H), 2.84-2.67 (m, 4H), 2.13 (s, 3H), 1.18-1.08 (m, 6H) | 0.156 |

TABLE 2-continued

REPRESENTATIVE COMPOUNDS AND IC50 VALUES
Physicochemical Characters

| SCID | Structure | IUPAC Name | Mass (m/e) | ¹H NMR | IC$_{50}$ (μM) |
|---|---|---|---|---|---|
| S01712 | 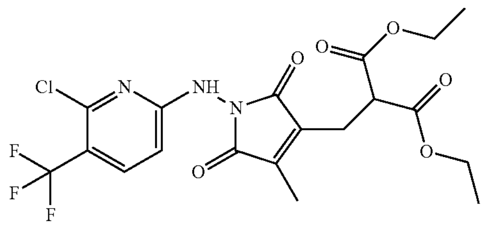 [SMILES: CCOC(=O)C(CC1=C(C)C(=O)N(Nc2ccc(C(F)(F)F)c(Cl)n2)C1=O)C(=O)OCC] | diethyl 2-[((1-{[6-chloro-5-(trifluoro-methyl)(2-pyridyl)]amino}-4-methyl-2,5-dioxoazolin-3-yl)methyl]propane-1,3-dioate | 476 (M⁻ − 1) | (CDCl$_3$, 300 MHz) δ: 7.79 (d, J = 8.6 Hz 1H), 6.94 (s, 1H), 6.50 (d, J = 8.2 Hz, 1H), 4.25-4.16 (m, 4H), 3.86 (t, J = 7.9 Hz, 1H), 3.05 (d, 7.9 Hz, 2H), 2.11 (s, 3H), 1.27 (t, J = 7.1 Hz, 6H). | 0.156 |
| S01758 | 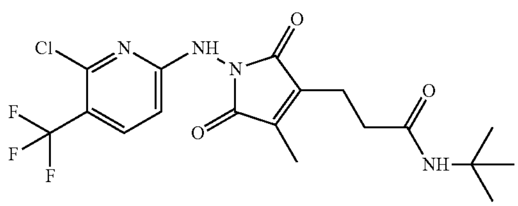 [SMILES: CC1=C(CCC(=O)NC(C)(C)C)C(=O)N(Nc2ccc(C(F)(F)F)c(Cl)n2)C1=O] | N-(tert-butyl)-3-(1-{[6-chloro-5-(trifluoromethyl)(2-pyridyl)]amino}-4-methyl-2,5-dioxoazolin-3-yl)propanamide | 431.3 (M⁻ − 1) | (CDCl$_3$, 300 MHz) δ: 7.79 (d, J = 8.6 Hz, 1H), 7.12 (s, 1H), 6.53 (d, J = 8.6 Hz, 1H), 5.33 (s, 1H), 2.79 (t, J = 7.2 Hz, 2H), 2.43 (t, J = 7.3 Hz, 2H), 2.10 (s, 3H), 1.32 (s, 9H). | 0.156 |
| S01925 | 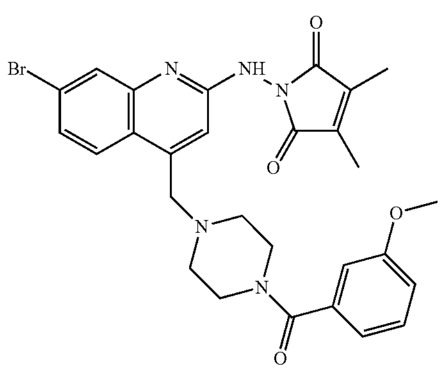 [SMILES: COc1cccc(C(=O)N2CCN(Cc3cc(NN4C(=O)C(C)=C(C)C4=O)nc4cc(Br)ccc34)CC2)c1] | 1-{[7-bromo-4-({4-[(3-methoxyphenyl)carbonyl]piperazinyl}methyl)(2-quinolyl)]amino}-3,4-dimethylazoline-2,5-dione | 576.3 (M⁻ − 1) | (CDCl$_3$, 300 MHz) δ: 7.87-7.83 (m, 2H), 7.41-7.37 (dd, J = 1.2 Hz, 1.4 Hz, 1H), 7.33-7.27 (m, 1H), 6.96-6.93 (m, 3H) 6.85 (s, 1H), 3.90-3.60 (br, 2H), 3.82 (s, 3H), 3.69 (s, 2H), 3.42 (br, 2H), 2.54 (br, 2H), 2.41 (br, 2H), 2.09 (s, 6H) | 0.156 |
| S00994 | 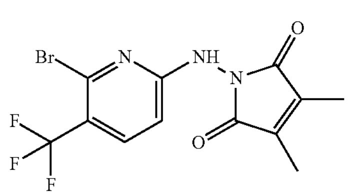 [SMILES: CC1=C(C)C(=O)N(Nc2ccc(C(F)(F)F)c(Br)n2)C1=O] | 1-{[6-bromo-5-(trifluoromethyl)(2-pyridyl)amino}-3,4-dimethylazoline-2,5-dione | 362.0 (M⁻ − 1) | (CDCl$_3$, 300 MHz) δ: 7.76-7.73 (d, J = 8.4 Hz, 1H), 6.77 (br, 1H), 6.53-6.50 (d, J = 8.7 Hz, 1H), 2.08 (s, 6H) | 0.2 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01005 | 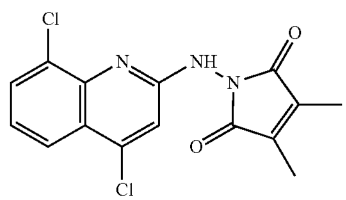 [SMILES: CC1=C(C)C(=O)N(Nc2cc(Cl)c3cccc(Cl)c3n2)C1=O] | 1-[(4,8-dichloro (2-quinolyl)) amino]-3,4-dimethylazoline-2,5-dione | 336.4 (M$^+$ + 1) | (CDCl$_3$, 300 MHz) δ: 7.95-7.91 (dd, J = 8.4 Hz, 1.5 Hz, 1H), 7.73-7.69 (dd, J = 7.8 Hz, 1.5 Hz, 1H), 7.33-7.29 (d, J = 8.1 Hz, 1H), 6.94 (s, 1H), 2.11 (s, 6H) | 0.2 |
| S01266 | 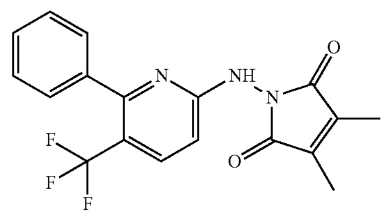 [SMILES: CC1=C(C)C(=O)N(Nc2ccc(C(F)(F)F)c(-c3ccccc3)n2)C1=O] | 3,4-dimethyl-1-{[6-phenyl-5-(trifluoromethyl) (2-pyridyl)]amino} azoline-2,5-dione | 360.2 (M$^-$ − 1) | (CDCl$_3$, 300 MHz) δ: 7.86-7.82 (d, J = 9.0 Hz, 1H), 7.45-7.35 (m, 5H), 6.48-6.44 (d, J = 9.0 Hz, 1H), 2.02 (s, 6H) | 0.2 |
| S01470 | 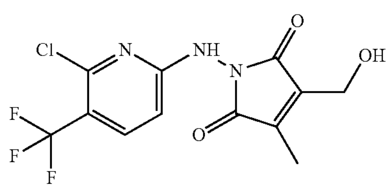 [SMILES: CC1=C(CO)C(=O)N(Nc2ccc(C(F)(F)F)c(Cl)n2)C1=O] | 1-{[6-chloro-5-(trifluoromethyl) (2-pyridyl)]amino}-3-(hydroxy-methyl)-4-methylazoline-2,5-dione | 336 (M$^+$ + 1) | (CDCl$_3$, 300 MHz) δ: 7.93-7.90 (d, J = 8.5 Hz, 1H), 7.69 (s, 1H), 6.28-6.25 (d, J = 8.5 Hz, 1H), 3.69 (s, 2H), 2.90-2.70 (br, 1H), 2.14 (s, 3H) | 0.2 |
| S01473 | 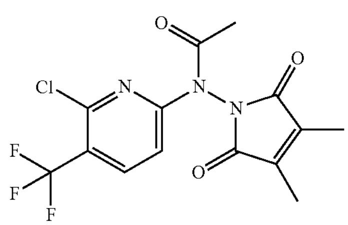 [SMILES: CC(=O)N(c1ccc(C(F)(F)F)c(Cl)n1)N1C(=O)C(C)=C(C)C1=O] | N-(3,4-dimethyl-2,5-dioxoazolinyl)-N-[6-chloro-5-(trifluoromethyl) (2-pyridyl)]acetamide | 360.0 (M$^-$ − 1) | (CDCl$_3$, 300 MHz) δ: 8.28-8.25 (m, 1H), 7.99-7.97 (d, J = 6.6 Hz, 1H), 2.28 (s, 3H), 2.11 (s, 6H) | 0.2 |
| S01878 | 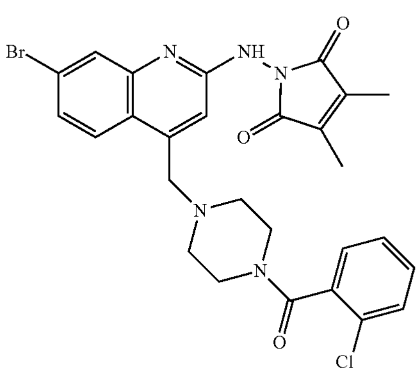 [SMILES: CC1=C(C)C(=O)N(Nc2cc(CN3CCN(C(=O)c4ccccc4Cl)CC3)c3ccc(Br)cc3n2)C1=O] | 1-{(7-bromo-4-({4-[(2-chlorophenyl) carbonyl]piperazinyl} methyl) (2-quinolyl)] amino}-3,4-dimethylazoline-2,5-dione | 582 (M$^+$ + 1) | (CDCl$_3$, 300 MHz) δ: 7.87-7.83 (m, 2H), 7.41-7.26 (m, 5H), 6.85 (s, 1H), 3.84-3.80 (m, 2H), 3.71 (s, 2H), 3.26-3.18 (m, 2H), 2.61-2.57 (m, 2H), 2.47-2.44 (m, 1H), 2.37-2.34 (m, 1H), 2.10 (s, 6H) | 0.234 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01883 | 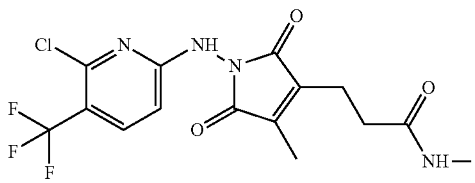 [SMILES: CNC(=O)CCC1=C(C)C(=O)N(Nc2ccc(C(F)(F)F)c(Cl)n2)C1=O] | 3-(1-{[6-chloro-5-(trifluoromethyl)(2-pyridyl)]amino}-4-methyl-2,5-dioxoazolin-3-yl)-N-methylpropanamide | 389.1 (M$^-$ − 1) | (CDCl$_3$, 300 MHz) δ: 7.80-7.77 (d, J = 8.4 Hz, 1H), 7.08 (s, 1H), 6 56-6.53 (d, J = 8.4 Hz, 1H), 5.60-5.50 (br, 1H), 2.90-2.75 (m, 5H), 2.55- 2.50 (t, J = 7.2 Hz, 2H), 2.10 (s, 3H) | 0.234 |
| S00585 | 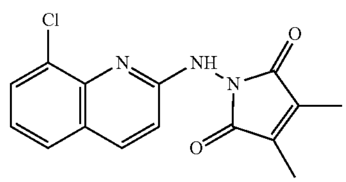 [SMILES: CC1=C(C)C(=O)N(Nc2ccc3cccc(Cl)c3n2)C1=O] | 1-[(8-chloro(2-quinolyl))amino]-3,4-dimethylazoline-2,5-dione | 302.1 (M$^+$ + 1) | (CDCl$_3$, 300 MHz) δ: 7.92-7.89 (d, J = 6.9 Hz, 1H), 7.66-7.63 (dd, J = 8.4 Hz, 1.2 Hz, 1H), 7.56-7.53 (dd, J = 6.3 Hz, 1.2 Hz, 1H), 7.24-7.19 (m, 1H), 6.87-6.84 (d, J = 6.6 Hz, 1H), 2.10 (s, 6H) | 0.3 |
| S00832 | 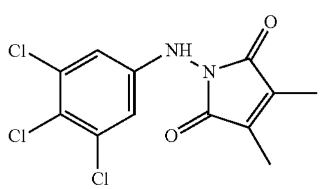 [SMILES: CC1=C(C)C(=O)N(Nc2cc(Cl)c(Cl)c(Cl)c2)C1=O] | 3,4-dimethyl-1-[(3,4,5-trichlorophenyl)amino]azoline-2,5-dione | No Mass | (CDCl$_3$, 300 MHz) δ: 6.75 (s, 2H), 6.04 (s, 1H), 2.06 (s, 6H) | 0.3 |
| S00873 | 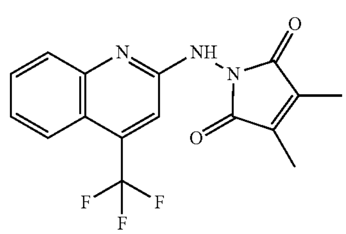 [SMILES: CC1=C(C)C(=O)N(Nc2cc(C(F)(F)F)c3ccccc3n2)C1=O] | 3,4-dimethyl-1-{[4-(trifluoromethyl)(2-quinolyl)]amino}azoline-2,5-dione | 336.0 (M$^+$ + 1) | (CDCl$_3$, 300 MHz) δ: 7.97-7.73 (d, J = 8.7 Hz, 1H), 7.78-7.74 (m, 1H), 7.67-7.61 (m, 1H), 7.47-7.41 (m, 1H), 7.13 (s, 1H), 6.88 (s, 1H), 2.11 (s, 6H) | 0.3 |
| S01311 | 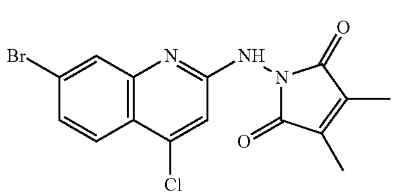 [SMILES: CC1=C(C)C(=O)N(Nc2cc(Cl)c3ccc(Br)cc3n2)C1=O] | 1-[(7-bromo-4-chloro(2-quinolyl))amino]-3,4-dimethylazoline-2,5-dione | 380.2 (M$^+$ + 1) | (CDCl$_3$, 300 MHz) δ: 7.89-7.84 (m, 2H), 7.50-7.48 (m, 1H), 6.90 (s, 1H), 2.11 (s, 6H) | 0.3 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01313 | 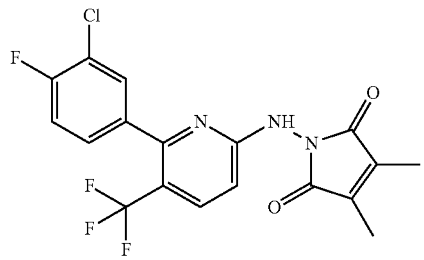 [SMILES: CC1=C(C)C(=O)N(Nc2ccc(C(F)(F)F)c(-c3ccc(F)c(Cl)c3)n2)C1=O] | 1-{[6-(3-chloro-4-fluorophenyl)-5-(trifluoromethyl)(2-pyridyl)]amino}-3,4-dimethylazoline-2,5-dione | 414.0 (M$^+$ + 1) | (CDCl$_3$, 300 MHz) δ: 7.89-7.85 (d, J = 8.4 Hz, 1H), 7.51-7.47 (dd, J = 7.5 Hz, 2.1 Hz, 1H), 7.40-7.35 (br, 1H), 7.18-7.12 (m, 1H), 6.82 (s, 1H), 6.62-6.58 (d, J = 8.7 Hz, 1H), 2.05 (s, 6H) | 0.3 |
| S01457 | 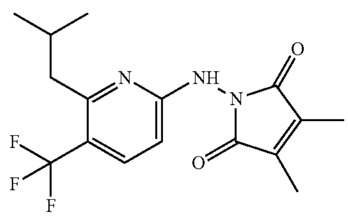 [SMILES: CC1=C(C)C(=O)N(Nc2ccc(C(F)(F)F)c(CC(C)C)n2)C1=O] | 3,4-dimethyl-1-{[6-(2-methyl-propyl)-5-(trifluoromethyl)(2-pyridyl)]amino}azoline-2,5-dione | 340.3 (M$^+$ + 1) | (CDCl$_3$, 300 MHz) δ: 7.70-7.67 (d, J = 6.3 Hz, 1H), 6.65 (br, 1H), 6.47-6.44 (d, J = 6.6 Hz, 1H), 2.61 (d, J = 5.4 Hz, 2H), 2.07 (s, 6H), 0.85 (s, 3H), 0.84 (s, 3H) | 0.3 |
| S01737 | 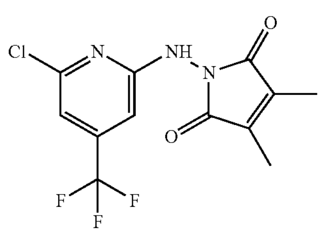 [SMILES: CC1=C(C)C(=O)N(Nc2cc(C(F)(F)F)cc(Cl)n2)C1=O] | 1-{[6-chloro-4-(trifluoromethyl)(2-pyridyl)]amino}-3,4-dimethylazoline-2,5-dione | 320 (M$^+$ + 1) | (CDCl$_3$, 300 MHz) δ: 7.03 (s, 1H), 6.93 (s, 1H), 6.62 (s, 1H), 2.07 (s, 6H) | 0.312 |
| S01865 | 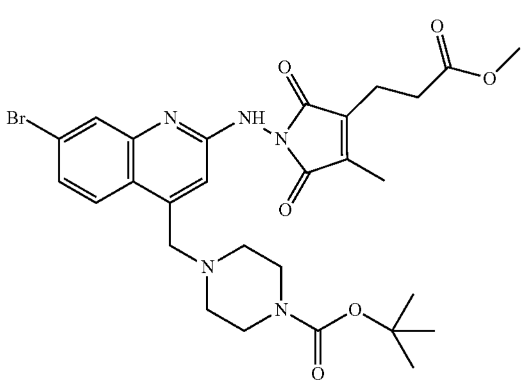 [SMILES: COC(=O)CCC1=C(C)C(=O)N(Nc2cc(CN3CCN(C(=O)OC(C)(C)C)CC3)c3ccc(Br)cc3n2)C1=O] | methyl 3-(1-{[4-({4-[(tert-butyl)oxycarbonyl]piperazinyl}methyl)-7-bromo(2-quinolyl)]amino}-4-methyl-2,5-dioxoazolin-3-yl)propanoate | 616 (M$^+$ + 1) | (CDCl$_3$, 300 MHz) δ: 7.86-7.79 (m, 2H), 7.40-7.37 (d*d, J$_1$ = 8.7 Hz, J$_2$ = 2.1 Hz, 1H), 6.85 (s, 1H), 3.72 (s, 3H), 3.65 (s, 2H), 3.42-3.39 (m, 4H), 2.83-2.81 (t, 2H), 2.74-2.72 (t, 2H), 2.40 (m, 4H), 2.14 (s, 3H), 1.46 (s, 9H) | 0.312 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01880 | 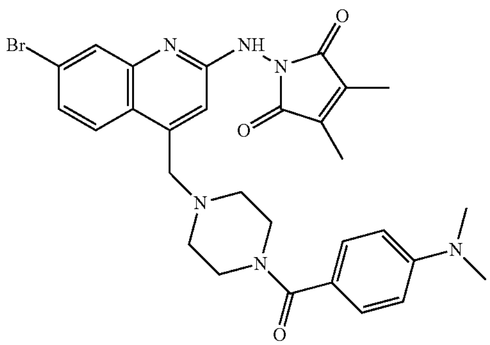 [SMILES: CC1=C(C)C(=O)N(Nc2cc(CN3CCN(C(=O)c4ccc(N(C)C)cc4)CC3)c3ccc(Br)cc3n2)C1=O] | 1-({4-[(4-([4-(dimethylamino)phenyl]carbonyl)piperazinyl)methyl]-7-bromo(2-quinolyl)}amino)-3,4-dimethylaxoline-2,5-dione | 591 (M$^+$ + 1) | (CDCl$_3$, 300 MHz) δ: 7.89-7.84 (m, 2H), 7.42-7.33 (m, 3H), 6.88 (s, 1H), 6.67-6.64 (d*d, J$_1$ = 7.2 Hz, J$_2$ = 2.1 Hz, 2H), 3.74 (s, 2H), 3.63 (m, 4H), 2.99 (s, 6H), 2.50 (m, 4H), 2.10 (s, 6H) | 0.312 |
| S01098 | 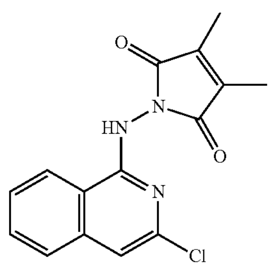 [SMILES: CC1=C(C)C(=O)N(Nc2nc(Cl)cc3ccccc23)C1=O] | 1-[(3-chloroisoquinolyl)amino]-3,4-dimethylazoline-2,5-dione | 302.2 (M$^+$ + 1) | (CDCl$_3$, 300 MHz) δ: 7.78-7.74 (m, 2H), 7.56-7.47 (m, 2H), 7.38-7.32 (m, 1H), 7.04 (s, 1H), 2.10 (s, 6H) | 0.45 |
| S01553 | 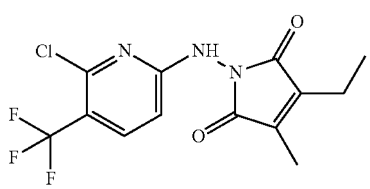 [SMILES: CCC1=C(C)C(=O)N(Nc2ccc(C(F)(F)F)c(Cl)n2)C1=O] | 1-{[6chloro-5-(trifluoromethyl)(2-pyridyl)]amino}-3-ethyl-4-methylazoline-2,5-dione | 332 (M$^-$ − 1) | (CDCl$_3$, 300 MHz) δ: 7.79-7.76 (d, J = 8.4 Hz, 1H), 6.95 (s, 1H), 6.50-6.47 (d, J = 8.4 Hz, 1H), 2.54-2.46 (m, 2H), 2.07 (s, 3H), 1.27-1.17 (m, 3H) | 0.45 |
| S01734 | 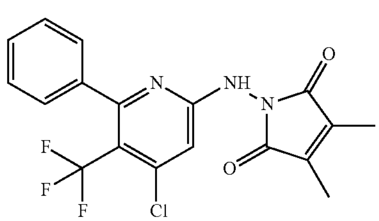 [SMILES: CC1=C(C)C(=O)N(Nc2cc(Cl)c(C(F)(F)F)c(-c3ccccc3)n2)C1=O] | 1-{[4-chloro-6-phenyl-5-(trifluoromethyl)(2-pyridyl)]amino}-3,4-dimethylazoline-2,5-dione | 396.3 (M$^+$ + 1) | (CDCl$_3$, 300 MHz) δ: 7.52 (br, 1H), 7.37-7.33 (m, 5H), 6.49 (s, 1H), 2.02 (s, 6H) | 0.45 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01864 | 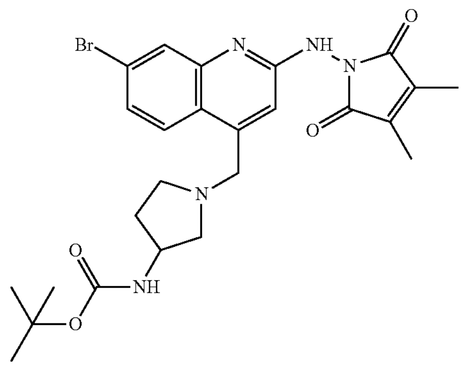 [SMILES: CC1=C(C)C(=O)N(Nc2cc(CN3CCC(NC(=O)OC(C)(C)C)C3)c3ccc(Br)cc3n2)C1=O] | N-[1-({2-[(3,4-dimethyl-2,5-dioxoalinyl)amino]-7-bromo(4-quinolyl)}methyl)pyrrolidin-3-yl](tert-butoxy)carboxamide | 542.2 (M$^-$ − 1) | (CDCl$_3$, 300 MHz) δ: 7.82-7.70 (m, 3H), 7.40-7.35 (dd, J = 9.0 Hz, 2.1 Hz, 1H), 6.86 (s, 1H), 4.90-4.80 (br, 0.5H), 4.20-4.10 (br, 0.5H), 3.80 (s, 2H), 2.90-2.80 (m, 1H), 2.70-2.55 (m, 2H), 2.40-2.20 (m, 2H), 2.00 (s, 6H), 1.70-1.50 (m, 2H), 1.43 (s, 9H) | 0.468 |
| S01877 | 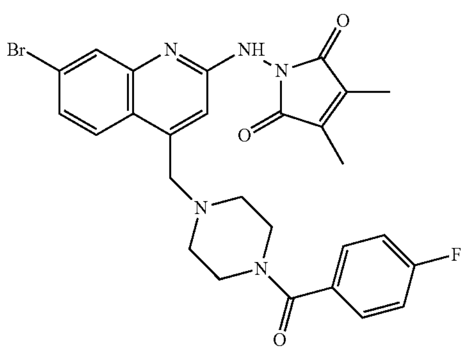 [SMILES: CC1=C(C)C(=O)N(Nc2cc(CN3CCN(C(=O)c4ccc(F)cc4)CC3)c3ccc(Br)cc3n2)C1=O] | 1-{[7-bromo-4-({4-[(4-fluorophenyl)carbonyl]piperazinyl}methyl)(2-quinolyl)]amino}-3,4-dimethylazoline-2,5-dione | 566 (M$^+$ + 1) | (CDCl$_3$, 300 MHz) δ: 7.86-7.83 (m, 2H), 7.43-7.37 (m, 3H), 7.11-7.06 (m, 2H) 6.82 (s, 1H), 3.77-3.44 (m, 6H), 2.52-2.11 (m, 4H), 2.10 (s, 6H) | 0.468 |
| S01475 | 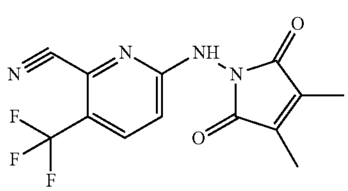 [SMILES: CC1=C(C)C(=O)N(Nc2ccc(C(F)(F)F)c(C#N)n2)C1=O] | 6-[(3,4-dimethyl-2,5-dioxoazolinyl)amino]-3-(trifluoromethyl)pyridine-2-carbonitrile | 309.2 (M$^-$ − 1) | (CDCl$_3$, 300 MHz) δ: 7.83-7.81 (d, J = 6.6 Hz, 1H), 7.31 (s, 1H), 6.86-6.84 (d, J = 6.6 Hz, 1H), 2.08 (s, 6H) | 0.5 |
| S00186 | 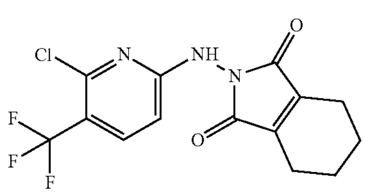 [SMILES: O=C1C2=C(CCCC2)C(=O)N1Nc1ccc(C(F)(F)F)c(Cl)n1] | 2-{[6-chloro-5-(trifluoromethyl)-2-pyridyl]amino}-4,5,6,7-tetrahydroisoindole-1,3-dione | | (CDCl$_3$, 300 MHz) δ: 7.80-7.70 (d, J = 8.7 Hz, 1H), 6.55-6.45 (d, J = 8.7 Hz, 1H), 2.50-2.30 (m, 4H), 1.90-1.75 (m, 4H) | 0.625 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S00516 | 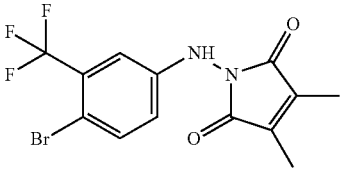 [SMILES: CC1=C(C)C(=O)N(Nc2ccc(Br)c(C(F)(F)F)c2)C1=O] | 1-{[4-bromo-3-(trifluoromethyl)phenyl]amino}-3,4-dimethylazoline-2,5-dione | 360.9 (M$^-$ − 1) | (CDCl$_3$, 300 MHz) δ: 7.54-7.50 (d, J = 9.0 Hz, 1H), 7.07-7.05 (d, J = 3.0 Hz, 1H), 6.76-6.72 (dd, J = 8.7 Hz, 2.7 Hz, 1H), 6.10 (s, 1H), 2.08 (s, 6H) | 0.625 |
| S00738 | 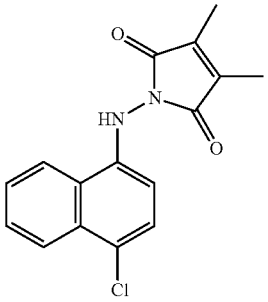 | 1-[(4-chloronaphthyl)amino]-3,4-dimethylazoline-2,5-dione | No Mass | (CDCl$_3$, 300 MHz) δ: 8.27-8.23 (dd, J = 8.7 Hz, 1.5 Hz, 1H), 8.01-7.97 (d, J = 8.7 Hz, 1H), 7.65-7.52 (m, 1H), 7 38-7.35 (d, J = 8.1 Hz, 1H), 6.60 (s, 1H), 6.57-6.53 (d, J = 8.4 Hz, 1H), 2.09 (s, 6H) | 0.625 |
| S00935 | 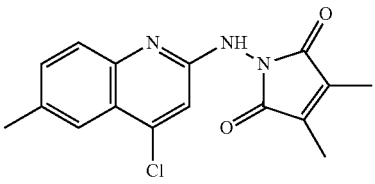 | 1-[(4-chloro-6-methyl(2-quinolyl))amino]-3,4-dimethylazoline-2,5-dione | 315.9 (M$^+$ + 1) | (CDCl$_3$, 300 MHz) δ: 7.79 (s, 1H), 7.61-7.57 (d, J = 8.4 Hz, 1H), 7.45-7.42 (d, 8.7 Hz, 1H), 6.86 (s, 1H), 2.49 (s, 3H), 2.08 (s, 6H) | 0.625 |
| S00942 | 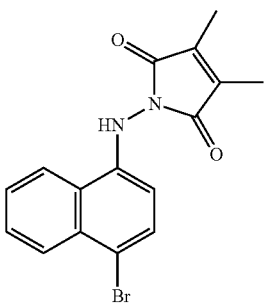 [SMILES: CC1=C(C)C(=O)N(Nc2ccc(Br)c3ccccc23)C1=O] | 1-[(4-bromonaphthyl)amino]-3,4-dimethylazoline-2,5-dione | 342.9 (M$^-$ − 1) | (CDCl$_3$, 300 MHz) δ: 8.25-8.21 (d, J = 8.1 Hz, 1H), 7.99-7.95 (d, J = 8.4 Hz, 1H), 7.65-7.52 (m, 3H), 6.56 (s, 1H), 6.52-6.49 (d, J = 8.4 Hz, 1H), 2.08 (s, 6H) | 0.625 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01037 | 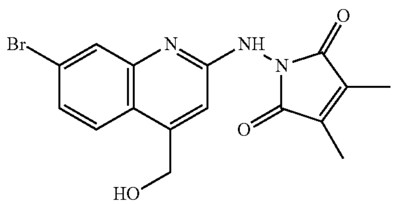 [SMILES: CC1=C(C)C(=O)N(Nc2cc(CO)c3ccc(Br)cc3n2)C1=O] | 1-{[7-bromo-4-(hydroxymethyl) 2-quinolyl)] amino}-3,4-dimethylazoline-2,5-dione | 376.1 (M$^+$ + 1) | (CDCl$_3$, 300 MHz) δ: 7.85-7.84 (d, J = 1.8 Hz, 1H), 7.52-7.49 (d, J = 8.7 Hz, 1H), 7.40-7.36 (dd, J = 8.7 Hz, 1.8 Hz, 1H), 6.99 (s, 1H), 4.99 (s, 2H), 2.11 (s, 1H), 2.10 (s, 6H) | 0.625 |
| S01047 | 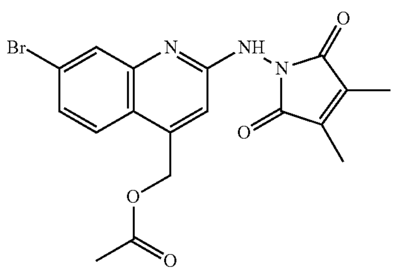 [SMILES: CC(=O)OCc1cc(NN2C(=O)C(C)=C(C)C2=O)nc2cc(Br)ccc12] | {2-[(3.4-dimethyl-2,5-dioxoazolinyl) amino]-7-bromo-4-quinolyl} methyl acetate | 418.0 (M$^+$ + 1) | (CDCl$_3$, 300 MHz) δ: 7.86-7.85 (d, J = 1.8 Hz, 1H), 7.58-7.54 (d, J = 8.7 Hz, 1H), 7.45-7.41 (dd, J = 9.0 Hz, 2.1 Hz, 1H), 6.85 (s, 1H), 5.27 (s, 2H), 2.13 (s, 3H), 2.02 (s, 6H) | 0.625 |
| S01191 | 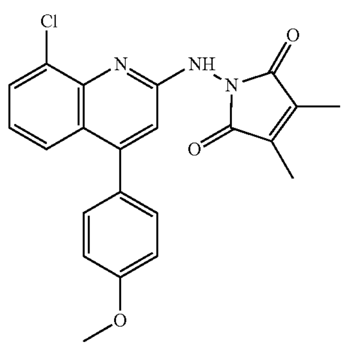 [SMILES: COc1ccc(-c2cc(NN3C(=O)C(C)=C(C)C3=O)nc3c(Cl)cccc23)cc1] | 1-{[8-chloro-4-(4-methoxyphenyl) (2-quinolyl)] amino}-3,4-dimethylazoline-2,5-dione | 408.2 (M$^+$ + 1) | (CDCl$_3$, 300 MHz) δ: 7.67-7.60 (m, 2H), 7.37-7.32 (m, 2H), 7.18-7.13 (m, 1H), 7.05-7.01 (m, 2H), 6.84 (br, 1H), 6.78 (s, 1H), 3.88 (s, 1H), 2.10 (s, 6H) | 0.625 |
| S01207 | 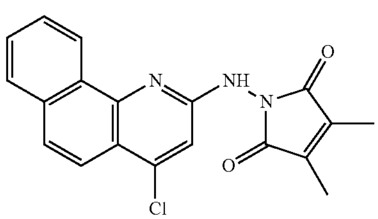 [SMILES: CC1=C(C)C(=O)N(Nc2cc(Cl)c3ccc4ccccc4c3n2)C1=O] | 1-[(4-chlorobenzo[h] quinolin-2-yl) amino]-3,4-dimethylazoline-2,5-dione | 352.2 (M$^+$ + 1) | (CDCl$_3$, 300 MHz) δ: 8.81-8.78 (d, J = 8.7 Hz, 1H), 7.99-7.96 (d, J = 8.7 Hz, 1H), 7.87-7.83 (d, 9.0 Hz, 1H), 7.73-7.69 (d, J = 9.0 Hz, 1H), 7.67-7.55 (m, 2H), 7.00 (s, 1H), 6.84 (br, 1H), 2.02 (s, 6H) | 0.625 |

TABLE 2-continued

REPRESENTATIVE COMPOUNDS AND IC50 VALUES
Physicochemical Characters

| SCID | Structure | IUPAC Name | Mass (m/e) | ¹H NMR | IC$_{50}$ (μM) |
|---|---|---|---|---|---|
| S01268 | 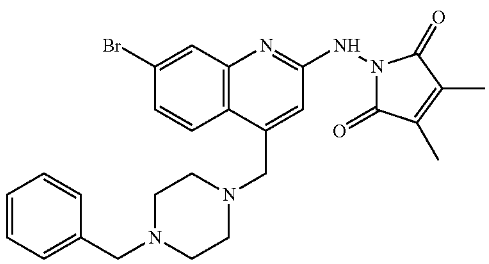 [SMILES: CC1=C(C)C(=O)N(Nc2cc(CN3CCN(Cc4ccccc4)CC3)c3ccc(Br)cc3n2)C1=O] | 1-[(7-bromo-4-{(4-benzylpiperazinyl]methyl}(2-quinolyl))amino]-3,4-dimethylazoline-2,5-dione | 534.3 (M$^+$ + 1) | (CDCl$_3$, 300 MHz) δ: 7.88-7.82 (m, 2H), 7.40-7.25 (m, 6H), 6.89 (s, 1H), 3.73 (s, 2H), 3.51 (s, 2H), 2.60-2.40 (m, 8H), 2.09 (s, 6H) | 0.625 |
| S01371 | 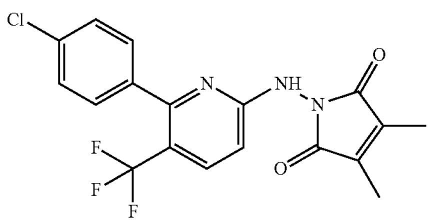 [SMILES: CC1=C(C)C(=O)N(Nc2ccc(C(F)(F)F)c(-c3ccc(Cl)cc3)n2)C1=O] | 1-{[6-(4-chlorophenyl)-5-(trifluoromethyl)-(2-pyridyl)]amino}-3,4-dimethylazoline-2,5-dione | 394.4 (M$^-$ − 1) | (CDCl$_3$, 300 MHz) δ: 7.85-7.81 (d, J = 8.7 Hz, 1H), 7.57 (br, 1H), 7.38-7.31 (m, 4H), 6.47-6.44 (d, J = 8.4 Hz, 1H), 2.04 (s, 6H) | 0.625 |
| S01393 | 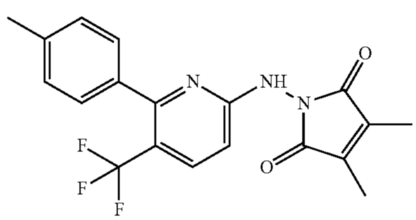 | 3,4-dimethyl-1-{[6-(4-methylphenyl)-5-(trifluoromethyl)(2-pyridyl)]amino}azoline-2,5-dione | 374.3 (M$^-$ − 1) | (CDCl$_3$, 300 MHz) δ: 7.87-7.84 (d, J = 9.0 Hz, 1H), 7.36-7.33 (d, J = 8.1 Hz, 2H), 7.21-7.18 (d, J = 8.1 Hz, 2H), 6.81 (s, 1H), 6.54-6.51 (d, J = 8.7 Hz, 1H), 2.39 (s, 3H), 2.04 (s, 6H) | 0.625 |
| S01474 | 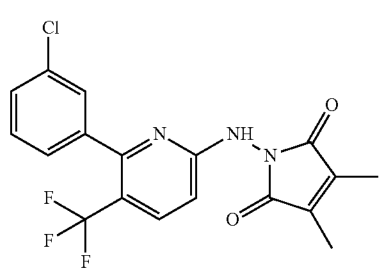 [SMILES: CC1=C(C)C(=O)N(Nc2ccc(C(F)(F)F)c(-c3cccc(Cl)c3)n2)C1=O] | 1-{[6-{3-chlorophenyl)-5-(trifluoromethyl)-2-pyridyl)]amino}-3,4-dimethylazoline-2,5-dione | 394 (M$^-$ − 1) | (CDCl$_3$, 300 MHz) δ: 7.87-7.84 (d, J = 6.6 Hz, 1H), 7.41-7.31 (m, 4H), 7.21 (br, 1H), 6.56-6.54 (d, J = 6.6 Hz, 1H), 2.04 (s, 6H) | 0.625 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01600 | 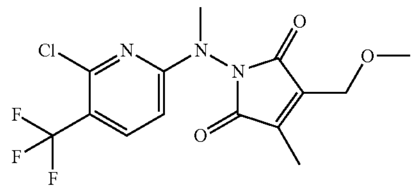 [SMILES: COCC1=C(C)C(=O)N(N(C)c2ccc(C(F)(F)F)c(Cl)n2)C1=O] | 1-{[6-chloro-5-(trifluoromethyl)-(2-pyridyl)]methylamino}-3-(methoxymethyl)-4-methylazoline-2,5-dione | 362 (M$^-$ − 1) | (CDCl$_3$, 300 MHz) δ: 7.77-7.74 (d, J = 8.6 Hz, 1H), 6.47-6.44 (d, J = 8.4 Hz, 1H), 4.37 (s, 2H), 3.45 (s, 3H), 3.44 (s, 3H), 2.20 (s, 3H) | 0.625 |
| S01683 | 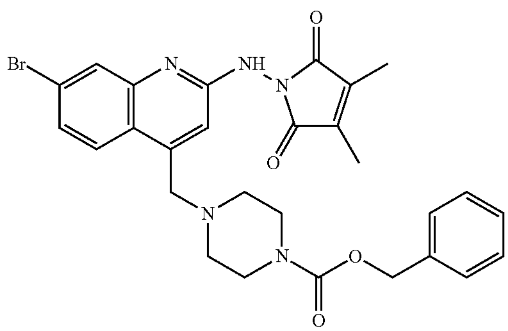 [SMILES: CC1=C(C)C(=O)N(Nc2cc(CN3CCN(C(=O)OCc4ccccc4)CC3)c3ccc(Br)cc3n2)C1=O] | phenylmethyl 4-({2-[(3,4-dimethyl-2,5-dioxoazolinyl)amino]-7-bromo-4-quinolyl}methyl)piperazine-carboxylate | 578 (M$^+$ + 1) | (CDCl$_3$, 300 MHz) δ: 7.84 (m, 2H), 7.41 (m, 1H), 7.37-7.30 (m, 5H), 6.86 (s, 1H), 6.76 (br, 1H), 5.14 (s, 2H), 3.70 (s, 2H), 3.50 (m, 4H), 2.44 (m, 4H) 2.09 (s, 6H) | 0.625 |
| S01688 | 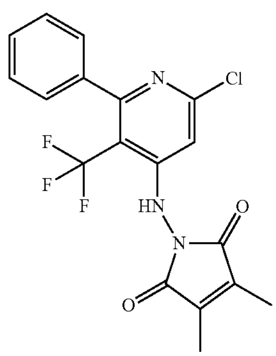 [SMILES: CC1=C(C)C(=O)N(Nc2cc(Cl)nc(-c3ccccc3)c2C(F)(F)F)C1=O] | 1-{[6-chloro-2-phenyl-3-(trifluoromethyl)(4-pyridyl)]amino}-3,4-dimethylazoline-2,5-dione | 394.3 (M$^-$ − 1) | (CDCl$_3$, 300 MHz) δ: 7.39-7.35 (m, 5H), 7.26 (s, 1H), 6.55 (d, J = 6.0 Hz, 1H), 2.03 (s, 6H) | 0.625 |
| S01691 | 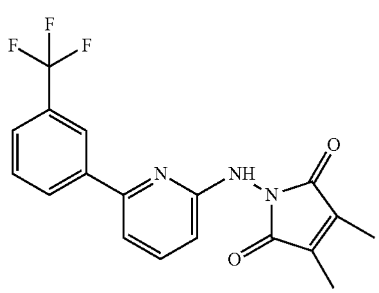 [SMILES: CC1=C(C)C(=O)N(Nc2cccc(-c3cccc(C(F)(F)F)c3)n2)C1=O] | 3,4-dimethyl-1-({6-[3-(trifluoromethyl)phenyl](2-pyridyl)}amino)azoline-2,5-dione | 362.3 (M$^+$ + 1) | (CDCl$_3$, 300 MHz) δ: 8.13 (br, 1H), 8.00-7.97 (d, J = 7.8 Hz, 1H), 7.65-7.58 (m, 2H), 7.52-7.47 (t, 1H), 7.33-7.31 (d, J = 7.5 Hz, 1H), 6.65-6.63 (t, 2H), 2.07 (s, 6H) | 0.625 |

TABLE 2-continued

REPRESENTATIVE COMPOUNDS AND IC50 VALUES
Physicochemical Characters

| SCID | Structure | IUPAC Name | Mass (m/e) | ¹H NMR | IC$_{50}$ (μM) |
|---|---|---|---|---|---|
| S01699 | 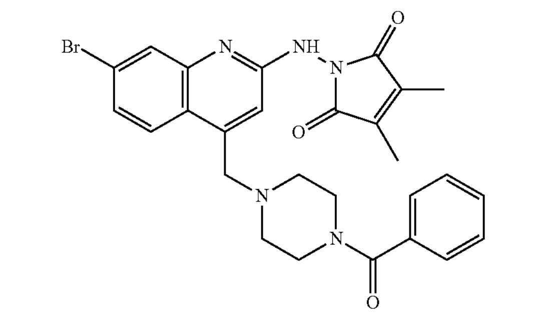 [SMILES: CC1=C(C)C(=O)N(Nc2cc(CN3CCN(C(=O)c4ccccc4)CC3)c3ccc(Br)cc3n2)C1=O] | 1-[(7-bromo-4-{[4-(phenylcarbonyl)piperazinyl]methyl}(2-quinolyl))amino]-3,4-dimethylazoline-2,5-dione | 548 (M⁺ + 1) | (CDCl$_3$, 300 MHz) δ: 7.88-7.84 (m, 2H), 7.41-7.38 (m, 6H), 6.86 (s, 1H), 3.79-3.73 (m, 4H), 3.42 (m, 2H), 2.54 (m, 4H), 2.09 (s, 6H) | 0.625 |
| S01759 | 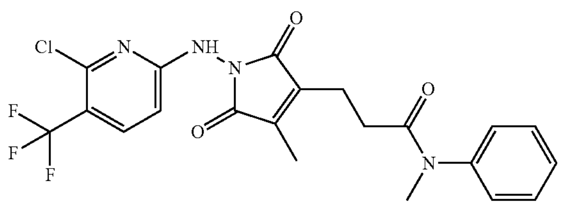 [SMILES: CC1=C(CCC(=O)N(C)c2ccccc2)C(=O)N(Nc2ccc(C(F)(F)F)c(Cl)n2)C1=O] | 3-(1-{[6-chloro-5-(trifluoromethyl)(2-pyridyl)]amino}-4-methyl-2,5-dioxoazolin-3-yl)-N-methyl-N-phenylpropanamide | 465.3 (M⁻ − 1) | (CDCl$_3$, 300 MHz) δ: 7.94 (s, 1H), 7.73 (d, J = 8.6 Hz, 1H), 7.43-7.33 (m, 3H), 7.19-7.16 (m, 2H), 6.51 (d, J = 8.5 Hz, 1H), 3.24 (s, 3H), 2.70 (t, J = 7.1 Hz, 2H), 2.41 (t, J = 7.2 Hz, 2H), 2.06 s, 3H). | 0.625 |
| S01762 | 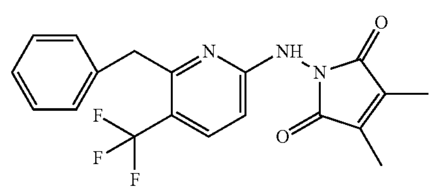 [SMILES: CC1=C(C)C(=O)N(Nc2ccc(C(F)(F)F)c(Cc3ccccc3)n2)C1=O] | 3,4-dimethyl-1-{[6-benzyl-5-(trifluoromethyl)(2-pyridyl)]amino}zoline-2,5-dione | 374.3 (M⁻ − 1) | (CDCl$_3$, 300 MHz) δ: 7.67-7.63 (d, J = 8.4 Hz, 1H), 7.22-7.12 (m, 5H), 6.84 (s, 1H), 6.45-6.41 (d, J = 8.7 Hz, 1H), 4.08 (s, 2H), 2.00 (s, 6H) | 0.625 |
| S01800 | 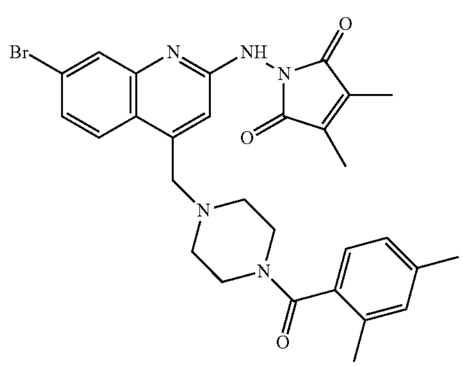 [SMILES: CC1=C(C)C(=O)N(Nc2cc(CN3CCN(C(=O)c4ccc(C)cc4C)CC3)c3ccc(Br)cc3n2)C1=O] | 1-{[4-({4-[(2,4-dimethylphenyl)carbonyl]piperazinyl}methyl)-7-bromo(2-quinolyl)lamino}-3,4-dimethylazoline-2,5-dione | 576 (M⁺ + 1) | (CDCl$_3$, 300 MHz) δ: 7.87-7.83 (m, 2H), 7.41-7.37 (d*d, J$_1$ = 8.7 Hz, J$_2$ = 2.1 Hz, 1H), 7.05-7.00 (m, 3H), 6.85 (s, 1H), 3.81 (m, 2H), 3.72 (s, 2H), 3.22 (m, 2H), 2.58-2.55 (m, 2H) 2.36-2.33 (m, 2H), 2.31 (s, 3H), 2.27 (s, 3H), 2.10 (s, 6H) | 0.625 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01801 | 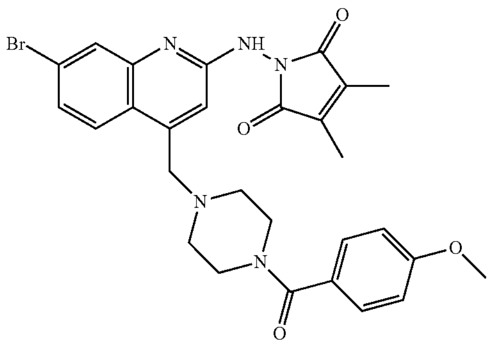 [SMILES: COc1ccc(C(=O)N2CCN(Cc3cc(NN4C(=O)C(C)=C(C)C4=O)nc4cc(Br)ccc34)CC2)cc1] | 1-{[7-bromo-4-({4-[(4-methoxy-phenyl)caxbonyl)piperazinyl}methyl)(2-quinolyl)]amino)-3,4-dimethylaxoline-2,5-dione | 578 (M$^+$ + 1) | (CDCl$_3$, 300 MHz) δ: 7.90-7.82 (m, 2H), 7.41-7.36 (m, 3H), 6.92-6.88 (m, 3H), 3.83 (s, 3H), 3.78 (s, 2H), 3.62 (m, 4H), 2.51 (m, 4H), 2.10 (s, 6H) | 0.625 |
| S01820 | 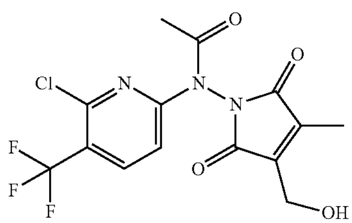 [SMILES: CC(=O)N(c1ccc(C(F)(F)F)c(Cl)n1)N1C(=O)C(C)=C(CO)C1=O] | N-[6-chloro-5-(trifluoromethyl)(2-pyridyl)]-N-[4-(hydroxymethyl)-3-methyl-2,5-dioxoazolinyl]acetamide | 376 (M$^-$ − 1) | (CDCl$_3$, 300 MHz) δ: 8.27-8.26 (m, 1H), 8.02-7.99 (t, 1H) 4.69-4.67 (d, J = 5.1 Hz, 2H), 2.31 (s, 3H), 2.28 (s, 3H) | 0.625 |
| S01822 | 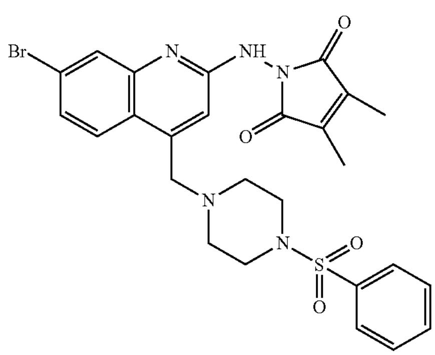 [SMILES: CC1=C(C)C(=O)N(Nc2cc(CN3CCN(S(=O)(=O)c4ccccc4)CC3)c3ccc(Br)cc3n2)C1=O] | 1-[(7-bromo-4-{[4-(phenylsulfonyl)piperazinyl]methyl}(2-quinolyl))amino]-3,4-dimethylazoline-2,5-dione | 584 (M$^+$ + 1) | (CDCl$_3$, 300 MHz) δ: 7.80-7.71 (m, 4H), 7.62-7.52 (m, 3H), 7.34-7.31 (d*d, J$_1$ = 8.7 Hz, J$_2$ = 2.1 Hz, 1H), 6.75 (s, 1H), 3.65 (s, 2H), 3.01 (m, 4H), 2.56-2.53 (m, 4H), 2.07 (s, 6H) | 0.625 |
| S00871 | 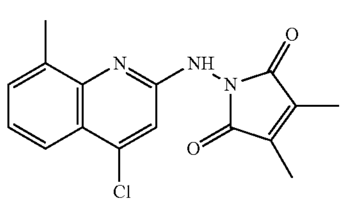 [SMILES: CC1=C(C)C(=O)N(Nc2cc(Cl)c3cccc(C)c3n2)C1=O] | 1-[(4-chloro-8-methyl(2-quinolyl))amino]-3,4-dimethylazoline-2,5-dione | 316 (M$^+$ + 1) | (CDCl$_3$, 300 MHz) δ: 7.91-7.88 (d, J = 8.4 Hz, 1H), 7.47-7.44 (d, J = 6.6 Hz, 1H), 7.32-7.28 (d, J = 8.4 Hz, 1H), 6 95 (s, 1H), 6.78 (br, 1H), 2.42 (s, 3H), 2.10 (s, 6H) | 0.625 |

TABLE 2-continued

REPRESENTATIVE COMPOUNDS AND IC50 VALUES
Physicochemical Characters

| SCID | Structure | IUPAC Name | Mass (m/e) | $^1$H NMR | IC$_{50}$ (μM) |
|---|---|---|---|---|---|
| S01862 | 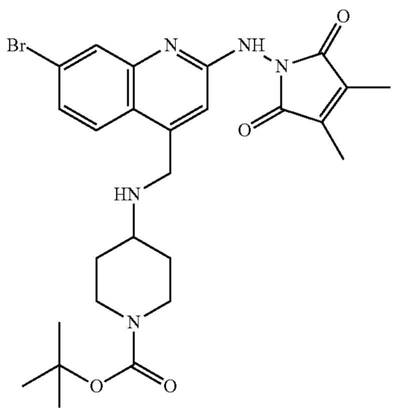 [SMILES: CC1=C(C)C(=O)N(Nc2cc(CNC3CCN(C(=O)OC(C)(C)C)CC3)c3ccc(Br)cc3n2)C1=O] | tert-butyl 4-({2-[(3,4-dimethyl-2,5-dioxoazolinyl)amino]-7-bromo-4-quinolyl}methyl)amino] piperidinecarboxylate | 556.2 (M$^-$ − 1) | (CDCl$_3$, 300 MHz) δ: 7.81-7.80 (d, J = 1.8 Hz, 1H), 7.60-7.55 (d, J = 9.0 Hz, 1H), 7.40-7.35 (dd, J = 8.7 Hz 2.1 Hz, 1H), 6.85 (s, 1H), 4.10-3.90 (m, 2H), 3.76 (s, 2H), 2.90-2.80 (m, 2H), 2.70-2.55 (m, 1H), 2.09 (s, 6H), 1.90-1.80 (m, 2H), 1.46 (s, 9H), 1.40-1.30 (m, 2H) | 0.937 |
| S01928 | 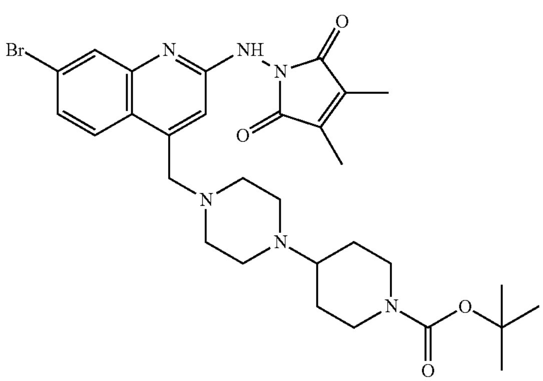 [SMILES: CC1=C(C)C(=O)N(Nc2cc(CN3CCN(C4CCN(C(=O)OC(C)(C)C)CC4)CC3)c3ccc(Br)cc3n2)C1=O] | tert-butyl 4-[4-((2-[(3,4-dimethyl-2,5-dioxoazolinyl)amino]-7-bromo-4-quinolyl)methyl) piperazinyl] piperidinecarboxylate | 627 (M$^+$ + 1) | (CDCl$_3$, 300 MHz) δ: 7.88-7.83 (m, 2H), 7.40-7.36 (m, 1H), 6.87 (s, 1H), 4.15-4.08 (m, 1H), 3.68 (s, 2H), 2.73-2.65 (m, 1H), 2.54-2.52 (m, 8H), 2.36 (m, 2H), 2.06 (s, 6H), 1.81-1.77 (m, 2H), 1.44 (s, 9H), 1.42-1.35 (m, 2H) | 0.9375 |
| S01929 | 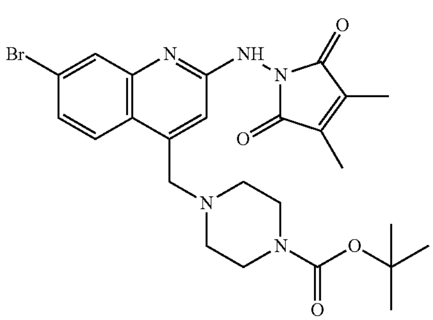 [SMILES: CC1=C(C)C(=O)N(Nc2cc(CN3CCN(C(=O)OC(C)(C)C)CC3)c3ccc(Br)cc3n2)C1=O] | 1-[(4-{(4-(3,3-dimethylbutanoyl) piperazinyl]methyl}-7-bromo(2-quinolyl))amino]-3,4-dimethylazoline-2,5-dione | 542 (M$^+$ + 1) | (CDCl$_3$, 300 MHz) δ: 7 89-7.84 (m, 2H), 7.42-7.38 (m, 1H), 6.87 (s, 1H), 3.72 (s, 2H), 3.67-3.63 (m, 2H), 3.49-3.46 (m, 2H), 2.50-2.41 (m, 4H), 2.25 (s, 2H), 2.10 (s, 6H), 1.05 (s, 9H) | 0.9375 |

TABLE 3

REPRESENTATIVE COMPOUNDS AND IC50 VALUES

| SCID | Structure | IUPAC Name | Mass (m/e) | $^1$H NMR | IC50 (μM) |
|---|---|---|---|---|---|
| S03518 | 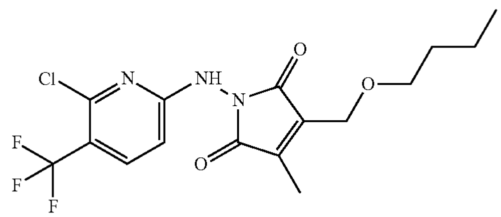 [SMILES: CCCCOCC1=C(C)C(=O)N(Nc2ccc(C(F)(F)F)c(Cl)n2)C1=O] | 3-(Butoxymethyl)-1-{[6-chloro-5-(trifluoromethyl)(2-pyridyl)]amino}-4-methylazoline-2,5-dione | 390.2 (M$^-$ − 1) | (CDCl$_3$, 300 MHz) δ: 0.90-0.95 (t, J = 7.2 Hz, 3H), 1.35-1.43 (m, 2H), 1.54-1.63 (m, 2H), 2.20 (s, 3H), 3.50-3.55 (t, J = 6.6 Hz, 2H), 4.41 (s, 2H), 6.49-6.52 (d, J = 8.4 Hz, 1H), 6.88 (s, 1H), 7.77-7.79 (d, J = 8.4 Hz, 1H) | 0.02 |
| S02225 | 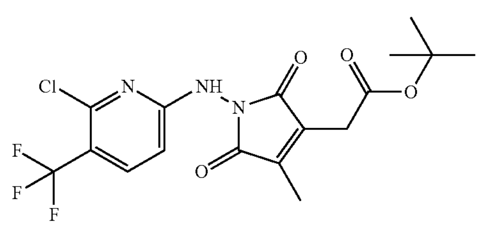 [SMILES: CC1=C(CC(=O)OC(C)(C)C)C(=O)N(Nc2ccc(C(F)(F)F)c(Cl)n2)C1=O] | tert-butyl 2-(1-{[6-chloro-5-(trifluoromethyl)(2-pyridyl)]amino}-4-methyl-2,5-dioxoazolin-3-yl)acetate | 418.0 (M$^-$ − 1) | (CDCl$_3$, 300 MHz) δ: 7.79-7.76 (d, J = 8.4 Hz, 1H), 7.04 (s, 1H), 6.51-6.48 (d, J = 8.7 Hz, 1H), 3.45 (s, 2H), 2.11 (s, 3H), 1.25 (s, 9H) | 0.03 |
| S02264 | 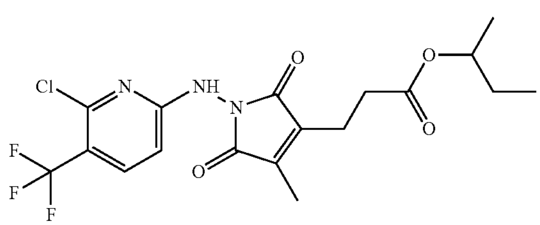 [SMILES: CCC(C)OC(=O)CCC1=C(C)C(=O)N(Nc2ccc(C(F)(F)F)c(Cl)n2)C1=O] | 4-methylphenyl 3-(1-{[6-chloro-5-(trifluoromethyl)(2-pyridyl)]amino}-4-methyl-2,5-dioxoazolin-3-yl)propanoate | 433.9 (M$^+$ + 1) | (CDCl$_3$, 300 MHz) δ: 7.78-7.75 (d, J = 8.7 Hz, 1H), 7.08 (s, 1H), 6.50-6.47 (d, J = 8.4 Hz, 1H), 4.85-4.83 (m, 1H), 2.79-2.66 (m, 4H), 1.59-1.52 (m, 2H), 1.21-1.18 (d, J = 6.3 Hz, 3H), 0.90-0.86 (t, 3H) | 0.04 |

TABLE 3-continued

REPRESENTATIVE COMPOUNDS AND IC50 VALUES

| SCID | Structure | IUPAC Name | Mass (m/e) | $^1$H NMR | IC50 (μM) |
|---|---|---|---|---|---|
| S02366 | 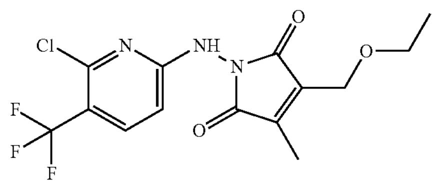 [SMILES: CCOCC1=C(C)C(=O)N(Nc2ccc(C(F)(F)F)c(Cl)n2)C1=O] | 1-{[6-Chloro-5-(trifluoromethyl)(2-pyridyl)]amino}-3-(ethoxymethyl)-4-methylazoline-2,5-dione | 364.0 (M$^+$ + 1) | (CDCl$_3$, 300 MHz) δ: 1.23-1.28 (t, J = 6.9 Hz, 3H), 2.21 (t, J = 1.2 Hz, 3H), 3.56-3.63 (q, J = 6.9 Hz, 2H), 4.41 (q, J = 1.2 Hz, 2H), 6.48-6.51 (d, J = 8.7 Hz, 1H), 7.0 (s, 1H), 7.75-7.78 (d, J = 8.4 Hz, 1H) | 0.04 |
| S03405 | 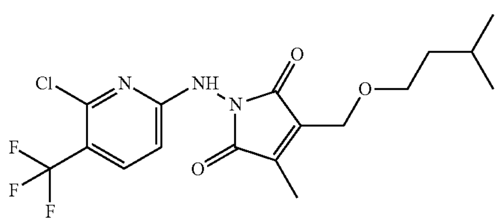 [SMILES: CC1=C(COCCC(C)C)C(=O)N(Nc2ccc(C(F)(F)F)c(Cl)n2)C1=O] | 1-{[6-Chloro-5-(trifluoromethyl)-(2-pyridyl)]amino}-4-methyl-3-[(3-methylbutoxy)methyl]azoline-2,5-dione | 404.2 (M$^-$ − 1) | (CDCl$_3$, 300 MHz) δ: 0.87-0.95 (m, 6H), 1.47-1.54 (m, 2H), 1.66-1.75 (m, 1H), 2.19 (s, 3H), 3.53-3.57 (t, J = 7.2 Hz, 2H), 4.41 (s, 2H), 6.49-6.52 (d, J = 8.4 Hz, 1H), 6.90 (s, 1H), 7.77-7.80 (d, J = 8.4 Hz, 1H) | <0.019 |
| S03448 | 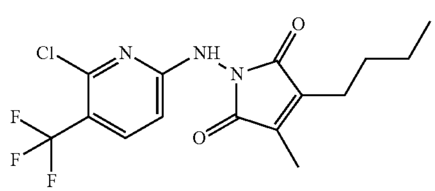 [SMILES: CCCCC1=C(C)C(=O)N(Nc2ccc(C(F)(F)F)c(Cl)n2)C1=O] | 3-butyl-1-{[6-chloro-5-(trifluoromethyl)(2-pyridyl)]amino}-4-methylazoline-2,5-dione | 360.0 (M$^+$ + 1) | (CDCl$_3$, 300 MHz) δ: 7.78-7.74 (d, J = 9.0 Hz, 1H), 7.05 (s, 1H), 6.50-6.46 (d, J = 8.7 Hz, 1H), 2.51-2.45 (t, J = 7.5 Hz, 2H), 2.07 (s, 3H), 1.60-1.52 (m, 2H), 1.42-1.34 (m, 2H), 0.97-0.92 (t, J = 7.2 Hz, 3H) | 0.156 |

TABLE 3-continued

REPRESENTATIVE COMPOUNDS AND IC50 VALUES

| SCID | Structure | IUPAC Name | Mass (m/e) | $^1$H NMR | IC50 ($\mu$M) |
|---|---|---|---|---|---|
| S03456 | 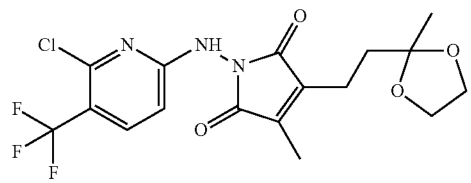 [SMILES: CC1=C(CCC2(C)OCCO2)C(=O)N(Nc2ccc(C(F)(F)F)c(Cl)n2)C1=O] | 1-{[6-Chloro-5-(trifluoromethyl)(2-pyridyl)]amino}-4-methyl-3-[2-(2-methyl(1,3-dioxolan-2-yl))ethyl]azoline-2,5-dione | 418.2 (M$^-$ − 1) | (CDCl$_3$, 300 MHz) δ: 1.35 (s, 3H), 1.98-2.03 (t, J = 7.2 Hz, 2H), 2.07 (s, 3H), 2.56-2.61 (t, J = 7.2 Hz, 2H), 3.88-4.00 (m, 4H), 6.47-6.50 (d, J = 8.7 Hz, 1H), 6.78 (s, 1H), 7.76-7.79 (d, J = 8.7 Hz, 1H) | 0.156 |
| S03552 | 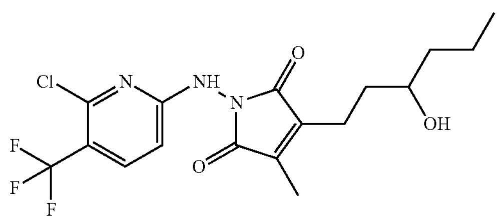 [SMILES: CCCC(O)CCC1=C(C)C(=O)N(Nc2ccc(C(F)(F)F)c(Cl)n2)C1=O] | 1-{[6-chloro-5-(trifluoromethyl)(2-pyridyl)]amino}-4-(3-hydroxyhexyl)-3-methylazoline-2,5-dione | 404.2 (M$^-$ − 1) | (CDCl$_3$, 300 MHz) δ: 7.77-7.74 (d, J = 8.7 Hz, 1H), 7.21 (br, 1H), 6.51-6.48 (d, J = 8.7 Hz, 1H), 3.61-3.59 (m, 1H), 2.65-2.60 (t, 2H), 2.09 (s, 3H), 1.77-1.62 (m, 3H), 1.47-1.25 (m, 4H), 0.94-0.90 (m, 3H) | 0.06 |
| S03742 | 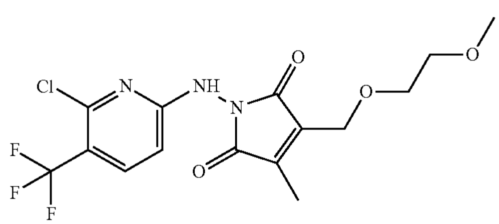 [SMILES: COCCOCC1=C(C)C(=O)N(Nc2ccc(C(F)(F)F)c(Cl)n2)C1=O] | 1-{[6-Chloro-5-(trifluoromethyl)(2-pyridyl)]amino}-3-[(2-methoxyethoxy)methyl]-4-methylazoline-2,5-dione | 392.0 (M$^-$ − 1) | (CDCl$_3$, 300 MHz) δ: 7.77-7.74 (d, J = 8.4 Hz, 1H), 7.20 (s, 1H), 6.52-6.49 (d, J = 8.4 Hz, 1H), 4.48 (s, 1H), 3.72-3.69 (m, 2H), 3.60-3.56 (m, 2H), 3.39 (s, 3H), 2.20 (s, 3H) | 0.12 |

TABLE 3-continued

REPRESENTATIVE COMPOUNDS AND IC50 VALUES

| SCID | Structure | IUPAC Name | Mass (m/e) | ¹H NMR | IC50 (μM) |
|---|---|---|---|---|---|
| S03745 | 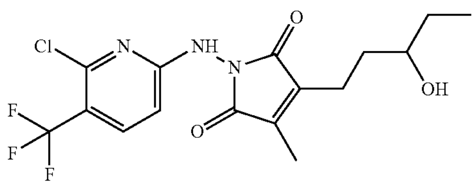 [SMILES: CCC(O)CCC1=C(C)C(=O)N(Nc2ccc(C(F)(F)F)c(Cl)n2)C1=O] | 1-{[6-chloro-5-(trifluoromethyl)(2-pyridyl)]amino}-4-(3-hydroxy-pentyl)-3-methylazoline-2,5-dione | 390.0 (M⁻ − 1) | (CDCl₃, 300 MHz) δ: 7.76-7.73 (d, J = 8.7 Hz, 1H), 7.36 (br, 1H), 6.51-6.48 (d, J = 8.7 Hz, 1H), 3.52-3.51 (m, 1H), 2.64-2.59 (t, 2H), 2.09 (s, 3H), 1.83-1.62 (m, 2H), 1.55-1.42 (m, 2H), 0.94-0.90 (m, 3H) | 0.06 |
| S03747 | 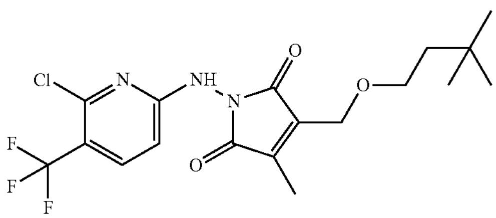 [SMILES: CC1=C(COCCC(C)(C)C)C(=O)N(Nc2ccc(C(F)(F)F)c(Cl)n2)C1=O] | 3-[(3,3-Dimethylbutoxy)methyl]-1-{[6-chloro-5-(trifluoromethyl)(2-pyridyl)]amino}-4-methylazoline-2,5-dione | 418.1 (M⁻ − 1) | (CDCl₃, 300 MHz) δ: 7.77-7.80 (d, J = 8.7 Hz, 1H), 6.77 (s, 1H), 6.49-6.52 (d, J = 8.4 Hz, 1H), 4.40 (s, 2H), 3.55-3.60 (t, J = 7.5 Hz, 2H), 2.20 (s, 3H), 1.53-1.58 (t, J = 6.9 Hz, 2H), 0.92-0.96 (s, 9H). | <0.019 |
| S03873 | 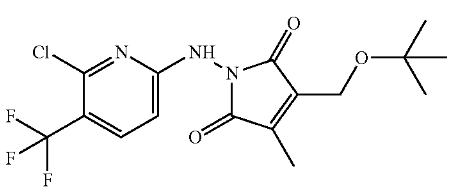 [SMILES: CC1=C(COC(C)(C)C)C(=O)N(Nc2ccc(C(F)(F)F)c(Cl)n2)C1=O] | 4-[(tert-Butoxy)methyl]-1-{[6-chloro-5-(trifluoromethyl)(2-pyridyl)]amino}-3-methylazoline-2,5-dione | 390.2 (M⁻ − 1) | (CDCl₃, 300 MHz) δ: 7.80-7.77 (d, J = 8.4 Hz, 1H), 6.85 (br, 1H), 6.51-6.49 (d, J = 8.4 Hz, 1H), 4.37 (s, 2H), 2.21 (s, 3H), 1.28 (s, 9H) | 0.02 |

TABLE 3-continued

REPRESENTATIVE COMPOUNDS AND IC50 VALUES

| SCID | Structure | IUPAC Name | Mass (m/e) | ¹H NMR | IC50 (μM) |
|---|---|---|---|---|---|
| S03955 | 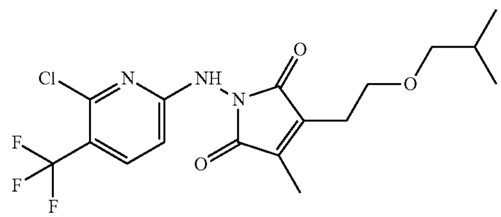 [SMILES: CC1=C(CCOCC(C)C)C(=O)N(Nc2ccc(C(F)(F)F)c(Cl)n2)C1=O] | 1-{[6-Chloro-5-(trifluoromethyl)(2-pyridyl)]amino}-4-methyl-3-[2-(2-methylpropoxy)ethyl]azoline-2,5-dione | 404.1 (M⁻ − 1) | (CDCl₃, 300 MHz) δ: 0.86-0.88 (d, J = 8.4 Hz, 6H), 1.79-1.83 (m, 1H), 2.21 (s, 3H), 2.72-2.76 (t, J = 6.6 Hz, 2H), 3.17-3.19 (d, J = 6.6 Hz, 2H), 3.60-3.64 (t, J = 6.6 Hz, 2H), 6.45-6.48 (d, J = 8.7 Hz, 1H), 7.03 (s, 1H), 7.75-7.78 (d, J = 8.4 Hz, 1H) | 0.06 |
| S03956 | 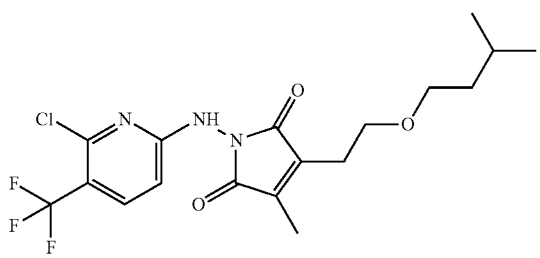 [SMILES: CC1=C(CCOCCC(C)C)C(=O)N(Nc2ccc(C(F)(F)F)c(Cl)n2)C1=O] | 1-{[6-Chloro-5-(trifluoromethyl)(2-pyridyl)]amino}-4-methyl-3-[2-(3-methylbutoxy)ethyl]azoline-2,5-dione | 418.3 M⁻ − 1) | (CDCl₃, 300 MHz) δ: 0.85-0.92 (d, J = 6.6 Hz, 6H), 1.39-1.46 (m, 2H), 1,60-1.69 (m, 1H), 2.09 (s, 3H), 2.72-2.76 (t, J = 6.6 Hz, 2H), 3.41-3.46 (d, J = 6.6 Hz, 2H), 3.60-3.64 (t, J = 6.6 Hz, 2H), 6.45-6.47 (d, J = 8.4 Hz, 1H), 7.38 (s, 1H), 7.73-7.76 (d, J = 8.4 Hz, 1H) | 0.156 |
| S03960 | 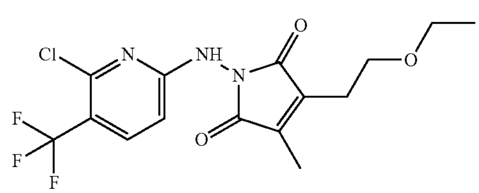 [SMILES: CCOCCC1=C(C)C(=O)N(Nc2ccc(C(F)(F)F)c(Cl)n2)C1=O] | 1-{[6-Chloro-5-(trifluoromethyl)(2-pyridyl)]amino}-3-{2-ethoxyethyl)-4-methylazoline-2,5-dione | 376.2 (M⁻ − 1) | (CDCl₃, 300 MHz) δ: 7.76-7.73 (d, J = 8.4 Hz, 1H), 7.41 (s, 1H ), 6.48-6.45 (d, J = 8.4 Hz, 1H), 3.65-3.61 (t, 2H), 3.52-3.45 (q, 2H), 2.76-2.72 (t, 2H), 2.09 (s, 3H), 1.19-1.14 (t, 3H) | 0.04 |

TABLE 3-continued

REPRESENTATIVE COMPOUNDS AND IC50 VALUES

| SCID | Structure | IUPAC Name | Mass (m/e) | ¹H NMR | IC50 (μM) |
|---|---|---|---|---|---|
| S03962 | 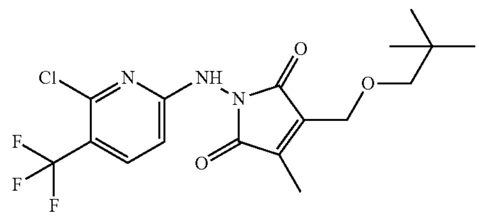 [SMILES: CC1=C(COCC(C)(C)C)C(=O)N(Nc2ccc(C(F)(F)F)c(Cl)n2)C1=O] | 3-[(2,2-Dimethylpropoxy)methyl]-1-{[6-chloro-5-(trifluoromethy)(2-pyridyl)]amino}-4-methylazoline-2,5-dione | 404.2 (M⁻ − 1) | (CDCl₃, 300 MHz) δ: 7.80-7.77 (d, J = 8.7 Hz, 1H), 6.83 (s, 1H), 6.53-6.50 (d, J = 8.7 Hz, 1H), 4.43 (s, 2H), 3.17 (s, 2H), 2.22 (s, 3H), 0.94 (s, 9H) | <0.019 |
| S03963 | 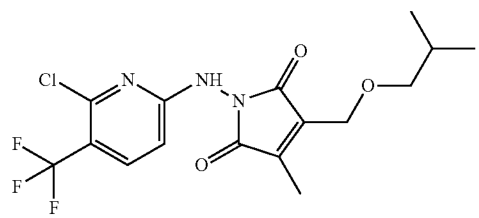 [SMILES: CC1=C(COCC(C)C)C(=O)N(Nc2ccc(C(F)(F)F)c(Cl)n2)C1=O] | 1-{[6-Chloro-5-(trifluoromethyl)(2-pyridyl)]amino}-4-methyl-3-[(2-methylpropoxy)methyl]azoline-2,5-dione | 390.2 (M⁻ − 1) | (CDCl₃, 300 MHz) δ: 7.78-7.75 (d, J = 8.7 Hz, 1H), 7.12 (s, 1H), 6.51-6.48 (d, J = 8.4 Hz, 1H), 4.41 (s, 2H), 3.30-3.28 (d, J = 6.6 Hz, 2H), 2.21 (s, 3H), 1.95-1.86 (m, 1H), 0.94-0.91 (d, J = 6.6 Hz, 6H) | <0.019 |
| S03964 | 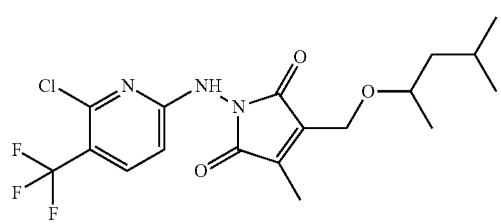 [SMILES: CC1=C(COC(C)CC(C)C)C(=O)N(Nc2ccc(C(F)(F)F)c(Cl)n2)C1=O] | 4-[(1,3-Dimethylbutoxy)methyl]-1-{[6-chloro-5-(trifluoromethyl)(2-pyridyl)]amino}-3-methyl azoline-2,5-dione | 418.1 (M⁻ − 1) | (CDCl₃, 300 MHz) δ: 7.77-7.74 (d, J = 8.4 Hz, 1H), 7.15 (br, 1H), 6.50-6-47 (d, J = 8.4 Hz, 1H), 4.51-4.30 (m, 2H), 3.64-3.57 (m, 1H), 2.20 (s, 3H), 1.76-1.69 (m, 1H), 1.56-1.49 (m, 1H), 1.27-1.23 (m, 1H), 1.21-1.18 (m, 3H), 0.92-0.88 (m, 6H) | 0.04 |

TABLE 3-continued

REPRESENTATIVE COMPOUNDS AND IC50 VALUES

| SCID | Structure | IUPAC Name | Mass (m/e) | ¹H NMR | IC50 (μM) |
|---|---|---|---|---|---|
| S04034 | 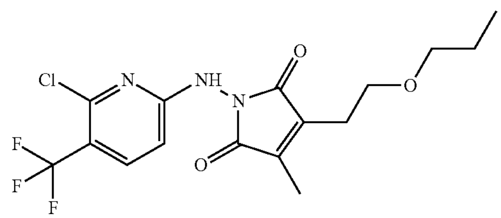 [SMILES: CCCOCCC1=C(C)C(=O)N(Nc2ccc(C(F)(F)F)c(Cl)n2)C1=O] | 1-{[6-chloro-5-(trifluoromethyl)(2-pyridyl)]amino}-3-methyl-4-(2-propoxyethyl)azoline-2,5-dione | 390.3 (M⁻ − 1) | (CDCl$_3$, 300 MHz) δ: 7.73 (s, 1H), 7.70 (br, 1H), 6.47-6.44 (d, J = 8.7 Hz, 1H), 3.64-3.60 (t, 2H), 3.39-3.50 (t, 2H), 2.76-2.72 (t, 2H ), 2.09 (s, 3H), 1.61-1.49 (m, 2H), 0.91-0.86 (t, 3H | 0.04 |

Example 7

Effects of S00109 Alone, and S00109 in Combination with Additional Anti-Cancer Treatments, on Normal Cells and on Cancer Cells The effects of S00109 alone, and S00109 in combination with well-known anti-cancer treatments, was determined for normal human dermal fibroblasts (NHDF), and human umbilical endothelial cells (HUVEC), and for MIAPaCa2 cells (pancreatic cancer-derived cell line), HCT116 cells (colon cancer-derived cell line), IM9 cells (multiple myeloma-derived cell line), ARH-77 cells (multiple myeloma-derived cell line), RPMI-8226 cells (multiple myeloma-derived cell line) and NCI-H929 cells (multiple myeloma-derived cell line).

Cells were treated as described in Tables 4-11, then harvested, stained with propidium iodide to allow measurement of DNA content, and analyzed by flow cytometry to determine the cell cycle stage of each cell present in each population following treatment. Thus, a "phenotype" or "predominant phenotype" or "cell cycle pattern" is determined on the basis of the percentage of cell in various cell cycle stages (G1, S, G2, M, subG1 (dead), and so on). Tables 4-11 report the predominant cell cycle pattern, or the most relevant change in the cell cycle pattern, corresponding to each treatment combination. For example, the result for one treatment combination may be reported as an increase in the number of cells in G2 phase after exposure to a certain S00109 concentration, compared with the predominant phenotype resulting from exposure to a lower S00109 concentration, for the same anti-cancer treatment. Similar, the result for a anti-cancer treatment, in the absence of S00109 treatment, may be reported as an increase in the number of cells in S phase, compared with the corresponding control (no anti-cancer treatment, no S00109, same culture conditions).

Normal human cells and human cancer cells were exposed to S00109 (abbreviated S109 in Tables 4-11) at various concentrations from no S00109, up to 100 μM S00109, as shown in the header for each column.

Normal human cells and human cancer cells were exposed to a variety of anti-cancer treatments including X-ray radiation, and the anti-cancer agents ("anti-cancer drugs") methotrexate, CPT-11 (irinotecan, Camptosar®), 5-FU (5-fluorouracil), CDDP (cisplatin), adriamycin, Gemzar® (gemcitabine), taxol, Velcade® (bortezomib), vincristine, dexamethasone, and melpharan. Treatments included simultaneous treatment with the anti-cancer agent and the indicated dose of S00109, as well as staggered treatment combinations, were cells were treated first with an anti-cancer treatment and then with the indicated dose of S00109. A key to the treatments as described in the legend for each row in Tables 4-11 is presented below.

Control experiments included experiments in which cells were treated with S109 at the indicated dose, and no additional treatment, indicated as "alone" in Tables 4-11, where "S109 at the indicated dose" includes no S00109, or S00109 at various concentrations up to 100 μM, as indicated in each column heading. Control experiments included experiments designed to test the effects of 24 hr and 48 culture times, as well as the effects of additional steps such as a change of culture media at 3 hours, or the addition of S00109 in a later step.

| Key to Treatments in Tables 4-11 | |
|---|---|
| alone 24 hr | Cells were cultured 24 hrs without any additional anti-cancer treatment, in culture media with the indicated dose of S109, where "the indicated dose of S109" includes "No S109" control treatments |
| X-ray 10 Gy 24 hr simul.stim. | Cells were irradiated with X-rays for a total dose of 10 Gy at the beginning of the experiment (requiring about 5-10 min), and cultured in the presence of the indicated dose of S109, for 24 hrs |
| X-ray 10 Gy pre irrad. | Cells were irradiated with X-rays for a total dose of 10 Gy (about 5-10 min) and cultured in culture media alone for 24 hrs, then at 24 hrs after the irradiation, the indicated dose of S109 was added to culture media and cells were cultured for an additional 24 hrs |
| MTX 0.4 24 hr | Cells were cultured in media containing 0.4 μg/ml methotrexate and the indicated dose of S109 for 24 hrs |
| MTX 2 24 hr | Cells were cultured in media containing 2 μg/ml methotrexate and the indicated dose of S109 for 24 hrs |
| MTX 10 24 hr | Cells were cultured in media containing 10 μg/ml methotrexate and the indicated dose of S109 for 24 hrs |
| alone 3 hr 24 hr culture | Cells were cultured for 3 hrs in media containing S109 at the indicated dose, then at 3 hrs, the culture media was replaced with fresh media without S109, and cells were cultured in the fresh media for an additional 24 hrs |

Key to Treatments in Tables 4-11

| | |
|---|---|
| CPT-11 50 | Cells were cultured for 3 hrs in media containing 50 µg/ml CPT-11 (irinotecan, Camptosar ®) and the indicated dose of S109, then at 3 hrs, the culture media was replaced with fresh media without CPT-11 or S109, and cells were cultured in the fresh media for an additional 24 hrs |
| 5-FU 20 | Cells were cultured for 3 hrs in media containing 20 µg/ml 5-FU (5-fluorouracil) and the indicated dose of S109, then at 3 hrs, the culture media was replaced with fresh media without 5-FU or S109, and cells were cultured in the fresh media for an additional 24 hrs |
| alone 3 hr 48 hr culture | Cells were cultured for 3 hrs in media containing the indicated dose of S109, then at 3 hrs, the culture media was replaced with fresh medium without S109, and cells were cultured in the fresh media for an additional 48 hrs |
| CDDP 3 | Cells were cultured for 3 hrs in media containing 3 µg/ml CDDP (cisplatin) and the indicated dose of S109, then at 3 hrs, the culture media was replaced with fresh media without CDDP or S109, and cells were cultured for an additional 48 hrs |
| CDDP 10 | Cells were cultured for 3 hrs in media containing 10 µg/ml CDDP and the indicated dose of S109, that at 3 hrs, the culture media was replaced with fresh media without CDDP or S109, and cells were cultured for an additional 48 hrs |
| ADR 1 | Cells were cultured for 3 hrs in media containing 1 µg/ml adriamycin and the indicated dose of S109, then at 3 hrs, the culture media was replaced with fresh media without adriamycin or S109, and cells were cultured for an additional 48 hrs |
| Gemzar 0.016 | Cells were cultured for 3 hrs in media containing 0.016 µg/ml Gemzar ® (Gemcitabine) and the indicated dose of S109, then at 3 hrs, the culture + media was replaced with fresh media without Gemzar ® or S109, and cells were cultured for an additional 48 hrs |
| Gemzar 0.08 | Cells were cultured for 3 hrs in media containing 0.08 µg/ml Gemzar ® and the indicated dose of S109, then at 3 hrs, the culture media was replace with fresh media with Gemzar ® or S109, and cells were cultured for and additional 48 hrs |
| Gemzar 0.4 | Cells were cultured for 3 hrs in media containing 0.04 µg/ml Gemzar ® and the indicated dose of S109, then at 3 hrs, the culture media was replaced with fresh media without Gemzar ® or S109, and cells were cultured for an additional 48 hrs |
| Gemzar 2 | Cells were cultured for 3 hrs in media containing 0.2 µg/ml Gemzar ® and the indicated dose of S109, then at 3 hrs, the culture media was replaced with fresh media without Gemzar ® or S109, and cells were cultured for an additional 48 hrs |
| Gemzar 10 | Cells were cultured for 3 hrs in media containing 10 µg/ml of Gemzar ® and the indicated dose of S109, then at 3 hrs, the culture media was replace with fresh media without Gemzar ® or S109, and cells were cultured for an additional 48 hrs |
| Gemzar 50 | Cells were cultured for 3 hrs in media containing 50 µg/ml of Gemzar ® and the indicated dose of S109, then at 3 hrs, the culture media was replace with fresh media without Gemzar ® or S109, and cells were cultured for an additional 48 hrs |
| Taxol 0.0032 | Cells were cultured for 3 hrs in media containing 0.0032 µg/ml Taxol and the indicated dose of S109, then at 3 hrs, the culture media was replaced with fresh media without Taxol or S109, and cells were cultured for an additional 48 hrs |
| Taxol 0.016 | Cells were cultured for 3 hrs in media containing 0.016 µg/ml Taxol and the indicated dose of S109, then at 3 hrs, the culture media was replaced with fresh media without Taxol or S109, and cells were cultured for an additional 48 hrs |
| Taxol 0.08 | Cells were cultured for 3 hrs in media containing 0.08 µg/ml Taxol and the indicated dose of S109, then at 3 hrs, the culture media was replaced with fresh media without Taxol or S109, and cells were cultured for an additional 48 hrs |
| Taxol 0.4 | Cells were cultured for 3 hrs in media containing 0.4 µg/ml Taxol and the indicated dose of S109, then at 3 hrs, the culture media was replaced with fresh media without Taxol or S109, and cells were cultured for an additional 48 hrs |
| Taxol 2 | Cells were cultured for 3 hrs in media containing 2 µg/ml Taxol and the indicated dose of S109, then at 3 hrs, the culture media was replaced with fresh media without Taxol or S109, and cells were cultured for an additional 48 hrs |
| Taxol 10 | Cells were cultured for 3 hrs in media containing 10 µg/ml Taxol and the indicated dose of S109, then at 3 hrs, the culture media was replaced with fresh media without Taxol or S109, and cells were cultured for an additional 48 hrs |
| 24 hr | Cells were cultured for 24 hrs with no additional anti-cancer treatment (same as "alone, 24 hr" above) |
| Velcade 3 | Cells were cultured for 24 hrs in media containing 3 µg/ml Velcade ® (bortezomib) and S109 at the indicated dose |
| Velcade 6 | Cells were cultured for 24 hrs in media containing 6 µg/ml Velcade ® (bortezomib) and S109 at the indicated dose |
| Vincristine 2 | Cells were cultured for 24 hrs in media containing 2 µg/ml Vincristine and S109 at the indicated dose |
| Vincristine 20 | Cells were cultured for 24 hrs in media containing 20 µg/ml Vincristine and S109 at the indicated dose |
| Dexamethasone 2 | Cells were cultured for 24 hrs in media containing 2 µg/ml Dexamethasone and S109 at the indicated dose |
| Dexamethasone 20 | Cells were cultured for 24 hrs in media containing 20 µg/ml Vincristine and S109 at the indicated dose |
| Dexamethasone 200 | Cells were cultured for 24 hrs in media containing 200 µg/ml Vincristine and S109 at the indicated dose |
| Sim24 hr ADR0.1 | Cells were cultured for 24 hrs in the presence of 0.1 µg/ml adriamycin and the indicated dose of S109 (i.e., simultaneously) |
| Sim24 hr ADR0.5 | Cells were cultured for 24 hrs in the presence of 0.5 µg/ml adriamycin and the indicated dose of S109 (i.e., simultaneously) |
| Sim24 hr Melph 1 | Cells were cultured for 24 hrs in the presence of 1 µg/ml melpharan and the indicated dose of S109 (i.e., simultaneously) |
| Sim24 hr Melph 4 | Cells were cultured for 24 hrs in the presence of 4 µg/ml melpharan and the indicated dose of S109 (i.e., simultaneously) |
| 48 hr | Cells were cultured for 48 hrs without any additional anti-cancer treatment and in the presence of the indicated dose of S109 |
| Sim48 hr ADR0.1 | Cells were cultured for 48 hrs in the presence of 0.1 µg/ml adriamycin and the indicated dose of S109 (i.e., simultaneously) |
| Sim48 hr ADR0.5 | Cells were cultured for 48 hrs in the presence of 0.5 µg/ml adriamycin and the indicated dose of S109 (i.e., simultaneously) |
| Sim48 hr Melph 1 | Cells were cultured for 48 hrs in the presence of 1 µg/ml melpharan and the indicated dose of S109 (i.e., simultaneously) |
| Sim48 hr Melph 4 | Cells were cultured for 48 hrs in the presence of 1 µg/ml melpharan and the indicated dose of S109 (i.e., simultaneously) |
| Add at 24 hr | Cells were cultured for 24 hrs in media alone, then at 24 hrs, the indicated dose of S109 was added to the culture media and the cells were cultured for an additional 24 hrs |
| Pre ADR0.1 Add 24 hr | Cells were cultured for 24 hrs in media containing 0.1 µg/ml adriamycin, then at 24 hrs, the indicated dose of S109 was added to the adriamycin-containing media and cells were cultured in the presence of adriamycin and S109 for an additional 24 hrs |
| Pre ADR0.5 Add 24 hr | Cells were cultured for 24 hrs in media containing 0.5 µg/ml adriamycin, then at 24 hrs, the indicated dose of S109 was added to the adriamycin-containing media and cells were cultured in the presence of adriamycin and S109 for an additional 24 hrs |

| Key to Treatments in Tables 4-11 | |
| --- | --- |
| Pre Mel 1<br>Add 24 hr | Cells were cultured for 24 hrs in media containing 1 μg/ml melpharan, then at 24 hrs, the indicated dose of S109 was added to the melpharan-containing media and cells were cultured in the presence of melpharan and S109 for an additional 24 hrs |
| Pre Mel 4<br>Add 24 hr | Cells were cultured for 24 hrs in media containing 4 μg/ml melpharan, then at 24 hrs, the indicated dose of S109 was added to the melpharan-containing media and cells were cultured in the presence of melpharan and S109 for an additional 24 hrs |
| Add at 48 hr | Cells were cultured in media alone for 48 hrs, then at 48 hrs, the indicated dose of S109 was added and cells were cultured for an additional 24 hrs |
| Pre ADR0.1<br>Add 48 hr | Cells were cultured in media containing 0.1 μg/ml adriamycin for 48 hrs, then at 48 hrs, the indicated dose of S109 was added and cells were cultured in the presence of adriamycin and S109 for an additional 24 hrs |
| Pre ADR0.5<br>Add 48 hr | Cells were cultured in media containing 0.5 μg/ml adriamycin for 48 hrs, then at 48 hrs, the indicated dose of S109 was added and cells were cultured in the presence of adriamycin and S109 for an additional 24 hrs |
| Pre Mel 1<br>Add 48 hr | Cells were cultured in media containing 1 μg/ml melpharan for 48 hrs, then at 48 hrs, the indicated dose of S109 was added and cells were cultured in the presence of melpharan and S109 for an additional 24 hrs |
| Pre Mel 4<br>Add 48 hr | Cells were cultured in media containing 4 μg/ml melpharan for 48 hrs, then at 48 hrs, the indicated dose of S109 was added and cells were cultured in the presence of melpharan and S109 for an additional 24 hrs |

In Tables 4-11, results were reported as follows.

| Key to Results in Tables 4-11 | |
| --- | --- |
| horizontal arrow → | The cell cycle pattern (phenotype) seen after this treatment is the same as the pattern seen for control (non-treated) cells under corresponding conditions, OR the pattern for this S00109 dose is the same as the pattern seen at the next lower dose of S00109 |
| slightly G2↑ or slight G2↑ | The percentage of cells in the G2 phase (the G2 cell population) is slightly increased, by about 5-10% |
| slightly dead or slight dead↑ | The percentage of cells in the subG1 cell population (where subG1 is the phenotype of a dead cell) is slightly increased, i.e., about a 5-10% increase in the subG1 population |
| G2↑ | The percentage of cells in G2cell population is increased (10%-20%) |
| Dull G1 | When the results of cell sorting by flow cytometry are plotted, the shape of the peak representing the G1 cell population has become "dull" (more rounded, more diffusely distributed, usually with longer tails) compared with a "sharp" peak seen in other cell populations |

| Key to Results in Tables 4-11 | |
| --- | --- |
| S delay | The percentage of cells in S phase (the S phase population) has increased |
| G2↑Death↑ | The G2 cell population is increased by about 10%-20%, and the subG1 population (i.e., dead cells) is also increased |
| Freezing or Freezing? | The cell cycle pattern observed for this treatment combination was the same as the untreated control (no anti-cancer treatment and no S00109, same culture conditions) even though these cells were subjected to the specified treatment combination. |
| Dull G1 G2↓ | The shape of the peak representing the G1 cell population has become "dull" (see above) and the percentage of cells in G2 phase (the "G2 cell population") is decreased |
| G2↓ | The G2 cell population is decreased |
| G2 | The G2 cell population is slightly increased |
| S/G2 | The percentage of cells in S/G2 phase (the "S/G2 cell population") is slightly increased |
| S/G2↑ | The percentage of cells in S/G2 phase (the "S/G2 cell population") is significantly increased |
| Death | The subG1 cell population (dead cells) is increased |
| NON or Cycle | The cell cycle pattern for this cell population is the same as the pattern of the corresponding non-treated control cells, despite the fact that this cell population was treated as indicated. |
| Dull | When the results of cell sorting by flow cytometry are plotted, the shapes of all the peaks corresponding to cells in different cell cycle phases is "dull" (rounded, diffusely distributed, not "sharp") |

Results

The results show that S00109 had more severe cytotoxic effects on cancer cells and little or no cytotoxic effects on normal cells Alternately expressed, the results show that most cancer cells are more sensitive to S00109 and than are most normal cells These results are in agreement with the results of the ARH-77 xenograft tumor transplant experiments of Example 4, where treatment of xenograft tumor-bearing mice with S00109, S01860, S03518, S03405 or S03747 resulted in dramatic increases in the survival rates of the tumor-bearing mice, indicating that S00109, S01860, S03518, S03405 or S03747 has specifically killed or suppressed the ARH-77 (multiple myeloma) cells in the xenograft tumors without having cytotoxic effects on the normal cells or organs of the mouse host.

A. Normal Human Dermal Fibroblasts (NHDF)

Normal human dermal fibroblasts (NHDF) were treated as described in the first cell of each row of Table 4, and exposed to no S00109 (Column 2) or S00109 at the concentrations listed in Columns 3-9. The predominant phenotype for each treatment combination is described in the corresponding cell.

TABLE 4

Phenotype of normal human dermal fibroblast cells (NHDF) treated with S00109 alone, or in combination with anti-cancer treatments

| NHDF Treatment | No S109 | 0.0064 μM S109 | 0.032 μM S109 | 0.16 μM S109 | 0.8 μM S109 | 4 μM S109 | 20 μM S109 | 100 μM S109 |
| --- | --- | --- | --- | --- | --- | --- | --- | --- |
| alone 24 hr | | → | → | → | slightly G2↑ | slightly G2↑ | slightly G2↑ | Slightly dead |
| X-ray 10Gy 24 hr simul. stim. | G2↑ | → | → | → | → | → | → | → |
| X-ray 10Gy pre irrad. | G2↑ | → | → | → | → | → | → | → |
| MTX 0.4 24 hr | dull G1 | → | → | → | slightly G2↑ | slightly G2↑ | slightly G2↑ | slightly G2↑ |
| MTX 2 24 hr | dull G1 | → | → | → | slightly G2↑ | slightly G2↑ | slightly G2↑ | slightly G2↑ |

TABLE 4-continued

Phenotype of normal human dermal fibroblast cells (NHDF) treated with S00109 alone, or in combination with anti-cancer treatments

| NHDF Treatment | No S109 | 0.0064 µM S109 | 0.032 µM S109 | 0.16 µM S109 | 0.8 µM S109 | 4 µM S109 | 20 µM S109 | 100 µM S109 |
|---|---|---|---|---|---|---|---|---|
| MTX 10 24 hr | dull G1 | → | → | → | slightly G2↑ | slightly G2↑ | slightly G2↑ | slightly G2↑ |
| alone 3 hr 24 hr culture | | → | → | → | → | → | → | Slightly dead |
| CPT-11 50 | S delay | → | → | → | → | → | → | → |
| 5-FU 20 | Slight G2↑ | → | → | → | → | → | → | → |
| alone 3 hr 48 hr culture | | → | → | → | → | G2↑Death↑ | G2↑Death↑ | G2↑Death↑ |
| CDDP 3 | Slight G2↑ | → | → | → | G2↑ | G2↑ | G2↑Death↑ | G2↑Death↑ |
| CDDP 10 | G2↑ | → | → | → | G2↓ | Freezing | Freezing | Freezing |
| ADR 1 | G2↑ | → | → | → | → | → | → | → |
| Gemzar 0.016 | Dull G1 G2↓ | → | → | → | → | Freezing | Freezing | G2↑ |
| Gemzar 0.08 | G2↓ | → | → | → | → | → | → | G2↑ |
| Gemzar 0.4 | S/G2 | → | → | → | → | → | → | G2 |
| Gemzar 2 | S/G2↑ | → | → | → | → | → | → | → |
| Gemzar 10 | S/G2↑ | → | → | → | → | → | → | → |
| Gemzar 50 | S/G2↑ | → | → | → | → | → | → | → |
| Taxol 0.0032 | Death | → | → | → | → | → | M↑ | M↑ |
| Taxol 0.016 | Death | → | → | → | → | → | M↑ | M↑ |
| Taxol 0.08 | Death | → | → | → | → | → | M↑ | M↑ |
| Taxol 0.4 | Death | → | → | → | → | Freezing | Freezing | |
| Taxol 2 | Death | → | → | → | → | Freezing | Freezing | |
| Taxol 10 | Death | → | → | → | → | Freezing | Freezing | |

B. Normal Human Umbilical Endothelial Cells (HUVEC)

Normal human umbilical endothelial cells (HUVEC) were treated as described in the first cell of each row of Table 5, and exposed to no S00109 (Column 2) or S00109 at the concentrations listed in Columns 3-9. The predominant phenotype for each treatment combination is described in the corresponding cell.

TABLE 5

Phenotype of normal human umbilical endothelial cells (HUVEC) treated with S00109 alone or in combination with anti-cancer treatments

| HUVEC Treatment | No S109 | 0.0064 µM S109 | 0.032 µM S109 | 0.16 µM S109 | 0.8 µM S109 | 4 µM S109 | 20 µM S109 | 100 µM S109 |
|---|---|---|---|---|---|---|---|---|
| alone 24 hr | | → | → | → | slightly G2↑ | slightly G2↑ | slightly G2↑ | Slightly dead |
| X-ray 10Gy 24 hr simul. stim. | G2↑ | → | → | → | → | → | → | → |
| X-ray 10Gy pre irrad. | G2↑ | → | → | → | → | → | → | → |
| MTX 0.4 24 hr | S/G2↑ | → | → | Cycle? | Cycle? | Cycle? | Cycle? | Slightly dead |
| MTX 2 24 hr | S/G2↑ | → | → | Cycle? | Cycle? | Cycle? | Cycle? | Slightly dead |
| MTX 10 24 hr | S/G2↑ | → | → | → | → | → | → | → |
| alone 3 hr 24 hr culture | | → | → | → | → | → | → | → |
| CPT-11 50 | S delay | → | → | → | → | → | → | → |
| 5-FU 20 | Slight G2↑ | → | → | → | → | → | → | → |
| alone 3 hr 48 hr culture | | → | → | → | → | → | → | → |
| CDDP 3 | Slight G2↑ | → | → | → | → | G2↑ | G2↑ | G2↑ |
| CDDP 10 | G2↑ | → | → | → | → | → | Freezing? | Freezing? |
| ADR 1 | Death G2↑ | → | → | → | → | → | → | Death |
| Gemzar 0.016 | Death | → | → | → | → | Freezing? | Freezing? | Freezing? |
| Gemzar 0.08 | Death | → | → | → | → | → | Freezing? | Freezing? |
| Gemzar 0.4 | Death | → | → | → | → | → | Freezing? | Freezing? |

TABLE 5-continued

Phenotype of normal human umbilical endothelial cells (HUVEC) treated with S00109 alone or in combination with anti-cancer treatments

| HUVEC Treatment | No S109 | 0.0064 µM S109 | 0.032 µM S109 | 0.16 µM S109 | 0.8 µM S109 | 4 µM S109 | 20 µM S109 | 100 µM S109 |
|---|---|---|---|---|---|---|---|---|
| Gemzar 2 | Death | → | → | → | → | → | Freezing? | Freezing? |
| Gemzar 10 | Death | → | → | → | → | → | Freezing? | Freezing? |
| Gemzar 50 | Death | → | → | → | → | → | Freezing? | Freezing? |
| Taxol 0.0032 | Death | → | → | → | → | → | → | → |
| Taxol 0.016 | Death | → | → | → | → | → | → | → |
| Taxol 0.08 | Death | → | → | → | → | → | → | Freezing? |
| Taxol 0.4 | Death | → | → | → | → | → | Freezing? | Freezing? |
| Taxol 2 | Death | → | → | → | → | → | Freezing? | Freezing? |
| Taxol 10 | M arrest | → | → | → | → | → | Freezing? | Freezing? |

C. Human Pancreatic Cancer-Derived Cell Line MIA-PaCa2

Cells of the human pancreatic cancer-derived cell line MIAPaCa2 were treated as described in the first cell of each row of Table 6, and exposed to no S00109 (Column 2) or S00109 at the concentrations listed in Columns 3-7. The predominant phenotype for each treatment combination is described in the corresponding cell.

TABLE 6

Phenotype of human pancreatic cancer cell line (MIAPaCa2) treated with S00109 alone or in combination with anti-cancer treatments

| MIAPaCa2 Treatment | No S109 | 0.032 µM S109 | 0.16 µM S109 | 0.8 µM S109 | 4 µM S109 | 20 µM S109 |
|---|---|---|---|---|---|---|
| alone 24 hr | NON | NON | NON | SG2↓ | SG2↓ | SG2↓ |
| X-ray 2Gy 24 hr simul. stim. | NON | NON | NON | SG2↓ | SG2↓ | SG2↓ |
| X-ray 10Gy 24 hr simul. stim. | G2↑ | → | → | → | G1↑ G2↓ | G1↑ G2↓ |
| X-ray 2Gy pre irrad. | G2↑ | → | SG2↓ | SG2↓ | SG2↓ | SG2↓ |
| X-ray 10Gy pre irrad. | G2↑ | → | G1↑ | G1↑ G2↓ | G1↑ G2↓ | G1↑ G2↓ |
| MTX 0.12 24 hr | SG2↓ | → | → | → | → | → |
| MTX 0.6 24 hr | SG2↓ | → | → | → | → | → |
| MTX 3 24 hr | SG2↓ | → | → | → | → | → |
| alone 3 hr 24 hr culture | NON | NON | NON | NON | NON | SG2↓ |
| CPT-11 50 | G2↑ | → | → | → | → | G1↑ G2↓ |
| 5-FU 20 | SG2↓ | → | → | → | → | → |
| alone 3 hr 48 hr culture | NON | NON | NON | NON | NON | NON |
| CDDP 3 | Slight G2↑ | → | → | → | → | → |
| CDDP 10 | G2↑ | → | → | → | → | G2↓ |
| ADR 1 | SG2↑ | → | → | → | → | G2↓ Death↑ |
| Gemzar 2 | SG2↓ | → | → | → | → | SG2↓ |
| Gemzar 10 | G1↓ | → | → | → | → | SG2↓ |
| Gemzar 50 | Dull | → | Dead | → | → | SG2↓ |
| Taxol 0.4 | Death | → | → | → | G2↑ | G2↑ |
| Taxol 2 | Death | → | → | → | → | G2↑ |
| Taxol 10 | Death | → | → | G2↑ | G2↑ | G2↑ |

D. Human Colon Cancer-Derived Cell Line HCT116

Cells of the human colon cancer-derived cell line HCT116 were treated as described in the first cell of each row of Table 7, and exposed to no S00109 (Column 2) or S00109 at the concentrations listed in Columns 3-8. The predominant phenotype for each treatment combination is described in the corresponding cell.

TABLE 7

Phenotype of human colon cancer cell line (HCT116) treated with S00109 alone or in combination with anti-cancer treatments

| HCT116 Treatment | No S109 | 0.032 μM S109 | 0.16 μM S109 | 0.8 μM S109 | 4 μM S109 | 20 μM S109 | 100 μM S109 |
|---|---|---|---|---|---|---|---|
| alone 24 hr | NON | NON | NON | S↓ | G2↑ | G2↑Death↑ | ND |
| X-ray 2Gy 24 hr simul. stim. | NON | NON | NON | S↓ | G2↑↑ | G2↑Death↑ | |
| X-ray 10Gy 24 hr simul. stim. | G2↑ | → | → | → | → | → | |
| X-ray 2Gy pre irrad. | NON | NON | NON | Death↑ | G2↑Death↑ | G2↑Death↑ | |
| X-ray 10Gy pre irrad. | G2↑ | → | → | → | Death | Death | |
| MTX 0.12 24 hr | G2↓ | → | → | → | → | → | |
| MTX 0.6 24 hr | G2↓ | → | → | → | → | → | |
| MTX 3 24 hr | G2↓ | → | → | → | → | → | |
| alone 3 hr 24 hr culture | NON | NON | NON | G2↑ | G2↑ | S↓ | |
| CPT-11 50 | G2↑ | → | → | → | G1 | G1↑ | |
| 5-FU 20 | NON | NON | NON | NON | NON | NON | |
| alone 3 hr 48 hr culture | NON | NON | NON | NON | NON | NON | |
| CDDP 3 | Slight G2↑ | → | → | → | → | → | |
| CDDP 10 | G2↑ | → | → | → | → | Death | |
| ADR 1 | G2↑ | | | Death↑ | G2↓Death↑ | G2↓Death↑ | |
| Gemzar 2 | Death G2↓ | → | → | → | → | Death | |
| Gemzar 10 | Death G2↓ | → | → | → | Death | Death | |
| Gemzar 50 | Death G2↓ | → | → | → | Death | Death | |
| Taxol 0.4 | Death | | | Death↑ | M↓Death↑ | M↓Death↑ | |
| Taxol 2 | Death | | | M↓Death↑ | M↓Death↑ | M↓Death↑ | |
| Taxol 10 | Death | | | | M↓Death↑ | M↓Death↑ | |

E. Human Multiple Myeloma-Derived Cell Line IM9

Cells of human multiple myeloma-derived cell line IM9 were treated as described in the first cell of each row of Table 8, and exposed to no S00109 (Column 2, Table 8A) or S00109 at the concentrations listed in Columns 3-7 of Table 8A and Columns 2-7 of Table 8B. The predominant phenotype for each treatment combination is described in the corresponding cell.

Table 8. Phenotype of human multiple myeloma cell line (IM9) treated with S00109 alone or in combination with anti-cancer treatments

TABLE 8A

Results for no S00109, and 0.02 to 0.3125 μM S00109

| IM9 Treatment | No S109 | 0.02 μM S109 | 0.039 μM S109 | 0.078 μM S109 | 0.156 μM S109 | 0.3125 μM S109 |
|---|---|---|---|---|---|---|
| X-ray 10Gy preirrad. 24 hr | G2↑Death | → | → | → | → | → |
| | | | S/G2↓ | S/G2↓ | S/G2↓ | S/G2↓Death↑ |
| Velcade 3 | → | → | → | → | → | G1↑S↓ |
| Velcade 6 | → | S/G2↓ | S/G2↓ | S/G2↓ | S/G2↓ | S/G2↓ |
| Vincristine 2 | → | → | G1↑ | G1↑S↓ | G1↑S↓ | G1↑S↓ |
| Vincristine 20 | Death S↓ | G1↑ | G1↑ | G1↑ | G1↑ | G1↑ |
| Dexamethasone 2 | → | → | → | → | → | S/G2↓Death↑ |
| Dexamethasone 20 | → | → | → | → | G1↑ | G1↑S↓ | S↓Death↑ |
| Dexamethasone 200 | → | → | → | → | G1↑S↓ | S↓Death↑ |
| Sim24hr ADR0.1 | G2↑ | | G1↑S/G2↓ | G1↑S/G2↓ | S/G2↓Death↑ | S/G2↓Death↑ |
| Sim24hr ADR0.5 | G2↑Death | | G1↑S/G2↓ | G1↑S/G2↓ | S/G2↓Death↑ | S/G2↓Death↑ |
| Sim24hr Melph 1 | S/G2↑ | | G1↑S/G2↓ | G1↑S/G2↓ | S/G2↓Death↑ | S/G2↓Death↑ |
| Sim24hr Melph 4 48 hr | S/G2↑ | | G1↑S/G2↓ | G1↑S/G2↓ | S/G2↓Death↑ | S/G2↓Death↑ |
| | | | → | → | Death↑ | Death↑ |
| Sim48hr ADR0.1 | G2↑Death | | G1↑S/G2↓ | G1↑S/G2↓ | S/G2↓Death↑ | S/G2↓Death↑ |
| Sim48hr ADR0.5 | G2↑Death | | G1↑S/G2↓ | G1↑S/G2↓ | G1↑S/G2↓ | G1↑S/G2↓ |
| Sim48hr Melph 1 | → | | G2↑ | G2↑Death↑ | G2↑Death↑ | S/G2↓Death↑ |
| Sim48hr Melph 4 | G2↑Death | | S/G2↓Death↑ | S/G2↓Death↑ | S/G2↓Death↑ | S/G2↓Death↑ |
| Add at 24 hr | | | → | → | G1↑ | G1↑ |

TABLE 8A-continued

Results for no S00109, and 0.02 to 0.3125 μM S00109

| IM9 Treatment | No S109 | 0.02 μM S109 | 0.039 μM S109 | 0.078 μM S109 | 0.156 μM S109 | 0.3125 μM S109 |
|---|---|---|---|---|---|---|
| Pre ADR0.1 Add 24 hr | G2↑Death | | → | → | → | → |
| Pre ADR0.5 Add 24 hr | Death | | → | G2↓ | G2↓ | → |
| Pre Mel 1 Add 24 hr | → | | → | G2↑ | G2↑ | G2↑ |
| Pre Mel 4 Add 24 hr | G2↑Death | | → | → | → | S/G2↓Death↑ |
| Pre S109 Add 24 hr ADR0.1 | G2↑Death | | → | → | → | → |
| Pre S109 Add 24 hr ADR0.5 | Death | | → | → | → | → |
| Pre S109 Add 24 hr Mel 1 | → | | → | → | → | → |
| Pre S109 Add 24 hr Mel 4 | → | | → | → | → | → |

TABLE 8B

Results for 0.625 to 20 μM S00109

| IM9 Treatment | 0.625 μM S109 | 1.25 μM S109 | 2.5 μM S109 | 5 μM S109 | 10 μM S109 | 20 μM S109 |
|---|---|---|---|---|---|---|
| X-ray 10Gy preirrad. 24 hr | → | → | → | → | → | → |
| | S/G2↓Death↑ | S↓Death↑ | S↓Death↑ | S↓Death↑ | S↓Death↑ | S↓Death↑ |
| Velcade 3 | G1↑S↓Death↑ | G1↑S↓Death↑ | G1↑S↓Death↑ | G1↑S↓Death↑ | G1↑S↓Death↑ | G1↑S↓Death↑ |
| Velcade 6 | S↓Death↑ | S↓Death↑ | S↓Death↑ | S↓Death↑ | S↓Death↑ | S↓Death↑ |
| Vincristine 2 | S↓Death↑ | S↓Death↑ | S↓Death↑ | S↓Death↑ | S↓Death↑ | S↓Death↑ |
| Vincristine 20 | Death↑ | Death↑ | Death↑ | Death↑ | Death↑ | Death↑ |
| Dexamethasone 2 | S/G2↓Death↑ | S/G2↓Death↑ | S/G2↓Death↑ | S/G2↓Death↑ | S/G2↓Death↑ | S/G2↓Death↑ |
| Dexamethasone 20 | S↓Death↑ | S↓Death↑ | S↓Death↑ | S↓Death↑ | S↓Death↑ | S↓Death↑ |
| Dexamethasone 200 | S↓Death↑ | S↓Death↑ | S↓Death↑ | S↓Death↑ | S↓Death↑ | S↓Death↑ |
| Sim24hr ADR0.1 | S/G2↓Death↑ | S/G2↓Death↑ | S/G2↓Death↑ | S/G2↓Death↑ | S/G2↓Death↑ | S/G2↓Death↑ |
| Sim24hr ADR0.5 | S/G2↓Death↑ | S/G2↓Death↑ | S/G2↓Death↑ | S/G2↓Death↑ | S/G2↓Death↑ | S/G2↓Death↑ |
| Sim24hr Melph 1 | S/G2↓Death↑ | S/G2↓Death↑ | S/G2↓Death↑ | S/G2↓Death↑ | S/G2↓Death↑ | S/G2↓Death↑ |
| Sim24hr Melph 4 | S/G2↓Death↑ | S/G2↓Death↑ | S/G2↓Death↑ | S/G2↓Death↑ | S/G2↓Death↑ | S/G2↓Death↑ |
| 48 hr | Death↑ | Death↑ | Death↑ | Death↑ | Death↑ | Death↑ |
| Sim48hr ADR0.1 | S/G2↓Death↑ | S/G2↓Death↑ | S/G2↓Death↑ | S/G2↓Death↑ | S/G2↓Death↑ | S/G2↓Death↑ |
| Sim48hr ADR0.5 | G1↑S/G2↓ | G1↑S/G2↓ | G1↑S/G2↓ | G1↑S/G2↓ | G1↑S/G2↓ | S/G2↓Death↑ |
| Sim48hr Melph 1 | S/G2↓Death↑ | S/G2↓Death↑ | S/G2↓Death↑ | S/G2↓Death↑ | S/G2↓Death↑ | S/G2↓Death↑ |
| Sim48hr Melph 4 | S/G2↓Death↑ | S/G2↓Death↑ | S/G2↓Death↑ | S/G2↓Death↑ | S/G2↓Death↑ | S/G2↓Death↑ |
| Add at 24 hr | G1↑ | non | non | non | G1↓G2↑Death↑ | G1↓G2↑Death↑ |
| Pre ADR0.1 Add 24 hr | → | → | → | → | → | G2↓ |
| Pre ADR0.5 Add 24 hr | → | → | → | Death↑ | Death↑ | Death↑ |
| Pre Mel 1 Add 24 hr | G2↑Death↑ | → | → | → | → | → |
| Pre Mel 4 Add 24 hr | → | → | → | → | → | → |
| Pre S109 Add 24 hr ADR0.1 | → | → | → | → | → | → |
| Pre S109 Add 24 hr ADR0.5 | → | → | → | → | → | → |
| Pre S109 Add 24 hr Mel 1 | → | → | → | → | → | → |
| Pre S109 Add 24 hr Mel 4 | → | → | → | → | → | Death |

F. Human Multiple Myeloma-Derived Cell Line ARH-77

Cells of human multiple myeloma-derived cell line ARH-77 were treated as described in the first cell of each row of Table 9, and exposed to no S00109 (Table 9A, Column 2) or S00109 at the concentrations listed in Columns 3-7 of Table 9A and 2-7 of Table 9B. The predominant phenotype for each treatment combination is described in the corresponding cell.

Table 9. Phenotype of Human Multiple Myeloma Cell Line (ARH-77) Treated with S00109 alone or in Combination with Anti-Cancer Treatments.

TABLE 9A

Results for no S00109, and 0.02 to 0.3125 µM S00109

| ARH-77 Treatment | No S109 | 0.02 µM S109 | 0.039 µM S109 | 0.078 µM S109 | 0.156 µM S109 | 0.3125 µM S109 |
|---|---|---|---|---|---|---|
| X-ray 10Gy preirrad. 24 hr | G2↑Death | → | → | → | → | → |
| Velcade 3 | | | G1↑G2↓ | G1↑G2↓ | G1↑G2↓ | Death↑G2↓ |
| Velcade 6 | Death | → | → | G1↑G2↓ | G1↑G2↓ | S/G2↓Death↑ |
| Vincristine 2 | Death | → | → | → | → | Death↑G2↓ |
| Vincristine 20 | Death M↑ | G1↑ | G1↑ | G1↑ | G1↑ | G1↑ |
| Dexamethasone 2 | Death | G1↑ | G1↑ | G1↑ | G1↑ | Death↑ |
| Dexamethasone 20 | Death | → | → | → | Death↑G2↓ | Death↑G2↓ |
| Dexamethasone 200 | Death | → | Death↑G2↓ | Death↑G2↓ | Death↑G2↓ | Death↑G2↓ |
| Sim24hr ADR0.1 | G2↑ | → | Death↑G2↓ | Death↑G2↓ | Death↑G2↓ | Death↑G2↓ |
| Sim24hr ADR0.5 | G2↑Death | G1↑S/G2↓ | G1↑S/G2↓ | S/G2↓Death↑ | S/G2↓Death↑ | |
| Sim24hr Melph 1 | S/G2↑ | G1↑S/G2↓ | G1↑S/G2↓ | S/G2↓Death↑ | S/G2↓Death↑ | S/G2↓Death↑ |
| Sim24hr Melph 4 48 hr | S/G2↑ | → | G1↑S/G2↓ | S/G2↓Death↑ | S/G2↓Death↑ | S/G2↓Death↑ |
| Sim48hr ADR0.1 | G2↑ | → | → | S/G2↓Death↑ | S/G2↓Death↑ | S/G2↓Death↑ |
| Sim48hr ADR0.5 | G2↑Death | G1↑S/G2↓ | G1↑S/G2↓ | G1↑S/G2↓ | G1↑S/G2↓ | |
| Sim48hr Melph 1 | | → | → | S/G2↓Death↑ | S/G2↓Death↑ | |
| Sim48hr Melph 4 | G2↑Death | S/G2↓Death↑ | S/G2↓Death↑ | S/G2↓Death↑ | S/G2↓Death↑ | |
| Add at 24 hr | → | → | → | → | → | |
| Pre ADR0.1 Add 24 hr | G2↑Death | → | → | → | → | |
| Pre ADR0.5 Add 24 hr | G2↑Death | → | → | G2↓ | → | |
| Pre Mel 1 Add 24 hr | → | → | G2↑ | G2↑ | G2↑Death↑ | |
| Pre Mel 4 Add 24 hr | G2↑Death | G2↓Death↑ | → | → | → | |
| Add at 48 hr | → | → | → | → | → | |
| Pre ADR0.1 Add 48 hr | G2↑Death | → | → | → | → | |
| Pre ADR0.5 Add 48 hr | G2↑Death | → | → | → | → | |
| Pre Mel 1 Add 48 hr | → | → | → | → | → | |
| Pre Mel 4 Add 48 hr | G2↑Death | → | → | → | → | |

TABLE 9B

Results for 0.625 to 20 µM S00109

| ARH-77 Treatment | 0.625 µM S109 | 1.25 µM S109 | 2.5 µM S109 | 5 µM S109 | 10 µM S109 | 20 µM S109 |
|---|---|---|---|---|---|---|
| X-ray 10Gy preirrad. 24 hr | → | → | → | → | Death | Death |
| Velcade 3 | Death↑G2↓ | Death↑G2↓ | Death↑G2↓ | Death↑G2↓ | Death↑G2↓ | Death↑G2↓ |
| Velcade 6 | S/G2↓Death↑ | S/G2↓Death↑ | S/G2↓Death↑ | S/G2↓Death↑ | S/G2↓Death↑ | S/G2↓Death↑ |
| Vincristine 2 | Death↑G2↓ | Death↑G2↓ | Death↑G2↓ | Death↑G2↓ | Death↑G2↓ | Death↑G2↓ |
| Vincristine 20 | G1↑ | G1↑ | G1↑ | G1↑ | G1↑ | G1↑ |
| Dexamethasone 2 | Death↑ | Death↑ | Death↑ | Death↑ | Death↑ | Death↑ |
| Dexamethasone 20 | Death↑G2↓ | Death↑G2↓ | Death↑G2↓ | Death↑G2↓ | Death↑G2↓ | Death↑G2↓ |
| Dexamethasone 200 | Death↑G2↓ | Death↑G2↓ | Death↑G2↓ | Death↑G2↓ | Death↑G2↓ | Death↑G2↓ |
| Sim24hr ADR0.1 | S/G2↓Death↑ | S/G2↓Death↑ | S/G2↓Death↑ | S/G2↓Death↑ | S/G2↓Death↑ | S/G2↓Death↑ |
| Sim24hr ADR0.5 | S/G2↓Death↑ | S/G2↓Death↑ | S/G2↓Death↑ | S/G2↓Death↑ | S/G2↓Death↑ | S/G2↓Death↑ |
| Sim24hr Melph 1 | S/G2↓Death↑ | S/G2↓Death↑ | S/G2↓Death↑ | S/G2↓Death↑ | S/G2↓Death↑ | S/G2↓Death↑ |
| Sim24hr Melph 4 48 hr | S/G2↓Death↑ | S/G2↓Death↑ | S/G2↓Death↑ | S/G2↓Death↑ | S/G2↓Death↑ | S/G2↓Death↑ |

TABLE 9B-continued

| Results for 0.625 to 20 µM S00109 | | | | | | |
|---|---|---|---|---|---|---|
| ARH-77 Treatment | 0.625 µM S109 | 1.25 µM S109 | 2.5 µM S109 | 5 µM S109 | 10 µM S109 | 20 µM S109 |
| Sim48hr ADR0.1 | S/G2↓Death↑ | S/G2↓Death↑ | S/G2↓Death↑ | S/G2↓Death↑ | S/G2↓Death↑ | S/G2↓Death↑ |
| Sim48hr ADR0.5 | G1↑S/G2↓ | G1↑S/G2↓ | G1↑S/G2↓ | G1↑S/G2↓ | G1↑S/G2↓ | S/G2↓Death↑ |
| Sim48hr Melph 1 | S/G2↓Death↑ | S/G2↓Death↑ | S/G2↓Death↑ | S/G2↓Death↑ | S/G2↓Death↑ | S/G2↓Death↑ |
| Sim48hr Melph 4 | S/G2↓Death↑ | S/G2↓Death↑ | S/G2↓Death↑ | S/G2↓Death↑ | S/G2↓Death↑ | S/G2↓Death↑ |
| Add at 24 hr | → | → | G2↑Death↑ | G2↑Death↑ | G2↑Death↑ | G2↑Death↑ |
| Pre ADR0.1 Add 24 hr | → | G1↓Death↑ | → | → | → | → |
| Pre ADR0.5 Add 24 hr | → | → | → | → | → | → |
| Pre Mel 1 Add 24 hr | → | → | → | → | → | → |
| Pre Mel 4 Add 24 hr | → | → | → | → | → | → |
| Add at 48 hr | → | → | → | → | → | → |
| Pre ADR0.1 Add 48 hr | → | → | → | → | → | → |
| Pre ADR0.5 Add 48 hr | → | → | → | → | → | → |
| Pre Mel 1 Add 48 hr | → | → | → | → | Death↑ | Death↑ |
| Pre Mel 4 Add 48 hr | → | → | Death↑ | → | → | → |

G. Human Multiple Myeloma-Derived Cell Line RPMI-8226

Cells from human multiple myeloma-derived cell line RPMI-8226 were treated as described in the first cell of each row of Table 10, and exposed to no S00109 (Column 2, Table 10A) or S00109 at the concentrations listed in Columns 3-7 of Column 10A and Columns 2-7 of Column 10B. The predominant phenotype for each treatment combination is described in the corresponding cell.

Table 10. Phenotype of Human Multiple Myeloma Cell Line (RPMI-8226) Treated with S00109 Alone or in Combination with Anti-Cancer Treatments

TABLE 10A

| Results for no S00109, and 0.02 to 0.3125 µM S00109 | | | | | | |
|---|---|---|---|---|---|---|
| RPMI-8226 Treatment | No S109 | 0.02 µM S109 | 0.039 µM S109 | 0.078 µM S109 | 0.156 µM S109 | 0.3125 µM S109 |
| X-ray 10Gy preirrad. 24 hr | G2↑Death | → | → | G2↓ | G1↑G2↓ | G1↑G2↓ |
| Sim24hr ADR0.1 | → | → | → | → | G2↓ | G2↓ |
| Sim24hr Melph 1 | S arrest | | → | → | → | G1↑S/G2↓ |
| Sim24hr Melph 4 | S arrest | | → | → | → | G1↑ |
| 48 hr | | | → | G1↑S/G2↓ | DeathG1↑ S/G2↓ | S/G2↓Death↑ |
| Velcade 3 | Death | Death | Death | Death | Death | Death |
| Velcade 6 | Death | Death | Death | Death | Death | Death |
| Vincristine 2 | Death | Death | Death | Death | Death | Death |
| Vincristine 20 | Death | Death | Death | Death | Death | Death |
| Dexamethasone 2 | | | Death↑ | Death↑ | S/G2↓Death↑ | S/G2↓Death↑ |
| Dexamethasone 20 | S/G2↓Death↑ | | G1↑ | G1↑ | G1↑ | G1↑ |
| Dexamethasone 200 | Death | | S/G2↓Death↑ | S/G2↓Death↑ | S/G2↓Death↑ | S/G2↓Death↑ |
| Sim48hr ADR0.1 | G2↑ | | → | → | → | G1↑S/G2↓ |
| Sim48hr Melph 1 | → | | → | → | → | → |
| Sim48hr Melph 4 | G2↑ | | → | → | G1↑S/G2↓ | G1↑S/G2↓ |
| Add at 48 hr | | | → | → | → | → |
| Pre ADR0.1 Add 48 hr | G2↑ | | → | → | → | → |
| Pre Mel 1 Add 48 hr | → | | → | → | → | → |
| Pre Mel 4 Add 48 hr | G2↑ | | → | → | → | → |

TABLE 10B

| | Results for 0.625 to 20 μM S00109 | | | | | |
|---|---|---|---|---|---|---|
| RPMI-8226 Treatment | 0.625 μM S109 | 1.25 μM S109 | 2.5 μM S109 | 5 μM S109 | 10 μM S109 | 20 μM S109 |
| X-ray 10Gy preirrad. | → | → | → | → | → | → |
| 24 hr | G1↑G2↓ | G1↑G2↓ | G1↑G2↓ | G1↑G2↓ | Death↑G2↓ | Death↑G2↓ |
| Sim24hr ADR0.1 | G2↓ | G2↓ | G2↓ | G2↓ | Death↑G2↓ | Death↑G2↓ |
| Sim24hr Melph 1 | G1↑S/G2↓ | G1↑S/G2↓ | G1↑S/G2↓ | G1↑S/G2↓ | G1↑S/G2↓ | G1↑S/G2↓ |
| Sim24hr Melph 4 | G1↑ | G1↑ | G1↑ | G1↑ | G1↑ | G1↑ |
| 48 hr | S/G2↓Death↑ | S/G2↓Death↑ | S/G2↓Death↑ | S/G2↓Death↑ | S/G2↓Death↑ | S/G2↓Death↑ |
| Velcade 3 | Death | Death | Death | Death | Death | Death |
| Velcade 6 | Death | Death | Death | Death | Death | Death |
| Vincristine 2 | Death | Death | Death | Death | Death | Death |
| Vincristine 20 | Death | Death | Death | Death | Death | Death |
| Dexamethasone 2 | S/G2↓Death↑ | S/G2↓Death↑ | S/G2↓Death↑ | S/G2↓Death↑ | S/G2↓Death↑ | S/G2↓Death↑ |
| Dexamethasone 20 | G1↑ | G1↑ | G1↑Death↑ | G1↑Death↑ | G1↑Death↑ | G1↑Death↑ |
| Dexamethasone 200 | S/G2↓Death↑ | S/G2↓Death↑ | S/G2↓Death↑ | S/G2↓Death↑ | S/G2↓Death↑ | S/G2↓Death↑ |
| Sim48hr ADR0.1 | G1↑S/G2↓ | G1↑S/G2↓ | G1↑S/G2↓ | G1↑S/G2↓ | G1↑S/G2↓ | G1↑S/G2↓ |
| Sim48hr Melph 1 | → | → | Death | Death | Death | Death |
| Sim48hr Melph 4 | G1↑S/G2↓ | G1↑S/G2↓ | G1↑S/G2↓ | G1↑S/G2↓ | Death↑G2↓ | Death↑G2↓ |
| Add at 48 hr | → | → | → | → | → | → |
| Pre ADR0.1 Add 48 hr | → | → | → | → | → | → |
| Pre Mel 1 Add 48 hr | → | → | → | → | → | → |
| Pre Mel 4 Add 48 hr | → | → | → | → | → | → |

H. Human Myeloma-Derived Cell Line NCI-H929

Cells of human myeloma-derived cell line NCI-H929 were treated as described in the first cell of each row of Table 11, and exposed to no S00109 (Column 2, Table 11A) or S00109 at the concentrations listed in Columns 3-7 of Table 11A and Columns 2-7 of Table 11B. The predominant phenotype for each treatment combination is described in the corresponding cell.

Table 11. Phenotype of Human Multiple Myeloma Cell Line (NCI-H929) Treated with S00109 Alone or in Combination with Anti-Cancer Treatments

TABLE 11A

| | Results for no S00109, and 0.02 to 0.3125 μM S00109 | | | | | |
|---|---|---|---|---|---|---|
| NCI-H929 Treatment | No S109 | 0.02 μM S109 | 0.039 μM S109 | 0.078 μM S109 | 0.156 μM S109 | 0.3125 μM S109 |
| X-ray 10Gy preirrad. | Slight G2↑Death | → | → | → | → | → |
| 24 hr | | | → | → | → | → |
| Sim24hr ADR0.1 | G2↑ | → | → | → | G1↑S/G2↓ | G1↑S/G2↓ |
| Sim24hr ADR0.5 | SG2↑ | → | → | → | → | → |
| Sim24hr Melph 0.25 | → | → | → | → | → | → |
| Sim24hr Melph 1 | → | → | → | → | → | → |
| Sim24hr Melph 4 | SG2↑ | → | G1↑S/G2↓ | G1↑S/G2↓ | G1↑S/G2↓ | G1↑S/G2↓ |
| 48 hr | | | → | → | Death | Death |
| Sim48hr ADR0.1 | G2↑ | → | → | → | → | S/G2↓ |
| Sim48hr ADR0.5 | Death | → | → | → | → | → |
| Sim48hr Melph 0.25 | → | → | → | → | → | Death |
| Sim48hr Melph 1 | → | → | → | → | → | Death |
| Sim48hr Melph 4 | G2↑ | → | → | → | → | Death |
| Add at 48 hr | | → | → | → | → | → |
| Pre ADR0.1 Add 48 hr | Death G2↑ | → | → | → | → | S/G2↓Death↑ |
| Pre ADR0.5 Add 48 hr | Death | → | → | → | → | → |
| Pre Mel0.25 Add 48 hr | → | → | → | → | → | → |

TABLE 11A-continued

Results for no S00109, and 0.02 to 0.3125 µM S00109

| NCI-H929 Treatment | No S109 | 0.02 µM S109 | 0.039 µM S109 | 0.078 µM S109 | 0.156 µM S109 | 0.3125 µM S109 |
|---|---|---|---|---|---|---|
| Pre Mel 1 Add 48 hr | → | | → | → | → | → |
| Pre Mel 4 Add 48 hr | SG2↑ | | → | → | → | → |

TABLE 11B

Results for Results for 0.625 to 20 µM S00109

| NCI-H929 Treatment | 0.625 µM S109 | 1.25 µM S109 | 2.5 µM S109 | 5 µM S109 | 10 µM S109 | 20 µM S109 |
|---|---|---|---|---|---|---|
| X-ray 10Gy preirrad. 24 hr | Death↑G2↓ → | Death↑G2↓ → | Death↑G2↓ → | Death↑G2↓ Death | Death↑G2↓ Death | Death↑G2↓ Death |
| Sim24hr ADR0.1 | G1↑S/G2↓ | G1↑S/G2↓ | G1↑S/G2↓ | G1↑S/G2↓ | G1↑S/G2↓ | G1↑S/G2↓ |
| Sim24hr ADR0.5 | → | → | → | → | → | → |
| Sim24hr Melph 0.25 | → | → | Death | Death | Death | Death |
| Sim24hr Melph 1 | → | → | → | → | Death | Death |
| Sim24hr Melph 4 48 hr | G1↑S/G2↓ Death | G1↑S/G2↓ Death | Death Death | Death Death | Death Death | Death Death |
| Sim48hr ADR0.1 | S/G2↓ | Death↑G2↓ | Death↑G2↓ | Death↑G2↓ | Death↑G2↓ | Death↑G2↓ |
| Sim48hr ADR0.5 | → | → | → | → | → | → |
| Sim48hr Melph 0.25 | Death | Death | Death | Death | Death | Death |
| Sim48hr Melph 1 | Death | Death | Death | Death | Death | Death |
| Sim48hr Melph 4 | Death | Death | Death | Death | Death | Death |
| Add at 48 hr | Death | Death | Death | Death | Death | Death |
| Pre ADR0.1 Add 48 hr | → | → | → | → | → | → |
| Pre ADR0.5 Add 48 hr | → | → | → | → | → | Death |
| Pre Mel0.25 Add 48 hr | Death | Death | Death | Death | Death | Death |
| Pre Mel 1 Add 48 hr | Death | Death | Death | Death | Death | Death |
| Pre Mel 4 Add 48 hr | → | → | → | → | Death | Death |

Example 8

Synthesis of Representative Compounds

The following examples are intended to serve as illustrations, and all compounds of this invention could be synthesized using methods similar to those described in these examples.

General Procedure for the Synthesis of Substituted 2-pyridylhydrazines

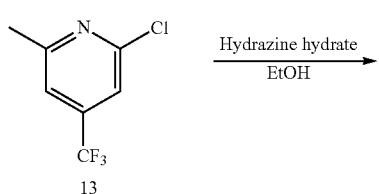

13

-continued

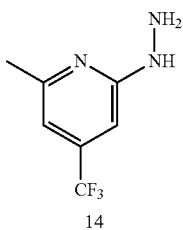

14

The general procedure for the synthesis of substituted 2-pyridylhydrazines is represented here in the synthesis of 4-(trifluoromethyl)-6-methyl-2-pyridylhydrazine (14). One equivalent of 2-chloro-4-(trifluoromethyl)-6-methylpyridine (13) and 1.5 equivalent of hydrazine hydrate were mixed in ethanol. The solution turned yellow after being stirred for several minutes. The reaction mixture was refluxed until TLC analysis showed no starting material left. The solvent was then removed under vacuum, and the resulting slurry was extracted with ether three times. The combined ether solution was dried over anhydrous MgSO$_4$ and evaporated to afford the crude product, which was then re-crystallized from ethanol to give compound 14.

Synthesis of S00069

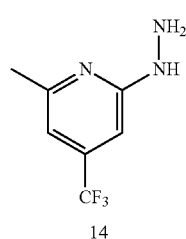
14

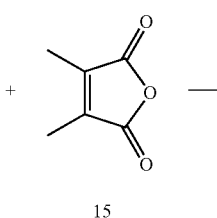
15

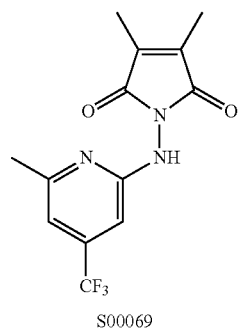
S00069

The anhydride 15 (1 eq.) was added to a solution of the hydrazine 14 (1.0 mmol) in chloroform and stirred under reflux for 4 hr. The reaction was determined to be completed by TLC (petroleum ether: ethyl acetate=3:1). The solvent was evaporated and the residue was purified by flash chromatography (petroleum ether: ethyl acetate=2:1) to give the product.

Synthesis of S00084

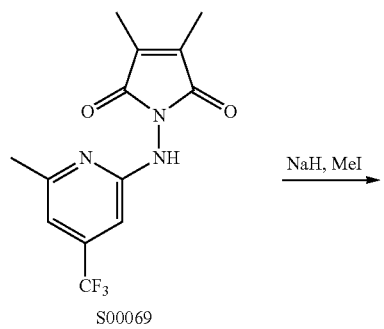
S00069

NaH, MeI →

-continued

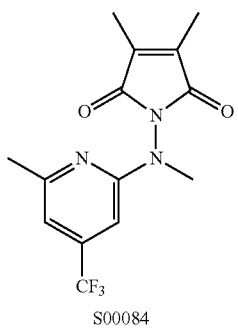
S00084

To a solution of S00069 (35 mg, 0.117 mmol) in THF (6 mL) at 0° C. was added NaH (60% in mineral oil, 8 mg, 0.12 mmol). The mixture was stirred for 30 min, and then MeI (20 mg) was added. The reaction mixture was stirred for 2 h at room temperature, and then poured into the saturated aqueous NH$_4$Cl. This was extracted with CHCl$_3$. The organic layer was dried over anhydrous Na$_2$SO$_4$. The solvent was removed and the residue was purified by preparative TLC (5:1 petroleum ether/diethyl ether) to afford S00084 (3 mg).

Synthesis of S00109

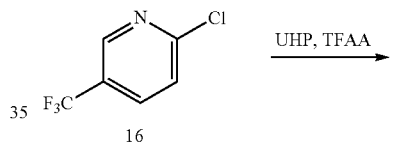

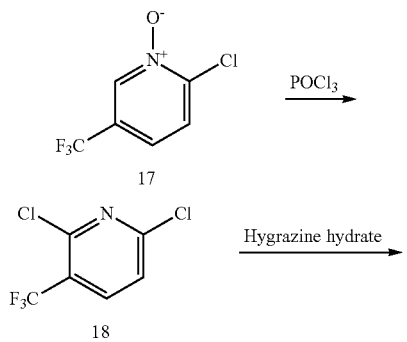

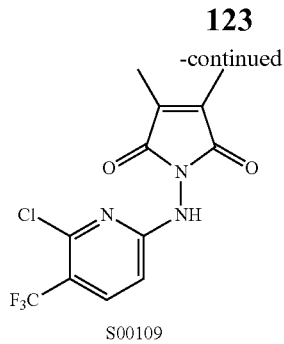

S00109

Step 1: Synthesis of 2-Chloro-5-trifluoromethyl-pyridine-N-oxide (17)

2-Chloro-5-trifluoromethyl-pyridine (16, 10 mmol) was dissolved in $CH_2Cl_2$ (20 mL) and UHP (Urea-hydrogen peroxide addition compound, 21 mmol) was added. The mixture was cooled to 0° C., trifluoroacetic anhydride (20 mmol) was then slowly added to the reaction mixture. It was allowed to warm to room temperature and stirred until the reaction was completed judged by TLC. The reaction was quenched with aqueous $Na_2SO_3$, stirred for 4 h, washed with saturated aqueous $NaHCO_3$, and dried over anhydrous $MgSO_4$. Column chromatography afforded 1.8 g of compound 17 as oil.

Step 2: Synthesis of 2,6-Dichloro-5-trifluoromethyl-pyridine (18)

2-Chloro-5-trifluoromethyl-pyridine-N-oxide (17, 4 mmol) was dissolved in freshly distilled $POCl_3$ (4.5 mL). The reaction mixture was heated to 80° C. for 17 h. After cooling to room temperature, the solvent was removed under reduced pressure. Ice was added, and the mixture was allowed to stand for 4 h. The mixture was partition between $CH_2Cl_2$ (50 mL) and saturated aqueous $NaHCO_3$. Column chromatography afforded compound 18 as yellow oil (yield: 50%).

Step 3: Synthesis of 6-Chloro-5-trifluoromethyl-2-pyridylhydrazine (19)

To the solution of 2,6-Dichloro-5-trifluoromethyl-pyridine (18, 2 g, 9.26 mmol) in ethanol (30 mL) was added hydrazine hydrate (2.9 g, 46 mmol). The reaction mixture was stirred for 4 h at room temperature, then concentrated to remove the solvent, and added ethyl acetate, washed with water. The organic layer was dried over anhydrous $Na_2SO_4$. Column chromatography (Silica, petroleum ether/ethyl acetate=4/1~3/1) afforded compound 19 as white solid (yield: 56%) and another isomer 20 (yield: 18%).

Step 4: Synthesis of S00109

2,3-Dimethylmaleic anhydride (15, 0.126 g, 1.0 mmol) was added to a solution of 6-chloro-5-trifluoromethyl-2-pyridylhydrazine (19, 0.211 g, 1.0 mmol) in 5 ml of chloroform and the mixture was refluxed for 4 hours. The solvent was removed and the residue was purified by flash chromatography (5:1 to 2:1 petroleum ether/ethyl acetate) to give S00109 (0.21 g).

Synthesis of S00170

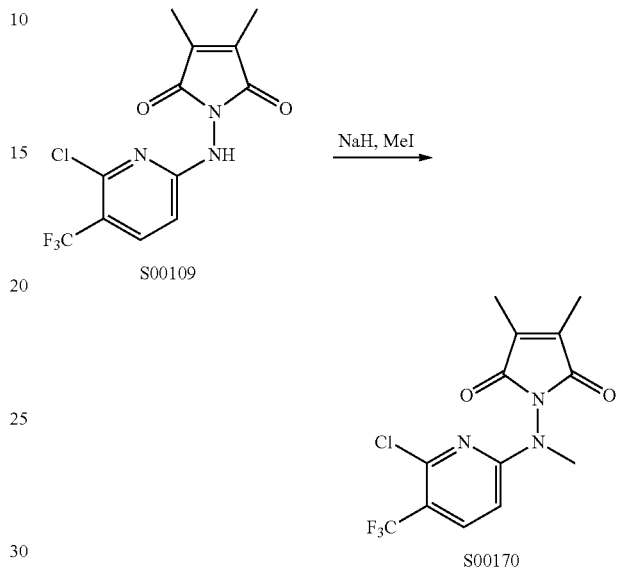

Compound S00109 (40 mg, 0.125 mmol) and NaH (60% in mineral oil, 7 mg, 0.188 mmol) were suspended in 2 ml of anhydrous THF and the mixture was stirred at 0° C. for 30 min. Methyl iodide (21 mg, 0.150 mmol) was added slowly to the solution at the same temperature and the mixture was then warmed to 25~30° C. and stirred for overnight. The solvent was evaporated, and acetic acid was added to make the solution at pH=4. This was extracted with chloroform three times, and the combined organic phase was washed with 1N HCl, and then saturated aqueous $NaHCO_3$. It was then dried over anhydrous $Na_2SO_4$. The solvent was removed and the residue was purified by preparative TLC (4:1 petroleum ether/diethyl ether) to give compound S00170 (4.2 mg).

Synthesis of S00585

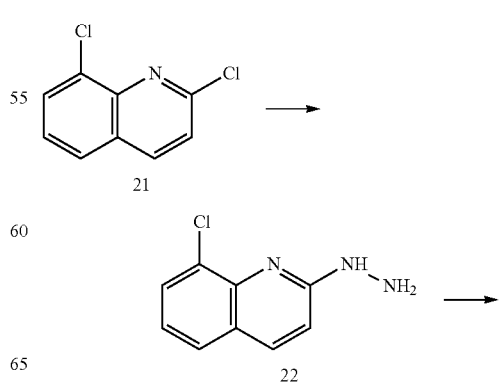

-continued

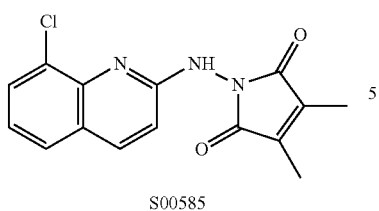
S00585

Compound 21 was converted to Compound 22 using a procedure similar to that described in Example 1. Compound 22 was converted to Compound S00585 using a procedure similar to that described in Example 2.

General Procedure for the Synthesis of Substituted Phenylhydrazines

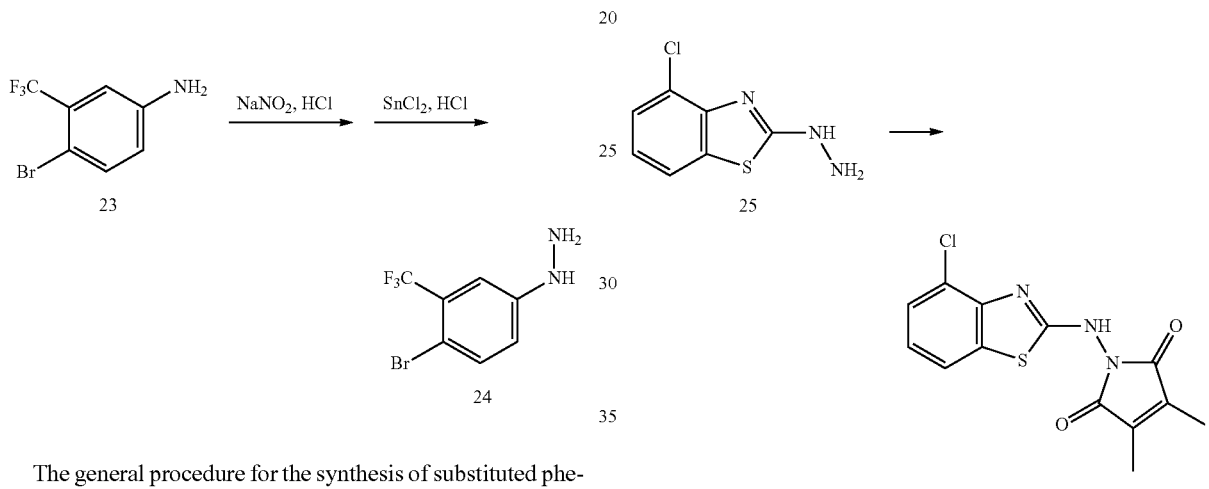

The general procedure for the synthesis of substituted phenylhydrazines is represented here in the synthesis of 3-(trifluoromethyl)-4-bromophenylhydrazine (24). The corresponding benzylamine 23 (0.08 mol) was added to conc. HCl (40 mL). The mixture was cooled to −5° C. by ice and salt with stirring. Then sodium nitrite (5.52 g, 0.08 mol) dissolved in water (20 mL) was added. Stirring was continued for 1 h, and stannous chloride (30 g) in conc. HCl (30 mL) was added slowly over a period of two hours, while keeping the temperature below 0° C. The mixture was stirred for another hour after the addition and filtered. The filtered solid was treated with dilute aqueous sodium hydroxide and the then extracted with ether. The ether layer was washed with water, dried over anhydrous Na$_2$SO$_4$. The solvent was removed and the residue was crystallized from hexane to give the Compound 24.

Synthesis of S00516

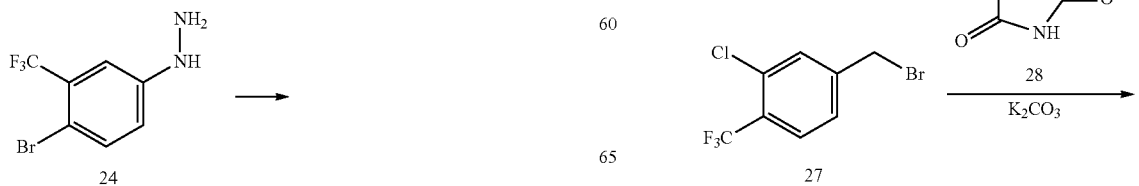

-continued

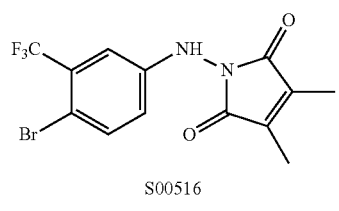
S00516

Compound S00516 was synthesized from the corresponding hydrazine 24 using a procedure similar to that described in Example 2.

Synthesis of S00756

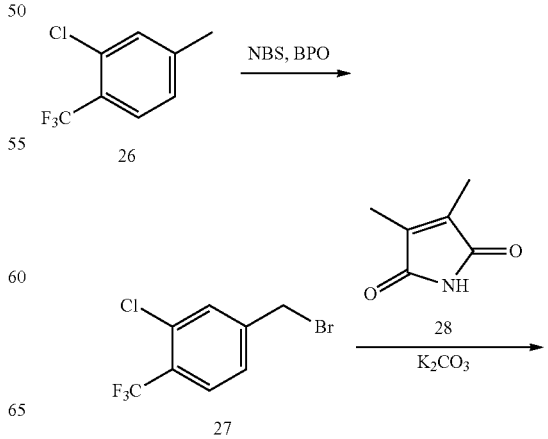
S00756

Compound 25 was synthesized according to literature procedure (Eur. J. Med. Chem. Chim. Ther. 1997, 32(5), 397-408). It was converted to Compound S00756 using a method similar to that described in Example 2.

Synthesis of S00513

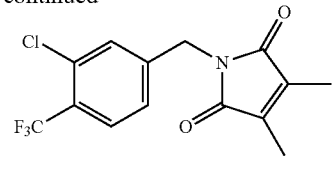

S00513

Step 1: 3-Chloro-4-trifluoromethylbenzylbromide 27

A mixture of 2-chloro-4-methyl-1-trifluoromethylbenzene 26 (0.20 g, 1 mmol), N-bromosuccinimide (0.17 g, 1 mmol) and benzoyl peroxide (7.4 mg, 0.03 mmol) in carbon tetrachloride (2 mL) was heated to reflux for 2 hours. Another portion of benzoyl peroxide (20 mg, 0.08 mmol) was added. The mixture was heated to reflux for another 0.5 hours. The reaction mixture was further stirred at room temperature for 16 hours. The solid was removed by filtration. The solvent was removed under reduced pressure. The crude product was purified by flash chromatography on silica, using petroleum ether as eluent, to give 0.22 g (80%) of Compound 27.

Step 2: Compound S00513

To a solution of 3,4-dimethylmaleimide 28 (43 mg, 0.34 mmol) in 1.3 mL of acetone was added anhydrous potassium carbonate (50 mg, 0.37 mmol) and Compound 27 (100 mg, 0.37 mmol). The reaction mixture was stirred at room temperature overnight. Water was added and the mixture was extracted with ethyl acetate. The organic extract was washed with brine, dried (Na$_2$SO$_4$), and concentrated under reduced pressure. The crude product was purified by chromatography on silica, using petroleum ether/ethyl acetate (10:1) as eluent, to give 70 mg (60%) of Compound S00513.

Synthesis of S00628

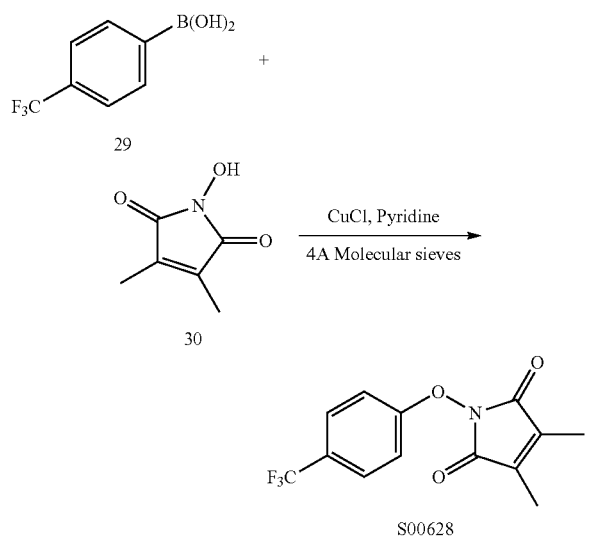

Into a solution of 1-hydroxy-3,4-dimethylazoline-2,5-dione 30 (56 mg, 0.39 mmol, 1 equiv) in 1,2-dichloroethane (2.5 mL), CuCl (39 mg, 0.39 mmol, 1 equiv), freshly activated 4 Å molecular sieves (~100 mg), and 4-trifluoromethylphenylboronic acid 29 (150 mg, 0.78 mmol, 2 equiv) were added, followed by pyridine (34 mg, 0.43 mmol, 1.1 equiv). The resulting light brown suspension was stirred for 16 h. The reaction mixture was filtered. Chromatography of the filtrate (petroleum ether/ethyl acetate=7:1) afforded Compound S00628 as a white solid (65 mg, 59%).

Example 9

Synthetic Procedures

All compounds listed in Tables 1, 2, and 3 were synthesized using methods identical to or similar to those described in the examples below.

General Procedure for the Synthesis from Halide-Substituted Pyridine Analogs to Target Compounds Scheme 1

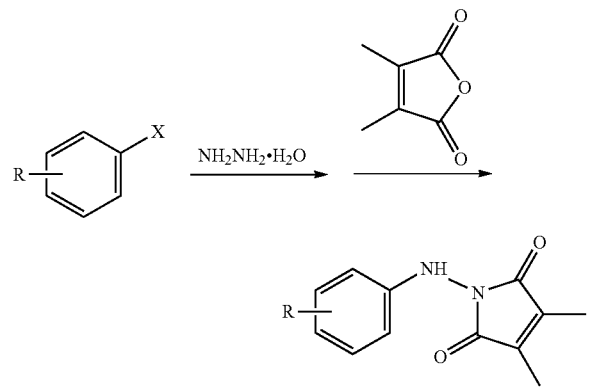

Starting material dissolved in ethanol and hydrazine hydrate (10.0 eq) was added to form a mixture, the mixture was stirred at 50-60° C. (oil temperature) for several hours (completion was checked by TLC), the solvent was evaporated, water was added and the resulting mixture was extracted with ethyl acetate, dried and concentrated to form a crude preparation that was used without further purification for the next step. The crude preparation was dissolved in chloroform (or toluene, acetic acid, or another suitable solvent), anhydride was added (1.0 eq), the mixture was heated at 50-60° C. (oil temperature) for several hours (completion checked by TLC), the solvent was evaporated, and the preparation was purified by Prep-TLC to provide the desired compound.

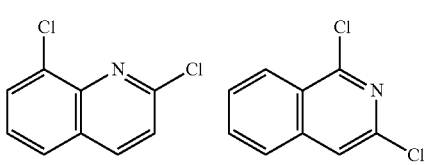

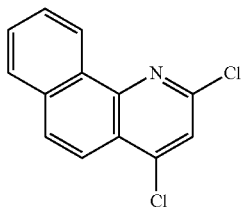

The starting materials were commercially available, so the synthetic route of compounds S00585, S01098, S01207 was similar to general procedure.

Compound S00109

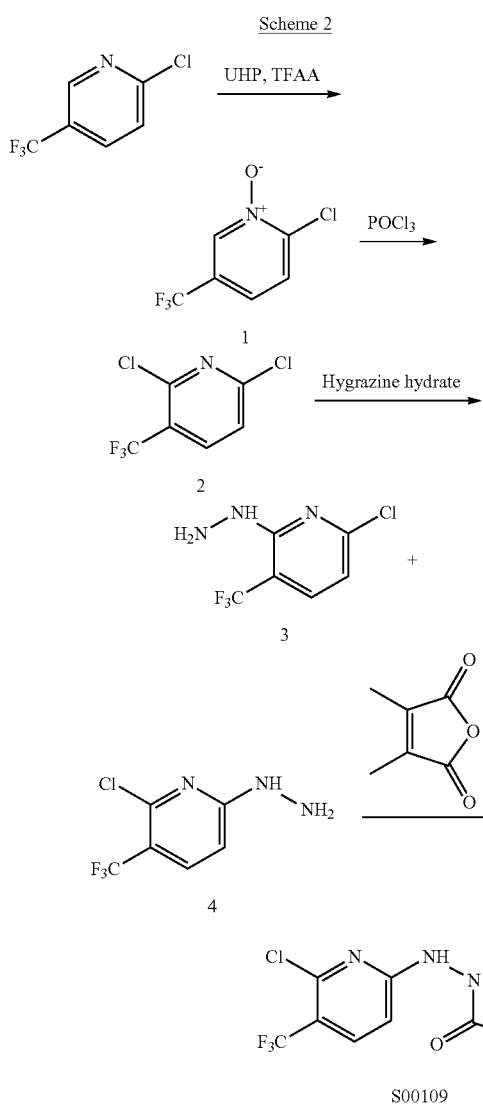

Intermediate 1

2-Chloro-5-trifluoromethyl-pyridine (10 mmol) was dissolved in CH$_2$Cl$_2$ (20 mL) and UHP (Urea-hydrogen peroxide addition compound, 21 mmol) was added. The mixture was cooled to 0° C., trifluoroacetic anhydride (20 mmol) was then slowly added to the reaction mixture. It was allowed to warm to room temperature and stirred until the reaction was completed monitored by TLC. The reaction was quenched with aqueous Na$_2$S$_2$O$_3$, stirred for 4 h, washed with saturated aqueous NaHCO$_3$, and dried over anhydrous MgSO$_4$. Column chromatography afforded 1.8 g of compound 1 as oil.

Intermediate 2

1 (4 mmol) was dissolved in freshly distilled POCl$_3$ (4.5 mL). The reaction mixture was heated to 80° C. for 17 h. After cooling to room temperature, the solvent was removed under reduced pressure. Ice was added, and the mixture was allowed to stand for 4 h. The mixture was partition between CH$_2$Cl$_2$ (50 mL) and saturated aqueous NaHCO$_3$. Column chromatography afforded compound 2 as yellow oil (yield: 50%).

Intermediate 4

To the solution of 2 (2 g, 9.26 mmol) in ethanol (30 mL) was added hydrazine hydrate (2.9 g, 46 mmol). The reaction mixture was stirred for 4 h at room temperature, then concentrated to remove the solvent, and added ethyl acetate, washed with water. The organic layer was dried over anhydrous Na$_2$SO$_4$. Column chromatography (Silica, petroleum ether/ethyl acetate=4/1~3/1) afforded compound 4 as white solid (yield: 56%) and another isomer 3 (yield: 18%).

Compound S00109

The synthetic procedure was similar to general procedure.

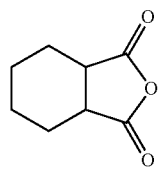 [SMILES: O=C1OC(=O)C2CCCCC12]

Compound S00186

The starting material (anhydride) was commercial available, so the synthetic route of compounds S00186 was similar to general procedure (anhydride react with intermediate 4).

Compound S00994

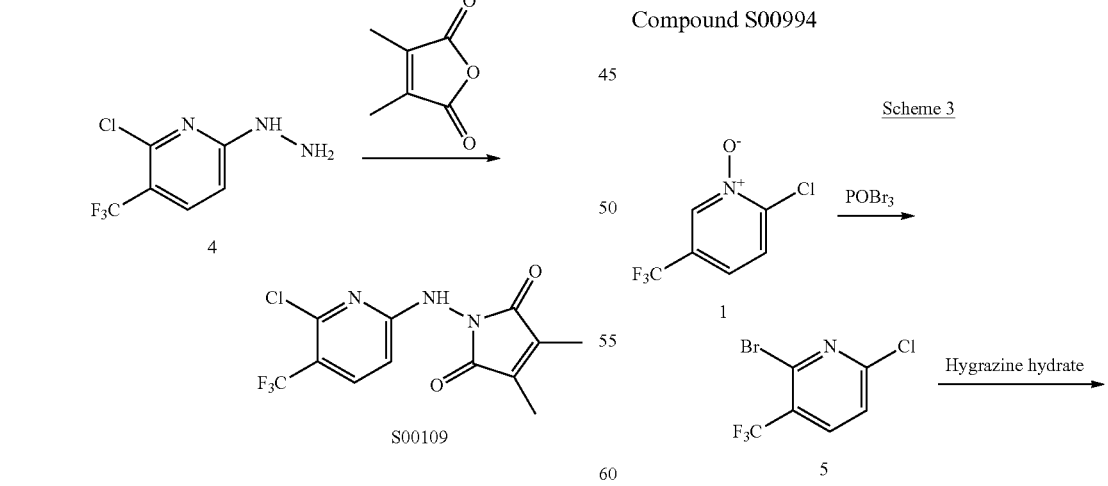

-continued

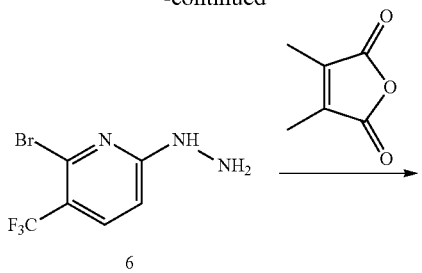

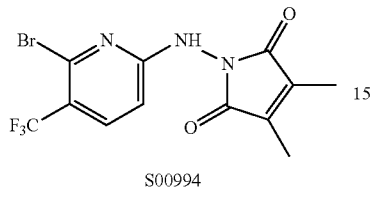

Intermediate 5

1 (4 mmol) was dissolved in freshly distilled POBr$_3$ (4.5 mL). The reaction mixture was heated to 80° C. for 17 h. After cooling to room temperature, the solvent was removed under reduced pressure. Ice was added, and the mixture was allowed to stand for 4 h. The mixture was partitioned between CH$_2$Cl$_2$ (50 mL) and saturated aqueous NaHCO$_3$. Column chromatography afforded compound 5 as yellow oil (yield: 50%).

Intermediate 6

Hydrazine hydrate was added to the solution of 5 in ethanol. The reaction mixture was stirred for 4 h at room temperature, then concentrated to remove the solvent, ethyl acetate was added, and the mixture was washed with water. The organic layer was dried over anhydrous Na$_2$SO$_4$. Column chromatography (Silica, petroleum ether/ethyl acetate=4/1~3/1) afforded compound 6 as a white solid.

Compound S00994

The synthetic procedure was similar to general procedure.

Compound S01860

Scheme 4

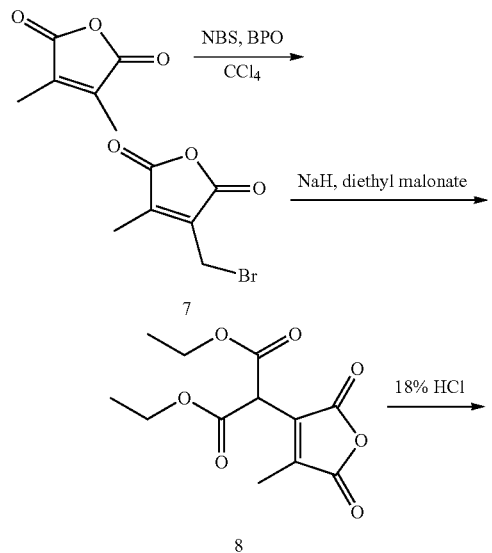

-continued

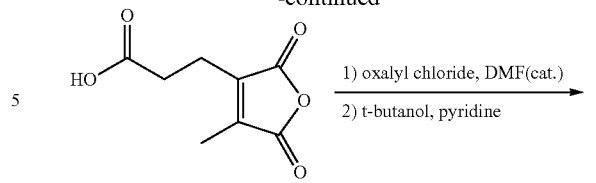

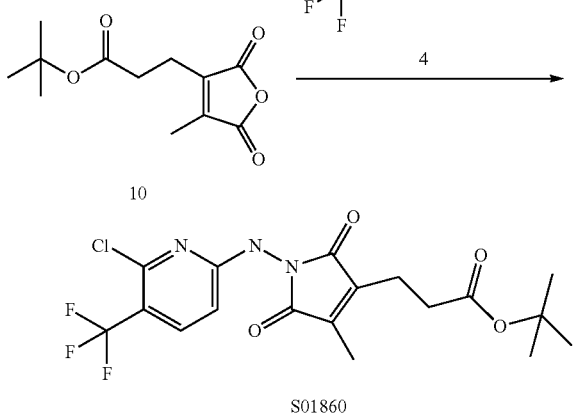

Intermediate 7

A solution of starting material (5.0 g, 0.040 mol), NBS (10.6 g, 0.059 mol), BPO (296 mg) in 300 ml CCl$_4$ was stirred under reflux for 5 hrs. The reaction mixture was then cooled to room temperature, and another portion of BPO (296 mg) was added, and the reaction was stirred under reflux for another 5 hrs. The reaction mixtures was then held at room temperature overnight. Then it was filtered and the residue was washed by CCl$_4$ for three (3) times, and the combined organic layer was washed by water and brine, then dried and concentrated and purified by column chromatography (PE: EA=4:1) to give crude product that was then was purified by distillation. The second fraction obtained at 128° C.~135° C. (3 mmHg) was intermediate 7.

Intermediate 8

To the slurry of sodium hydride (60 mg, 1.5 mmol) in benzene (5 mL), diethylmalonate (320 mg, 2.0 mmol) was added dropwise at room temperature. The reaction mixture was stirred for 5 min, then a solution of 7 (210 mg, 1.0 mmol) in benzene (5 mL) was added. The mixture was stirred at room temperature for another 8 h. Then the mixture was acidified with diluted HCl and extracted with EtOAc (2×15 mL). The combined organic layers were washed with water, brine and dried over anhydrous Na$_2$SO$_4$. Concentration of the organic layers in vacuo followed by silica gel column chromatographic purification of the residue (petroleum ether: EtOAc=4:1) furnished the product as a thick oil. Yield was 200 mg, (74.0%).

Intermediate 9

A solution of 8 (80 mg, 0.3 mmol) in diluted hydrochloride (2 mL, 18%) was refluxed with stirring for 12 h. The reaction mixture was cooled to room temperature, and saturated by adding solid sodium chloride. The filtered aqueous layer was extracted with EtOAc, dried over anhydrous Na$_2$SO$_4$ and concentrated to furnish pure acid. Yield was 50 mg (90.6%).

Intermediate 10

To a stirred solution of 9 (0.46 g, 2.5 mmol) and two drops of DMF in DCM (10 ml) was added oxalyl chloride (0.48 g, 3.75 mmol) dropwise. The mixture stirred at room temperature (oil temperature 20-30° C.) for two hours, then the solvent was evaporated. The residue and tert-butanol (0.22 g, 3 mmol) were dissolved in 10 ml of DCM, pyridine (0.3 g, 3.75 mmol) was added to this solution dropwise at room temperature. The resulting mixture stirred at room temperature. for an hour. Added sat. $NH_4Cl$ to quench the reaction, adjusted pH to 2 with 1N HCl and extracted with ethyl acetate, the combined organic layer dried over $Na_2SO_4$, filtered and evaporated. The residue purified by flash chromatography to give 10 as white solid (0.42 g, 70%).

Compound S01860

Intermediates 10 (119 mg, 0.45 mmol) and 4 (95 mg, 0.49 mmol) were added to 5 ml of DCM and refluxed overnight, then the solvent was evaporated and the residue purified by Prep-TLC to give the product. (Yield=150 mg, 77%)

Compound S01861

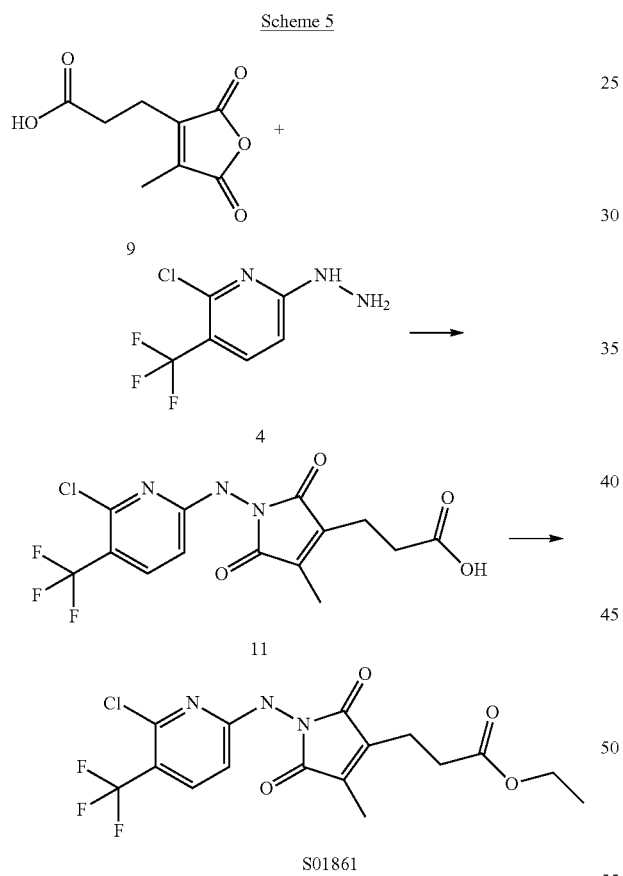

Intermediate 11

9 (1.0 g, 5.43 mmol) and 4 (1.15 g, 5.43 mmol) dissolved in 20 ml of chloroform and refluxed for 48 h, then evaporated the solvent and the residue recrystallized to give 11 (1.4 g, 68.2%).

Compound S01861

Intermediate 11 (15 mg, 0.04 mmol), EDCI (45 mg, 0.24 mmol), $Et_3N$ (1 drop) and ethanol (1 mL) was stirred at room temperature for about 3 h. Then the solvent was removed under vacuum. The product was separated by Prep-TLC. Yield was 12 mg (76.7%).

Compounds S01648, S01796, S01711, S01758, S01883, and S01759

The synthetic route of compounds S01648, S01796, S01711, S01758, S01883, and S01759 was similar to S01861, i.e., intermediate 11 coupled to different chemicals).

Compound S01589

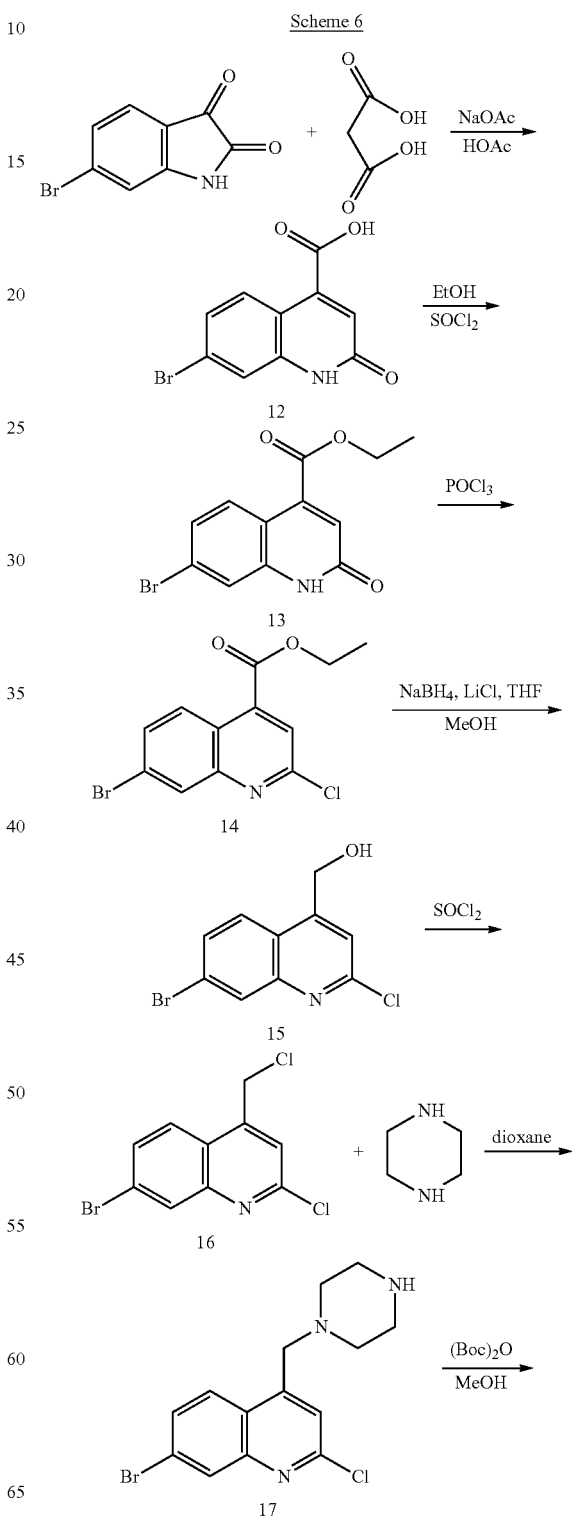

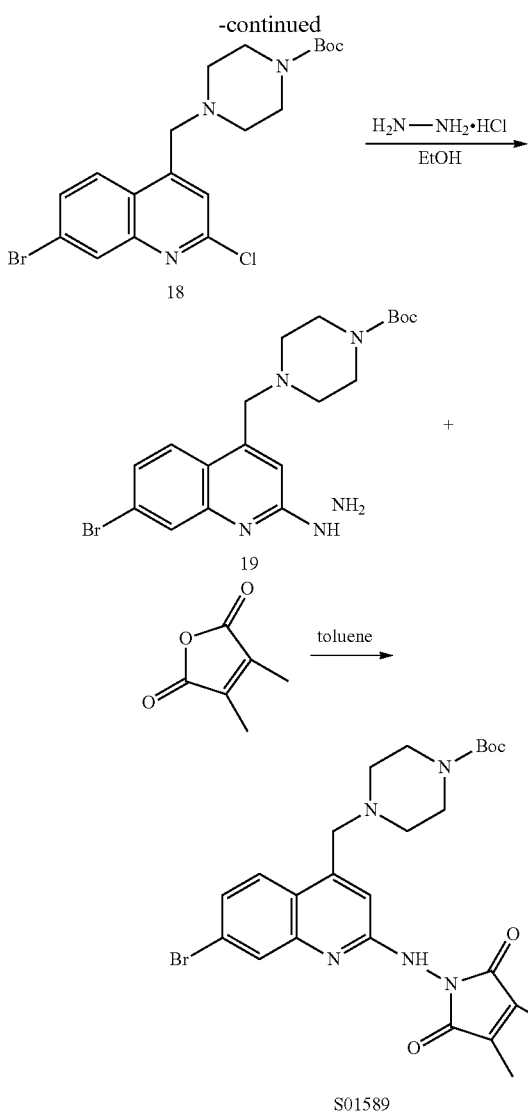

Intermediate 12

The mixture of starting material (6.5 g, 28.7 mmol), malonic acid (3.3 g, 31.7 mmol), HOAc (60 ml), NaOAc (2.95 g, 36 mmol) were stirred at RT. After 6-7 hrs, NaOAc (2.95 g, 36 mmol) was added additional, then refluxed overnight. After cooling, the mixture was filtered and the filtrate was washed with water and ethyl acetate, then dried under reduced pressure. 5 g thin brown solid was collected (yield=65.4%).

Intermediate 13

Four (4) ml of $SOCl_2$ was added dropwise to a suspension of compound 12 and EtOH, in an ice bath, and the mixture was stirred for 30 min at room temperature, then refluxed for 6 hrs. After cooling, the mixture was filtered and washed with chilled EtOH, and dried in vacuo to obtain 5.25 g pale grey powder (yield=95%)

Intermediate 14

A mixture of compound 13 and $POCl_3$ (15 ml) was stirred at room temperature for 15 min, then refluxed for 2 hrs. The mixture was concentrated in vacuo. The residue was quenched with cooled water and extracted with ethyl acetate, washed with saturated $NaHCO_3$ and brine, dried over MgSO4, concentrated and 4.68 g thin brown solid was collected.

Intermediate 15

To a solution of THF and MeOH, compound 14 (4.68 g, 14.9 mmol) and LiCl was added with ice-salt bath, $NaBH_4$ was added by portions. After addition, the reaction mixture was stirred at room temperature, checked by TLC, concentrated in vacuo, and dilute HCl was added slowly to the residue over an ice bath until the mixture reached pH7. The mixture was then extracted with ethyl acetate and washed with saturated $NaHCO_3$, $NH_4Cl$, NaCl solutions (in sequence), dried over $MgSO_4$, concentrated, and 4.15 g thin brown solid was collected.

Intermediate 16

Compound 15 (4.15 g) was dissolved in $SOCl_2$ and refluxed overnight. The solvent was evaporated, water was added to the residue, the mixture was extracted with ethyl acetate, the combined organic layer was dried over anhydrous $Na_2SO_4$, the solvent was evaporated, and 4.0 g compound 16 was collected.

Intermediate 17

Compound 16 (200 mg, 0.69 mmol) was dissolved in dioxane, and anhydrous piperazine (177 mg, 2.05 mmol) was added, and the mixture was stirred overnight. The mixture was filtered, the filtrate was concentrated in vacuo, and 250 mg crude product was collected.

Intermediate 18

A solution of di-tert-butyl dicarbonate (0.246 g, 1.13 mmol) in MeOH was added dropwise to compound 17 (0.35 g, 1.03 mmol) in MeOH at room temperature. The reaction mixture was stirred overnight at room temperature. The solvent was evaporated, the residue was extracted in the usual manner as described above, and the extract was purified by chromatography column (EA:PE=1:10). The product was obtained as a white solid.

Compound S01589

The synthetic procedure from intermediate 18 to compound S01589 was similar to general procedure described herein.

Compounds S01037 and S01047

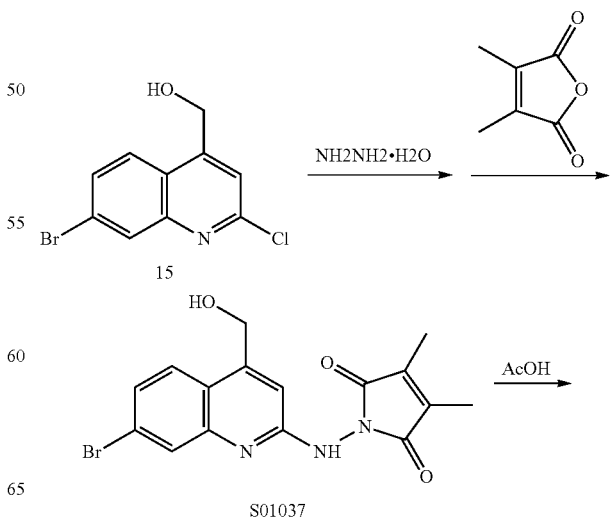

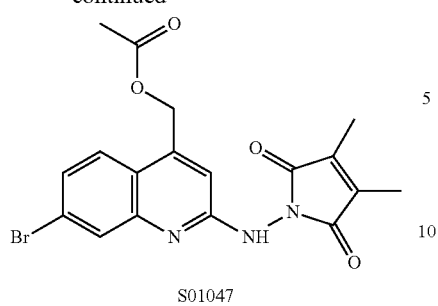

S01047

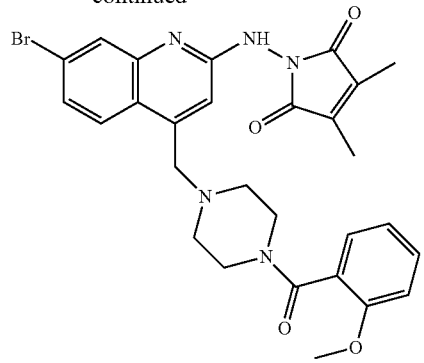

S01879

Compound S01037

The synthetic procedure from intermediate 15 to compound S01037 is similar to general procedure.

Compound S01047

Starting material (0.145 g, 0.54 mmol) was dissolved in 5 ml of acetic acid and the mixture was heated with refluxing for 1 h, then evaporated and purified by Prep-TLC (petroleum ether:ethyl acetate=1:1) to give the product.

Compound S01879

Scheme 8

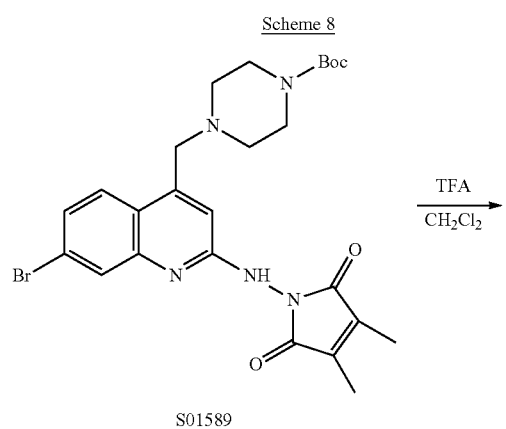

S01589

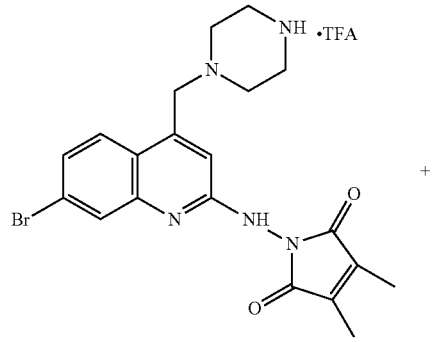

20

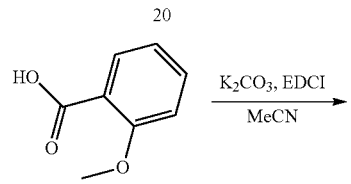

Intermediate 20

Starting material (50 mg, 0.09 mmol) was dissolved in 5 ml of $CH_2Cl_2$ and TFA (5 ml) was added dropwise to the stirred mixture over an ice bath. The resulting mixture was stirred for 1 h at room temperature and checked by TLC. The solvent was evaporated to give the product as yellow solid which was used without further purification. (40 mg).

Compound S01879

Compound 20 was dissolved in MeCN, and $K_2CO_3$ (3 eq) was added, after which the mixture was stirred for about 30 min, and benzoic acid (1 eq) and EDCl (2 eq) was added and the mixture was stirred overnight, then concentrated and worked up in the usual manner described above. The final preparation was purified by Prep plate TLC and product was obtained as a thin yellow solid.

Compounds S01925, S01878, S01877, S01699, S01800, S01801, S01822, S01880, S01683, S01928, S01929

The synthetic route of compounds S01925, S01878, S01877, S01699, S01800, S01801, S01822, S01880, S01683, S01928, S01929 was similar to S01879 (intermediate 20 coupled with different chemicals).

Compound S01981

Scheme 9

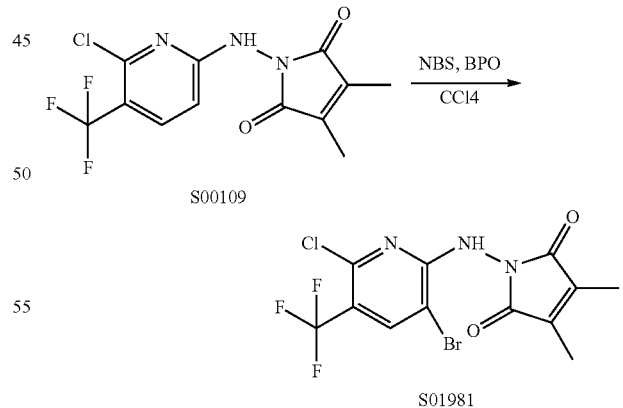

S01981

Starting material (100 mg, 0.314 mmol) was dissolved in $CCl_4$, NBS (112 mg, 0.629 mmol) and BPO (1.5 mg, 0.0062 mmol) were added, and the mixture was refluxed for about 4 hrs. The reaction mixture was quenched with water, extracted with ethyl acetate, the organic layer washed with brine, dried over $MgSO_4$ and concentrated in vacuo, then purified by prep plate to obtain product.

Compound S00170

Scheme 10

S00109

S00170

NaH (8 mg, 0.12 mmol) was added dropwise to a solution of hydrazine (35 mg, 0.117 mmol) in THF (6 mL), at 0° C. The mixture was stirred for 30 min, then added MeI (20 mg). The reaction mixture was stirred for 2 h at room temperature, then poured into the Sat. NH$_4$Cl aq.; extracted with CHCl$_3$. The organic layer was dried over Na2SO4, then chromatography (PE/AE, 5/1) to obtain the product (3 mg).

Compounds S01007, S01473

The synthetic route of compounds S01007, S01473 was similar to S00170.

Compound S01470

Scheme 11

7

21

S01470

Intermediate 21

Compound 2 (1 g, 4.9 mmol) was added to an ice cold solution of 4N aq. KOH (5 ml), and the mixture was stirred at room temperature for 5 hrs. The mixture was slowly acidified with 6N H$_2$SO$_4$ (5 ml), then saturated with solid NaCl and stirred at room temperature for 30 min. The aqueous layer was extracted with ethyl acetate and the organic layer was washed with brine and dried. The organic layer was concentrated in vacuo and the concentrate was applied to silica gel (PE: EA=1:1) to furnish 355 mg of product.

Compound S01470

The synthetic procedure was similar to general procedure.

Compounds S01599 and S01600

Scheme 12

S01470

S01599

S01600

Starting material (80 mg, 0.24 mmol), MeI (40 uL, 0.64 mmol), and KOH (30 mg, 0.54 mmol) in DMSO (5 mL) was stirred at room temperature for 1 h, then diluted with EtOAc, washed with water, brine, dried over anhydrous Na$_2$SO$_4$. The solvent was removed in vacuum and the residue was purified by Prep-TLC to obtain the two target compounds.

Compound S01712

Scheme 13

8

141

-continued

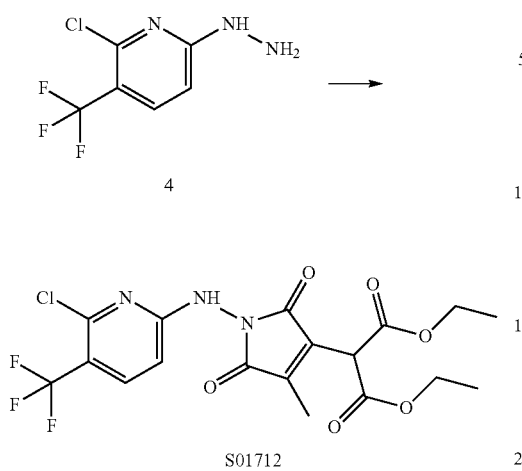

The synthetic procedure was similar to general procedure.
Compound S01266

Scheme 14

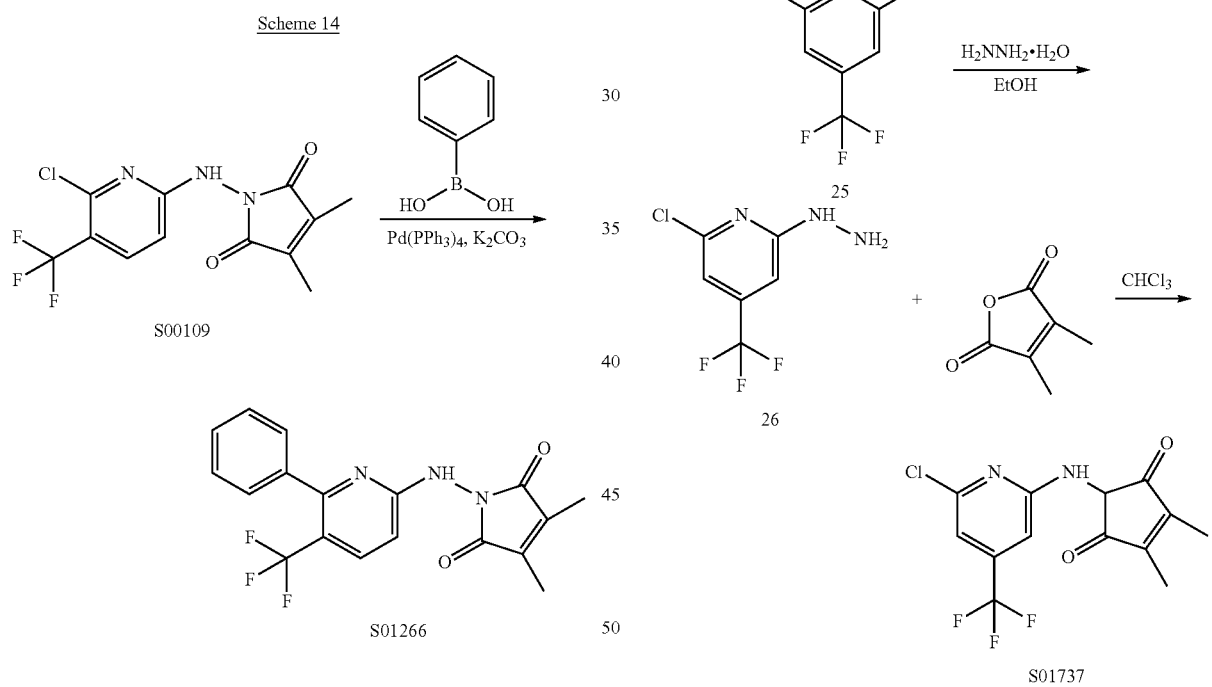

Pd(PPh₃)₄ (16 mg) was added to a mixture of starting material (50 mg, 0.14 mmol), benzeneboronic acid (19 mg, 0.15 mmol), potassium carbonate (59 mg, 0.43 mmol) in 10 ml of toluene under a nitrogen atmosphere. The resulting mixture was refluxed for 16 h, after which the solvent was evaporated and the residue purified by preparative TLC to give 4 mg of product.

Compounds S01313, S01457, S01691, S01371, S01393, S01474

The synthetic route of compounds S01313, S01457, S01691, S01371, S01393, S01474 was similar to S01266.

142

Compound S01737

Scheme 15

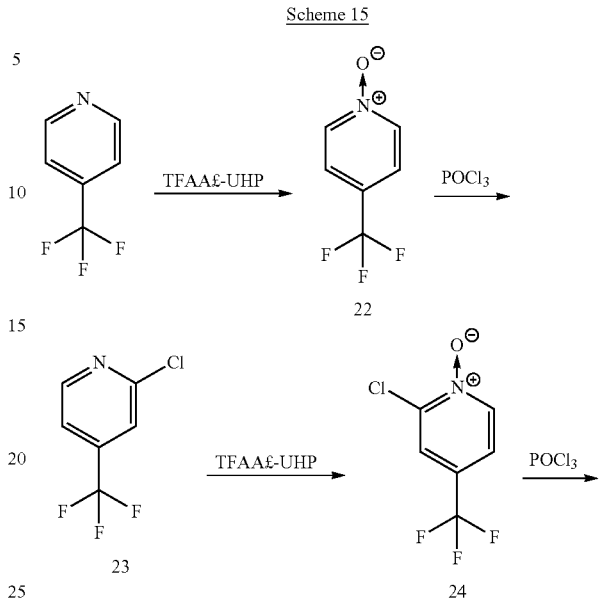

Intermediate 22

The pyridine (500 mg, 3.4 mmol) was dissolved in CH₂Cl₂ and UHP (700 mg, 7.4 mmol) was added, which was cooled to 0° C., TFAA (1.43 g, 6.8 mmol) was then slowly added to the reaction mixture. After TLC indicated starting material was consumed, work up as usual manner to afford 420 mg of target compound.

Intermediate 23

Compound 22 (420 mg, 2.57 mmol) was dissolved in POCl₃ (3 ml), then heated at 90° C. overnight. The reaction mixture was quenched to water carefully, extracted by CH₂Cl₂, washed with brine and dried over MgSO₄, concentrated in vacuo. Purified by chromatography column (CH₂Cl₂:PE=1:3) then obtained 300 mg target compound.

143

Intermediate 24

The reaction and work-up procedure was same as for intermediate 22, and 170 mg target compound was obtained.

Intermediate 25

The reaction and work-up procedure was same as for intermediate 23, and 120 mg target compound was obtained.

Compound S01737

The synthetic procedure from intermediate 25 to target compound was similar to the general procedure.

Compound S01865

144

Intermediate 27

Two starting materials were dissolved in CHCl₃ and refluxed overnight, then concentrated and purified by chromatography column (EA:PE=1:1). The product was obtained as a light yellow solid.

Compound S01865

Compound 27 was dissolved in anhydrous MeOH, EDCI was added, then stirred overnight. Concentrated in vacuo, work up as usual manner and purified by Prep-TLC to obtain the final product as light yellow solid.

Compounds S01734 and S01688

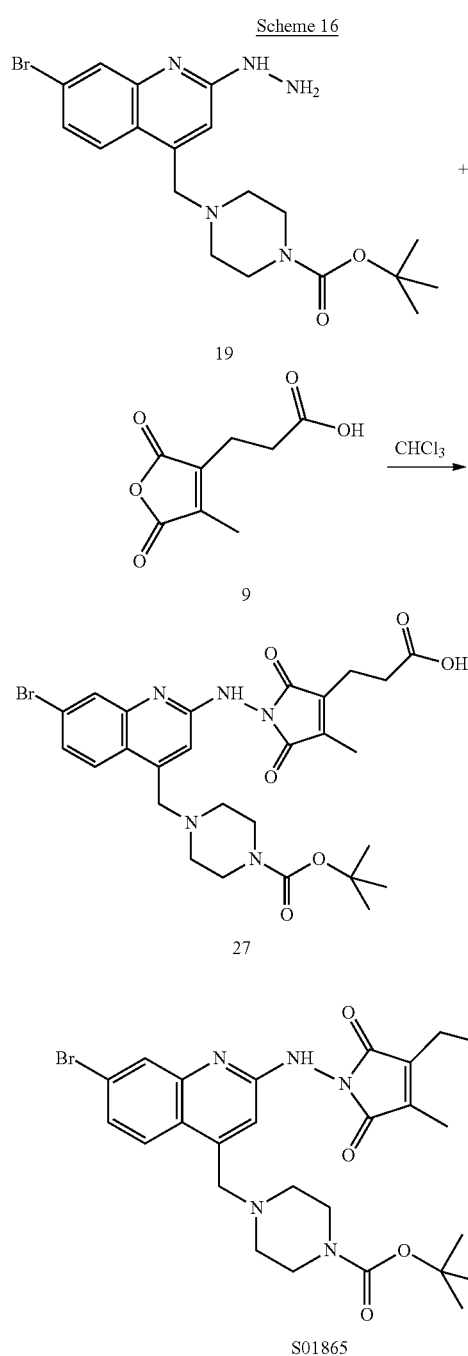

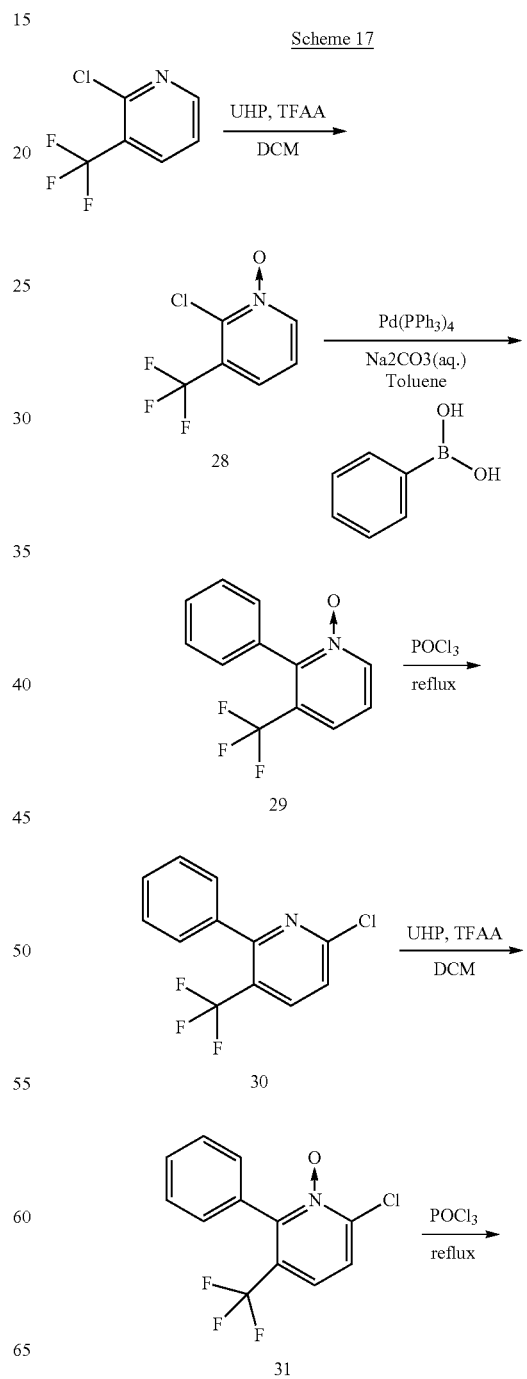

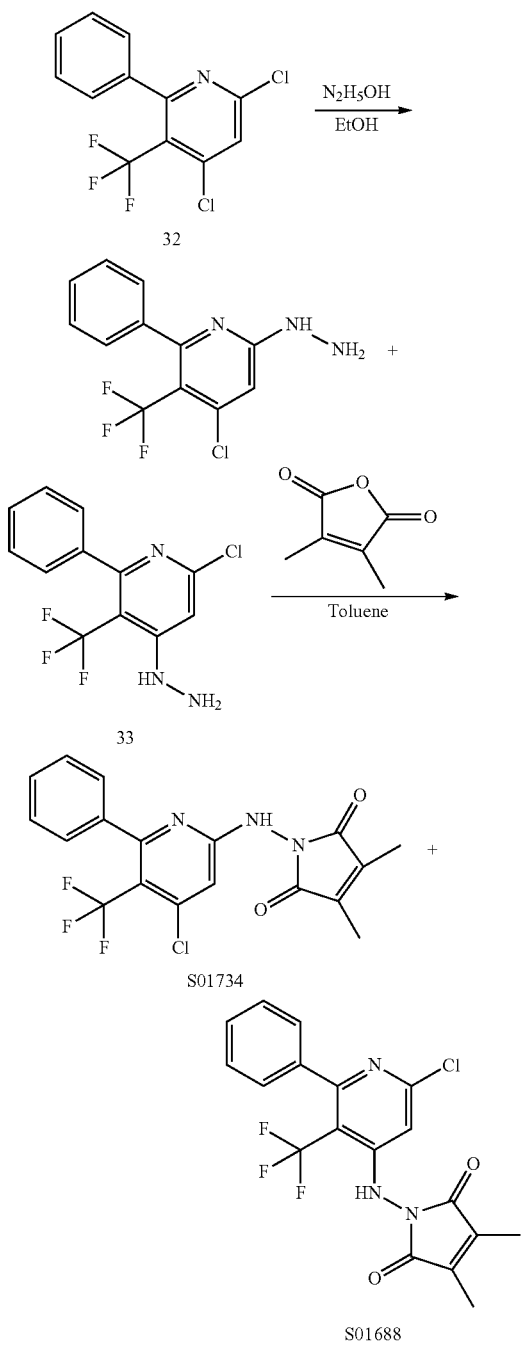

Intermediate 28

To a solution of starting material (9.26 g, 0.05 mol), UHP (9.9 g, 0.105 mol) was added. With ice-bath, TFAA (21 g, 0.100 mol) was added dropwise. After addition, the reaction was maintained at room temperature. for 4 hrs. Neutralize the reaction with $Na_2CO_3$ (aq.).and the mixture was extracted with DCM for 3 times. The organic layer was collected, dried and concentrated and purified by flash chromatography (PE: EA=3:1) to give the pure product 8.1 g.

Intermediate 29

A solution of compound 28 (0.8 g, 4.07 mmol) and in 2 ml $Na_2CO_3$ (aq. 2N) and 3 ml toluene was stirred under an atmosphere of $N_2$ and at room temperature. Then $Pd(PPh_3)_4$ was added. The mixture was stirred under reflux at an atmosphere of $N_2$ for 3 hrs. Then the solvent was removed under vacuum. The residue was treated with water and extracted with EA, and the organic phase was collected, dried and concentrated to be purified by recrystallization to give.0.75 g of pale yellow powder.

Intermediate 31

A solution of compound 29 (0.75 g, 3.15 mmol) in 5 ml $POCl_3$ and the mixture was stirred under reflux for 5 hrs. Then the reaction mixture was poured into ice and the aqueous layer was extracted with ethyl acetate for 3 times. Then the organic phase was collected, washed with $Na_2CO_3$ aqueous solution and then dried, concentrated and to be purified by column chromatography to afford 800 mg intermediate 30, which was dissolved in 5 ml DCM and UHP, followed by TFAA was added to the above mixture under ice-bath. Then the reaction mixture was stirred at room temperature. overnight. Then neutralized the reaction mixture by $Na_2CO_3$ aqueous solution and the aqueous phase was extracted by DCM for 3 times. The organic phase was collected, dried, concentrated and purified by column chromatography (PE: EA=5:1) to give 350 mg of pure compound 31.

Intermediate 32

A solution of compound 31 (350 mg, 1.28 mmol) in 5 ml $POCl_3$ was stirred under reflux for 4 hrs. Then the mixture was poured into ice water and extracted with ethyl acetate. The organic layer was washed with $Na_2CO_3$ aqueous solution and dried, concentrated and purified to give 180 mg pure compound 32.

Compounds S01734 and S01688

The synthetic procedure from intermediate 32 to target compounds was similar to the general procedure.

Compound S01864

Scheme 18

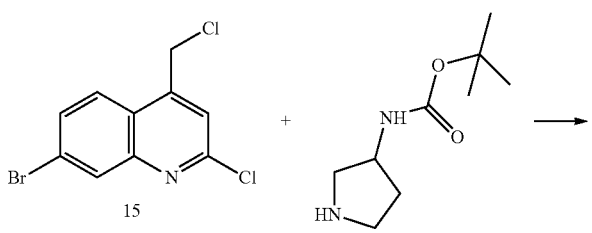

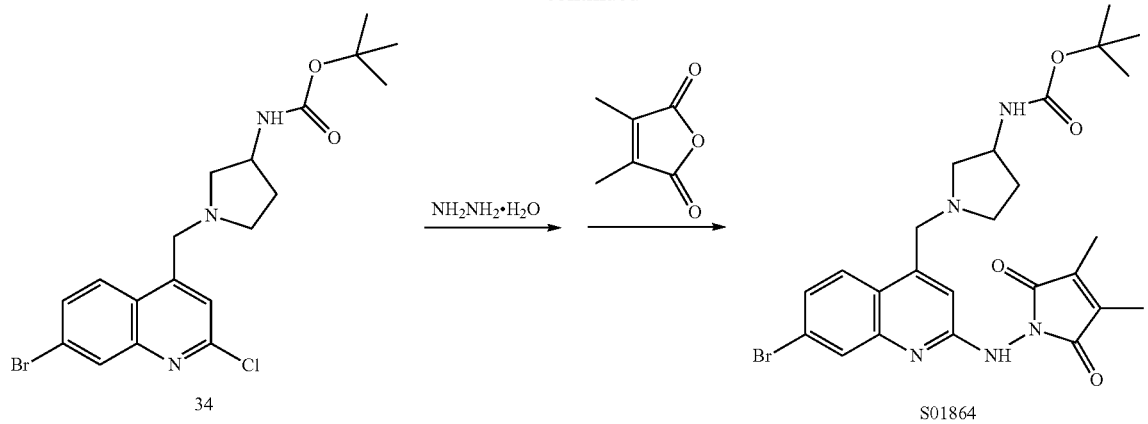

Intermediate 34

Starting material and intermediate 15 were dissolved in acetonitrile and stirred at room temperature overnight, then filtered and the solvent was evaporated. The residue was purified by preparative TLC to afford the product.

Compound S01864

The synthetic procedure from intermediate 34 to target compound is similar to general procedure.

Compounds S01268 and S01862

The synthetic route for compounds S01268 and S01862 was similar to that for compound S01864

Compound S01475

TEA (4.55 g, 45 mmol, 6.3 ml) in 25 ml of acetonitrile at room temperature. The mixture was then heated to 110° C. (oil bath temperature) for 12 h, cooled down to room temperature, and the solvent was evaporated. DCM and saturate NaHCO₃ (aq.) were added and the layers were separated. The organic layer was dried over anhydrous Na₂SO₄ and evaporated. The residue was washed with ether and filtered, then evaporated to give the crude product as a black oil that was then purified by flash chromatography to give the product as a yellow oil. Yield was 4.4 g (71%).

Compound S01475

The synthetic procedure from intermediate 35 to Compound S01475 was similar to the general procedure.

Compound S01762

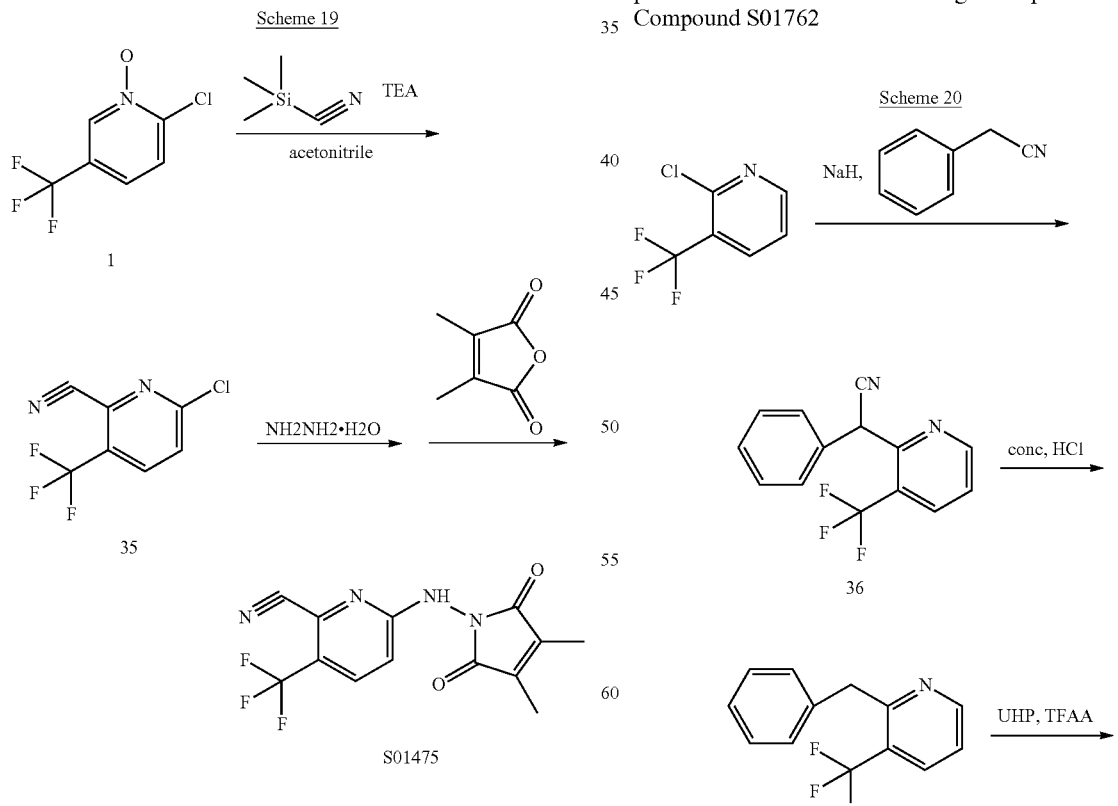

Intermediate 35

Trimethylsilyl cyanide (7.44 g, 75 mmol, 10 ml) was added to a stirred solution of intermediate 35 (5.92 g, 30 mmol) and

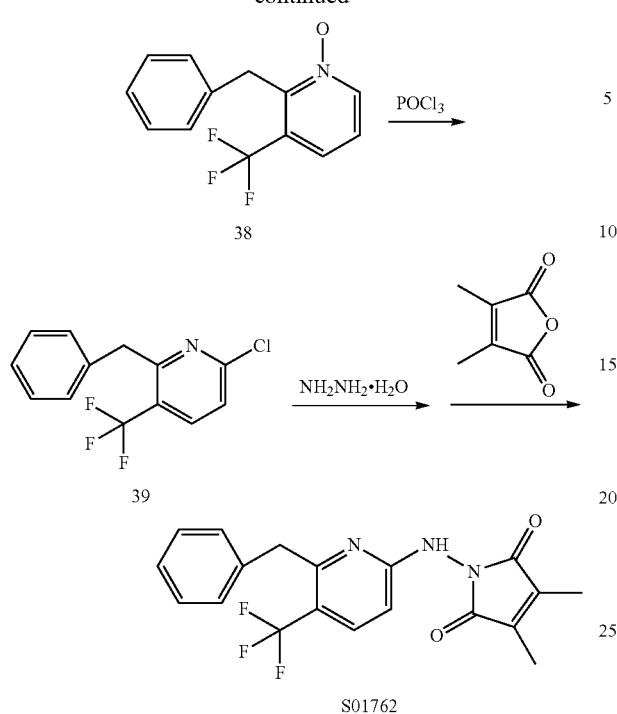

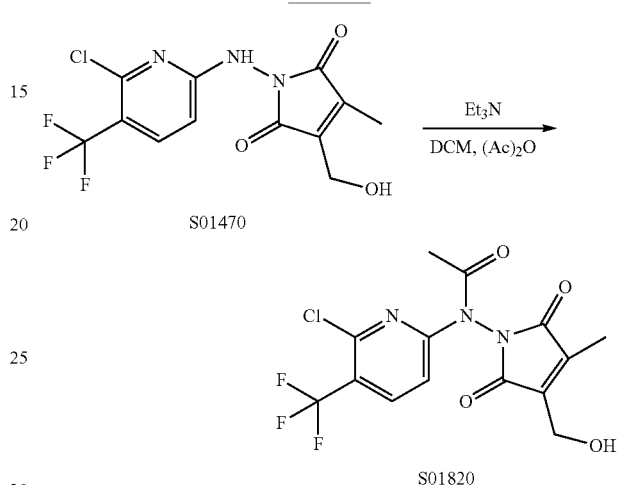

organic layer was washed with sat.NaHCO$_3$, dried over Na$_2$SO$_4$ and evaporated. The residue was purified by preparative TLC to afford 0.13 g of product (yield=87%).

Compound S01762

The synthetic procedure from intermediate 39 to compound S01762 was similar to the general procedure.

Compound S01820

Intermediate 36

Sodium hydride (0.264 g, 6.6 mmol, 60%) was added to a stirred solution of benzyl cyanide (0.645 g, 5.5 mmol) in 10 ml of DMF at room temperature. Starting material (1.0 g, 5.5 mmol) was added to the mixture after 30 min and the resulting mixture was stirred at room temperature for 2 h. Brine was added to quench the reaction and the mixture was extracted with ethyl acetate. The combined organic layer was dried over anhydrous sodium sulfate and evaporated. The residue was purified by flash chromatography (eluted with petroleum ether:ethyl acetate=8:1 to 5:1) to give 0.475 g of product (yield=33%).

Intermediate 37

Intermediate 36 (0.15 g, 0.57 mmol) mixed with 5 ml of concentrated HCl and refluxed overnight. Then the mixture cooled to room temperature, 15 ml of water was added, the pH was adjusted to 8-9 with sodium carbonate, and the mixture was extracted with ethyl acetate (10 ml). The combined organic layer was dried over anhydrous sodium sulfate and evaporated to give 0.14 g grams of product (yield=100%), which was used without further purification for the next step.

Intermediate 38

Intermediate 37 (0.14 g, 0.57 mmol) was dissolved in 5 ml of DCM, then UHP (0.17 g, 1.77 mmol) was added and after that, TFAA (0.36 g, 1.71 mmol, 0.24 ml) was added dropwise with ice-bath cooling. The mixture was then warmed to room temperature and stirred overnight at the same temperature. Five (5) ml of water was added and the mixture was neutralized with sodium carbonate to pH 8-9 and then extracted with DCM. The combined organic layer was dried over anhydrous sodium sulfate and evaporated to give 0.14 g of the crude product (yield=95%), which was used without further purification for next step.

Intermediate 39

Intermediate 38 (0.14 g, 0.55 mmol) was dissolved in 5 ml of POCl$_3$ and the mixture was heated to 80-90° C. for 2 h. The mixture was then cooled to room temperature, poured into ice-water, and extracted with ethyl acetate. The combined A solution of S01470 in 3 ml DCM was stirred at room temperature and Et$_3$N was added. Then Ac$_2$O was added under ice-bath. The reaction mixture was warmed to room temperature and stirred overnight. The reaction was then quenched and worked-up in the usual manner as described above. The residue was purified by prep-TLC (PE:EA=3:1) to furnish pure compound S01820.

Compound S00935

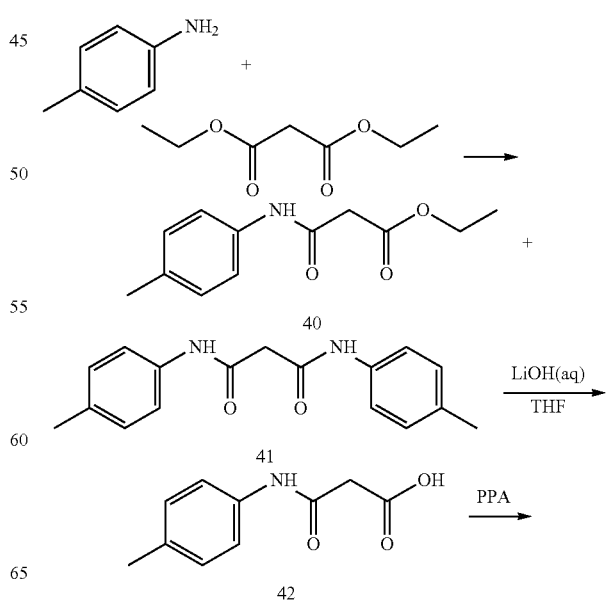

151

-continued

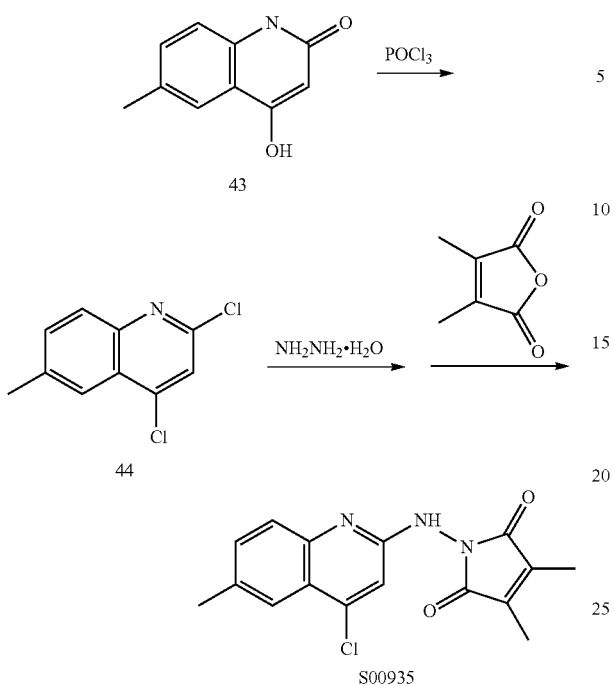

Compound S00516

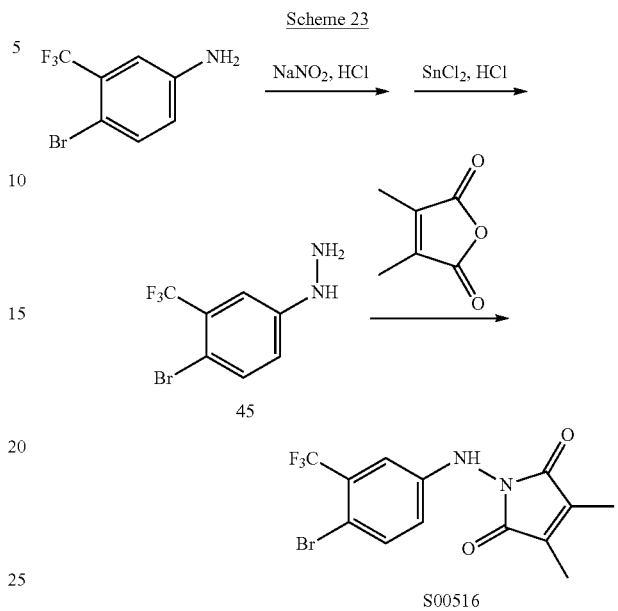

Intermediate 40

Starting material (9.08 g, 84.4 mmol) was added to 19.2 ml of diethyl malonate, the mixture was heated to 150° C. (oil bath temperature) for 6 h, evaporated, filtered and washed with ethyl acetate to give 3.7 g of white solid, it was intermediate 41 (check it by LC-MS), the filtrate was evaporated, the residue cooled to afford second batch solid, washed with a solution of Petroleum ether: Ethyl acetate equal to 5:1, check it by LC-MS, it was intermediate 40 (5.42 g).

Intermediate 42

To a stirred solution of intermediate 40 (5.42 g, 24.5 mmol) in THF, 60 ml of 2N LiOH was added and the resulting mixture was stirred at room temperature for 3 h. The solvent was evaporated, the residue washed with ethyl acetate, filtered, and the cake was added to 10 ml of concentrated HCl and stirred for 30 min, then the cake was filtered and dried to give 3.1 g of product.

Intermediate 43

Intermediate 42 (3.1 g, 16 mmol) was added to 20 ml of PPA and the mixture was heated to 150° C. for 4 h. The reaction mixture was poured into ice-water with stirring, then filtered, and the cake was washed with water and dried to give 2.92 g of product.

Intermediate 44

Intermediate 43 (0.47 g, 2.7 mmol) was added to 10 ml of POCl$_3$, and the mixture was heated with refluxing for 5 h. The resulting mixture was cooled to room temperature and poured into ice-water, then extracted with ethyl acetate. The combined organic layer was dried over Na$_2$SO$_4$, and evaporated to give the crude product (0.45 g) which was used without further purification.

Compound S00935

From intermediate 43 to compound S00935, the synthetic procedure was similar to the general procedure.

Compounds S00871, S01005, S01078, S01247, and S01311

The synthetic route of compounds S00871, S01005, S01078, S01247, and S01311 is similar to compound S00935.

Intermediate 45

Starting material (0.08 mol) was added to conc. HCl (40 mL). The mixture was cooled to −5° C. by ice and salt with stirring. Then sodium nitrite (5.52 g, 0.08 mol) dissolved in water (20 mL) was added. Stirring was continued for 1 h, and stannous chloride (30 g) in conc. HCl (30 mL) was added slowly over a period of two hours, while keeping the temperature below 0° C. The mixture was stirred for another hour after the addition and filtered. The filtered solid was treated with dilute aqueous sodium hydroxide and the then extracted with ether. The ether layer was washed with water, dried over anhydrous Na$_2$SO$_4$. The solvent was removed and the residue was crystallized from hexane to give the Compound 45.

Compound S00516

The synthetic procedure is similar to general procedure.

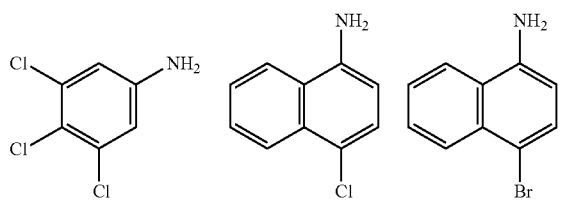

Compounds S00738, S00832, S00942

The starting materials are commercially available, so the synthetic route of compounds S00738, S00832, S00942 was similar to S00516.

Compound S01191

Scheme 24

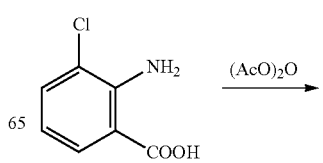

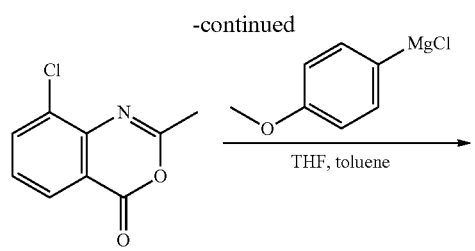

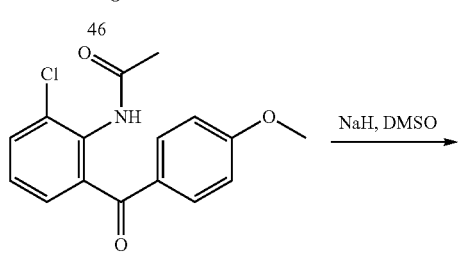

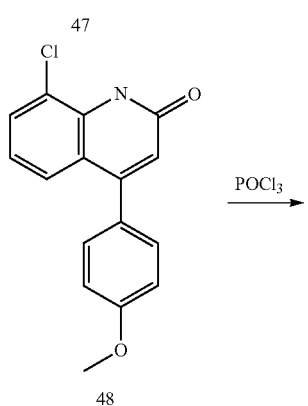

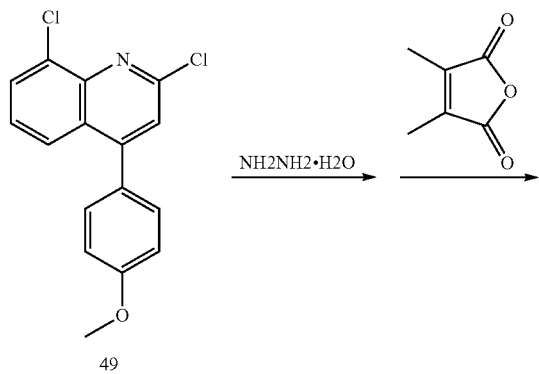

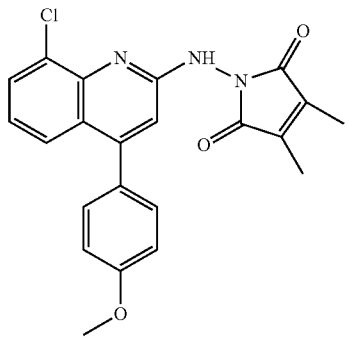

S01191

Intermediate 46

A mixture of 2-amino-3-chlorobenzoic acid (500 mg, 2.91 mmol) and acetic anhydride (1.2 mL) was heated with refluxing for 1 hour, and excess acetic anhydride was removed under vacuum. The residue was cooled and treated with diethyl ether to give a bulk precipitate, which was filtered off, washed with cold ether and dried to give 550 mg of the desired product as a pale yellow solid (yield=97%).

Intermediate 47

Into a three-necked flask, which had been oven dried and flushed with $N_2$, was added a small amount of $I_2$ to a mixture of magnesium (59 mg, 2.47 mmol) in 0.5 mL of dry THF. When the reaction mixture became colorless, a solution of 4-bromoanisole (440 mg, 2.35 mmol) in 1.5 mL of dry THF was added to the mixture. The reaction mixture was stirred at room temperature until Mg was eliminated.

The Grignard reagent from 4-bromoanisole in 2 mL of THF was treated with compound 46 (460 mg, 2.35 mmol) in 4.5 mL dry toluene at 0° C. for 1 hour and at 30° C. for an additional 1 hour. The solution was carefully acidified with dilute sulphuric acid, and washed with aqueous $NaHCO_3$ and water. The organic layer was dried over anhydrous $Na_2SO_4$ and evaporated to give an oil. The residue was purified by silica gel chromatography (petroleum ether/ethyl acetate=4:1) to give 450 mg of the desired product as pale brown solid (yield=63%).

Intermediate 48

A mixture of compound 47 (400 mg, 1.32 mmol), NaH (60% in oil, 316 mg, 13.20 mmol) in 1 mL of DMSO was heated at 60-70° C. overnight. The reaction mixture was poured into ice-water and extracted with ethyl acetate, then washed with water and brine. The organic layer was dried over anhydrous $Na_2SO_4$ and evaporated to dryness. The residue was recrystallized from ethanol to give 80 mg of the desired compound 48 as a brown solid (yield=21%).

Compound S01191

The synthetic procedure from intermediate 48 to target compound was similar to the general procedure.

Compound S01553

Scheme 25

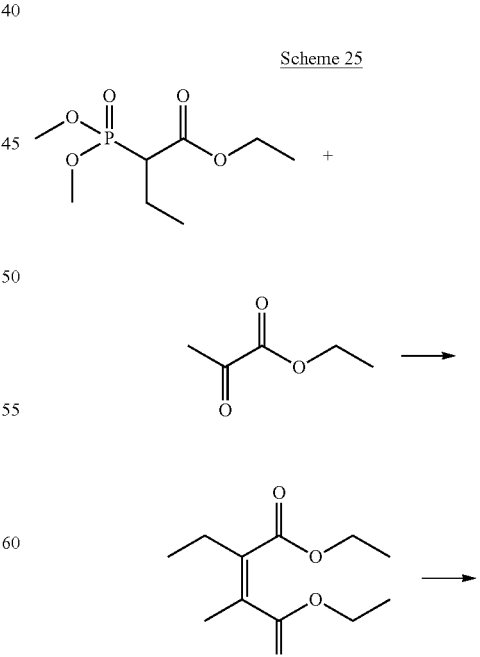

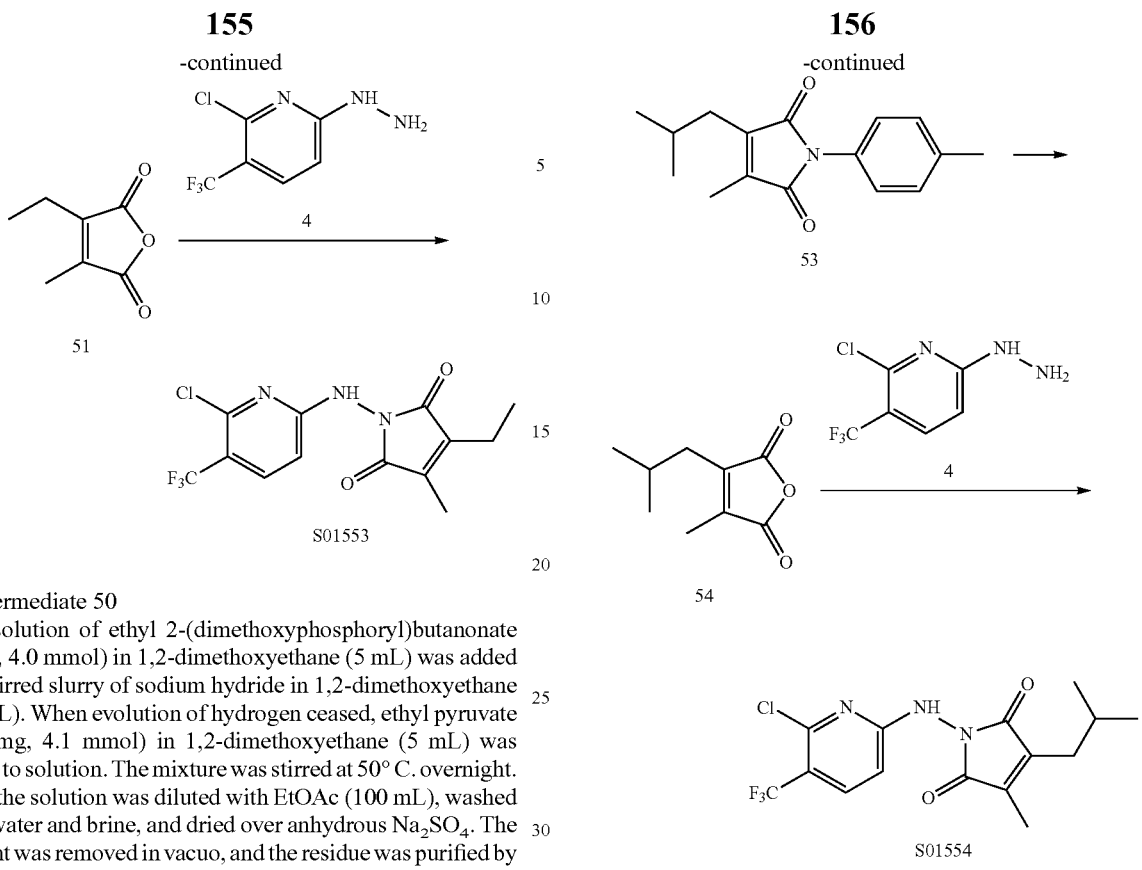

Intermediate 50

A solution of ethyl 2-(dimethoxyphosphoryl)butanonate (1.0 g, 4.0 mmol) in 1,2-dimethoxyethane (5 mL) was added to a stirred slurry of sodium hydride in 1,2-dimethoxyethane (10 mL). When evolution of hydrogen ceased, ethyl pyruvate (480 mg, 4.1 mmol) in 1,2-dimethoxyethane (5 mL) was added to solution. The mixture was stirred at 50° C. overnight. Then the solution was diluted with EtOAc (100 mL), washed with water and brine, and dried over anhydrous $Na_2SO_4$. The solvent was removed in vacuo, and the residue was purified by chromatography to give the product. Yield was 710 mg (87.2%)

Intermediate 51

A solution of diethyl 2-ethyl-3-methylmaleate (75 mg, 0.35 mmol) in ethanol (0.8 mL) was added dropwise to aqueous NaOH (2M, 0.4 mL) dropwise. The mixture was stirred at room temperature for 30 min, then diluted with water (10 mL) and washed with ether (5 mL). The aqueous layer was acidified with 5% aq. then extracted with EtOAc. The organic layer was washed with brine and dried over anhydrous $Na_2SO_4$. The solvent was removed in vacuo, and the residue was purified by chromatography on a silica gel column. Yield was 41 mg (83.7%)

Compound S01553

The synthetic procedure from intermediate 51 to compound S01553 was similar to the general procedure.

Compound S01554

Scheme 26

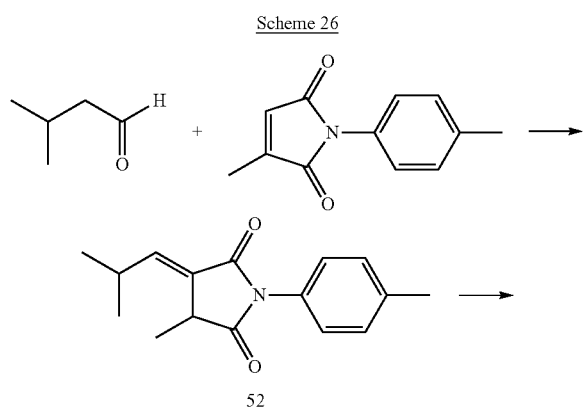

Intermediate 52

A mixture of citraconimide (200 mg, 1.0 mmol) and $PPh_3$ (320 mg, 1.2 mmol) in glacial AcOH (7 mL) was stirred at room temperature for 1 hour. Isovaleraldehyde (160 μl, 1.5 mmol), was added and the reaction mixture was refluxed with stirring for 24 hours. HOAc was distilled off in vacuo, the residue was dissolved in EtOAc (30 mL), and the organic layer was washed with $H_2O$, brine and dried over anhydrous $NaSO_4$. The solvent was removed in vacuo and the residue was purified by chromatography on a silica gel column. Yield: (90 mg, 35.0%)

Intermediate 53

To a stirred solution of 52 (90 mg) in THF (2 mL) was added $Et_3N$ (0.4 mL). The reaction mixture was refluxed for 48 hours, and then was concentrated in vacuo. The residue was dissolved in EtOAc and the organic layer washed with water, brine and dried over anhydrous $Na_2SO_4$. The solvent was removed in vacuo and the residue was purified by chromatography on a silica gel column. Yield: (85 mg, 94.4%).

Intermediate 54

To the solution of 53 (50 mg, 0.19 mmol) in THF (0.3 mL) and MeOH (0.6 mL) was added aq. KOH (1 mL, 30%) and the reaction mixture was refluxed for 12 hours with stirring. Then the reaction mixture was concentrated in vacuo, the obtained residue was acidified with dilute aq. HCl and extracted with EtOAc (20 mL). The organic layer was washed with water, brine and dried over anhydrous $Na_2SO_4$. The solvent was removed in vacuo and the residue was purified by chromatography on a silica gel column. Yield: (26 mg, 81.3%).

Compound S01554

The synthetic procedure from intermediate 54 to compound S01554 was similar to the general procedure.

Compound S00873

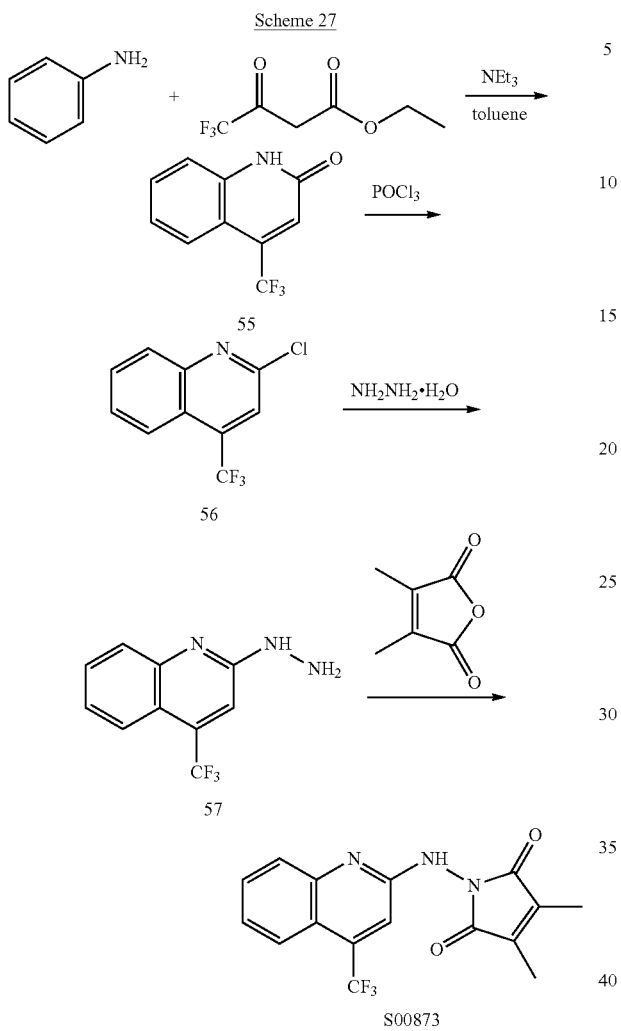

Intermediate 55

To a solution of the ester (5.46 mmol) and triethylamine (101 g, 10.86 mmol) in toluene (5 mL) was added a solution of aniline (6.52 mmol) in toluene (2 mL) at room temperature. The reaction mixture was refluxed until the reaction was complete. After workup, compound 56 was obtained, which was pure enough to be used in the next step.

Intermediate 57

The mixture of 55 and POCl₃ (5 mL) was refluxed for 5 h, and then poured into the ice water. The ether extract was washed with brine and dried over anhydrous Na₂SO₄, and then concentrated to afford the compound 56, which was directly used in next step.

The mixture of 56 and hydrazine hydrate in 5 mL of ethanol was refluxed for several hours until the starting material disappeared. After workup, compound 57 was obtained.

Compound S00873

The synthetic procedure from intermediate 57 to compound S00873 was similar to the general procedure.

Compound S01455

The synthetic route of compound S01455 is similar to compound S00873.

We claim:

1. A method for treating a cell proliferation disorder in a subject, comprising administering to the subject a compound having the formula of Structure (II):

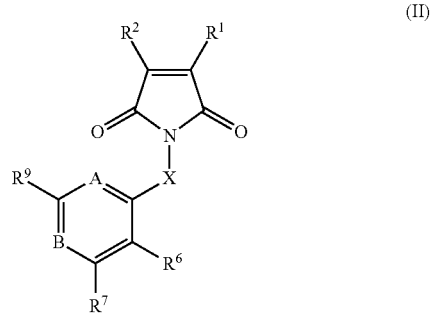

wherein $R^1$ and $R^2$ are independently chosen from alkyl, substituted alkyl, and optionally substituted alkoxy, wherein at least one of $R^1$ and $R^2$ is methyl, and where $R^1$ and $R^2$ can be part of a cyclic alkylene chain that forms a fused ring structure;

X is $NR^3$;

$R^3$ is H, alkyl, or acyl;

A is N or CH;

B is $CR^8$;

$R^6$ is selected from H, alkyl, substituted alkyl, and halogen, $R^7$ is selected from H, alkyl, substituted alkyl, halogen, optionally substituted aryl, optionally substituted heteroaryl, optionally substituted alkoxy, optionally substituted aryloxy, cyano, optionally substituted alkylthio, optionally substituted alkylsufinyl, optionally substituted alkylsulfonyl, optionally substituted arylthio, optionally substituted acyl, optionally substituted amino, carboxyl, optionally substituted alkoxycarbonyl, optionally substituted carbamoyl, and wherein $R^6$ and $R^7$ can form an aryl group forming a fused ring structure when each of $R^6$ and $R^7$ is alkyl;

$R^8$ is selected from H, alkyl, substituted alkyl, halogen, and $R^9$ is selected from H, alkyl, substituted alkyl, halogen, optionally substituted aryl, and cyano, wherein $R^8$ and $R^9$ can form one or more optionally substituted aryl groups forming a fused ring structure when each of $R^8$ and $R^9$ is alkyl or substituted alkyl and wherein at least one of $R^6$, $R^7$, $R^8$, and $R^9$ is halogen selected from Br or Cl, or substituted alkyl substituted with halogen selected from Br, Cl, or F;

or a salt thereof.

2. The method of claim 1, wherein one of $R^1$ and $R^2$ is methyl, and the other of $R^1$ and $R^2$ is alkyl or alkyl substituted with alkoxy, hydroxy, carboxy, or alkoxycarbonyl.

3. The method of claim 1, wherein $R^3$ is H, methyl, or acyl.

4. The method of claim 2, wherein one of $R^1$ and $R^2$ is methyl, and the other of $R^1$ and $R^2$ is alkyl or alkyl substituted with alkoxy, hydroxy, carboxy, alkoxycarbonyl, wherein alkoxy includes cyclic alkoxy, and $R^6$ is H, $R^7$ is H, $R^8$ is $CF_3$, and $R^9$ is Cl.

5. A method for treating a cell proliferation disorder in a subject, comprising administering to the subject a compound having the formula of Structure (II):

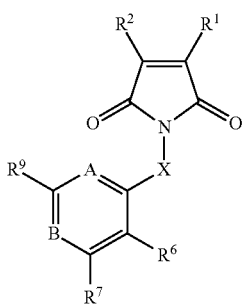

(II)

wherein
R¹ and R² are independently chosen from alkyl, substituted alkyl, and optionally substituted alkoxy, optionally substituted alkylthio, halogen, optionally substituted aryl, optionally substituted aryloxy, optionally substituted arylthio, or H, where R¹ and R² can be part of a cyclic alkylene chain that forms a fused ring structure;
X is NR³;
R³ is H, alkyl, or acyl;
A is N or CH;
B is CR⁸ or N;
R⁶, R⁷, R⁸, and R⁹ are independently chosen from H, alkyl, substituted alkyl, halogen, optionally substituted aryl, optionally substituted heteroaryl, optionally substituted alkoxy, optionally substituted aryloxy, cyano, optionally substituted alkylthio, optionally substituted alkylsufinyl, optionally substituted alkylsulfonyl, optionally substituted arylthio, optionally substituted acyl, optionally substituted amino, carboxyl, optionally substituted alkoxycarbonyl, optionally substituted carbamoyl, wherein R⁶ and R⁷, or R⁷ and R⁸, or R⁸ and R⁹ can be part of a cyclic alkylene group forming a fused ring structure;
wherein the compound is selected from the group consisting of
tert-butyl 3-(1-{[6-chloro-5-(trifluoromethyl)(2-pyridyl)]amino}-4-methyl-2,5-dioxoazolin-3-yl)propanoate (S01860);
ethyl 3-{[6-chloro-5-(trifluoromethyl)(2-pyridyl)]amino}-4-methyl-2,5-dioxoazolin-3-yl)propanoate (S01861),
3,4-dimethyl-1-[(4,7,8-trichloro(2-quinolyl))amino]azoline-2,5-dione (S01078),
1-[(8-bromo-4-chloro(2-quinolyl))amino]-3,4-dimethylazoline-2,5-dione (S01247),
tert-butyl 4-({2-[(3,4-dimethyl-2,5-dioxoazolinyl)amino]-7-bromo-4-quinolyl}methyl)piperazinecarboxylate (S01589),
methyl 3-(1-{[6-chloro-5-(trifluoromethyl)(2-pyridyl)]amino}-4-methyl-2,5-dioxoazolin-3-yl)propanoate (S01648),
3-(1-{[6-chloro-5-(trifluoromethyl)(2-pyridyl)]amino}-4-methyl-2,5-dioxoazolin-3-yl)-N-methoxy-N-methylpropanamide (S01796),
1-{[7-bromo-4-({4-[2-methoxyphenyl)carbonyl]piperazinyl}methyl) (2-quinolyl)]amino}-3,4-dimethylazoline-2,5-dione (S01879),
1-{[3-bromo-6-chloro-5-(trifluoromethyl)(2-pyridyl)]amino}-3,4-dimethylazoline-2,5-dione (S01981),
1-{[6-chloro-3-(trifluoromethyl)(2-pyridyl)]amino}-3,4-dimethylazoline-2,5-dione (S00109),
1-{[6-chloro-5-(trifluoromethyl)(2-pyridyl)]methylamino}-3,4-dimethylazoline-2,5-dione (S00170),
1-{[6-bromo-5-(trifluoromethyl)(2-pyridyl)]methylamino}-3,4-dimethylazoline-2,5-dione (S01007),
1-{[6-chloro-5-(trifluoromethyl)(2-pyridyl)]amino}-4-methyl-3-(3-methylbutyl)azoline-2,5-dione (S01554),
1-{[6-chloro-5-(trifluoromethyl)(2-pyridyl)]amino}-3-(methoxymethyl)-4-methylazoline-2,5-dione (S01599),
1-{[7,8-dichloro-4-(trifluoromethyl)(2-quinolyl)]amino}-3,4-dimethylazoline-2,5-dione (S01455),
3-(1-{[6-chloro-5-(trifluoromethyl)(2-pyridyl)]amino}-4-methyl-2,5-dioxoazolin-3-yl)-N,N-diethylpropanamide (S01711),
diethyl 2-[(1-{[6-chloro-5-(trifluoromethyl)(2-pyridyl)]amino}-4-methyl-2,5-dioxoazolin-3-yl)methyl]propane-1,3-dioate (S01712),
N-(tert-butyl)-3-(1-{[6-chloro-5-(trifluoromethyl)(2-pyridyl)]amino}-4-methyl-2,5-dioxoazolin-3-yl)propanamide (S01758),
1-{[7-bromo-4-({4-[(3-methoxyphenyl)carbonyl]piperazinyl}methyl) (2-quinolyl)]amino}-3,4-dimethylazoline-2,5-dione (S01925),
1-{[6-bromo-5-(trifluoromethyl)(2-pyridyl)]amino}-3,4-dimethylazoline-2,5-dione (S00994),
1-[(4,8-dichloro(2-quinolyl))amino]-3,4-dimethylazoline-2,5-dione (S01005),
3,4-dimethyl-1-{[6-phenyl-5-(trifluoromethyl)(2-pyridyl)]amino}azoline-2,5-dione (S01266),
1-{[6-chloro-5-(trifluoromethyl)(2-pyridyl)]amino}-3-(hydroxymethyl)-4-methylazoline-2,5-dione (S01470),
N-(3,4-dimethyl-2,5-dioxoazolinyl)-N-[6-chloro-5-(trifluoromethyl)(2-pyridyl)]acetamide (S01473),
1-{[7-bromo-4-({4-[(2-chlorophenyl)carbonyl]piperazinyl}methyl)(2-quinolyl)]amino}-3,4-dimethylazoline-2,5-dione (S01878),
3-(1-{[6-chloro-5-(trifluoromethyl)(2-pyridyl)]amino}-4-methyl-2,5-dioxoazolin-3-yl)-N-methylpropanamide (S01883),
1-[(8-chloro(2-quinolyl))amino]-3,4-dimethylazoline-2,5-dione (S00585),
3,4-dimethyl-1-[(3,4,5-trichlorophenyl)amino]azoline-2,5-dione (S00832),
3,4-dimethyl-1-{[4-(trifluoromethyl)(2-quinolyl)]amino}azoline-2,5-dione (S00873),
1-[(7-bromo-4-chloro(2-quinolyl))amino]-3,4-dimethylazoline-2,5-dione (S01311),
1-{[6-(3-chloro-4-fluorophenyl)-5-(trifluoromethyl)(2-pyridyl)]amino}-(3,4-dimethylmethylazoline-2,5-dione (S01313),
3,4-dimethyl-1-{[6-(2-methylpropyl)-5-(trifluoromethyl)(2-pyridyl)]amino}azoline-2,5-dione (S01457),
1-{[6-chloro-4-(trifluoromethyl)(2-pyridyl)]amino}-3,4-dimethylazoline-2,5-dione (S01737),
Methyl 3-(1-{[4-({4-[(tert-butyl)oxycarbonyl]piperazinyl}methyl)-7-bromo (2-quinolyl)]amino}-4-methyl-2,5-dioxoazolin-3-yl)propanoate (S01865),
1-({4-[(4-{[4-(dimethylamino)phenyl]carbonyl}piperazinyl)methyl]-7-bromo (2-quinolyl)}amino)-3,4-dimethylazoline-2,5-dione (S01880),
1-[(3-chloroisoquinolyl)amino]-3,4-dimethylazoline-2,5-dione (S01098),
1-{[6-chloro-5-(trifluoromethyl)(2-pyridyl)]amino}-3-ethyl-4-methylazoline-2,5-dione (S01553),
1-{[4-chloro-6-phenyl-5-(trifluoromethyl)(2-pyridyl)]amino}-3,4-dimethylazoline-2,5-dione (S01734),
N-[1-({2-[(3,4-dimethyl-2,5-dioxoazolinyl)amino]-7-bromo(4-quinolyl)}methyl)pyrrolidin-3-yl](tert-butoxy)carboxamide (S01864), 1-{[7-bromo-4-({4-[(4-fluorophenyl)carbonyl]
piperazinyl}methyl)(2-quinolyl)]amino}-3,4-dimethylazoline-2,5-dione (S01877),
6-[(3,4-dimethyl-2,5-dioxoazolinyl)amino]-3-(trifluoromethyl)pyridine-2-carbonitrile (S01475),
2-{[6-chloro-5-(trifluoromethyl)-2-pyridyl]amino}-4,5,6,7-tetrahydroisoindole-1,3-dione (S00186),
1-{[4-bromo-3-(trifluoromethyl)phenyl]amino}-3,4-dimethylazoline-2,5-dione (S00516),
1-[(4-chloronaphthyl)amino]-3,4-dimethylazoline-2,5-dione (S00738),
1-[(4-chloro-6-methyl(2-quinolyl))amino]-3,4-dimethylazoline-2,5-dione (S00935),
1-[(4-bromonaphthyl)amino]-3,4-dimethylazoline-2,5-dione (S00942),
1-{[7-bromo-4-(hydroxymethyl)(2-quinolyl)]amino}-3,4-dimethylazoline-2,5-dione (S01037),
{2-[(3,4-dimethyl-2,5-dioxoazolinyl)amino]-7-bromo-4-quinolyl}methyl acetate (S01047),
1-{[8-chloro-4-(4-methoxyphenyl)(2-quinolyl)]amino}-3,4-dimethylazoline-2,5-dione (S01191),
1-[(4-chlorobenzo[h]quinolin-2-yl)amino]-3,4-dimethylazoline-2,5-dione (S01207),
1-[(7-bromo-4-{[4-benzylpiperazinyl]methyl}(2-quinolyl))amino]-3,4-dimethylazoline-2,5-dione (S01268),
1-{[6-(4-chlorophenyl)-5-(trifluoromethyl)(2-pyridyl)]amino}-3,4-dimethylazoline-2,5-dione (S01371),
3,4-dimethyl-1-{[6-(4-methylphenyl)-5-(trifluoromethyl)(2-pyridyl)]amino} azoline-2,5-dione (S01393),
1-{[6-(3-chlorophenyl)-5-(trifluoromethyl)(2-pyridyl)]amino}-3,4-dimethylazoline-2,5-dione (S01474),
1-{[6-chloro-5-(trifluoromethyl)(2-pyridyl)]methylamino}-3-(methoxymethyl)-4-methylazoline-2,5-dione (S01600),
phenylmethyl 4-({2-[(3,4-dimethyl-2,5-dioxoazolinyl)amino]-7-bromo-4-quinolyl}methyl)piperazinecarboxylate (S01683),
1-{[6-chloro-2-phenyl-3-(trifluoromethyl)(4-pyridyl)]amino}-3,4-dimethylazoline-2,5-dione (S01688),
3,4-dimethyl-1-({6-[3-(trifluoromethyl)phenyl] (2-pyridyl)}amino)azoline-2,5-dione (S01691),
1-[(7-bromo-4-{[4-(phenylcarbonyl)piperazinyl]methyl}(2-quinolyl))amino]-3,4-dimethylazoline-2,5-dione (S01699),
3-(1-{[6-chloro-5-(trifluoromethyl)(2-pyridyl)]amino}-4-methyl-2,5-dioxoazolin-3-yl)-N-methyl-N-phenylpropanamide (S01759),
3,4-dimethyl-1-{[6-benzyl-5-(trifluoromethyl)(2-pyridyl)]amino}azoline-2,5-dione (S01762),
1-{[4-({4-[(2,4-dimethylphenyl)carbonyl]piperazinyl}methyl)-7-bromo (2-quinolyl)]amino}-3,4-dimethylazoline-2,5-dione (S01800),
1-{[7-bromo-4-({4-[(4-methoxyphenyl)carbonyl]piperazinyl}methyl)(2-quinolyl)]amino}-3,4-dimethylazoline-2,5-dione (S01801),
N-[6-chloro-5-(trifluoromethyl)(2-pyridyl)]-N-[4-(hydroxymethyl)-3-methyl-2,5-dioxoazolinyl]acetamide (S01820),
1-[(7-bromo-4-{[4-(phenylsulfonyl)piperazinyl]methyl}(2-quinolyl))amino]-3,4-dimethylazoline-2,5-dione (S01822),
1-[(4-chloro-8-methyl(2-quinolyl))amino]-3,4-dimethylazoline-2,5-dione (S00871),
tert-butyl 4-[({2-[(3,4-dimethyl-2,5-dioxoazolinyl)amino]-7-bromo-4-quinolyl}methyl)amino]piperidinecarboxylate (S01862),
tert-butyl 4-[4-({2-[(3,4-dimethyl-2,5-dioxoazolinyl)amino]-7-bromo-4-quinolyl}methyl)piperazinyl]piperidinecarboxylate (S01928),
1-[(4-{[4-(3,3-dimethylbutanoyl)piperazinyl]methyl}-7-bromo (2-quinolyl))amino]-3,4-dimethylazoline-2,5-dione (S01929),
Methylethyl 3-(1-{[6-chloro-5-(trifluoromethyl)(2-pyridyl)]amino}-4-methyl-2,5-dioxoazolin-3-yl)propanoate (S02022)
Methylpropyl 3-(1-{[6-chloro-5-(trifluoromethyl)(2-pyridyl)]amino}-4-methyl-2,5-dioxoazolin-3-yl)propanoate (S02264)
tert-Butyl 2-(1-{[6-chloro-5-(trifluoromethyl)(2-pyridyl)]amino}-4-methyl-2,5-dioxoazolin-3-yl)acetate (S02225)
1-{[6-Chloro-5-(trifluoromethyl)(2-pyridyl)]amino}-3-(ethoxymethyl)-4-methylazoline-2,5-dione (S02366)
3-Butyl-1-{[6-chloro-5-(trifluoromethyl)(2-pyridyl)]amino}-4-methylazoline-2,5-dione (S03448)
1-{[6-Chloro-5-(trifluoromethyl)(2-pyridyl)]amino}-4-methyl-3-[2-(2-methyl(1,3-dioxolan-2-yl))ethyl]azoline-2,5-dione (S03456)
1-{[6-Chloro-5-(trifluoromethyl)(2-pyridyl)]amino}-3-[(2-methoxyethoxy)methyl]-4-methylazoline-2,5-dione (S03742)
1-{[6-Chloro-5-(trifluoromethyl)(2-pyridyl)]amino}-4-(3-hydroxyhexyl)-3-methylazoline-2,5-dione (S03552)
1-{[6-Chloro-5-(trifluoromethyl)(2-pyridyl)]amino}-4-(3-hydroxypentyl)-3-methylazoline-2,5-dione (S03745)
1-{[6-Chloro-5-(trifluoromethyl)(2-pyridyl)]amino}-4-methyl-3-[(3-methylbutoxy)methyl]azoline-2,5-dione (S03405)
3-(Butoxymethyl)-1-{[6-chloro-5-(trifluoromethyl)(2-pyridyl)]amino}-4-methylazoline-2,5-dione (S03518)
3-[(3,3-Dimethylbutoxy)methyl]-1-{[6-chloro-5-(trifluoromethyl)(2-pyridyl)]amino}-4-methylazoline-2,5-dione (S03747)
1-{[6-Chloro-5-(trifluoromethyl)(2-pyridyl)]amino}-3-(2-ethoxyethyl)-4-methylazoline-2,5-dione (S03960)
1-{[6-Chloro-5-(trifluoromethyl)(2-pyridyl)]amino}-4-methyl-3-[(2-methylpropoxy)methyl]azoline-2,5-dione (S03963)
3-[(2,2-Dimethylpropoxy)methyl]-1-{[6-chloro-5-(trifluoromethyl)(2-pyridyl)]amino}-4-methylazoline-2,5-dione (S03962)
4-[(1,3-Dimethylbutoxy)methyl]-1-{[6-chloro-5-(trifluoromethyl)(2-pyridyl)]amino}-3-methylazoline-2,5-dione (S03964)
4-[(tert-Butoxy)methyl]-1-{[6-chloro-5-(trifluoromethyl)(2-pyridyl)]amino}-3-methylazoline-2,5-dione (S03873)
1-{[6-Chloro-5-(trifluoromethyl)(2-pyridyl)]amino}-4-methyl-3-[2-(2-methylpropoxy)ethyl]azoline-2,5-dione (S03955)
1-{[6-Chloro-5-(trifluoromethyl)(2-pyridyl)]amino}-4-methyl-3-[2-(3-methylbutoxy)ethyl]azoline-2,5-dione (S03956)
1-{[6-Chloro-5-(trifluoromethyl)(2-pyridyl)]amino}-3-methyl-4-(2-propoxyethyl)azoline-2,5-dione (S04034);
and salts thereof.

6. The method of claim 5, wherein the compound is tert-butyl 3-(1-{[6-chloro-5-(trifluoromethyl)(2-pyridyl)]

amino}-4-methyl-2,5-dioxoazolin-3-yl)propanoate (S01860) or a salt thereof; having the following structure:

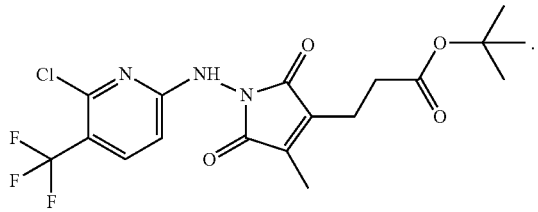 [SMILES: CC1=C(CCC(=O)OC(C)(C)C)C(=O)N(Nc2ccc(C(F)(F)F)c(Cl)n2)C1=O]

7. The method of claim 5, wherein the compound is ethyl 3-(1-{[6-chloro-5-(trifluoromethyl)(2-pyridyl)]amino}-4-methyl-2,5-dioxoazolin-3-yl)propanoate (S01861) or a salt thereof, having the following structure:

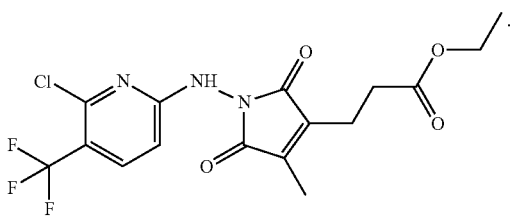 [SMILES: CCOC(=O)CCC1=C(C)C(=O)N(Nc2ccc(C(F)(F)F)c(Cl)n2)C1=O]

8. The method of claim 5, wherein the compound is 3,4-dimethyl-1-[(4,7,8-trichloro(2-quinolyl))amino]azoline-2,5-dione (S01078) or a salt thereof, having the following structure:

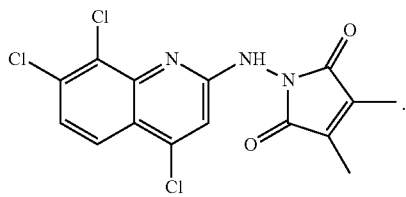 [SMILES: CC1=C(C)C(=O)N(Nc2cc(Cl)c3ccc(Cl)c(Cl)c3n2)C1=O]

9. The method of claim 5, wherein the compound is 1-[(8-bromo-4-chloro(2-quinolyl))amino]-3,4-dimethylazoline-2,5-dione (S01247) or a salt thereof, having the following structure:

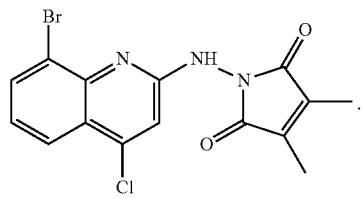 [SMILES: CC1=C(C)C(=O)N(Nc2cc(Cl)c3cccc(Br)c3n2)C1=O]

10. The method of claim 5, wherein the compound is tert-butyl 4-({2-[(3,4-dimethyl-2,5-dioxoazolinyl)amino]-7-bromo-4-quinolyl}methyl)piperazinecarboxylate (S01589) or a salt thereof, having the following structure:

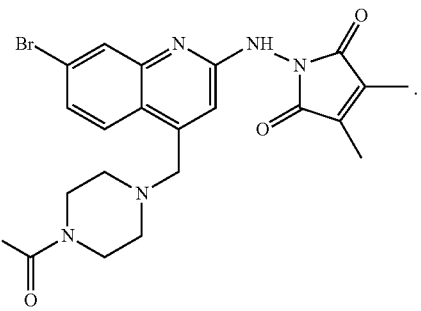

11. The method of claim 5, wherein the compound is methyl 3-(1-{[6-chloro-5-(trifluoromethyl)(2-pyridyl)]amino}-4-methyl-2,5-dioxoazolin-3-yl)propanoate (S01648) or a salt thereof, having the following structure:

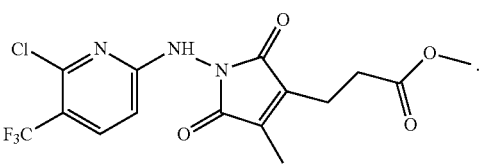 [SMILES: COC(=O)CCC1=C(C)C(=O)N(Nc2ccc(C(F)(F)F)c(Cl)n2)C1=O]

12. The method of claim 5, wherein the compound is 3-(1-{[6-chloro-5-(trifluoromethyl)(2-pyridyl)]amino}-4-methyl-2,5-dioxoazolin-3-yl)-N-methoxy-N-methylpropanamide (S01796) or a salt thereof, having the following structure:

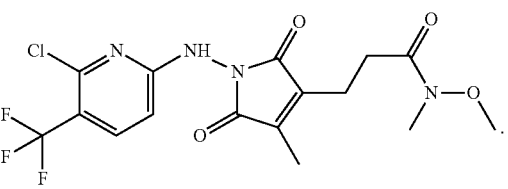 [SMILES: CON(C)C(=O)CCC1=C(C)C(=O)N(Nc2ccc(C(F)(F)F)c(Cl)n2)C1=O]

13. The method of claim 5, wherein the compound is 1-{[7-bromo-4-({4-[(2-methoxyphenyl)carbonyl]piperazinyl}methyl)(2-quinolyl)]amino}-3,4-dimethylazoline-2,5-dione (S01879) or a salt thereof, having the following structure:

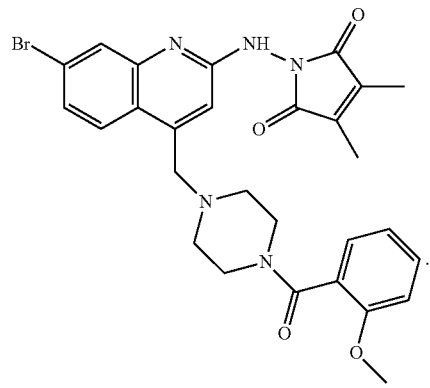 [SMILES: COc1ccccc1C(=O)N1CCN(Cc2cc(NN3C(=O)C(C)=C(C)C3=O)nc3cc(Br)ccc23)CC1]

14. The method of claim 5, wherein the compound is 1-{[3-bromo-6-chloro-5-(trifluoromethyl)(2-pyridyl)]amino}-

3,4-dimethylazoline-2,5-dione (S01981) or a salt thereof, having the following structure:

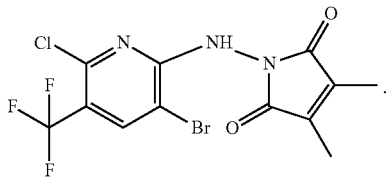 [SMILES: CC1=C(C)C(=O)N(Nc2nc(Cl)c(C(F)(F)F)cc2Br)C1=O]

15. The method of claim 5, wherein the compound is 1-{[6-chloro-3-(trifluoromethyl)(2-pyridyl)]amino}-3,4-dimethylazoline-2,5-dione (S00109) or a salt thereof, having the following structure:

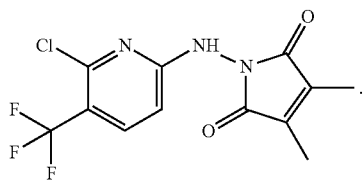 [SMILES: CC1=C(C)C(=O)N(Nc2ccc(C(F)(F)F)c(Cl)n2)C1=O]

16. The method of claim 5, wherein the compound is 1-{[6-chloro-5-(trifluoromethyl)(2-pyridyl)]methylamino}-3,4-dimethylazoline-2,5-dione (S00170) or a salt thereof, having the following structure:

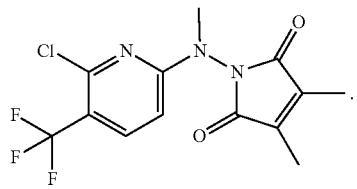 [SMILES: CC1=C(C)C(=O)N(N(C)c2ccc(C(F)(F)F)c(Cl)n2)C1=O]

17. The method of claim 5, wherein the compound is 1-{[6-bromo-5-(trifluoromethyl)(2-pyridyl)]methylamino}-3,4-dimethylazoline-2,5-dione (S01007) or a salt thereof, having the following structure:

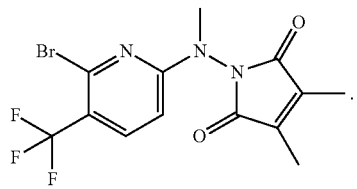 [SMILES: CC1=C(C)C(=O)N(N(C)c2ccc(C(F)(F)F)c(Br)n2)C1=O]

18. The method of claim 5, wherein the compound is 1-{[6-chloro-5-(trifluoromethyl)(2-pyridyl)]amino}-4-methyl-3-(3-methylbutyl)azoline-2,5-dione (S01554), or a salt thereof, having the following structure:

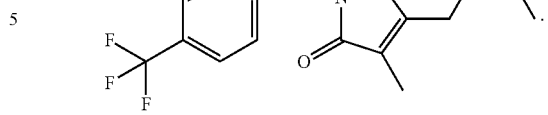

19. The method of claim 5, wherein the compound is 1-{[6-chloro-5-(trifluoromethyl)(2-pyridyl)]amino}-3-(methoxymethyl)-4-methylazoline-2,5-dione (S01599) or a salt thereof, having the following structure:

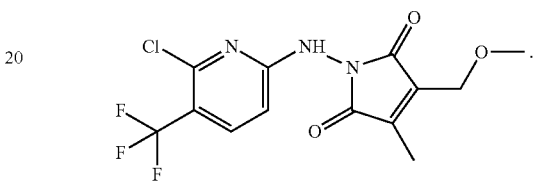

20. The method of claim 5, wherein the compound is 1-{[7,8-dichloro-4-(trifluoromethyl)(2-quinolyl)]amino}-3,4-dimethylazoline-2,5-dione (S01455) or a salt thereof, having the following structure:

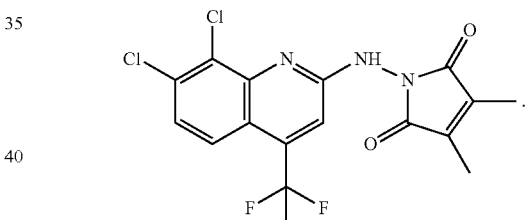

21. The method of claim 5, wherein the compound is 3-(1-{[6-chloro-5-(trifluoromethyl)(2-pyridyl)]amino}-4-methyl-2,5-dioxoazolin-3-yl)-N,N-diethylpropanamide (S01711) or a salt thereof, having the following structure:

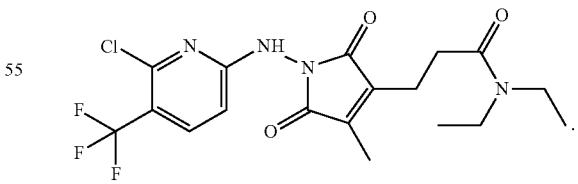

22. The method of claim 5, wherein the compound is diethyl 2-[(1-{[6-chloro-5-(trifluoromethyl)(2-pyridyl)]amino}-4-methyl-2,5-dioxoazolin-3-yl)methyl]propane-1,3-dioate (S01712) or a salt thereof, having the following structure:

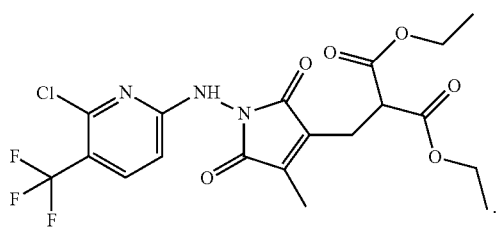 [SMILES: CCOC(=O)C(CC1=C(C)C(=O)N(Nc2ccc(C(F)(F)F)c(Cl)n2)C1=O)C(=O)OCC]

23. The method of claim 5, wherein the compound is N-(tert-butyl)-3-(1-{[6-chloro-5-(trifluoromethyl)(2-pyridyl)]amino}-4-methyl-2,5-dioxoazolin-3-yl)propanamide (S01758) or a salt thereof, having the following structure:

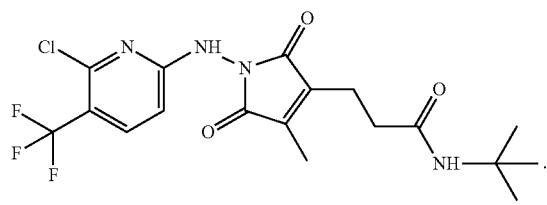 [SMILES: CC1=C(CCC(=O)NC(C)(C)C)C(=O)N(Nc2ccc(C(F)(F)F)c(Cl)n2)C1=O]

24. The method of claim 5, wherein the compound is 1-{[7-bromo-4-({4-[(3-methoxyphenyl)carbonyl]piperazinyl}methyl)(2-quinolyl)]amino}-3,4-dimethylazoline-2,5-dione (S01925) or a salt thereof, having the following structure:

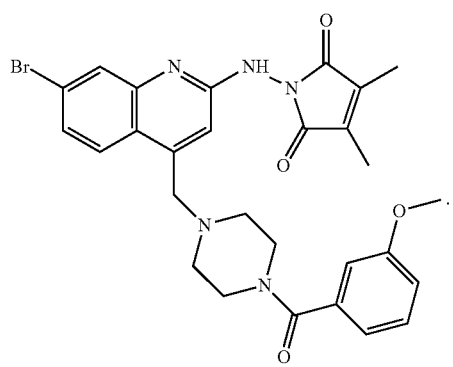 [SMILES: COc1cccc(C(=O)N2CCN(Cc3cc(NN4C(=O)C(C)=C(C)C4=O)nc4cc(Br)ccc34)CC2)c1]

25. The method of claim 5, wherein the compound is 1-{[6-bromo-5-(trifluoromethyl)(2-pyridyl)]amino}-3,4-dimethylazoline-2,5-dione (S00994) or a salt thereof, having the following structure:

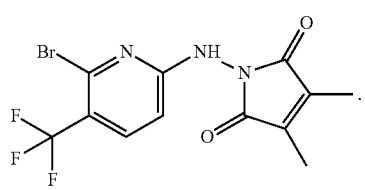 [SMILES: CC1=C(C)C(=O)N(Nc2ccc(C(F)(F)F)c(Br)n2)C1=O]

26. The method of claim 5, wherein the compound is 1-[(4,8-dichloro(2-quinolyl))amino]-3,4-dimethylazoline-2,5-dione (S01005) or a salt thereof, having the following structure:

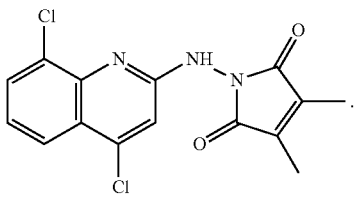 [SMILES: CC1=C(C)C(=O)N(Nc2cc(Cl)c3cccc(Cl)c3n2)C1=O]

27. The method of claim 5, wherein the compound is 3,4-dimethyl-1-{[6-phenyl-5-(trifluoromethyl)(2-pyridyl)]amino}azoline-2,5-dione (S01266) or a salt thereof, having the following structure:

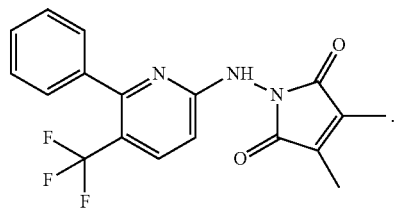 [SMILES: CC1=C(C)C(=O)N(Nc2ccc(C(F)(F)F)c(-c3ccccc3)n2)C1=O]

28. The method of claim 5, wherein the compound is 1-{[6-chloro-5-(trifluoromethyl)(2-pyridyl)]amino}-3-(hydroxymethyl)-4-methylazoline-2,5-dione (S01470) or a salt thereof, having the following structure:

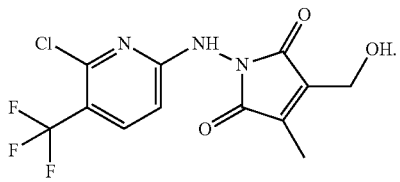 [SMILES: CC1=C(CO)C(=O)N(Nc2ccc(C(F)(F)F)c(Cl)n2)C1=O]

29. The method of claim 5, wherein the compound is N-(3,4-dimethyl-2,5-dioxoazolinyl)-N-[6-chloro-5-(trifluoromethyl)(2-pyridyl)]acetamide (S01473) or a salt thereof, having the following structure:

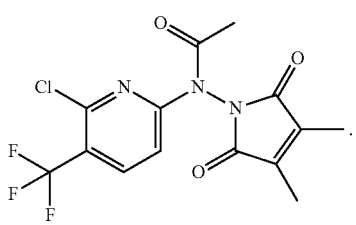 [SMILES: CC(=O)N(c1ccc(C(F)(F)F)c(Cl)n1)N1C(=O)C(C)=C(C)C1=O]

30. The method of claim 5, wherein the compound is 1-{[7-bromo-4-({4-[(2-chlorophenyl)carbonyl]piperazinyl}methyl)(2-quinolyl)]amino}-3,4-dimethylazoline-2,5-dione (S01878) or a salt thereof, having the following structure:

35. The method of claim 5, wherein the compound is 1-[(7-bromo-4-chloro(2-quinolyl))amino]-3,4-dimethylazoline-2,5-dione (S01311) or a salt thereof, having the following structure:

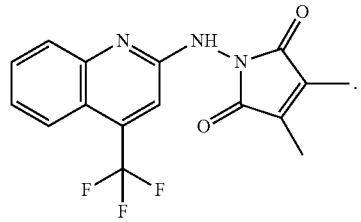

31. The method of claim 5, wherein the compound is 3-(1-{[6-chloro-5-(trifluoromethyl)(2-pyridyl)]amino}-4-methyl-2,5-dioxoazolin-3-yl)-N-methylpropanamide (S01883) or a salt thereof, having the following structure:

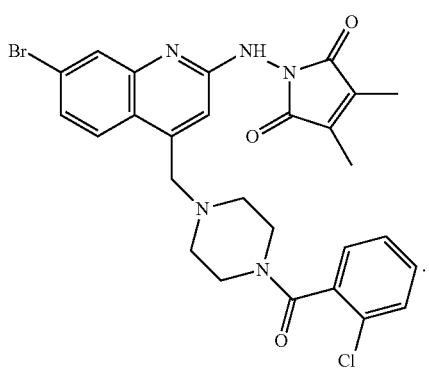 [SMILES: CC1=C(C)C(=O)N(Nc2cc(CN3CCN(C(=O)c4ccccc4Cl)CC3)c3ccc(Br)cc3n2)C1=O]

32. The method of claim 5, wherein the compound is 1-[(8-chloro(2-quinolyl))amino]-3,4-dimethylazoline-2,5-dione (S00585) or a salt thereof, having the following structure:

36. The method of claim 5, wherein the compound is 1-{[6-(3-chloro-4-fluorophenyl)-5-(trifluoromethyl)(2-pyridyl)]amino}-(3,4-dimethylazoline-2,5-dione (S01313) or a salt thereof, having the following structure:

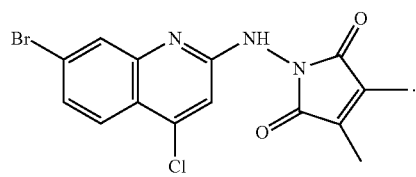

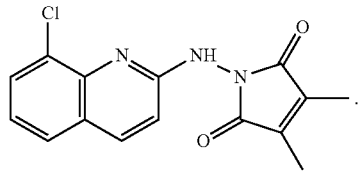 [SMILES: CC1=C(C)C(=O)N(Nc2ccc3cccc(Cl)c3n2)C1=O]

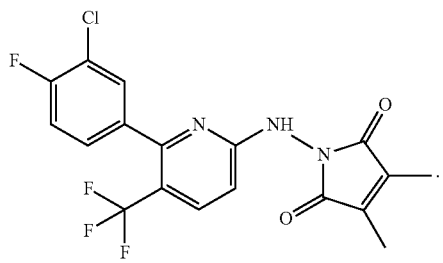 [SMILES: CC1=C(C)C(=O)N(Nc2ccc(C(F)(F)F)c(-c3ccc(F)c(Cl)c3)n2)C1=O]

33. The method of claim 5, wherein the compound is 3,4-dimethyl-1-[(3,4,5-trichlorophenyl)amino]azoline-2,5-dione (S00832) or a salt thereof, having the following structure:

37. The method of claim 5, wherein the compound is 3,4-dimethyl-1-{[6-(2-methylpropyl)-5-(trifluoromethyl)(2-pyridyl)]amino}azoline-2,5-dione (S01457) or a salt thereof, having the following structure:

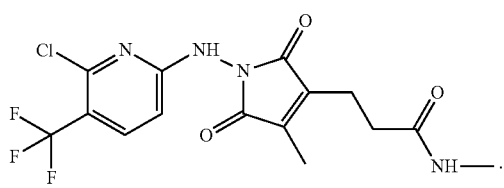

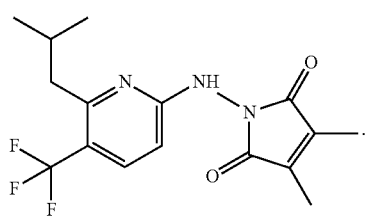 [SMILES: CC1=C(C)C(=O)N(Nc2ccc(C(F)(F)F)c(CC(C)C)n2)C1=O]

34. The method of claim 5, wherein the compound is 3,4-dimethyl-1-{[4-(trifluoromethyl)(2-quinolyl)]amino}azoline-2,5-dione (S00873) or a salt thereof, having the following structure:

38. The method of claim 5, wherein the compound is 1-{[6-chloro-4-(trifluoromethyl)(2-pyridyl)]amino}-3,4-dimethylazoline-2,5-dione (S01737) or a salt thereof, having the following structure:

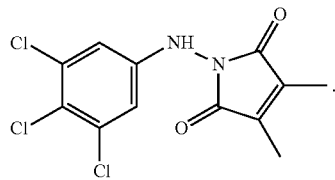

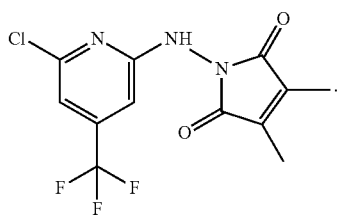 [SMILES: CC1=C(C)C(=O)N(Nc2cc(C(F)(F)F)cc(Cl)n2)C1=O]

39. The method of claim 5, wherein the compound is methyl 3-(1-{[4-({4-[(tert-butyl)oxycarbonyl]piperazinyl}methyl)-7-bromo(2-quinolyl)]amino}-4-methyl-2,5-dioxoazolin-3-yl)propanoate (S01865) or a salt thereof, having the following structure:

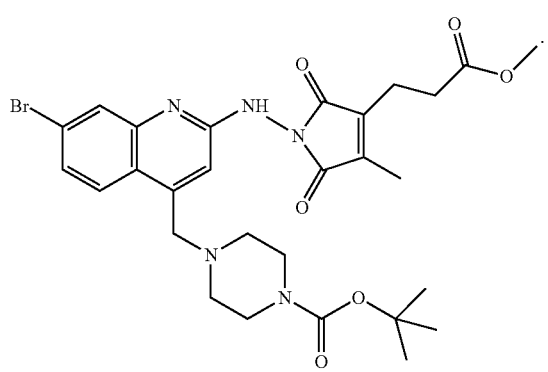 [SMILES: COC(=O)CCC1=C(C)C(=O)N(Nc2cc(CN3CCN(C(=O)OC(C)(C)C)CC3)c3ccc(Br)cc3n2)C1=O]

40. The method of claim 5, wherein the compound is 1-({4-[(4-{[4-(dimethylamino)phenyl]carbonyl}piperazinyl)methyl]-7-bromo (2-quinolyl)}amino)-3,4-dimethylazoline-2,5-dione (S01880) or a salt thereof, having the following structure:

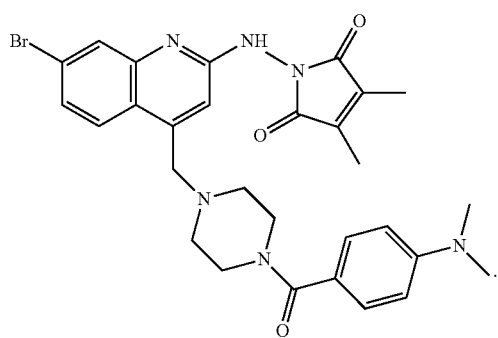 [SMILES: CC1=C(C)C(=O)N(Nc2cc(CN3CCN(C(=O)c4ccc(N(C)C)cc4)CC3)c3ccc(Br)cc3n2)C1=O]

41. The method of claim 5, wherein the compound is 1-[(3-chloroisoquinolyl)-amino]-3,4-dimethylazoline-2,5-dione (S01098) or a salt thereof, having the following structure:

42. The method of claim 5, wherein the compound is 1-{[6-chloro-5-(trifluoromethyl)(2-pyridyl)]-amino}-3-ethyl-4-methylazoline-2,5-dione (S01553) or a salt thereof, having the following structure:

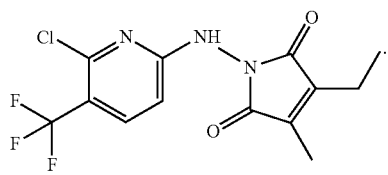 [SMILES: CCC1=C(C)C(=O)N(Nc2ccc(C(F)(F)F)c(Cl)n2)C1=O]

43. The method of claim 5, wherein the compound is 1-{[4-chloro-6-phenyl-5-(trifluoromethyl)(2-pyridyl)]amino}-3,4-dimethylazoline-2,5-dione (S01734) or a salt thereof, having the following structure:

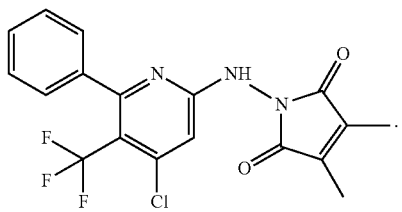 [SMILES: CC1=C(C)C(=O)N(Nc2cc(Cl)c(C(F)(F)F)c(-c3ccccc3)n2)C1=O]

44. The method of claim 5, wherein the compound is N-[1-({2-[(3,4-dimethyl-2,5-dioxoazolinyl)amino]-7-bromo(4-quinolyl)}-methyl)pyrrolidin-3-yl] (tert-butoxy)carboxamide (S01864) or a salt thereof, having the following structure:

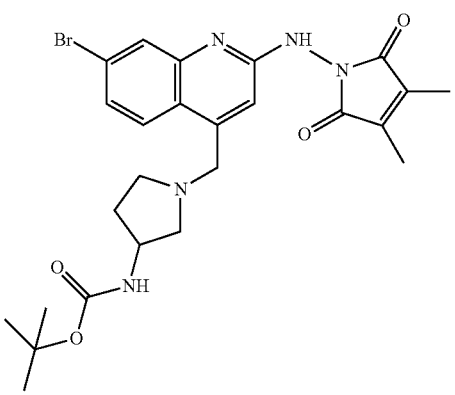

45. The method of claim 5, wherein the compound is 1-{[7-bromo-4-({4-[(4-fluorophenyl)carbonyl]

piperazinyl}methyl)(2-quinolyl)]amino}-3,4-dimethylazoline-2,5-dione (S01877) or a salt thereof, having the following structure:

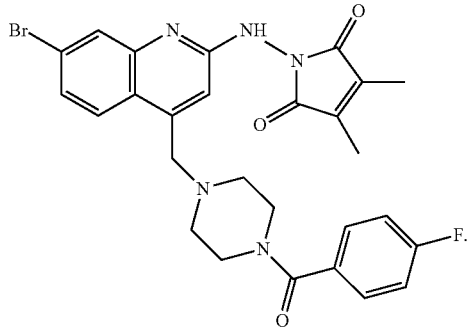 [SMILES: CC1=C(C)C(=O)N(Nc2cc(CN3CCN(C(=O)c4ccc(F)cc4)CC3)c3ccc(Br)cc3n2)C1=O]

46. The method of claim 5, wherein the compound is 6-[(3,4-dimethyl-2,5-dioxoazolinyl)amino]-3-(trifluoromethyl)pyridine-2-carbonitrile (S01475) or a salt thereof, having the following structure:

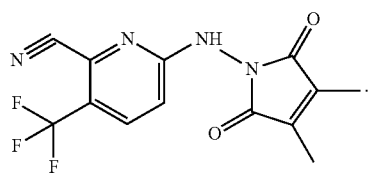 [SMILES: CC1=C(C)C(=O)N(Nc2ccc(C(F)(F)F)c(C#N)n2)C1=O]

47. The method of claim 5, wherein the compound is 2-{[6-chloro-5-(trifluoromethyl)-2-pyridyl]amino}-4,5,6,7-tetrahydroisoindole-1,3-dione (S00186) or a salt thereof, having the following structure:

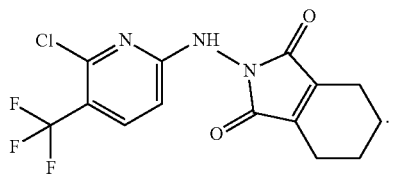 [SMILES: O=C1C2=C(CCCC2)C(=O)N1Nc1ccc(C(F)(F)F)c(Cl)n1]

48. The method of claim 5, wherein the compound is 1-{[4-bromo-3-(trifluoromethyl)phenyl]amino}-3,4-dimethylazoline-2,5-dione (S00516) or a salt thereof, having the following structure:

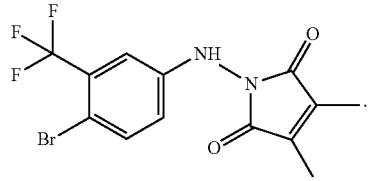 [SMILES: CC1=C(C)C(=O)N(Nc2ccc(Br)c(C(F)(F)F)c2)C1=O]

49. The method of claim 5, wherein the compound is 1-[(4-chloronaphthyl)amino]-3,4-dimethylazoline-2,5-dione (S00738) or a salt thereof, having the following structure:

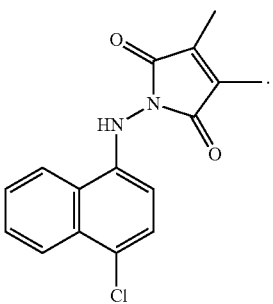 [SMILES: CC1=C(C)C(=O)N(Nc2ccc(Cl)c3ccccc23)C1=O]

50. The method of claim 5, wherein the compound is 1-[(4-chloro-6-methyl(2-quinolyl))amino]-3,4-dimethylazoline-2,5-dione (S00935) or a salt thereof, having the following structure:

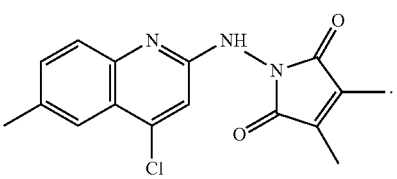

51. The method of claim 5, wherein the compound is 1-[(4-bromonaphthyl)amino]-3,4-dimethylazoline-2,5-dione (S00942) or a salt thereof, having the following structure:

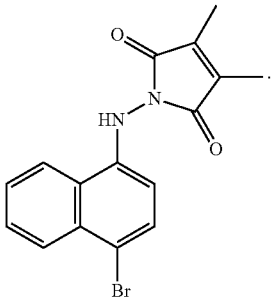

52. The method of claim 5, wherein the compound is 1-{[7-bromo-4-(hydroxymethyl)(2-quinolyl)]amino}-3,4-dimethylazoline-2,5-dione (S01037) or a salt thereof, having the following structure:

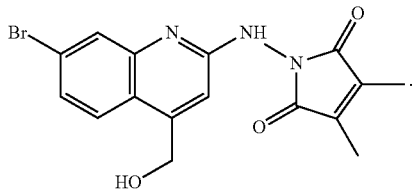 [SMILES: CC1=C(C)C(=O)N(Nc2cc(CO)c3ccc(Br)cc3n2)C1=O]

53. The method of claim 5, wherein the compound is {2-[(3,4-dimethyl-2,5-dioxoazolinyl)amino]-7-bromo-4-quinolyl}methyl acetate (S01047) or a salt thereof, having the following structure:

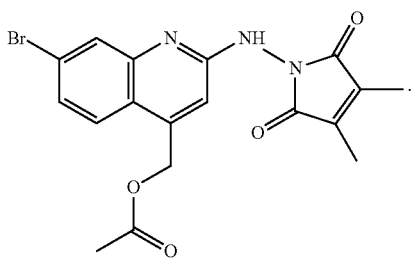 [SMILES: CC(=O)OCc1cc(NN2C(=O)C(C)=C(C)C2=O)nc2cc(Br)ccc12]

54. The method of claim 5, wherein the compound is 1-{[8-chloro-4-(4-methoxyphenyl)(2-quinolyl)]amino}-3,4-dimethylazoline-2,5-dione (S01191) or a salt thereof, having the following structure:

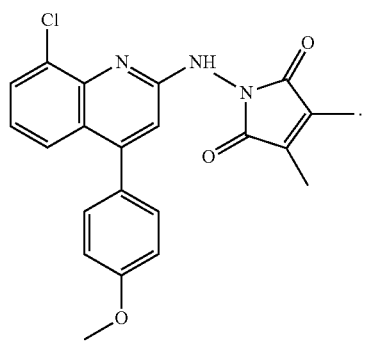 [SMILES: COc1ccc(-c2cc(NN3C(=O)C(C)=C(C)C3=O)nc3c(Cl)cccc23)cc1]

55. The method of claim 5, wherein the compound is 1-[(4-chlorobenzo[h]quinolin-2-yl)amino]-3,4-dimethylazoline-2,5-dione (S01207) or a salt thereof, having the following structure:

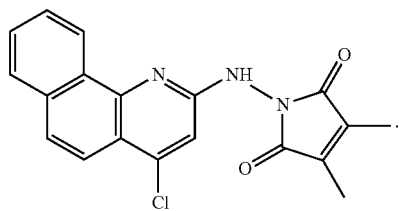 [SMILES: CC1=C(C)C(=O)N(Nc2cc(Cl)c3ccc4ccccc4c3n2)C1=O]

56. The method of claim 5, wherein the compound is 1-[(7-bromo-4-{[4-benzylpiperazinyl]methyl}(2-quinolyl))amino]-3,4-dimethylazoline-2,5-dione (S01268) or a salt thereof, having the following structure:

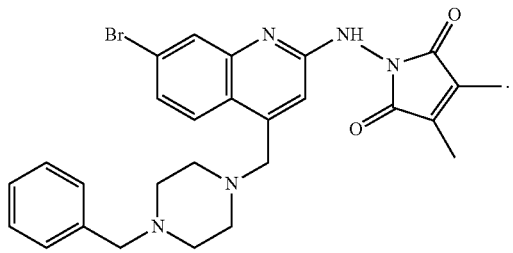 [SMILES: CC1=C(C)C(=O)N(Nc2cc(CN3CCN(Cc4ccccc4)CC3)c3ccc(Br)cc3n2)C1=O]

57. The method of claim 5, wherein the compound is 1-{[6-(4-chlorophenyl)-5-(trifluoromethyl)(2-pyridyl)]amino}-3,4-dimethylazoline-2,5-dione (S01371) or a salt thereof, having the following structure:

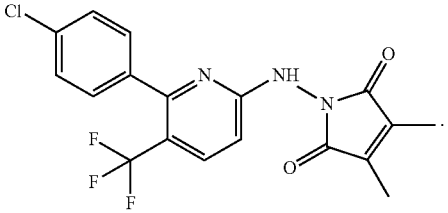 [SMILES: CC1=C(C)C(=O)N(Nc2ccc(C(F)(F)F)c(-c3ccc(Cl)cc3)n2)C1=O]

58. The method of claim 5, wherein the compound is 3,4-dimethyl-1-{[6-(4-methylphenyl)-5-(trifluoromethyl)(2-pyridyl)]amino}azoline-2,5-dione (S01393) or a salt thereof, having the following structure:

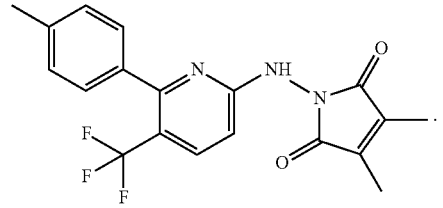

59. The method of claim 5, wherein the compound is 1-{[6-(3-chlorophenyl)-5-(trifluoromethyl)(2-pyridyl)]amino}-3,4-dimethylazoline-2,5-dione (S01474) or a salt thereof, having the following structure:

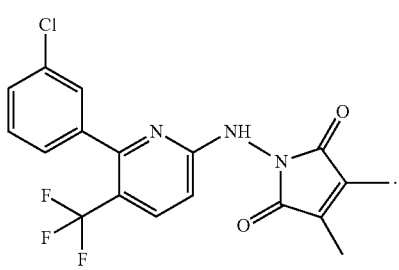 [SMILES: CC1=C(C)C(=O)N(Nc2ccc(C(F)(F)F)c(-c3cccc(Cl)c3)n2)C1=O]

60. The method of claim 5, wherein the compound is 1-{[6-chloro-5-(trifluoromethyl)(2-pyridyl)]methylamino}-3-(methoxymethyl)-4-methylazoline-2,5-dione (S01600) or a salt thereof, having the following structure:

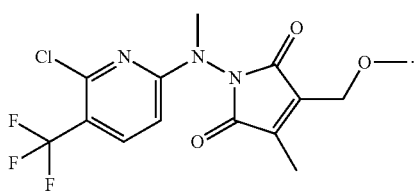 [SMILES: COCC1=C(C)C(=O)N(N(C)c2ccc(C(F)(F)F)c(Cl)n2)C1=O]

61. The method of claim 5, wherein the compound is phenylmethyl 4-({2-[3,4-dimethyl-2,5-dioxoazolinyl)amino]-7-bromo-4-quinolyl}methyl)piperazinecarboxylate (S01683) a salt thereof, having the following structure:

62. The method of claim 5, wherein the compound is 1-{[6-chloro-2-phenyl-3-(trifluoromethyl)(4-pyridyl]amino}-3,4-dimethylazoline-2,5-dione (S01688) or a salt thereof, having the following structure:

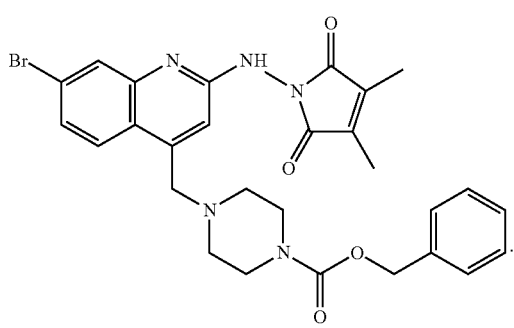 [SMILES: CC1=C(C)C(=O)N(Nc2cc(CN3CCN(C(=O)OCc4ccccc4)CC3)c3ccc(Br)cc3n2)C1=O]

63. The method of claim 5, wherein the compound is 3,4-dimethyl-1-({6-[3-(trifluoromethyl)phenyl](2-pyridyl)}amino)azoline-2,5-dione (S01691) or a salt thereof, having the following structure:

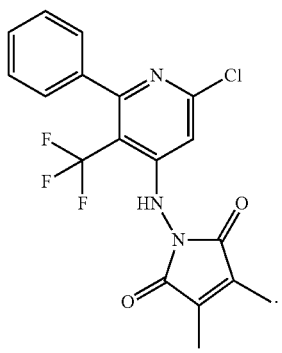 [SMILES: CC1=C(C)C(=O)N(Nc2cc(Cl)nc(-c3ccccc3)c2C(F)(F)F)C1=O]

64. The method of claim 5, wherein the compound is 1-[(7-bromo-4-{[4-(phenylcarbonyl)piperazinyl]methyl}(2-quinolyl)amino]-3,4-dimethylazoline-2,5-dione (S01699) or a salt thereof, having the following structure:

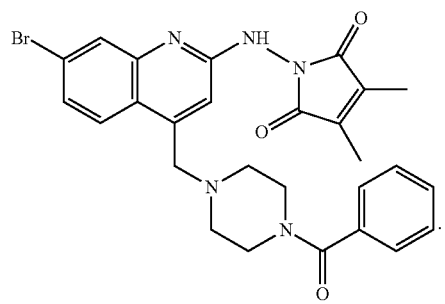 [SMILES: CC1=C(C)C(=O)N(Nc2cc(CN3CCN(C(=O)c4ccccc4)CC3)c3ccc(Br)cc3n2)C1=O]

65. The method of claim 5, wherein the compound is 3-(1-{[6-chloro-5-(trifluoromethyl)(2-pyridyl)]amino}-4-methyl-2,5-dioxoazolin-3-yl)-N-methyl-N-phenylpropanamide (S01759) or a salt thereof, having the following structure:

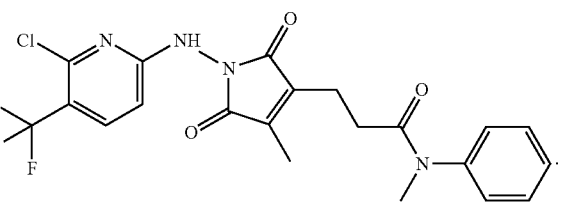

66. The method of claim 5, wherein the compound is 3,4-dimethyl-1-{[6-benzyl-5-(trifluoromethyl)(2-pyridyl)]amino}azoline-2,5-dione (S01762) or a salt thereof, having the following structure:

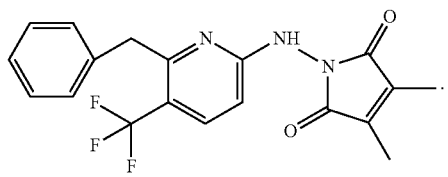 [SMILES: CC1=C(C)C(=O)N(Nc2ccc(C(F)(F)F)c(Cc3ccccc3)n2)C1=O]

67. The method of claim 5, wherein the compound is 1-{[4-({4-[(2,4-dimethylphenyl)carbonyl]piperazinyl}methyl)-7-bromo(2-quinolyl)]amino}-3,4-dimethylazoline-2,5-dione (S01800) or a salt thereof, having the following structure:

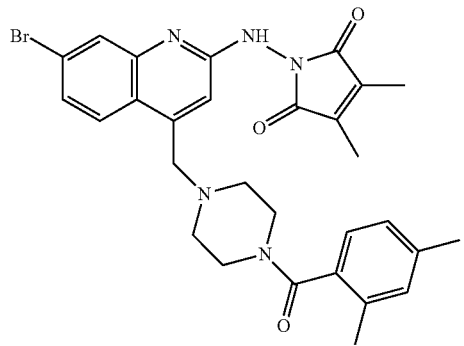

68. The method of claim 5, wherein the compound is 1-{[7-bromo-4-({4-[(4-methoxyphenyl)carbonyl]

piperazinyl}methyl)(2-quinolyl)]amino}-3,4-dimethylazoline-2,5-dione (S01801) or a salt thereof, having the following structure:

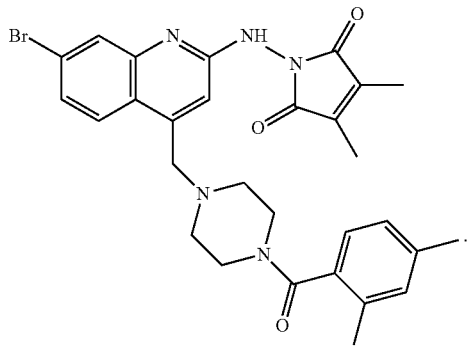 [SMILES: CC1=C(C)C(=O)N(Nc2cc(CN3CCN(C(=O)c4ccc(C)cc4C)CC3)c3ccc(Br)cc3n2)C1=O]

69. The method of claim 5, wherein the compound is N-[6-chloro-5-(trifluoromethyl)(2-pyridyl)]-N-[4-(hydroxymethyl)-3-methyl-2,5-dioxoazolinyl]acetamide (S01820) or a salt thereof, having the following structure:

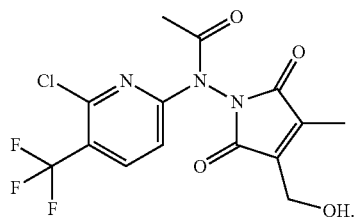 [SMILES: CC(=O)N(c1ccc(C(F)(F)F)c(Cl)n1)N1C(=O)C(C)=C(CO)C1=O]

70. The method of claim 5, wherein the compound is 1-[(7-bromo-4-{[4-(phenylsulfonyl)piperazinyl]methyl}(2-quinolyl))amino]-3,4-dimethylazoline-2,5-dione (S01822) or a salt thereof, having the following structure:

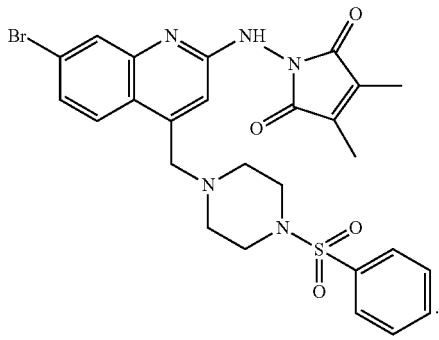 [SMILES: CC1=C(C)C(=O)N(Nc2cc(CN3CCN(S(=O)(=O)c4ccccc4)CC3)c3ccc(Br)cc3n2)C1=O]

71. The method of claim 5, wherein the compound is 1-[(4-chloro-8-methyl(2-quinolyl))amino]-3,4-dimethylazoline-2,5-dione (S00871) or a salt thereof, having the following structure:

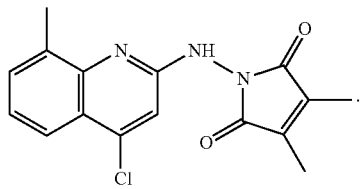 [SMILES: CC1=C(C)C(=O)N(Nc2cc(Cl)c3cccc(C)c3n2)C1=O]

72. The method of claim 5, wherein the compound is tert-butyl 4-[({2-[(3,4-dimethyl-2,5-dioxoazolinyl)amino]-7-bromo-4-quinolyl}methyl)amino]piperidinecarboxylate (S01862) or a salt thereof, having the following structure:

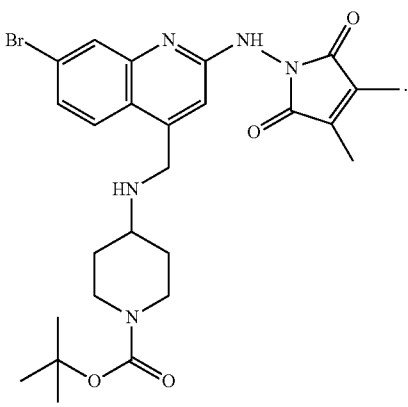 [SMILES: CC1=C(C)C(=O)N(Nc2cc(CNC3CCN(C(=O)OC(C)(C)C)CC3)c3ccc(Br)cc3n2)C1=O]

73. The method of claim 5, wherein the compound is tert-butyl 4-[4-({2-[(3,4-dimethyl-2,5-dioxoazolinyl)amino]-7-bromo-4-quinolyl}methyl)piperazinyl]piperidinecarboxylate (S01928) or a salt thereof, having the following structure:

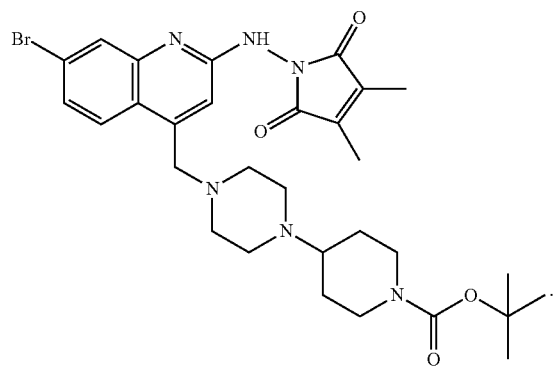 [SMILES: CC1=C(C)C(=O)N(Nc2cc(CN3CCN(C4CCN(C(=O)OC(C)(C)C)CC4)CC3)c3ccc(Br)cc3n2)C1=O]

74. The method of claim 5, wherein the compound is 1-[(4-{[4-(3,3-dimethylbutanoyl)piperazinyl]methyl}-7-bromo(2-quinolyl))amino]-3,4-dimethylazoline-2,5-dione (S01929) or a salt thereof, having the following structure:

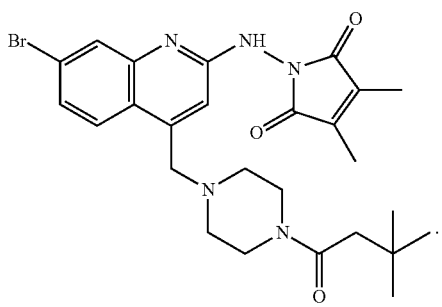 [SMILES: CC1=C(C)C(=O)N(Nc2cc(CN3CCN(C(=O)CC(C)(C)C)CC3)c3ccc(Br)cc3n2)C1=O]

75. The method of claim 5, wherein the compound is methylethyl 3-(1-{[6-chloro-5-(trifluoromethyl)(2-pyridyl)]amino}-4-methyl-2,5-dioxoazolin-3-yl)propanoate (S02022) or a salt thereof, having the following structure:

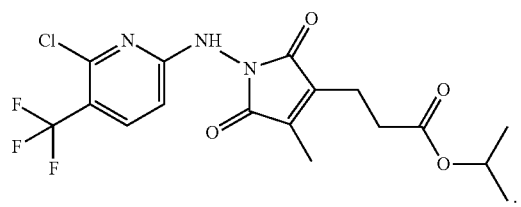 [SMILES: CC1=C(CCC(=O)OC(C)C)C(=O)N(Nc2ccc(C(F)(F)F)c(Cl)n2)C1=O]

76. The method of claim 5, wherein the compound is methylpropyl 3-(1-{[6-chloro-5-(trifluoromethyl)(2-pyridyl)]amino}-4-methyl-2,5-dioxoazolin-3-yl)propanoate (S02264) or a salt thereof, having the following structure:

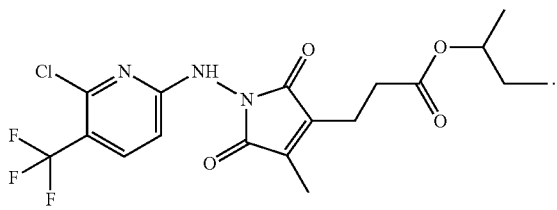 [SMILES: CCC(C)OC(=O)CCC1=C(C)C(=O)N(Nc2ccc(C(F)(F)F)c(Cl)n2)C1=O]

77. The method of claim 5, wherein the compound is tert-butyl 2-(1-{[6-chloro-5-(trifluoromethyl)(2-pyridyl)]amino}-4-methyl-2,5-dioxoazolin-3-yl)acetate (S02225) or a salt thereof, having the following structure:

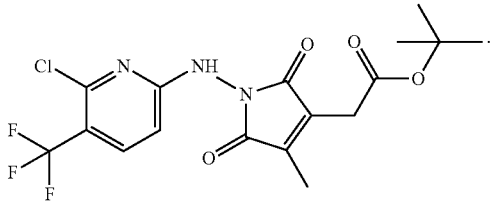 [SMILES: CC1=C(CC(=O)OC(C)(C)C)C(=O)N(Nc2ccc(C(F)(F)F)c(Cl)n2)C1=O]

78. The method of claim 5, wherein the compound is 1-{[6-Chloro-5-(trifluoromethyl)(2-pyridyl)]amino}-3-(ethoxymethyl)-4-methylazoline-2,5-dione (S02366) or a salt thereof, having the following structure:

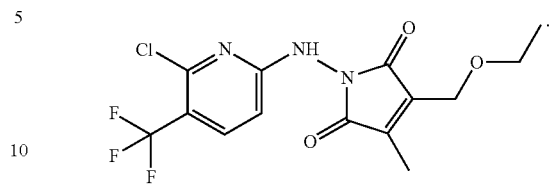

79. The method of claim 5, wherein the compound is 3-Butyl-1-{[6-chloro-5-(trifluoromethyl)(2-pyridyl)]amino}-4-methylazoline-2,5-dione (S03448) or a salt thereof, having the following structure:

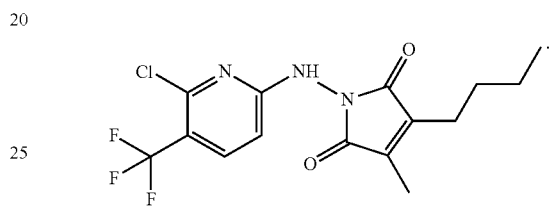

80. The method of claim 5, wherein the compound is 1-{[6-Chloro-5-(trifluoromethyl)(2-pyridyl)]amino}-4-methyl-3-[2-(2-methyl(1,3-dioxolan-2-yl))ethyl]azoline-2,5-dione (S03456) or a salt thereof, having the following structure:

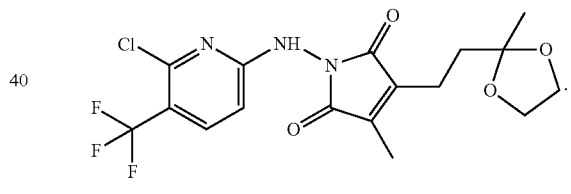

81. The method of claim 5, wherein the compound is 1-{[6-Chloro-5-(trifluoromethyl)(2-pyridyl)]amino}-3-[(2-methoxyethoxy)methyl]-4-methylazoline-2,5-dione (S03742) or a salt thereof, having the following structure:

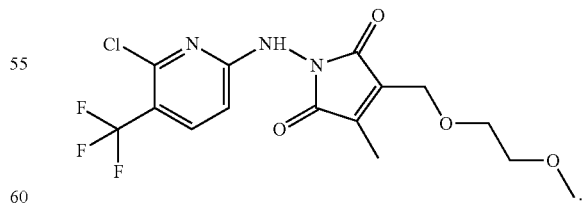

82. The method of claim 5, wherein the compound is 1-{[6-Chloro-5-(trifluoromethyl)(2-pyridyl)]-amino}-4-(3-hydroxyhexyl)-3-methylazoline-2,5-dione (S03552) or a salt thereof, having the following structure:

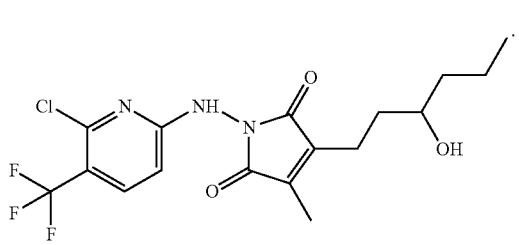 [SMILES: CCCC(O)CCC1=C(C)C(=O)N(Nc2ccc(C(F)(F)F)c(Cl)n2)C1=O]

83. The method of claim 5, wherein the compound is 1-{[6-Chloro-5-(trifluoromethyl)(2-pyridyl)]amino}-4-(3-hydroxypentyl)-3-methylazoline-2,5-dione (S03745) or a salt thereof, having the following structure:

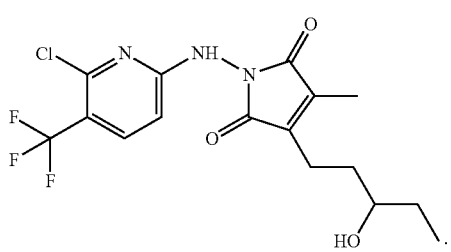 [SMILES: CCC(O)CCC1=C(C)C(=O)N(Nc2ccc(C(F)(F)F)c(Cl)n2)C1=O]

84. The method of claim 5, wherein the compound is 1-{[6-Chloro-5-(trifluoromethyl)(2-pyridyl)]-amino}-4-methyl-3-[(3-methylbutoxy)methyl]azoline-2,5-dione (S03405) or a salt thereof, having the following structure:

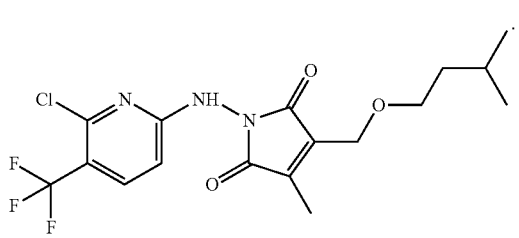 [SMILES: CC1=C(COCCC(C)C)C(=O)N(Nc2ccc(C(F)(F)F)c(Cl)n2)C1=O]

85. The method of claim 5, wherein the compound is 3-(Butoxymethyl)-1-{[6-chloro-5-(trifluoromethyl)(2-pyridyl)]amino}-4-methylazoline-2,5-dione (S03518) or a salt thereof, having the following structure:

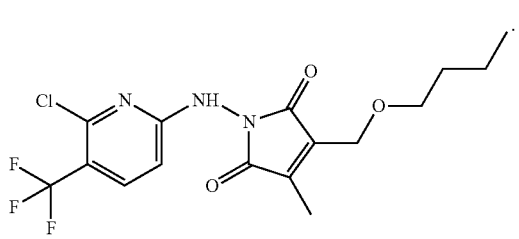 [SMILES: CCCCOCC1=C(C)C(=O)N(Nc2ccc(C(F)(F)F)c(Cl)n2)C1=O]

86. The method of claim 5, wherein the compound is 3-[(3,3-Dimethylbutoxy)methyl]-1-{[6-chloro-5-(trifluoromethyl)(2-pyridyl)]amino}-4-methylazoline-2,5-dione (S03747) or a salt thereof, having the following structure:

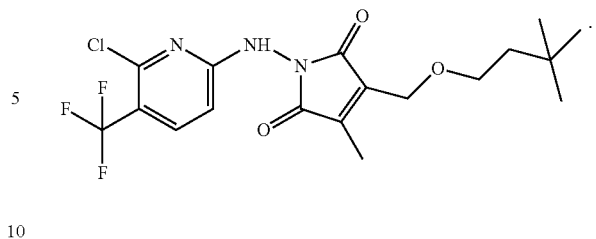

87. The method of claim 5, wherein the compound is 1-{[6-Chloro-5-(trifluoromethyl)(2-pyridyl)]amino}-3-(2-ethoxyethyl)-4-methylazoline-2,5-dione (S03960) or a salt thereof, having the following structure:

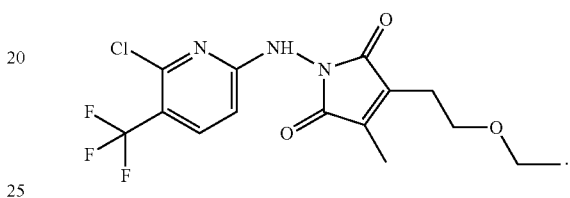

88. The method of claim 5, wherein the compound is 1-{[6-Chloro-5-(trifluoromethyl)(2-pyridyl)]amino}-4-methyl-3-[(2-methylpropoxy)methyl]azoline-2,5-dione (S03963) or a salt thereof, having the following structure:

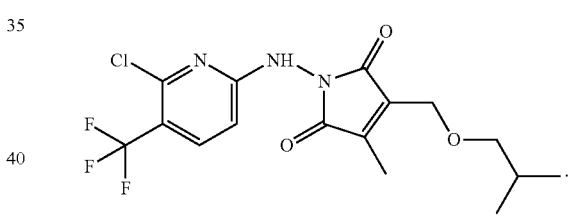

89. The method of claim 5, wherein the compound is 3-[(2,2-Dimethylpropoxy)methyl]-1-{[6-chloro-5-(trifluoromethyl)(2-pyridyl)]amino}-4-methylazoline-2,5-dione (S03962) or a salt thereof, having the following structure:

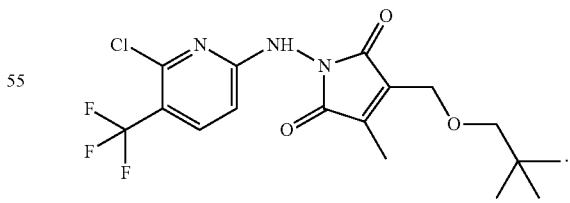

90. The method of claim 5, wherein the compound is 4-[(1,3-Dimethylbutoxy)methyl]-1-{[6-chloro-5-(trifluoromethyl)(2-pyridyl)]amino}-3-methylazoline-2,5-dione (S03964) or a salt thereof, having the following structure:

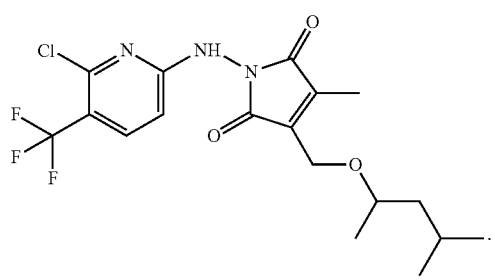 [SMILES: CC1=C(COC(C)CC(C)C)C(=O)N(Nc2ccc(C(F)(F)F)c(Cl)n2)C1=O]

91. The method of claim 5, wherein the compound is 4-[(tert-Butoxy)methyl]-1-{[6-chloro-5-(trifluoromethyl)(2-pyridyl)]amino}-3-methylazoline-2,5-dione (S03873) or a salt thereof, having the following structure:

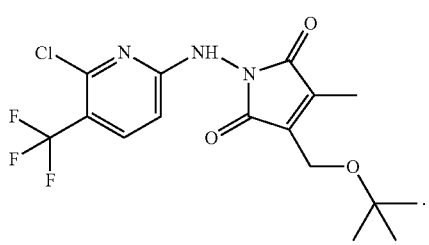 [SMILES: CC1=C(COC(C)(C)C)C(=O)N(Nc2ccc(C(F)(F)F)c(Cl)n2)C1=O]

92. The method of claim 5, wherein the compound is 1-{[6-Chloro-5-(trifluoromethyl)(2-pyridyl)]amino}-4-methyl-3-[2-(2-methylpropoxy)ethyl]azoline-2,5-dione (S03955) or a salt thereof, having the following structure:

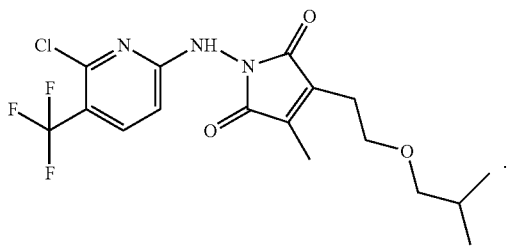 [SMILES: CC1=C(CCOCC(C)C)C(=O)N(Nc2ccc(C(F)(F)F)c(Cl)n2)C1=O]

93. The method of claim 5, wherein the compound is 1-{[6-Chloro-5-(trifluoromethyl)(2-pyridyl)]amino}-4-methyl-3-[2-(3-methylbutoxy)ethyl]azoline-2,5-dione (S03956) or a salt thereof, having the following structure:

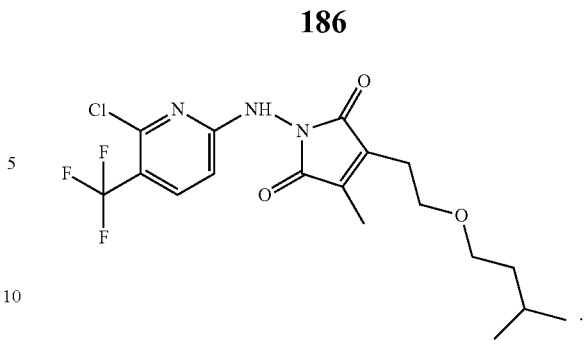

94. The method of claim 5, wherein the compound is 1-{[6-Chloro-5-(trifluoromethyl)(2-pyridyl)]amino}-3-methyl-4-(2-propoxyethyl)azoline-2,5-dione (S04034) or a salt thereof, having the following structure:

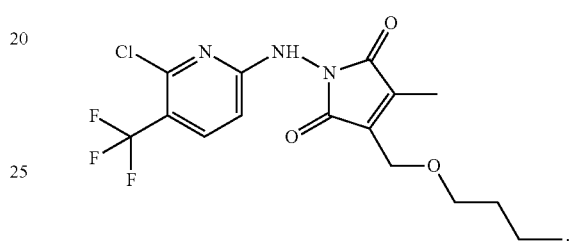

95. The method of claim 1 or 5, wherein the compound comprises a pharmaceutical composition.

96. The method of claim 1, comprising administering an effective amount of the compound to the subject.

97. The method of claim 1, wherein the cell proliferation disorder is cancer.

98. The method of claim 97, wherein the cancer is a lymphoma.

99. The method of claim 97, wherein the cancer is a myeloma.

100. The method of claim 97, wherein the cancer call is a leukemia.

101. The method of claim 1, further comprising administering at least one additional anti-cancer treatment.

102. The method of claim 101, wherein the anti-cancer treatment is a DNA-damaging agent or a DNA-damaging treatment.

103. The method of claim 5, further comprising administering at least one additional anti-cancer treatment.

104. The method of claim 103, wherein the anti-cancer treatment is a DNA-damaging agent or a DNA-damaging treatment.

* * * * *